United States Patent
Askem et al.

(10) Patent No.: US 11,903,798 B2
(45) Date of Patent: *Feb. 20, 2024

(54) REDUCED PRESSURE APPARATUS AND METHODS

(71) Applicant: Smith & Nephew PLC, Watford (GB)

(72) Inventors: Ben Alan Askem, Leeds (GB); Sarah Jenny Collinson, Hull (GB); John Cowan-Hughes, Bristol (GB); Christopher John Fryer, York (GB); Tom Moy, Norwish (GB); Paul Mullen, Bristol (GB); Derek Nicolini, Hull (GB); Neil Pryor, Bristol (GB); Philip Walsh, Bristol (GB); Ian Binder, Chippenham (GB)

(73) Assignee: Smith & Nephew PLC, Watford (GB)

( * ) Notice: Subject to any disclaimer, the term of this patent is extended or adjusted under 35 U.S.C. 154(b) by 304 days.

This patent is subject to a terminal disclaimer.

(21) Appl. No.: 17/397,860

(22) Filed: Aug. 9, 2021

(65) Prior Publication Data

US 2021/0361854 A1 Nov. 25, 2021

Related U.S. Application Data

(63) Continuation of application No. 16/047,786, filed on Jul. 27, 2018, now Pat. No. 11,129,931, which is a
(Continued)

(51) Int. Cl.
*A61F 13/02* (2006.01)
*A61M 1/00* (2006.01)
*A61F 13/00* (2006.01)

(52) U.S. Cl.
CPC .... *A61F 13/0246* (2013.01); *A61F 13/00042* (2013.01); *A61M 1/732* (2021.05);
(Continued)

(58) Field of Classification Search
CPC .. A61M 1/964; A61M 2205/82; A61M 1/962; A61M 1/985; A61M 1/80;
(Continued)

(56) References Cited

U.S. PATENT DOCUMENTS

| | | | |
|---|---|---|---|
| 3,874,387 | A | 4/1975 | Barbieri |
| 3,972,328 | A | 8/1976 | Chen |

(Continued)

FOREIGN PATENT DOCUMENTS

| | | |
|---|---|---|
| CN | 201664463 U | 12/2010 |
| DE | 9017289 U1 | 4/1992 |

(Continued)

OTHER PUBLICATIONS

Annex to the Communication, the Opposition of European Patent No. 2825220, mailed on May 10, 2019, 17 pages.
(Continued)

*Primary Examiner* — Adam Marcetich
(74) *Attorney, Agent, or Firm* — Knobbe, Martens, Olson & Bear, LLP

(57) ABSTRACT

Some embodiments have a pump assembly mounted to or supported by a dressing for reduced pressure wound therapy. The dressing can have visual pressure, saturation, and/or temperature sensors to provide a visual indication of the level of pressure, saturation, and/or temperature within the dressing. Additionally, the pump assembly can have a pressure sensor in communication with the flow pathway through the pump, and at least one switch or button supported by the housing, the at least one switch or button being accessible to a user and being in communication with the controller. The pump assembly can have a controller supported within or by the housing, the controller being configured to control an operation of the pump. The pump can be configured to be sterilized following the assembly of the
(Continued)

pump such that all of the components of the pump have been sterilized.

11 Claims, 105 Drawing Sheets

Related U.S. Application Data continuation of application No. 14/385,136, filed as application No. PCT/IB2013/000847 on Mar. 12, 2013, now Pat. No. 10,046,096.

(60) Provisional application No. 61/609,905, filed on Mar. 12, 2012.

(52) U.S. Cl.
CPC ............ *A61M 1/915* (2021.05); *A61M 1/962* (2021.05); *A61M 1/964* (2021.05); *A61F 2013/00536* (2013.01); *A61M 1/966* (2021.05); *A61M 1/982* (2021.05); *A61M 1/985* (2021.05); *A61M 2205/0216* (2013.01); *A61M 2205/42* (2013.01); *A61M 2205/80* (2013.01); *A61M 2205/82* (2013.01); *A61M 2205/8206* (2013.01); *A61M 2205/8293* (2013.01)

(58) Field of Classification Search
CPC .......... A61M 2205/8206; A61M 27/00; A61M 1/984; A61F 13/00068; A61F 2013/00536; A61F 2013/00544; A61F 13/0226
See application file for complete search history.

(56) References Cited

U.S. PATENT DOCUMENTS

| | | |
|---|---|---|
| 4,224,941 A | 9/1980 | Stivala |
| 4,398,910 A | 8/1983 | Blake et al. |
| 4,468,969 A | 9/1984 | Schwartz |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,846,164 A | 7/1989 | Martz |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,115,801 A | 5/1992 | Cartmell et al. |
| 5,152,757 A | 10/1992 | Eriksson |
| 5,160,328 A | 11/1992 | Cartmell et al. |
| 5,181,905 A | 1/1993 | Flam |
| 5,197,945 A | 3/1993 | Cole et al. |
| 5,238,732 A | 8/1993 | Krishnan |
| 5,266,928 A | 11/1993 | Johnson |
| 5,336,219 A | 8/1994 | Krantz |
| 5,354,261 A | 10/1994 | Clark et al. |
| 5,358,494 A | 10/1994 | Svedman |
| 5,364,381 A | 11/1994 | Soga et al. |
| 5,380,294 A | 1/1995 | Persson |
| D357,743 S | 4/1995 | Bilitz et al. |
| 5,417,743 A | 5/1995 | Dauber |
| 5,447,492 A | 9/1995 | Cartmell et al. |
| 5,456,660 A | 10/1995 | Reich et al. |
| 5,480,377 A | 1/1996 | Cartmell et al. |
| 5,497,788 A | 3/1996 | Inman et al. |
| 5,527,293 A | 6/1996 | Zamierowski |
| 5,538,500 A | 7/1996 | Peterson |
| 5,549,584 A | 8/1996 | Gross |
| 5,562,107 A | 10/1996 | Lavender et al. |
| 5,579,765 A | 12/1996 | Cox et al. |
| 5,603,946 A | 2/1997 | Constantine |
| 5,636,643 A | 6/1997 | Argenta et al. |
| 5,637,080 A | 6/1997 | Geng |
| 5,643,189 A | 7/1997 | Masini |
| 5,662,599 A | 9/1997 | Reich et al. |
| 5,702,356 A | 12/1997 | Hathman |
| 5,704,905 A | 1/1998 | Jensen et al. |
| 5,713,384 A | 2/1998 | Roach et al. |
| 5,759,570 A | 6/1998 | Arnold |
| 5,779,657 A | 7/1998 | Daneshvar |
| 5,827,213 A | 10/1998 | Jensen |
| 5,833,646 A | 11/1998 | Masini |
| 5,840,052 A | 11/1998 | Johns |
| 5,843,025 A | 12/1998 | Shaari |
| 5,887,437 A | 3/1999 | Maxim |
| 5,897,541 A | 4/1999 | Uitenbroek et al. |
| 5,902,256 A | 5/1999 | Benaron |
| 5,964,723 A | 10/1999 | Augustine |
| 6,040,493 A | 3/2000 | Cooke et al. |
| 6,071,267 A | 6/2000 | Zamierowski |
| 6,075,177 A | 6/2000 | Bahia et al. |
| 6,124,520 A | 9/2000 | Roberts |
| 6,124,521 A | 9/2000 | Roberts |
| 6,142,982 A | 11/2000 | Hunt et al. |
| 6,168,800 B1 | 1/2001 | Dobos et al. |
| 6,183,438 B1 | 2/2001 | Berguer |
| 6,189,327 B1 | 2/2001 | Strauss et al. |
| 6,225,523 B1 | 5/2001 | Masini |
| 6,261,276 B1 | 7/2001 | Reitsma |
| 6,261,283 B1 | 7/2001 | Morgan et al. |
| 6,297,423 B1 | 10/2001 | Schoenfeldt et al. |
| 6,362,390 B1 | 3/2002 | Carlucci et al. |
| 6,398,767 B1 | 6/2002 | Fleischmann |
| 6,468,295 B2 | 10/2002 | Augustine et al. |
| 6,471,982 B1 | 10/2002 | Lydon et al. |
| 6,506,175 B1 | 1/2003 | Goldstein |
| 6,528,696 B1 | 3/2003 | Ireland |
| 6,586,653 B2 | 7/2003 | Graeme, III et al. |
| 6,599,262 B1 | 7/2003 | Masini |
| 6,607,495 B1 | 8/2003 | Skalak et al. |
| 6,613,953 B1 | 9/2003 | Altura |
| 6,626,891 B2 | 9/2003 | Ohmstede |
| 6,685,681 B2 | 2/2004 | Lockwood et al. |
| 6,706,940 B2 | 3/2004 | Worthley |
| 6,719,742 B1 | 4/2004 | McCormack et al. |
| 6,752,794 B2 | 6/2004 | Lockwood et al. |
| 6,762,337 B2 | 7/2004 | Boukanov et al. |
| 6,764,459 B1 | 7/2004 | Donaldson |
| 6,776,769 B2 | 8/2004 | Smith |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,936,037 B2 | 8/2005 | Bubb et al. |
| 6,942,633 B2 | 9/2005 | Odland |
| 6,951,553 B2 | 10/2005 | Bubb et al. |
| 6,979,324 B2 | 12/2005 | Bybordi et al. |
| 6,998,511 B2 | 2/2006 | Worthley |
| 7,004,915 B2 | 2/2006 | Boynton et al. |
| 7,022,113 B2 | 4/2006 | Lockwood et al. |
| 7,041,057 B1 | 5/2006 | Faupel et al. |
| 7,049,478 B1 | 5/2006 | Smith |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,118,545 B2 | 10/2006 | Boyde |
| 7,216,651 B2 | 5/2007 | Argenta et al. |
| 7,294,751 B2 | 11/2007 | Propp et al. |
| 7,294,752 B1 | 11/2007 | Propp |
| 7,338,482 B2 | 3/2008 | Lockwood et al. |
| 7,361,184 B2 | 4/2008 | Joshi |
| 7,381,859 B2 | 6/2008 | Hunt et al. |
| 7,429,689 B2 | 9/2008 | Chen et al. |
| 7,476,205 B2 | 1/2009 | Erdmann |
| 7,498,802 B2 | 3/2009 | Takahata |
| 7,511,187 B2 | 3/2009 | Kelly |
| 7,524,315 B2 | 4/2009 | Blott et al. |
| 7,553,306 B1 | 6/2009 | Hunt et al. |
| 7,563,940 B2 | 7/2009 | Kurata |

(56) References Cited

U.S. PATENT DOCUMENTS

| | | |
|---|---|---|
| 7,569,742 B2 | 8/2009 | Haggstrom et al. |
| 7,576,256 B2 | 8/2009 | Bjornberg et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| D605,775 S | 12/2009 | Koch et al. |
| 7,625,362 B2 | 12/2009 | Boehringer et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,708,724 B2 | 5/2010 | Weston |
| 7,722,582 B2 | 5/2010 | Lina et al. |
| 7,723,561 B2 | 5/2010 | Propp |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| D625,422 S | 10/2010 | Arbesman et al. |
| 7,811,269 B2 | 10/2010 | Boynton et al. |
| 7,837,673 B2 | 11/2010 | Vogel |
| 7,838,717 B2 | 11/2010 | Haggstrom et al. |
| 7,846,141 B2 | 12/2010 | Weston |
| 7,896,864 B2 | 3/2011 | Lockwood et al. |
| 7,910,791 B2 | 3/2011 | Coffey |
| 7,922,676 B2 | 4/2011 | Daskal et al. |
| 7,922,703 B2 | 4/2011 | Riesinger |
| 7,935,066 B2 | 5/2011 | Shives et al. |
| 7,942,866 B2 | 5/2011 | Radl et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,988,673 B2 | 8/2011 | Wright et al. |
| 8,007,257 B2 | 8/2011 | Heaton et al. |
| 8,007,481 B2 | 8/2011 | Schuessler et al. |
| 8,021,253 B2 | 9/2011 | Dell et al. |
| 8,021,347 B2 | 9/2011 | Vitaris et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,092,436 B2 | 1/2012 | Christensen |
| 8,092,441 B2 | 1/2012 | Sugito |
| 8,118,794 B2 | 2/2012 | Weston |
| 8,158,844 B2 | 4/2012 | McNeil |
| 8,162,907 B2 | 4/2012 | Heagle |
| 8,167,869 B2 | 5/2012 | Wudyka |
| 8,168,848 B2 | 5/2012 | Lockwood et al. |
| 8,188,331 B2 | 5/2012 | Barta et al. |
| 8,192,409 B2 | 6/2012 | Hardman et al. |
| 8,207,392 B2 | 6/2012 | Haggstrom et al. |
| 8,212,100 B2 | 7/2012 | Moore |
| 8,212,101 B2 | 7/2012 | Propp |
| 8,215,929 B2 | 7/2012 | Shen et al. |
| 8,241,261 B2 | 8/2012 | Randolph et al. |
| 8,252,971 B2 | 8/2012 | Aali et al. |
| 8,282,611 B2 | 10/2012 | Weston |
| 8,303,552 B2 | 11/2012 | Weston |
| 8,314,283 B2 | 11/2012 | Kingsford et al. |
| 8,323,264 B2 | 12/2012 | Weston et al. |
| 8,328,858 B2 | 12/2012 | Barsky et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,403,899 B2 | 3/2013 | Sherman |
| 8,404,921 B2 | 3/2013 | Lee et al. |
| 8,409,157 B2 | 4/2013 | Haggstrom et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,444,612 B2 | 5/2013 | Patel et al. |
| 8,449,508 B2 | 5/2013 | Coulthard et al. |
| 8,460,255 B2 | 6/2013 | Joshi et al. |
| 8,500,776 B2 | 8/2013 | Ebner |
| 8,529,548 B2 | 9/2013 | Blott et al. |
| 8,535,296 B2 | 9/2013 | Blott et al. |
| 8,545,464 B2 | 10/2013 | Weston |
| 8,569,566 B2 | 10/2013 | Blott et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,628,505 B2 | 1/2014 | Weston |
| 8,641,691 B2 | 2/2014 | Fink et al. |
| 8,641,693 B2 | 2/2014 | Locke et al. |
| 8,663,198 B2 | 3/2014 | Buan et al. |
| 8,702,665 B2 | 4/2014 | Locke et al. |
| 8,715,256 B2 | 5/2014 | Greener |
| 8,764,732 B2 | 7/2014 | Hartwell |
| 8,791,316 B2 | 7/2014 | Greener |
| 8,795,243 B2 | 8/2014 | Weston |
| 8,795,247 B2 | 8/2014 | Bennett et al. |
| 8,795,257 B2 | 8/2014 | Coulthard et al. |
| 8,801,685 B2 | 8/2014 | Armstrong et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,829,263 B2 | 9/2014 | Haggstrom et al. |
| 8,834,451 B2 | 9/2014 | Blott et al. |
| 8,870,837 B2 | 10/2014 | Locke et al. |
| 8,915,895 B2 | 12/2014 | Jaeb et al. |
| 8,961,496 B2 | 2/2015 | Locke et al. |
| 8,974,429 B2 | 3/2015 | Gordon et al. |
| 9,050,209 B2 | 6/2015 | Coulthard et al. |
| 9,084,845 B2 | 7/2015 | Adie et al. |
| 9,089,630 B2 | 7/2015 | Perkins et al. |
| 9,168,330 B2 | 10/2015 | Joshi et al. |
| 9,198,802 B2 | 12/2015 | Robinson et al. |
| 9,254,353 B2 | 2/2016 | Locke et al. |
| 9,259,558 B2 | 2/2016 | Tsai |
| 9,265,665 B2 | 2/2016 | Robinson et al. |
| 9,265,867 B2 | 2/2016 | Coulthard et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,446,176 B2 | 9/2016 | Locke et al. |
| 9,452,088 B2 | 9/2016 | Shulman et al. |
| 9,452,245 B2 | 9/2016 | Jaeb et al. |
| 9,770,368 B2 | 9/2017 | Robinson et al. |
| 9,795,725 B2 | 10/2017 | Joshi et al. |
| 9,814,811 B2 | 11/2017 | Aalders et al. |
| 9,907,703 B2 | 3/2018 | Allen et al. |
| RE46,778 E | 4/2018 | Peron |
| 10,046,096 B2 | 8/2018 | Askem et al. |
| 10,384,041 B2 | 8/2019 | Patel et al. |
| 10,660,994 B2 | 5/2020 | Askem et al. |
| 11,730,877 B2 | 8/2023 | Askem |
| 2001/0034499 A1 | 10/2001 | Sessions et al. |
| 2001/0051178 A1 | 12/2001 | Blatchford et al. |
| 2002/0019602 A1 | 2/2002 | Geng |
| 2002/0072733 A1 | 6/2002 | Flaherty |
| 2002/0110672 A1 | 8/2002 | Muratore-Pallatino et al. |
| 2002/0169405 A1 | 11/2002 | Roberts |
| 2003/0009122 A1 | 1/2003 | Veras |
| 2003/0045825 A1 | 3/2003 | Etheredge, III |
| 2003/0069563 A1 | 4/2003 | Johnson |
| 2003/0114818 A1 | 6/2003 | Benecke et al. |
| 2003/0117371 A1 | 6/2003 | Roberts et al. |
| 2003/0180341 A1 | 9/2003 | Gooch et al. |
| 2003/0199800 A1 | 10/2003 | Levin |
| 2003/0212357 A1 | 11/2003 | Pace |
| 2003/0212359 A1 | 11/2003 | Butler |
| 2004/0064132 A1 | 4/2004 | Boehringer et al. |
| 2004/0073151 A1 | 4/2004 | Weston |
| 2004/0076662 A1 | 4/2004 | Riesinger |
| 2004/0078011 A1 | 4/2004 | Stevens |
| 2004/0087884 A1 | 5/2004 | Haddock et al. |
| 2004/0106888 A1 | 6/2004 | Lutri et al. |
| 2004/0138602 A1 | 7/2004 | Rossen |

(56) References Cited

U.S. PATENT DOCUMENTS

| | | |
|---|---|---|
| 2004/0162512 A1 | 8/2004 | Liedtke et al. |
| 2004/0167482 A1 | 8/2004 | Watson |
| 2004/0243042 A1 | 12/2004 | Lipman |
| 2005/0012616 A1 | 1/2005 | Forster et al. |
| 2005/0015036 A1 | 1/2005 | Lutri et al. |
| 2005/0045461 A1 | 3/2005 | Sweetland et al. |
| 2005/0065471 A1 | 3/2005 | Kuntz |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2005/0272142 A1 | 12/2005 | Horita |
| 2006/0003604 A1 | 1/2006 | Angerpointner |
| 2006/0009744 A1 | 1/2006 | Erdman et al. |
| 2006/0019144 A1 | 1/2006 | Hidaka et al. |
| 2006/0020234 A1 | 1/2006 | Chou et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0122548 A1 | 6/2006 | Abrams |
| 2006/0192259 A1 | 8/2006 | Silverbrook |
| 2006/0206047 A1 | 9/2006 | Lampe et al. |
| 2006/0213527 A1 | 9/2006 | Argenta et al. |
| 2006/0259102 A1 | 11/2006 | Slatkine |
| 2007/0003604 A1 | 1/2007 | Jones |
| 2007/0055209 A1 | 3/2007 | Patel et al. |
| 2007/0078366 A1 | 4/2007 | Haggstrom et al. |
| 2007/0078467 A1 | 4/2007 | Mullen |
| 2007/0091614 A1 | 4/2007 | Kaisser et al. |
| 2007/0100308 A1 | 5/2007 | Miyairi |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2007/0265586 A1 | 11/2007 | Joshi et al. |
| 2007/0282236 A1 | 12/2007 | LaGreca |
| 2008/0021356 A1 | 1/2008 | Castello Escude et al. |
| 2008/0021395 A1 | 1/2008 | Yodfat et al. |
| 2008/0051716 A1 | 2/2008 | Stutz |
| 2008/0058691 A1 | 3/2008 | Sorensen |
| 2008/0082059 A1 | 4/2008 | Fink et al. |
| 2008/0167592 A1 | 7/2008 | Greer |
| 2008/0200906 A1 | 8/2008 | Sanders et al. |
| 2008/0278336 A1 | 11/2008 | Ortega et al. |
| 2008/0281297 A1 | 11/2008 | Pesach et al. |
| 2008/0306456 A1 | 12/2008 | Riesinger |
| 2009/0012484 A1 | 1/2009 | Nielsen et al. |
| 2009/0048556 A1 | 2/2009 | Durand |
| 2009/0114293 A1 | 5/2009 | Kanai et al. |
| 2009/0125004 A1 | 5/2009 | Shen et al. |
| 2009/0129986 A1 | 5/2009 | Wimberger-Friedl et al. |
| 2009/0166411 A1 | 7/2009 | Kramer et al. |
| 2009/0227935 A1 | 9/2009 | Zanella et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0275896 A1 | 11/2009 | Kamen et al. |
| 2009/0299251 A1 | 12/2009 | Buan |
| 2009/0299306 A1 | 12/2009 | Buan |
| 2009/0320611 A1 | 12/2009 | Vasarhelyi et al. |
| 2010/0022990 A1 | 1/2010 | Karpowicz et al. |
| 2010/0036334 A1 | 2/2010 | Heagle et al. |
| 2010/0055158 A1 | 3/2010 | Vitaris et al. |
| 2010/0068820 A1 | 3/2010 | Meathrel et al. |
| 2010/0084074 A1 | 4/2010 | McClernon et al. |
| 2010/0087767 A1 | 4/2010 | McNeil |
| 2010/0100160 A1 | 4/2010 | Edman et al. |
| 2010/0106120 A1 | 4/2010 | Holm |
| 2010/0106121 A1 | 4/2010 | Holm |
| 2010/0125234 A1 | 5/2010 | Smith |
| 2010/0125258 A1 | 5/2010 | Coulthard et al. |
| 2010/0137775 A1 | 6/2010 | Hu et al. |
| 2010/0160881 A1 | 6/2010 | Lin et al. |
| 2010/0174250 A1 | 7/2010 | Hu et al. |
| 2010/0195318 A1 | 8/2010 | Jones |
| 2010/0217177 A1 | 8/2010 | Cali et al. |
| 2010/0262091 A1 | 10/2010 | Larsson |
| 2010/0265649 A1 | 10/2010 | Singh et al. |
| 2010/0280469 A1 | 11/2010 | Hall et al. |
| 2010/0286607 A1 | 11/2010 | Saltzstein |
| 2010/0292632 A1 | 11/2010 | Mulvihill et al. |
| 2010/0305490 A1* | 12/2010 | Coulthard ............ A61F 13/0206 604/313 |
| 2010/0305526 A1 | 12/2010 | Robinson et al. |
| 2010/0318052 A1 | 12/2010 | Ha et al. |
| 2010/0324510 A1 | 12/2010 | Andresen et al. |
| 2011/0004172 A1 | 1/2011 | Eckstein et al. |
| 2011/0040578 A1 | 2/2011 | Ramsey |
| 2011/0052664 A1 | 3/2011 | Tennican et al. |
| 2011/0054285 A1 | 3/2011 | Searle et al. |
| 2011/0054421 A1 | 3/2011 | Hartwell |
| 2011/0092927 A1 | 4/2011 | Wilkes et al. |
| 2011/0098621 A1 | 4/2011 | Fabo et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0137222 A1 | 6/2011 | Masini |
| 2011/0178375 A1 | 7/2011 | Forster |
| 2011/0178451 A1 | 7/2011 | Robinson et al. |
| 2011/0218509 A1 | 9/2011 | Dontas |
| 2011/0224631 A1 | 9/2011 | Simmons et al. |
| 2011/0230849 A1 | 9/2011 | Coulthard et al. |
| 2011/0236265 A1 | 9/2011 | Hasui et al. |
| 2011/0236277 A1 | 9/2011 | Lee et al. |
| 2011/0245788 A1 | 10/2011 | Marquez Canada |
| 2011/0247636 A1 | 10/2011 | Pollack |
| 2011/0270182 A1 | 11/2011 | Breznock et al. |
| 2011/0282309 A1 | 11/2011 | Adie et al. |
| 2011/0292623 A1 | 12/2011 | Stanley |
| 2011/0305736 A1 | 12/2011 | Wieland et al. |
| 2012/0016322 A1 | 1/2012 | Coulthard et al. |
| 2012/0016323 A1* | 1/2012 | Robinson ............ A61F 13/0216 604/319 |
| 2012/0041399 A1 | 2/2012 | Blott et al. |
| 2012/0053541 A1 | 3/2012 | Yao et al. |
| 2012/0059294 A1 | 3/2012 | Schubert et al. |
| 2012/0065664 A1 | 3/2012 | Avitable et al. |
| 2012/0095426 A1 | 4/2012 | Visscher et al. |
| 2012/0101465 A1 | 4/2012 | McGuire, Jr. |
| 2012/0109034 A1 | 5/2012 | Locke et al. |
| 2012/0109083 A1 | 5/2012 | Coulthard et al. |
| 2012/0123311 A1 | 5/2012 | Weidemann-Hendrickson et al. |
| 2012/0172778 A1 | 7/2012 | Rastegar et al. |
| 2012/0199125 A1 | 8/2012 | Bowditch et al. |
| 2012/0203145 A1 | 8/2012 | Nilsson |
| 2012/0203189 A1 | 8/2012 | Barta et al. |
| 2012/0232502 A1 | 9/2012 | Lowing |
| 2012/0238932 A1 | 9/2012 | Atteia et al. |
| 2013/0090615 A1 | 4/2013 | Jaeb et al. |
| 2013/0101804 A1 | 4/2013 | Brokken et al. |
| 2013/0102979 A1 | 4/2013 | Coulthard et al. |
| 2013/0116635 A1 | 5/2013 | Fleischmann |
| 2013/0138054 A1 | 5/2013 | Fleischmann |
| 2013/0138060 A1 | 5/2013 | Haggstrom et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0215638 A1 | 8/2013 | Dabov et al. |
| 2013/0218039 A1 | 8/2013 | Sotos et al. |
| 2013/0274688 A1 | 10/2013 | Weston |
| 2013/0331822 A1 | 12/2013 | Patel et al. |
| 2013/0338613 A1 | 12/2013 | Haggstrom et al. |
| 2014/0005618 A1 | 1/2014 | Locke et al. |
| 2014/0100536 A1 | 4/2014 | Angel |
| 2014/0114268 A1 | 4/2014 | Auguste et al. |
| 2014/0249493 A1 | 9/2014 | Hartwell |
| 2014/0316359 A1 | 10/2014 | Collinson et al. |
| 2014/0330227 A1 | 11/2014 | Coulthard et al. |
| 2014/0343518 A1 | 11/2014 | Riesinger |
| 2015/0057625 A1 | 2/2015 | Coulthard |
| 2015/0065965 A1 | 3/2015 | Haggstrom et al. |
| 2015/0073358 A1 | 3/2015 | Jaeb et al. |
| 2015/0159066 A1 | 6/2015 | Hartwell et al. |

(56) References Cited

U.S. PATENT DOCUMENTS

| | | |
|---|---|---|
| 2015/0202354 A1 | 7/2015 | Wall |
| 2015/0224238 A1 | 8/2015 | Hartwell |
| 2015/0250931 A1 | 9/2015 | Bharti et al. |
| 2015/0258256 A1 | 9/2015 | Jaeb et al. |
| 2016/0051737 A1 | 2/2016 | Joshi et al. |
| 2016/0058927 A1 | 3/2016 | Weston |
| 2016/0081859 A1 | 3/2016 | Hartwell |
| 2016/0144084 A1 | 5/2016 | Collinson et al. |
| 2016/0166438 A1 | 6/2016 | Rovaniemi |
| 2016/0206793 A1 | 7/2016 | Robinson et al. |
| 2016/0270967 A1 | 9/2016 | Hartwell |
| 2016/0361473 A1 | 12/2016 | Robinson et al. |
| 2017/0014556 A1 | 1/2017 | Haggstrom et al. |
| 2017/0296714 A1 | 10/2017 | Locke et al. |
| 2017/0304510 A1 | 10/2017 | Askem et al. |
| 2017/0319761 A1 | 11/2017 | Locke et al. |
| 2018/0021178 A1 | 1/2018 | Locke et al. |
| 2018/0028729 A1 | 2/2018 | Joshi et al. |
| 2018/0104393 A1 | 4/2018 | Wu et al. |
| 2018/0311078 A1 | 11/2018 | Hartwell |
| 2019/0142647 A1 | 5/2019 | Hartwell |

FOREIGN PATENT DOCUMENTS

| | | |
|---|---|---|
| DE | 19844355 A1 | 4/2000 |
| EP | 0208395 A1 | 1/1987 |
| EP | 0512543 A2 | 11/1992 |
| EP | 0541251 A1 | 5/1993 |
| EP | 0941726 A1 | 9/1999 |
| EP | 1411874 A1 | 4/2004 |
| EP | 1452156 A1 | 9/2004 |
| EP | 1455701 B1 | 3/2006 |
| EP | 1448261 B1 | 2/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 2161011 A1 | 3/2010 |
| EP | 1947987 B1 | 5/2010 |
| EP | 1358456 B1 | 7/2010 |
| EP | 2214728 A2 | 8/2010 |
| EP | 2302127 A1 | 3/2011 |
| EP | 2340064 A1 | 7/2011 |
| EP | 2346468 A2 | 7/2011 |
| EP | 2205190 B1 | 9/2011 |
| EP | 2366721 A1 | 9/2011 |
| EP | 2370116 A2 | 10/2011 |
| EP | 2462908 A1 | 6/2012 |
| EP | 2529767 A2 | 12/2012 |
| EP | 2531761 A1 | 12/2012 |
| EP | 2231088 B1 | 1/2013 |
| EP | 2015655 B1 | 3/2013 |
| EP | 2563421 A1 | 3/2013 |
| EP | 2049055 B1 | 4/2013 |
| EP | 2596815 A1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2305325 B1 | 4/2014 |
| EP | 2323712 B1 | 4/2014 |
| EP | 2345437 B1 | 4/2014 |
| EP | 2051675 B1 | 6/2014 |
| EP | 1485613 B1 | 7/2014 |
| EP | 1545644 B1 | 8/2014 |
| EP | 2416816 B1 | 10/2014 |
| EP | 2468323 B1 | 10/2014 |
| EP | 2658493 B1 | 10/2014 |
| EP | 2268348 B1 | 12/2014 |
| EP | 2561128 B1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |
| EP | 2438301 B1 | 10/2015 |
| EP | 2934402 A1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2293749 B1 | 8/2016 |
| EP | 3072542 A2 | 9/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2462956 B2 | 3/2017 |
| EP | 1587502 B1 | 5/2017 |
| EP | 1587554 B1 | 5/2017 |
| EP | 2731563 B1 | 5/2017 |
| EP | 2632613 B1 | 8/2017 |
| EP | 2888478 B1 | 8/2017 |
| EP | 2937107 B1 | 8/2017 |
| EP | 3062751 B1 | 8/2017 |
| EP | 2359784 B1 | 9/2017 |
| EP | 2367518 B1 | 10/2017 |
| EP | 2675493 B1 | 10/2017 |
| EP | 2736548 B1 | 11/2017 |
| EP | 2593058 B1 | 3/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 2941280 B1 | 10/2018 |
| EP | 3120879 B1 | 12/2018 |
| EP | 2370130 B1 | 3/2019 |
| EP | 3053609 B1 | 3/2019 |
| EP | 2285432 B2 | 6/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 2244756 B1 | 12/2019 |
| FR | 1163907 A | 10/1958 |
| FR | 2939320 A1 | 6/2010 |
| GB | 2099306 A | 12/1982 |
| GB | 2435422 A | 8/2007 |
| GB | 2435423 A | 8/2007 |
| GB | 2511523 A | 9/2014 |
| JP | H04354722 A | 12/1992 |
| RU | 2429887 C2 | 9/2011 |
| RU | 131622 U1 | 8/2013 |
| WO | WO-9423677 A2 | 10/1994 |
| WO | WO-9504511 A1 | 2/1995 |
| WO | WO-9514451 A1 | 6/1995 |
| WO | WO-9605873 A1 | 2/1996 |
| WO | WO-9621410 A1 | 7/1996 |
| WO | WO-9711658 A1 | 4/1997 |
| WO | WO-9939671 A1 | 8/1999 |
| WO | WO-0007653 A1 | 2/2000 |
| WO | WO-0042957 A1 | 7/2000 |
| WO | WO-0185248 A1 | 11/2001 |
| WO | WO-0217840 A1 | 3/2002 |
| WO | WO-0226180 A1 | 4/2002 |
| WO | WO-0238096 A2 | 5/2002 |
| WO | WO-02076379 A2 | 10/2002 |
| WO | WO-2004073566 A1 | 9/2004 |

(56) References Cited

FOREIGN PATENT DOCUMENTS

| | | |
|---|---|---|
| WO | WO-2005123170 A1 | 12/2005 |
| WO | WO-2006052839 A2 | 5/2006 |
| WO | WO-2007030598 A2 | 3/2007 |
| WO | WO-2007030601 A2 | 3/2007 |
| WO | WO-2008049277 A1 | 5/2008 |
| WO | WO-2008063281 A2 | 5/2008 |
| WO | WO-2008131895 A1 | 11/2008 |
| WO | WO-2009066105 A1 | 5/2009 |
| WO | WO-2009071935 A1 | 6/2009 |
| WO | WO-2009098696 A2 | 8/2009 |
| WO | WO-2009120951 A2 | 10/2009 |
| WO | WO-2009124100 A1 | 10/2009 |
| WO | WO-2009146441 A1 | 12/2009 |
| WO | WO-2009158128 A2 | 12/2009 |
| WO | WO-2010082872 A1 | 7/2010 |
| WO | WO-2010089448 A1 | 8/2010 |
| WO | WO-2010139926 A1 | 12/2010 |
| WO | WO-2010142959 A2 | 12/2010 |
| WO | WO-2010147533 A1 | 12/2010 |
| WO | WO-2011023650 A1 | 3/2011 |
| WO | WO-2011049562 A1 | 4/2011 |
| WO | WO-2011112724 A1 | 9/2011 |
| WO | WO-2011115908 A1 | 9/2011 |
| WO | WO-2011128651 A1 | 10/2011 |
| WO | WO-2011130570 A1 | 10/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2011146532 A2 | 11/2011 |
| WO | WO-2012009370 A2 | 1/2012 |
| WO | WO-2012069793 A1 | 5/2012 |
| WO | WO-2012069794 A1 | 5/2012 |
| WO | WO-2012074512 A1 | 6/2012 |
| WO | WO-2012131237 A1 | 10/2012 |
| WO | WO-2012140378 A1 | 10/2012 |
| WO | WO-2012143665 A1 | 10/2012 |
| WO | WO-2012146656 A1 | 11/2012 |
| WO | WO-2012150235 A1 | 11/2012 |
| WO | WO-2013010907 A1 | 1/2013 |
| WO | WO-2013076450 A1 | 5/2013 |
| WO | WO-2013083800 A1 | 6/2013 |
| WO | WO-2013118447 A1 | 8/2013 |
| WO | WO-2013136181 A2 | 9/2013 |
| WO | WO-2013149078 A1 | 10/2013 |
| WO | WO-2013175306 A2 | 11/2013 |
| WO | WO-2014016759 A1 | 1/2014 |
| WO | WO-2014020440 A1 | 2/2014 |
| WO | WO-2014020443 A2 | 2/2014 |
| WO | WO-2014099709 A1 | 6/2014 |
| WO | WO-2014108476 A1 | 7/2014 |
| WO | WO-2014113253 A1 | 7/2014 |
| WO | WO-2016107775 A2 | 7/2016 |
| WO | WO-2016174048 A1 | 11/2016 |

OTHER PUBLICATIONS

Closure of the appeal proceedings for European Patent No. 2825220 mailed on Oct. 14, 2020, 2 pages.
Communication of the registration of a transfer or change of name and or address for European Patent No. EP2825220, dated Jan. 27, 2021, 2 pages.
Grounds for the Decision and Annex to the Communication, Opposition of European Patent No. 2825220, mailed on Feb. 6, 2020, 184 pages.
Information about the Result of Oral Proceedings for the Opposition of European Patent No. 2825220, mailed on Dec. 5, 2019, 4 pages.
International Preliminary Report on Patentability for Application No. PCT/IB2013/000847, dated Sep. 25, 2014, 14 pages.
International Search Report and Written Opinion for Application No. PCT/IB2013/000847, dated Aug. 30, 2013, 20 pages.
Kendall ULTEC Hydrocolloid Dressing (4x4"), Product Ordering Page, web page downloaded on Jul. 13, 2014, 1 page.
Maintenance of the patent with the documents specified in the final decision for European patent No. 2825220 dated Oct. 13, 2020, 1 page.
Notice of Appeal against the Interlocutory Decision of the Opposition Division against European Patent No. 2825220, mailed on Apr. 6, 2020, 4 pages.
Notice of Opposition—Statement of Facts and Evidence for European Patent No. 2825220, mailed on Sep. 20, 2018, 15 pages.
Proprietor's Written Submission in Preparation for the Oral Proceedings for the Opposition of European Patent No. 2825220, mailed on Oct. 4, 2019, 13 pages.
Protz K., "Modern Wound Dressings Support the Healing Process," Wound care: Indications and Application, Geriatrie Journal, Apr. 2005, pp. 3333-3339 (17 pages with English translation).
Reply of the Patent Proprietor to the Notice of Opposition of the European Patent No. 2825220, mailed Feb. 13, 2019, 28 pages.
Statement of Ground of Appeal filed by proprietor for European patent No. 2825220 mailed on Jun. 5, 2020, 16 pages.
Termination of the opposition proceedings with maintenance of European Patent No. EP2825220, dated Jan. 29, 2021, 1 page.
Withdrawal of an appeal from the opponent for European patent No. 2825220 mailed on Oct. 7, 2020, 3 pages.

* cited by examiner

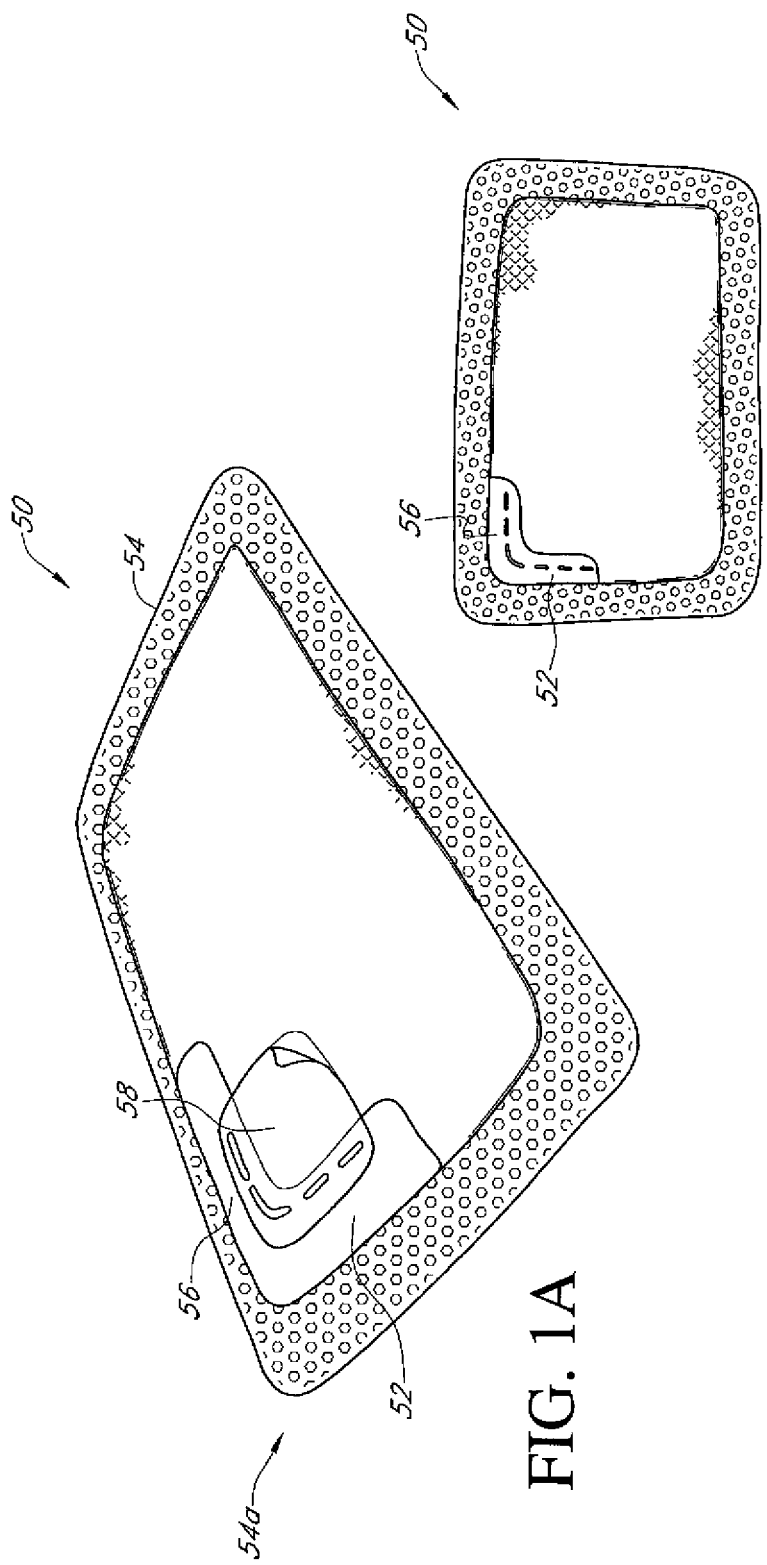

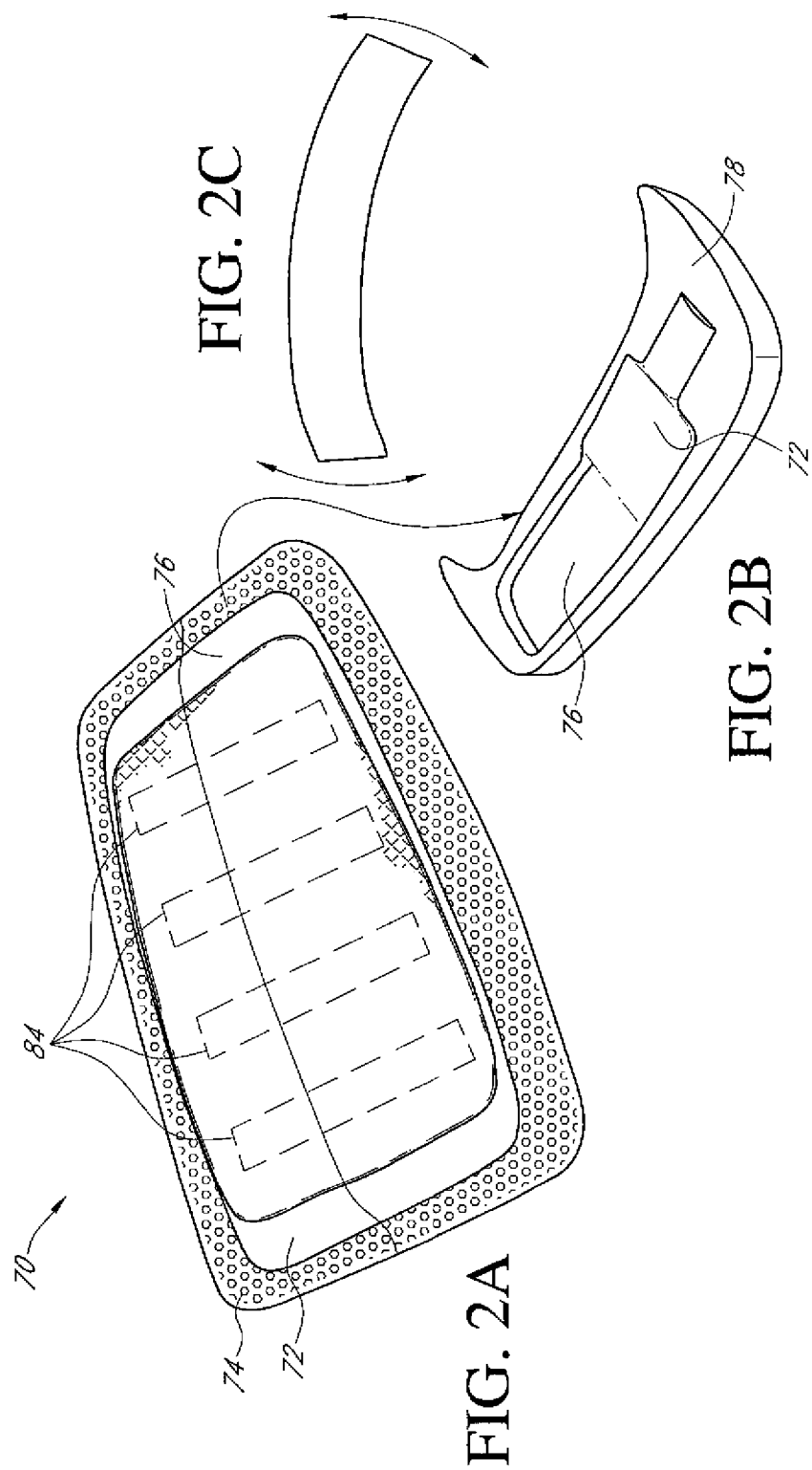

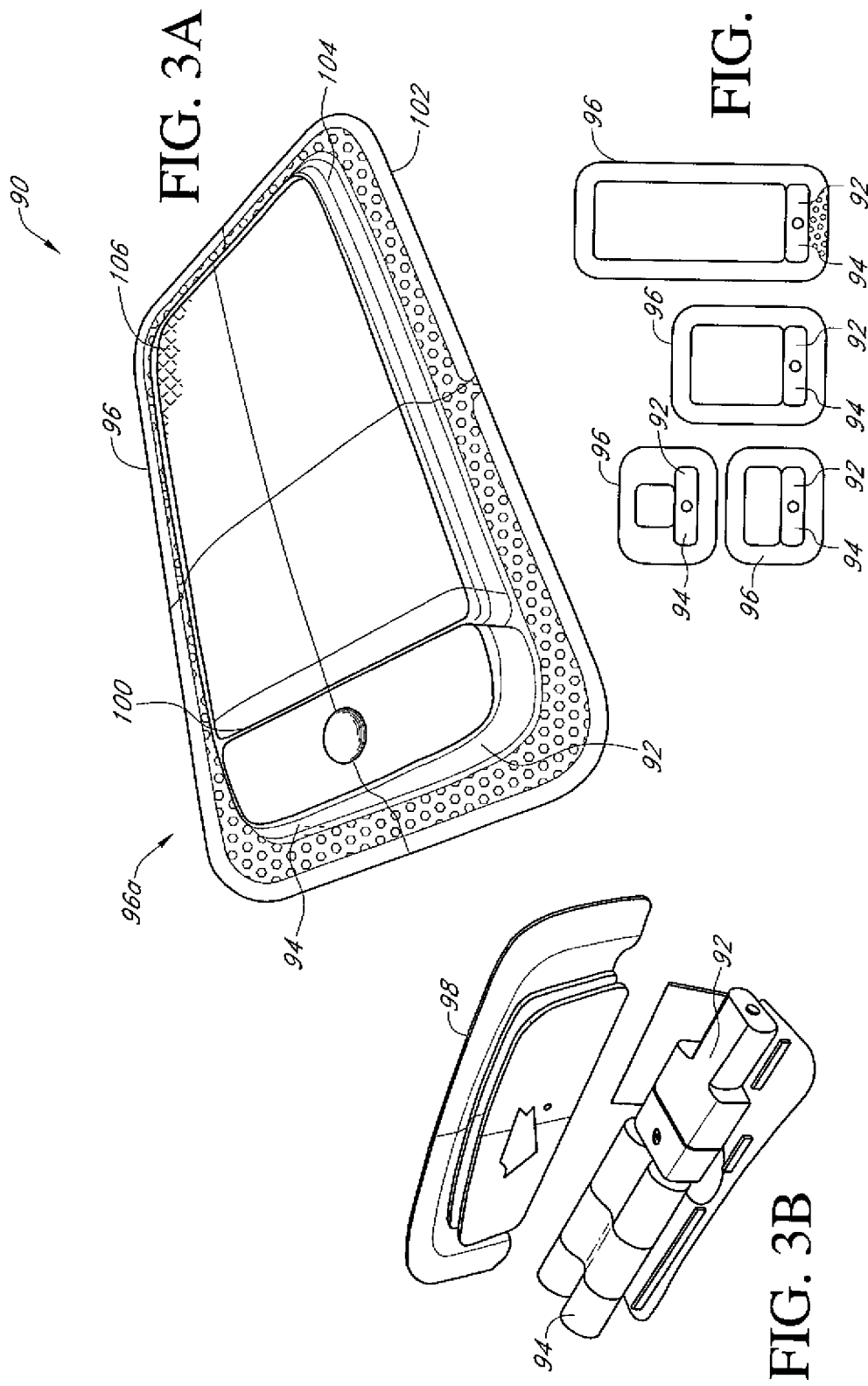

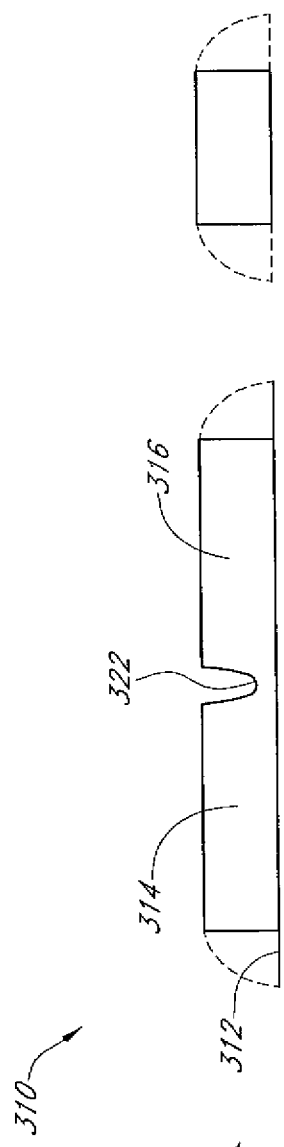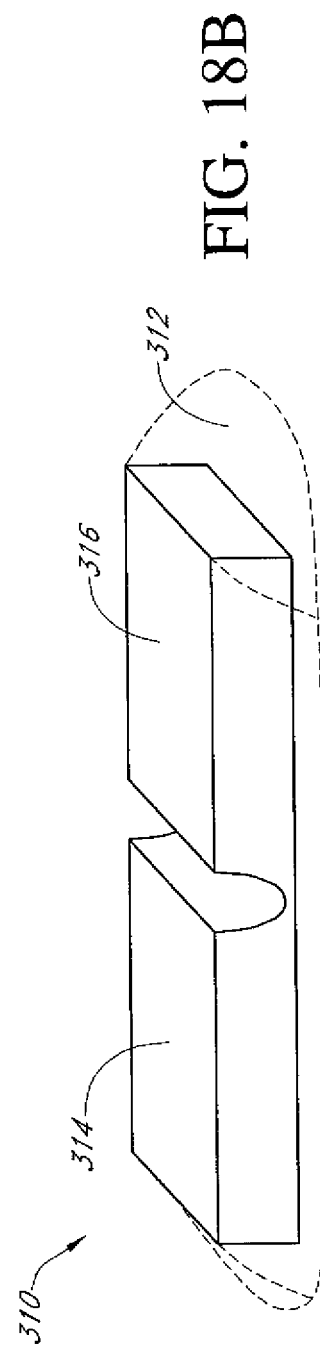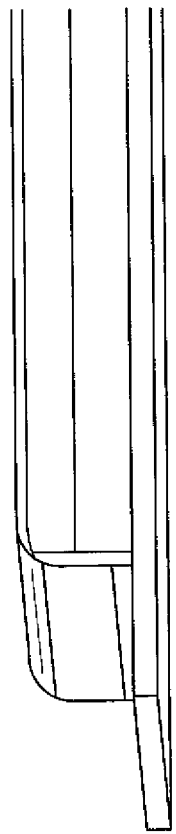

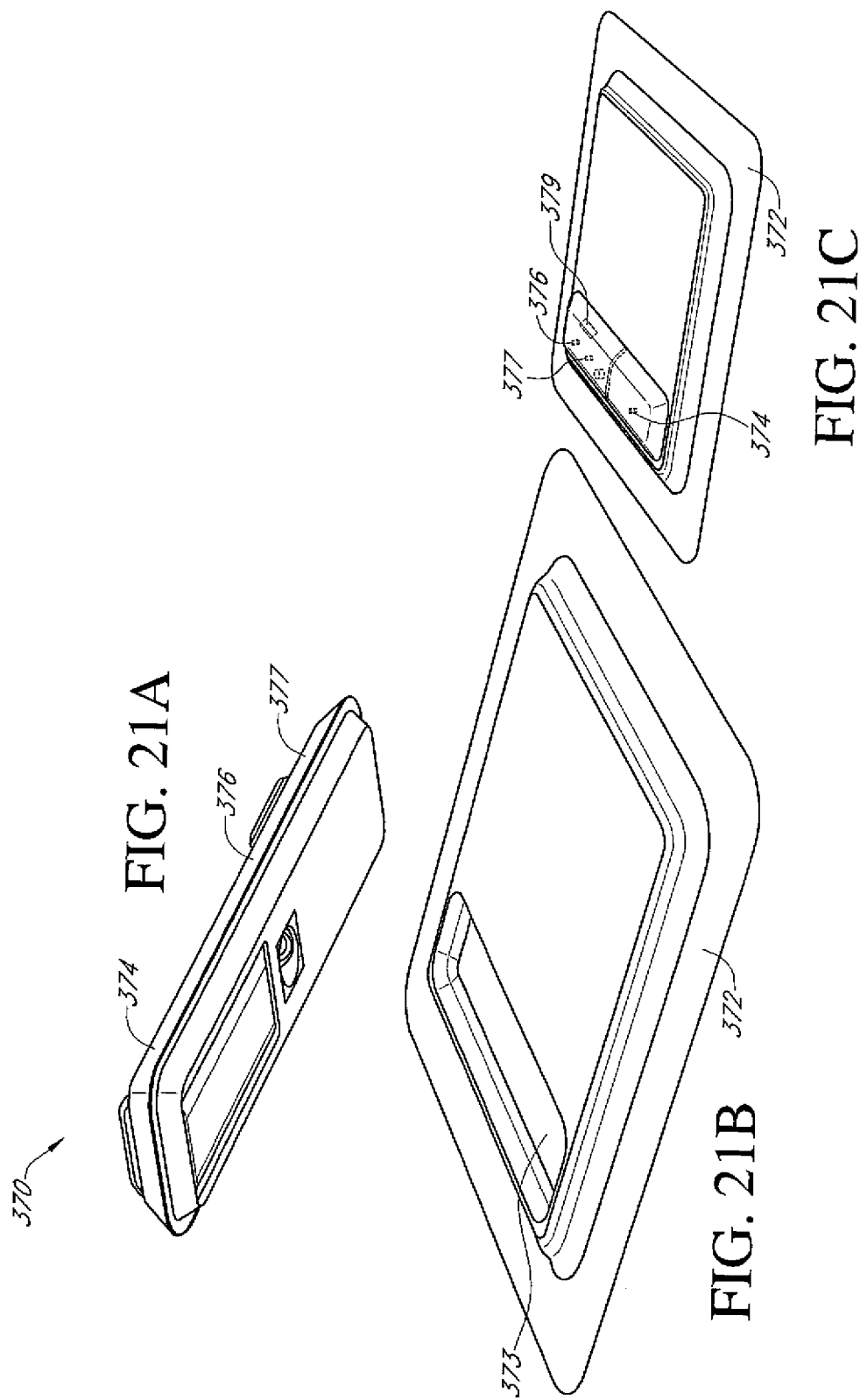

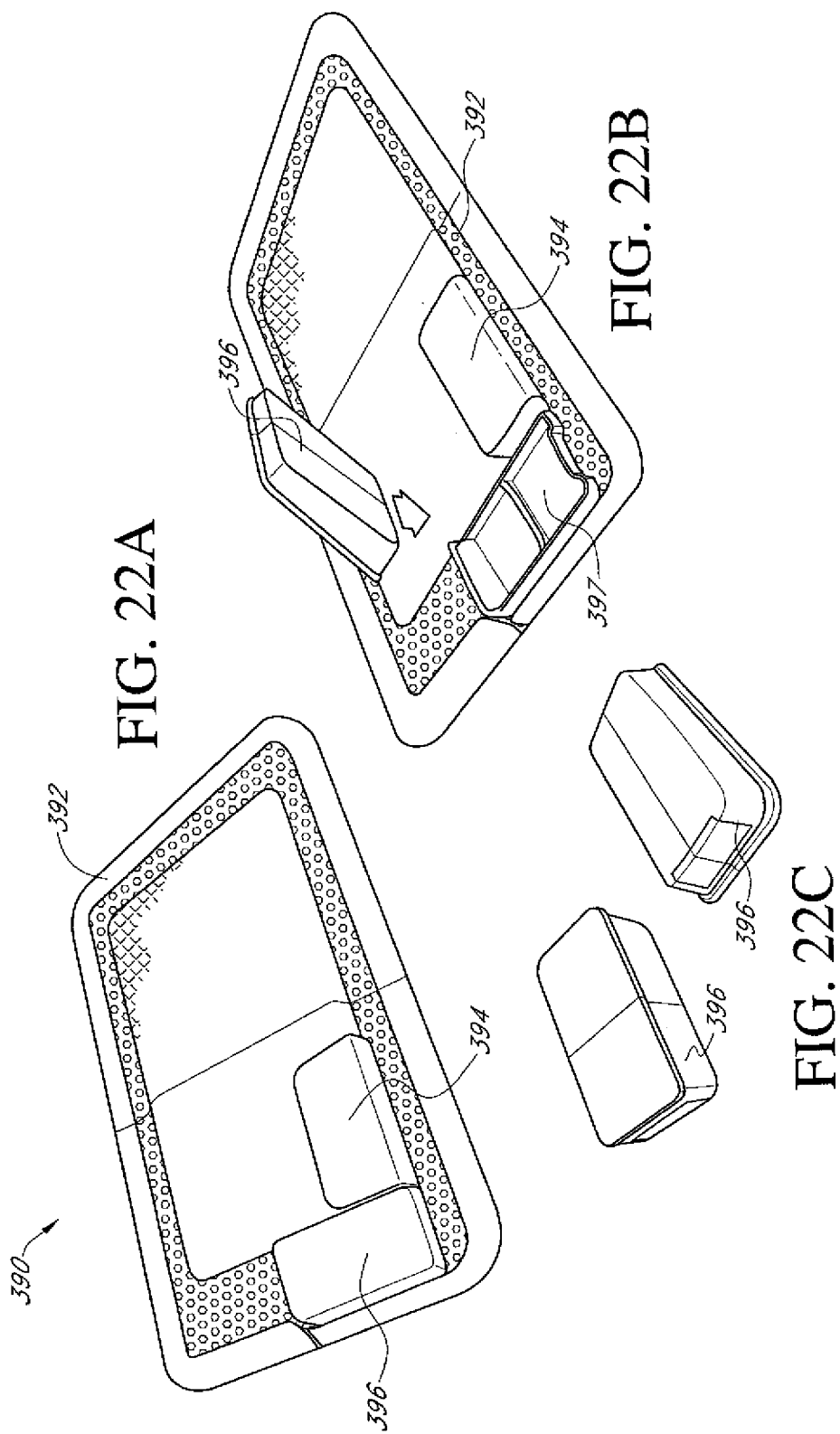

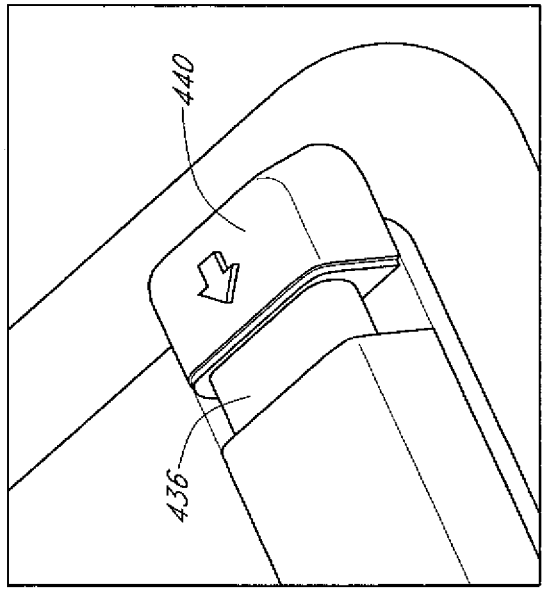
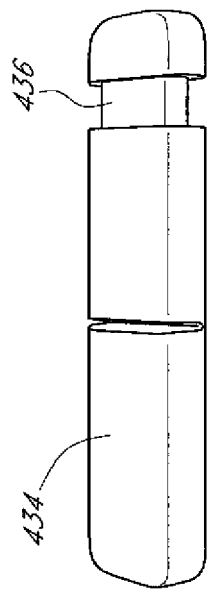
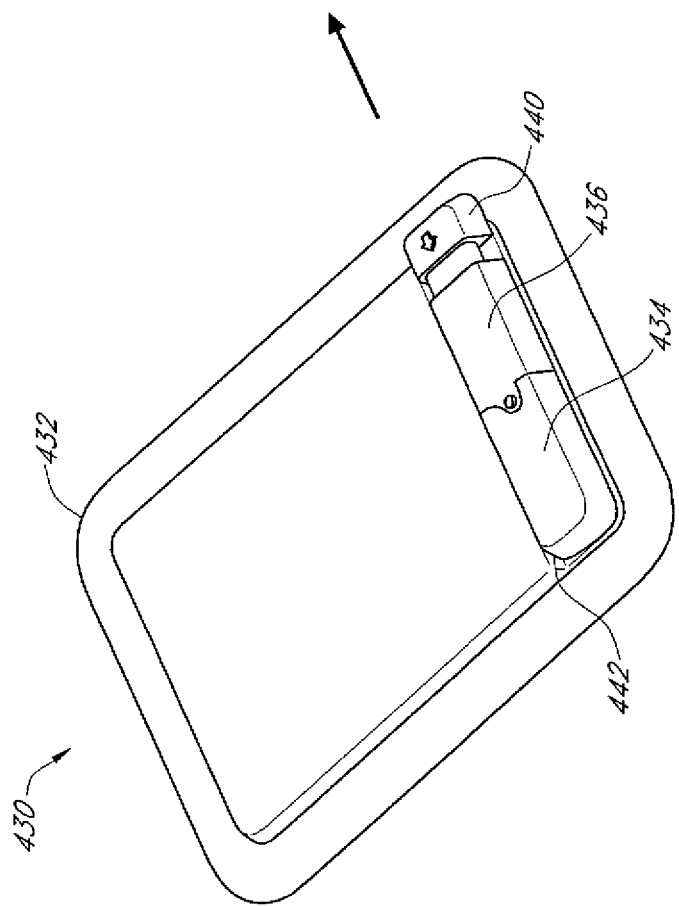
FIG. 24B
FIG. 24C
FIG. 24A

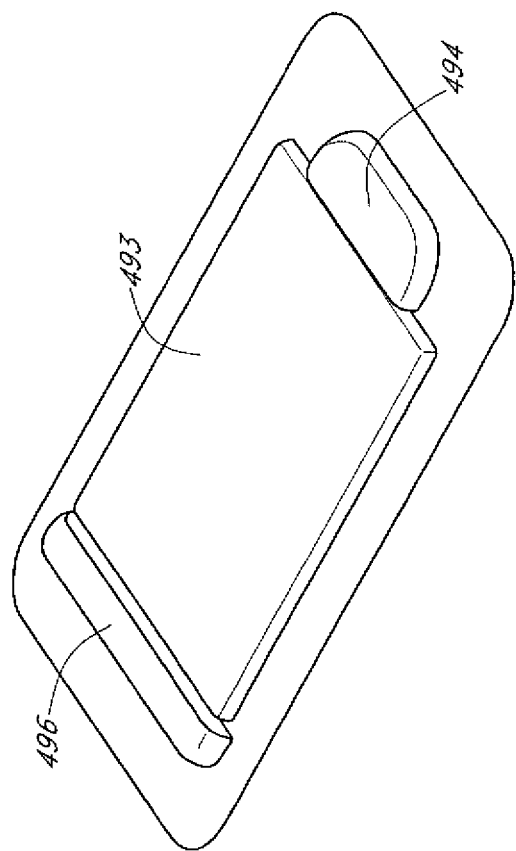
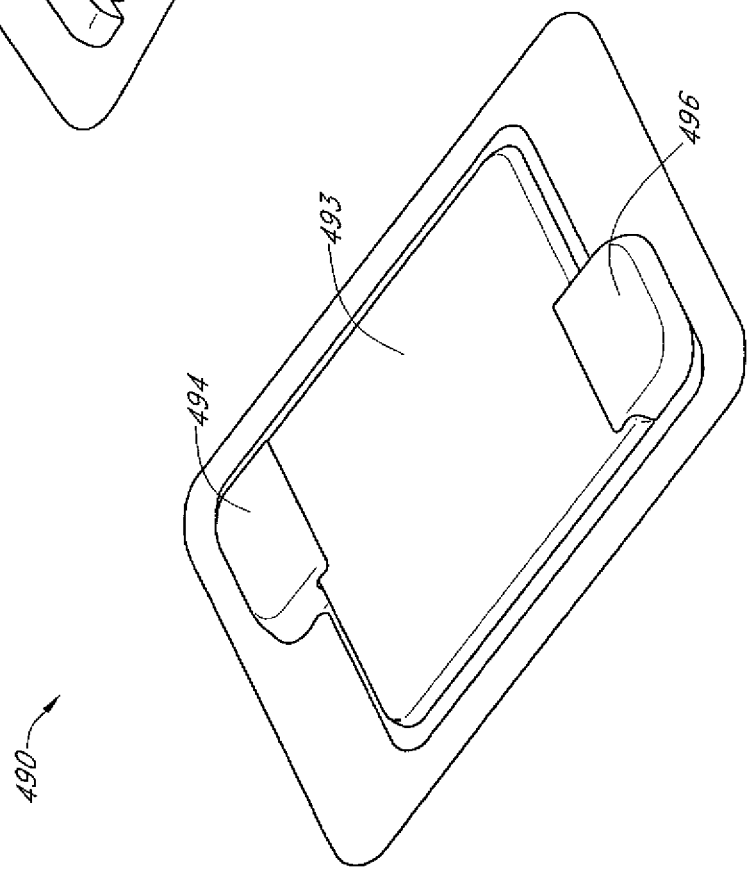

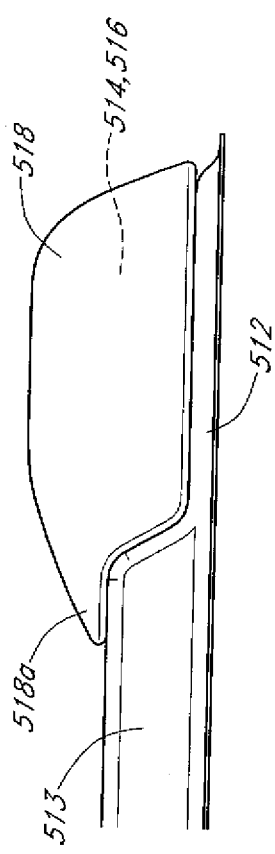
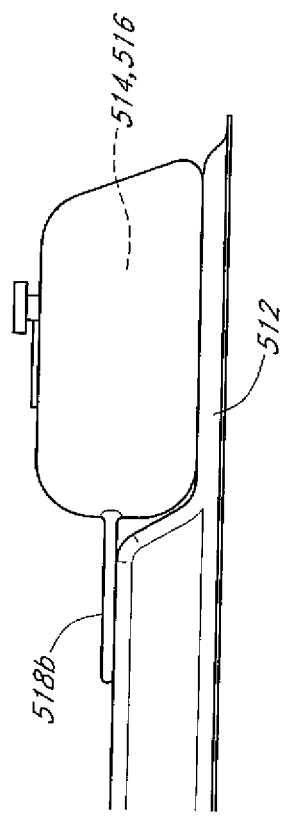
FIG. 28F
FIG. 28G

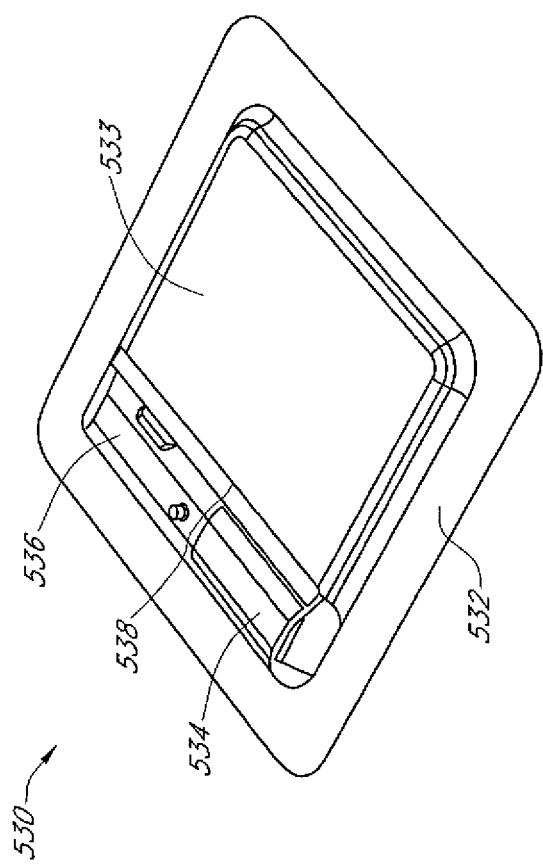
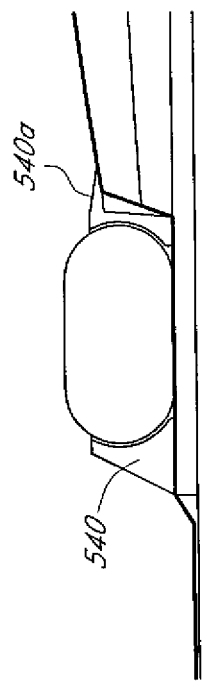
FIG. 29A
FIG. 29B

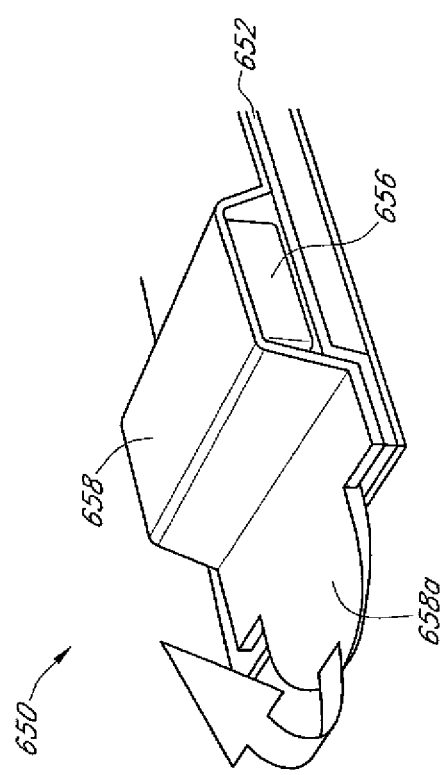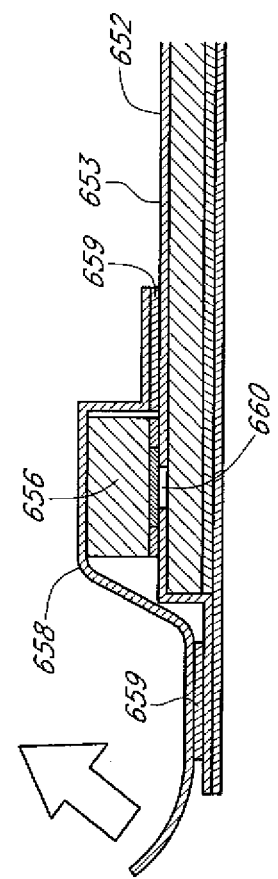

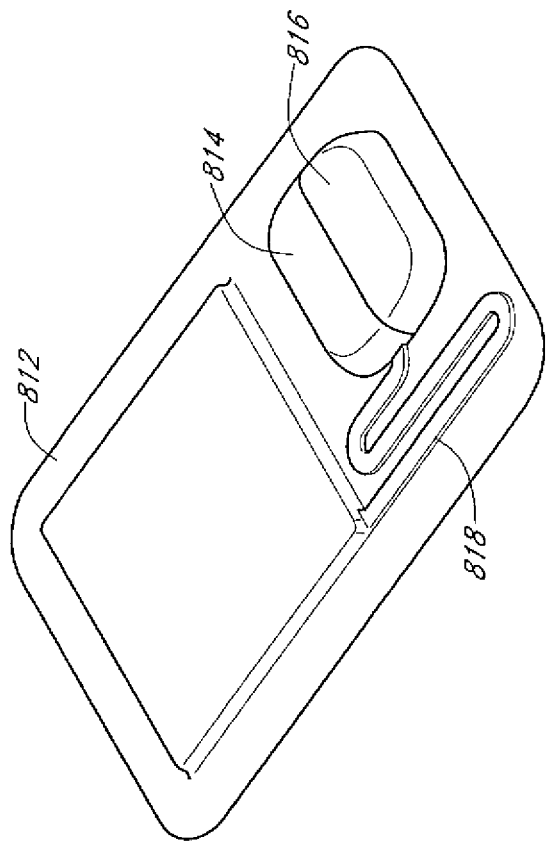
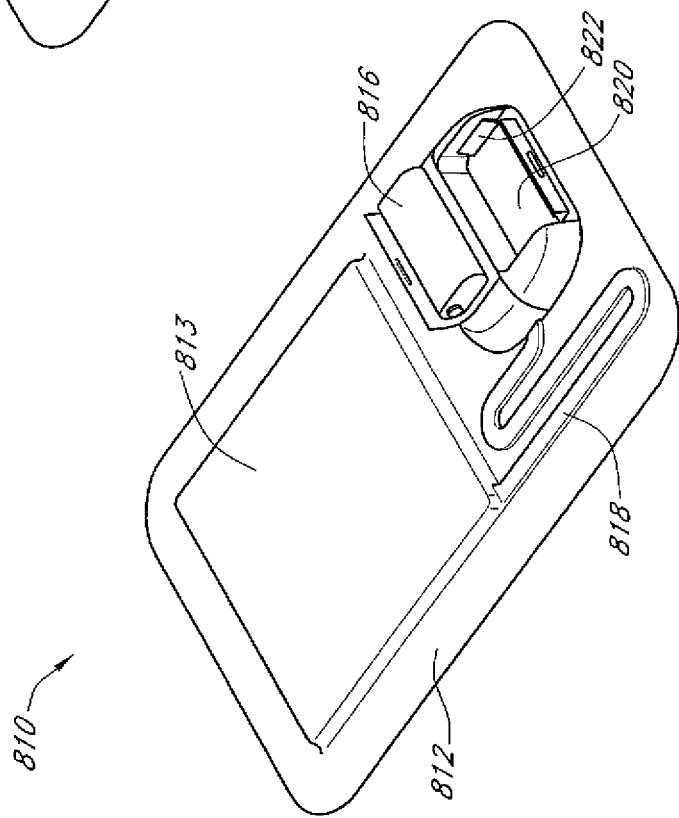
FIG. 43B
FIG. 43A

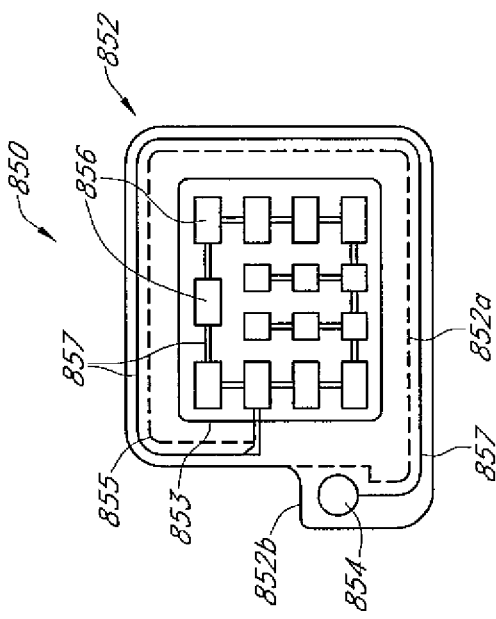
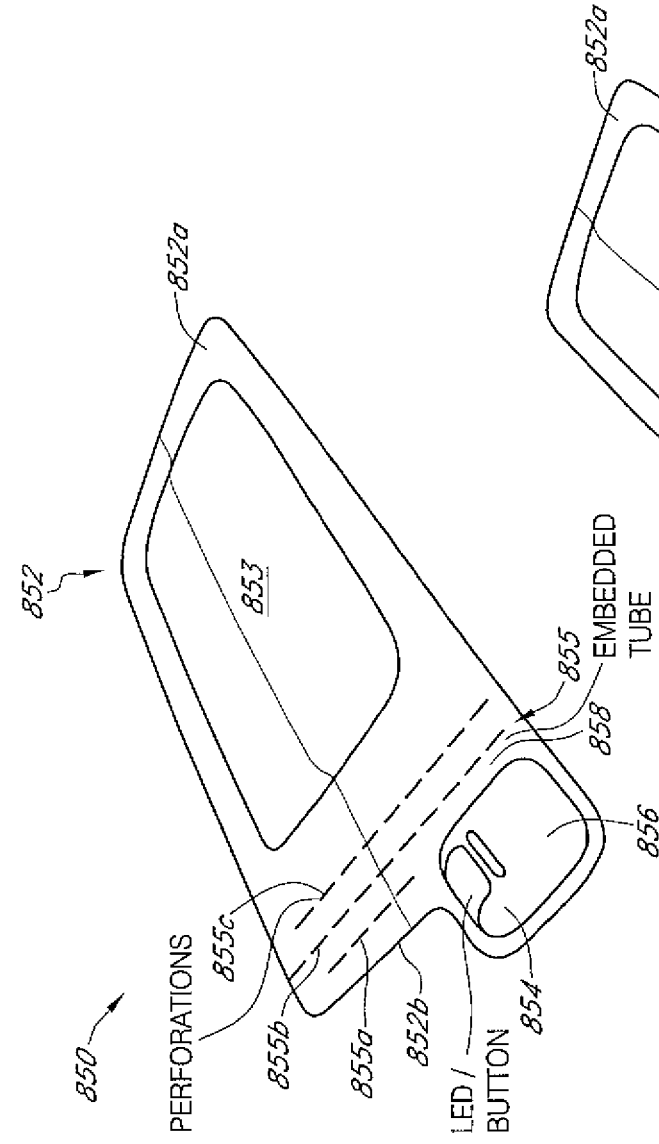
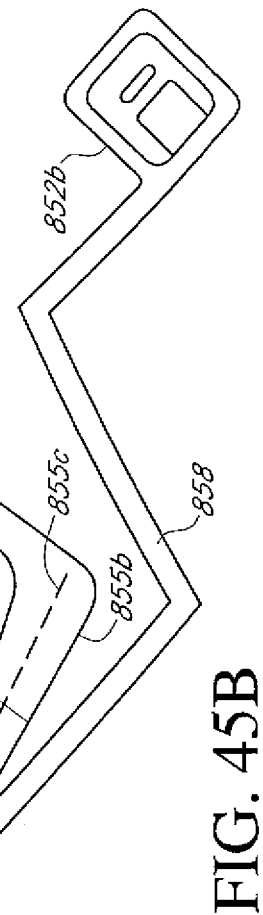
FIG. 45A
FIG. 45B
FIG. 45C

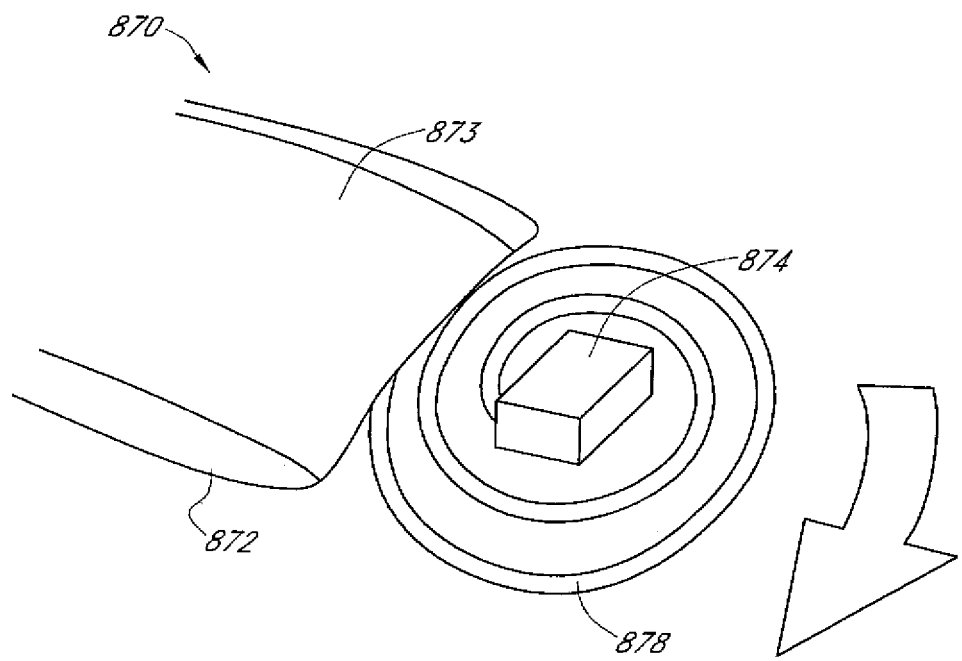
FIG. 46
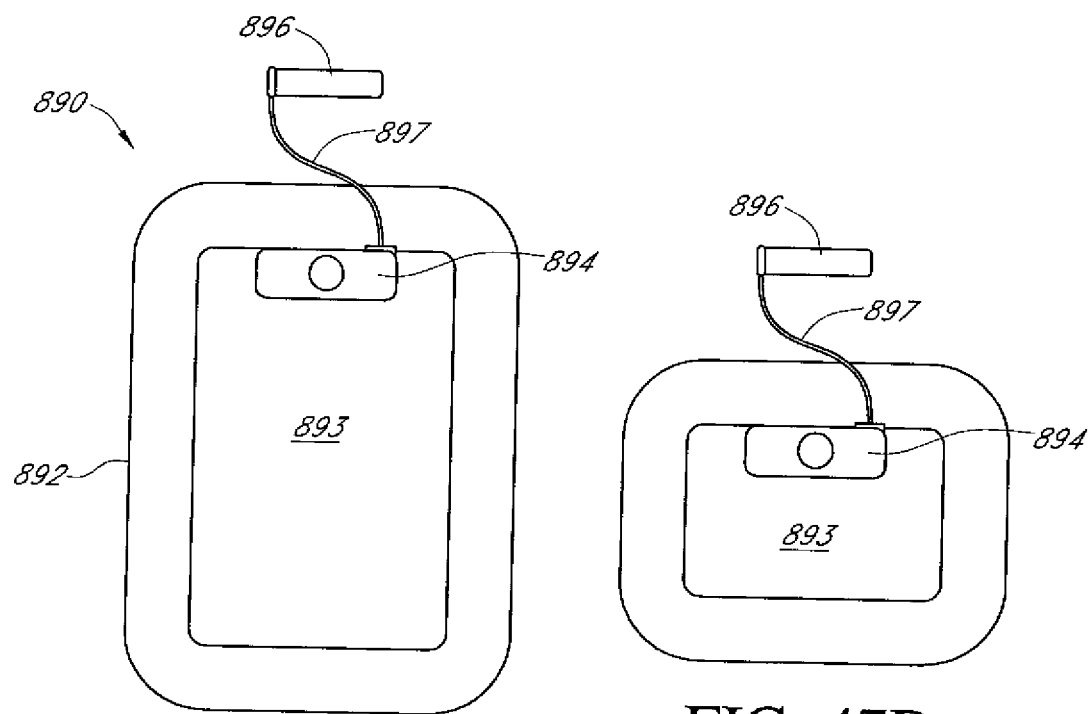
FIG. 47A
FIG. 47B

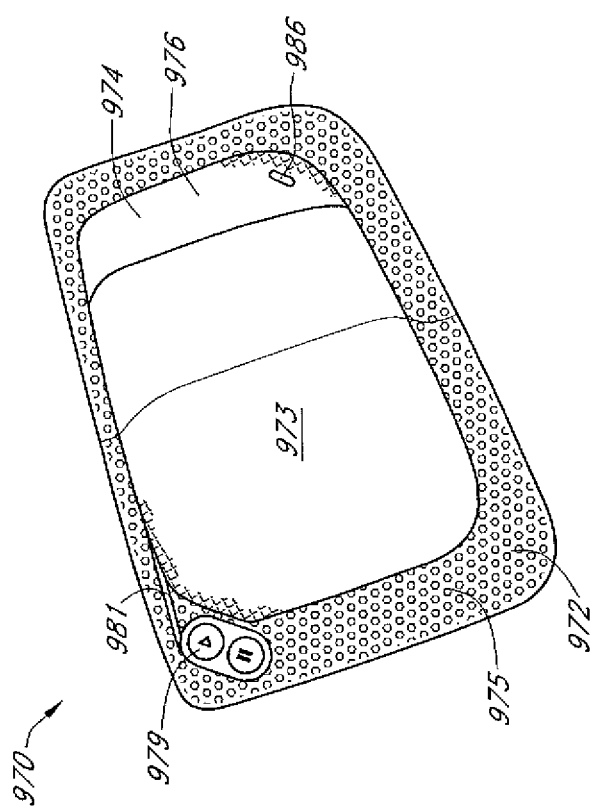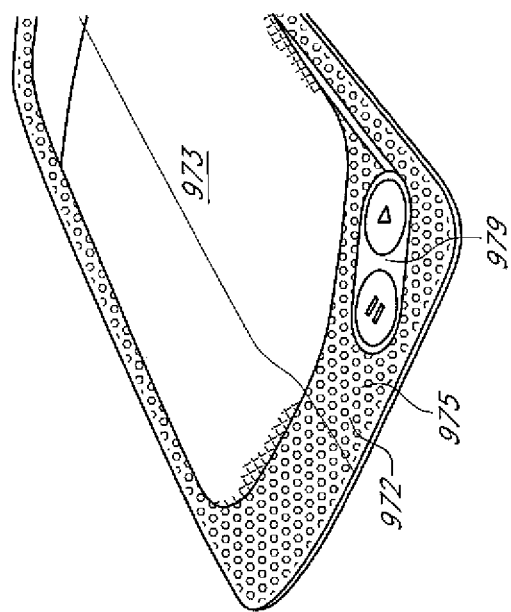
FIG. 51A
FIG. 51B

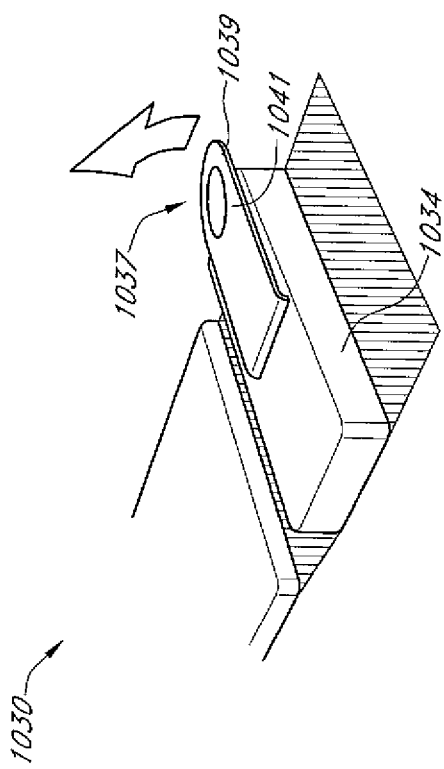
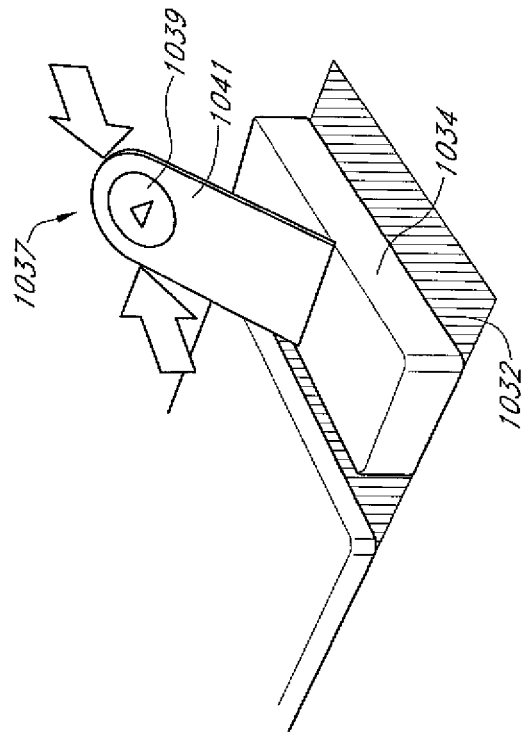
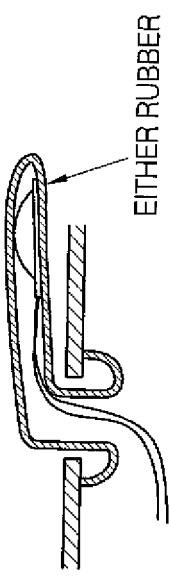
FIG. 54A
FIG. 54B
FIG. 54C

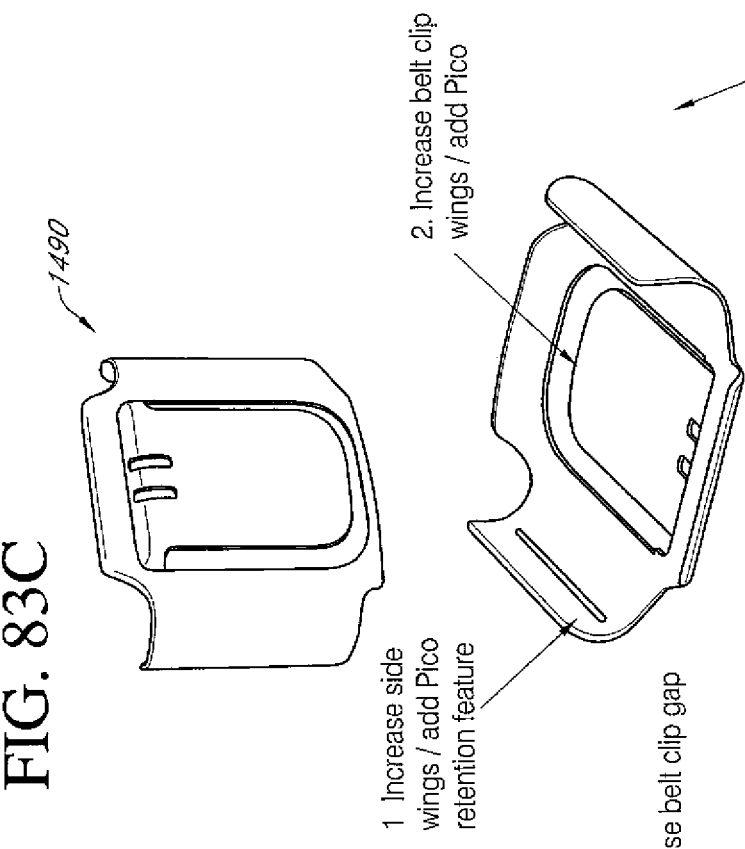
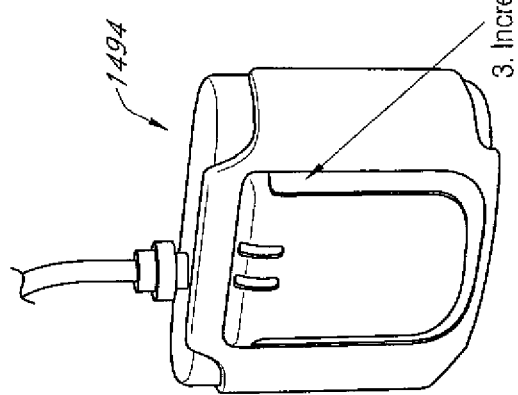
FIG. 83C
FIG. 83B
FIG. 83A
1. Increase side wings / add Pico retention feature
2. Increase belt clip wings / add Pico
3. Increase belt clip gap
4. Increase material thickness?

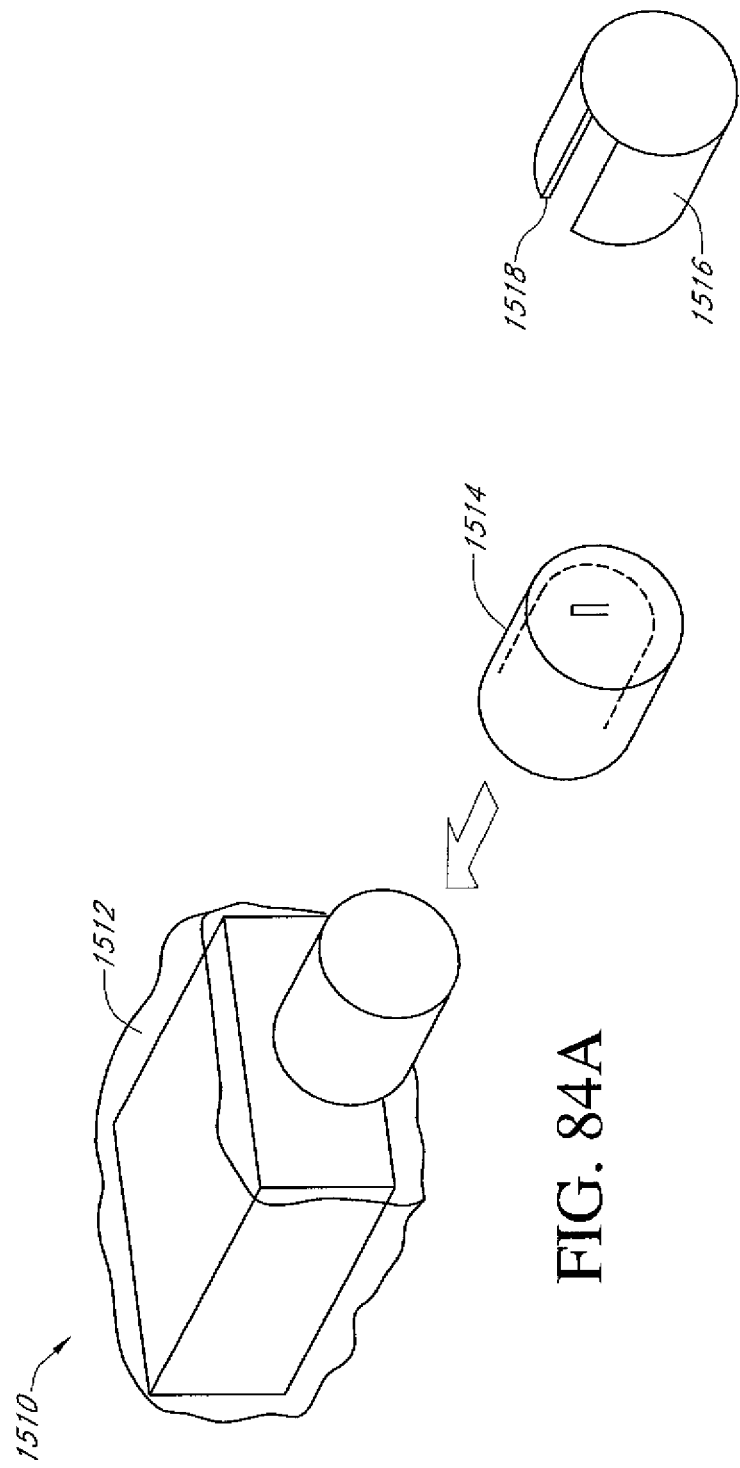

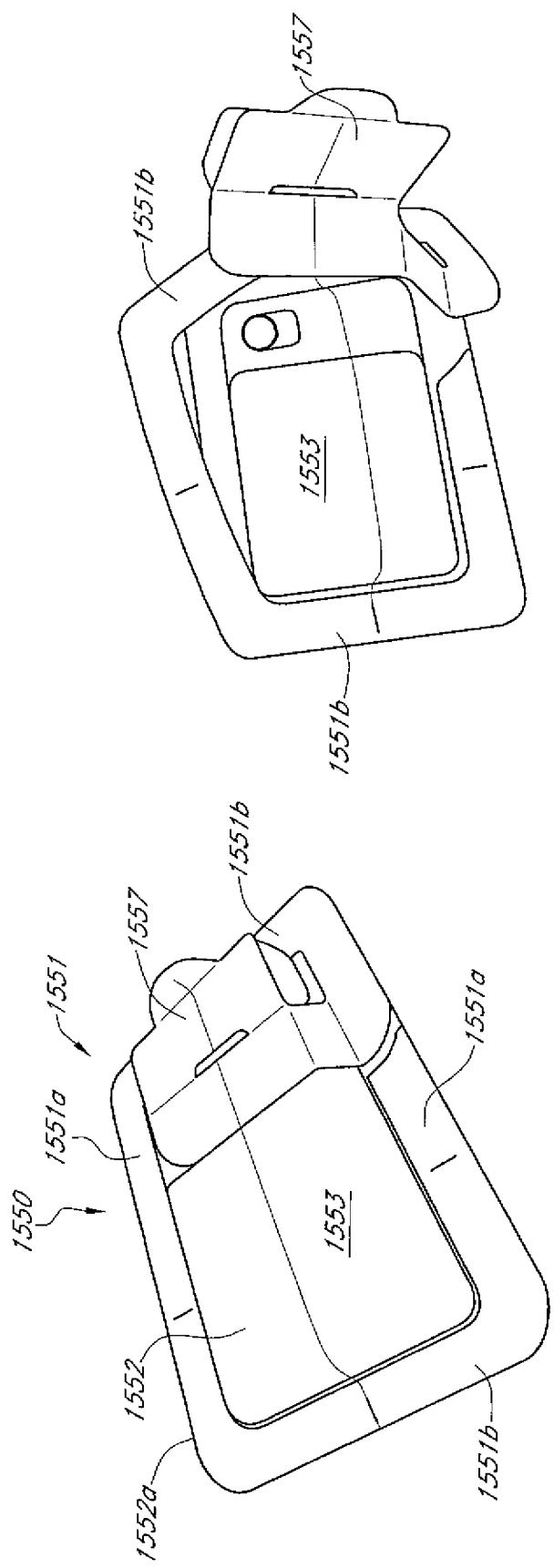

REDUCED PRESSURE APPARATUS AND METHODS

INCORPORATION BY REFERENCE

This application is a continuation application of U.S. application Ser. No. 16/047,786, filed Jul. 27, 2018, which is a continuation application of U.S. National Stage Patent Application No. 14/385,136, filed on Sep. 12, 2014 and now U.S. Pat. No. 10,046,096, which claims priority to International Patent Application No. PCT/IB2013/000847, filed on Mar. 12, 2013, which claims priority benefit of U.S. Provisional Patent Application No. 61/609,905 filed Mar. 12, 2012, titled REDUCED PRESSURE APPARATUS AND METHODS. The benefit of priority is claimed under the appropriate legal basis including, without limitation, under 35 U.S.C. § 119(e).

Additionally, further components and details of wound dressings, wound treatment apparatuses, and negative pressure wound treatment methods that may be used with any of the embodiments disclosed in this application are found in the following applications and/or patents, which are hereby incorporated by reference in their entireties as if fully set forth herein:

U.S. Patent Application Publication No. 2011/0282309 (Ser. No. 13/092,042). (titled WOUND DRESSING AND METHOD OF USE), filed on Apr. 21, 2011;

PCT Patent Application Publication No. WO 2011/087871 (International Patent Application No. PCT/US2010/061938), (titled APPARATUS AND METHODS FOR NEGATIVE PRESSURE WOUND THERAPY), filed internationally on Dec. 22, 2010;

U.S. Patent Publication No. 2009/0123513 (Ser. No. 11/922,894) (titled ANTIMICROBIAL BIGUANIDE METAL COMPLEXES), filed on May 21, 2008;

PCT Patent Publication No. WO/2011/135284 (International Patent Application No. PCT/GB11/000622) (titled WOUND DRESSING), filed internationally on Apr. 21, 2011;

PCT Patent Publication No. WO/2011/144888 (International Patent Application No. PCT/GB11/000621) (titled WOUND PROTECTION), filed internationally on Apr. 21, 2011;

PCT Patent Publication No. WO/2011/135285 (International Patent Application No. PCT/GB11/000625) (titled WOUND DRESSING), filed internationally on Apr. 21, 2011;

PCT Patent Publication No. WO/2011/135286 (International Patent Application No. PCT/GB11/000626) (titled MULTIPORT DRESSING), filed internationally on Apr. 21, 2011;

PCT Patent Publication No. WO/2011/135287 (International Patent Application No. PCT/GB11/000628) (titled SUCTION PORT), filed internationally on Apr. 21, 2011;

PCT Patent Publication No. WO/2012/038724 (International Patent Application No. PCT/GB11/051745) (titled PRESSURE CONTROL APPARATUS), filed internationally on Sep. 16, 2011;

U.S. patent application Ser. No. 13/287,897 (titled "REDUCED PRESSURE THERAPY APPARATUSES AND METHODS OF USING SAME,), filed on Nov. 2, 2011; and U.S. Patent Application Publication No. 2012/0136325 (Ser. No. 13/287,959), (titled SYSTEMS AND METHODS FOR CONTROLLING OPERATION OF A REDUCED PRESSURE THERAPY SYSTEM), filed on Nov. 2, 2011.

BACKGROUND OF THE INVENTION

Field of the Invention

Embodiments disclosed herein relate to methods and apparatuses for dressing and treating a wound with topical negative pressure (TNP) therapy, namely dressing kits for TNP.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates and may reduce bacterial load and thus, infection to the wound. Furthermore, TNP therapy permits less outside disturbance of the wound and promotes more rapid healing.

SUMMARY OF SOME EMBODIMENTS

Embodiments disclosed herein relate to methods and apparatuses for dressing and treating a wound with topical negative pressure (TNP) therapy. For example but without limitation, the embodiments disclosed herein relate to treating a wound with reduced pressure provided from a pump kit. Although not required, any embodiments of the pump kit can be integral, wherein the pump is mounted to or otherwise supported by or adjacent to the dressing. Additionally, although not required, any embodiments of the pump kit can be sterile. As another non-limiting example, some embodiments disclosed herein relate to apparatuses, features, and methods for controlling the operation of a TNP system and/or apparatuses, features, and methods for detecting one or more conditions or parameters of the dressing, such as pressure, temperature, or saturation level, and, although not required, controlling the operation of the pump or other components of the dressing kit accordingly. As another non-limiting example, any embodiments disclosed herein can be configured to provide a visual indication one or more conditions or parameters of the dressing, such as pressure, temperature, or saturation level.

Any of the features, components, or details of any of the arrangements or embodiments disclosed in this application, including those disclosed below, are interchangeably combinable with any other features, components, or details of any of the arrangements or embodiments disclosed herein to form new arrangements and embodiments. With that, the following arrangements are disclosed herein, inter alia.

1. A wound dressing kit for reduced pressure wound therapy, comprising:
   a pump assembly;

a power source; and a dressing member having one or more absorptive layers and a fluid impermeable backing layer, and defining a first dressing portion and a second dressing portion;

a score along at least a portion of the dressing member between the first and the second dressing portions, the score being configured to increase the tearability of the dressing member between the first and second dressing portions;

wherein:
the first dressing portion is configured to support the one or more absorptive layers; and
the second dressing portion is configured to support at least one of the pump assembly and the power source.

2. The wound dressing kit of Arrangement 1, comprising a conduit in fluid communication with the pump assembly and the dressing member.

3. The wound dressing kit of any one of the previous arrangements, comprising a conduit in fluid communication with the pump assembly and the dressing member, the conduit being selectively removable from the dressing member.

4. The wound dressing kit of any one of the previous arrangements, comprising a conduit positioned on a third dressing portion of the dressing member, the dressing member having a score along at least a portion of the dressing member between the first and the third dressing portions and/or the second and the third dressing portions, the score being configured to increase the tearability of the dressing member between the first and the third dressing portions and/or the second and the third dressing portions.

5. The wound dressing kit of any one of the previous arrangements, comprising a conduit having perforated edges therealong and being configured to extend about a perimeter of the first portion of the dressing member, the conduit being selectively detachable from the first portion of the dressing member by tearing the conduit along at least one perforated edge thereof.

6. The wound dressing kit of anyone of the previous arrangements, comprising a conduit in fluid communication with the pump assembly and the dressing member, the conduit being coiled about the pump assembly in a helical arrangement.

7. The wound dressing kit of any one of the previous arrangements, comprising a conduit in fluid communication with the pump assembly and the dressing member having a connector on an end portion thereof, the connector being configured to activate the pump assembly when engaged with a second connector supported by the first dressing portion.

8. The wound dressing kit of any one of the previous arrangements, wherein the pump assembly comprises a voice coil actuated pump.

9. The wound dressing kit of any one of the previous arrangements, wherein the score comprises a plurality of perforations, channels, partial thickness cuts, and notches configured to increase the tearability of the dressing along the score.

10. The wound dressing kit of any one of the previous arrangements, wherein the power source is removable from the pump assembly by tearing the dressing along a score in the second dressing portion between the power source and the pump assembly.

11. The wound dressing kit of any one of the previous arrangements, wherein the pump is powered by a single 1200 mAh lithium battery.

12. The wound dressing kit of any one of the previous arrangements, wherein the pump is powered by one or more printed batteries.

13. The wound dressing kit of any one of the previous arrangements, wherein the pump is powered by one or more flexible batteries having a thickness of from approximately 450 microns to approximately 770 microns.

14. The wound dressing kit of any one of the previous arrangements, wherein the pump is powered by one or more flexible batteries having a thickness of from approximately 450 microns to approximately 500 microns.

15. The wound dressing kit of any one of the previous arrangements, wherein the pump is powered by 10 or more interconnected batteries.

16. The wound dressing kit of any one of the previous arrangements, wherein the pump is powered by one or more flexible batteries having a thickness of less than approximately 500 microns.

17. The wound dressing kit of any one of the previous arrangements, wherein the pump assembly is powered by one or more flexible batteries positioned about at least one of the first dressing portion and a conduit configured to communicate a source of negative pressure from the pump assembly to the one or more absorptive layers.

18. The wound dressing kit of any one of the previous arrangements, wherein the pump assembly is powered by one or more flexible batteries supported by the first dressing portion beneath the backing layer.

19. The wound dressing kit of any one of the previous arrangements, wherein the pump assembly is powered by one or more flexible batteries supported by the first dressing portion, the one or more flexible batteries being embedded within the one or more absorptive layers.

20. The wound dressing kit of any one of the previous arrangements, wherein the pump assembly is powered by one or more flexible batteries supported by the first dressing portion outside of the backing layer.

21. The wound dressing kit of any one of the previous arrangements, wherein the pump assembly is powered by one or more air activatable batteries.

22. The wound dressing kit of any one of the previous arrangements, wherein the dressing member has a wound contact layer and a transmission layer positioned between the wound contact layer and the backing layer.

23. The wound dressing kit of any one of the previous arrangements, wherein the pump is at least partially powered by one or more photovoltaic cells.

24. The wound dressing kit of any one of the previous arrangements, wherein the pump is at least partially powered by one or more photovoltaic cells positioned about at least one of the dressing backing layer, a housing for the pump assembly, and a conduit configured to communicate a negative pressure provided by the pump assembly to the one or more absorptive layers.

25. The wound dressing kit of any one of the previous arrangements, wherein the pump is at least partially powered by one or more batteries attachable to the dressing member using snap connectors, adhesive, Velcro, a housing having a closeable opening, or a pouch supported by the dressing member.

26. The wound dressing kit of any one of the previous arrangements, further comprising a flexible hinge positioned between the power source and the pump assembly to improve the flexibility and conformability of the portion of the dressing kit supporting the pump and the power source.

27. The wound dressing kit of any one of the previous arrangements, comprising a V-shaped cut out in the dressing layer between the pump assembly and the power source.

28. The wound dressing kit of any one of the previous arrangements, comprising a OLED display.

29. The wound dressing kit of any one of the previous arrangements, comprising a one or more indicator lights configured to indicate a condition of the dressing kit.

30. The wound dressing kit of any one of the previous arrangements, comprising a pull tab, button, conductive label, or switch configured to activate the power source.

31. The wound dressing kit of any one of the previous arrangements, comprising a first packaging member configured prevent an electrical connection between the power source and the pump assembly while the power source is supported by the first packaging member.

32. The wound dressing kit of any one of the previous arrangements, comprising a pressure indicator supported by the first dressing portion configured to provide a visual indication of a level of pressure beneath the backing layer.

33. The wound dressing kit of any one of the previous arrangements, comprising a saturation indicator supported by the first dressing portion configured to provide a visual indication of a level of liquid saturation beneath the backing layer.

34. The wound dressing kit of any one of the previous arrangements, wherein the first portion of the dressing member has one or more features or colored regions detectable only when the backing layer is drawn against the one or more features or colored regions, the dressing kit being configured such that the backing layer is drawn against the one or more features or colored regions when a threshold level of negative pressure is achieved under the backing layer.

35. The wound dressing kit of any one of the previous arrangements, comprising n activation switch or button configured to move between a first on position and a second off position, the switch or button being configured to remain in the first position when a threshold level of negative pressure is maintained beneath the backing layer.

36. The wound dressing kit of Arrangement 36, wherein the switch or button is configured to move to the second position when the level of negative pressure under the backing layer is less than a threshold level of negative pressure and the pump assembly exceeds a threshold flow rate or has been operating continuously for a threshold period of time.

37. The wound dressing kit of Arrangement 36, wherein the switch or button is configured to move to the second position when the level of negative pressure under the backing layer is less than 60 mmHg and the pump assembly has been operating continuously for 4 minutes.

38. The wound dressing kit of Arrangement 36, wherein the switch or button comprises a depressible dome and a tact switch.

39. A wound dressing kit for reduced pressure wound therapy, comprising:
  a pump assembly;
  a dressing member; and
  a power source;
  wherein the pump assembly and the power source are supported by the dressing member.

40. The wound dressing kit of Arrangement 39, wherein:
  the power source comprises a plurality of batteries positioned about the dressing member;
  the plurality of batteries are configured to provide a source of power to at least the pump assembly; and
  each of the plurality of batteries has a thickness of from approximately 450 microns to approximately 700 microns.

41. The wound dressing kit of Arrangement 40, wherein the plurality of batteries each have a thickness of from approximately 450 microns to approximately 500 microns.

42. The wound dressing kit of any one of Arrangements 39-41, wherein:
  the dressing member comprises one or more absorptive layers and a fluid impermeable backing layer, and defines a first dressing portion and a second dressing portion;
  the dressing member comprises a score along at least a portion of the dressing member between the first and the second dressing portions, the score being configured to increase the tearability of the dressing member between the first and second dressing portions;
  wherein:
    the first dressing portion is configured to support the one or more absorptive layers; and
    the second dressing portion is configured to support the pump assembly.

43. The wound dressing kit of any one of Arrangements 39-42, comprising a conduit having perforated edges therealong and being configured to extend about a perimeter of the first portion of the dressing member, the conduit being selectively detachable from the first portion of the dressing member by tearing the conduit along at least one perforated edge thereof.

44. The wound dressing kit of any one of Arrangements 39-42, comprising a conduit in fluid communication with the pump assembly and the dressing member, the conduit being coiled about the pump assembly in a helical arrangement.

45. The wound dressing kit of any one of Arrangements 39-44, wherein the pump assembly comprises a voice coil actuated pump.

46. The wound dressing kit of any one of Arrangements 39-45, comprising a pull tab, button, conductive label, or switch configured to activate the power source.

47. The wound dressing kit of any one of Arrangements 39-46, comprising a pressure indicator supported by the dressing member configured to provide a visual indication of a level of pressure beneath the backing layer.

48. The wound dressing kit of any one of Arrangements 39-46, comprising a saturation indicator supported by the dressing member configured to provide a visual indication of a level of liquid saturation beneath the backing layer.

49. A wound dressing kit for reduced pressure wound therapy, comprising:
  a pump assembly;
  a power source configured to provide a source of power to at least the pump assembly; and
  a dressing member having a fluid impermeable backing layer;
  wherein:
    the pump assembly is supported by the dressing member; and
    the power source is supported by a separate support member and is positionable in a remote position spaced apart from the dressing member.

50. The wound dressing kit of Arrangement 49, wherein the dressing member comprises one or more absorptive layers and a fluid impermeable backing layer over the one or more absorptive layers, wherein the pump assembly is supported adjacent to one or more of the absorptive layers.

51. The wound dressing kit of any one of Arrangements 49-50, wherein the pump assembly comprises a voice coil actuated pump.

52. The wound dressing kit of any one of Arrangements 49-51, comprising a pull tab, button, conductive label, or switch configured to activate the power source.

53. The wound dressing kit of any one of Arrangements 49-52, comprising a pressure indicator supported by the dressing member configured to provide a visual indication of a level of pressure beneath the backing layer.

54. The wound dressing kit of any one of Arrangements 49-53, comprising a saturation indicator supported by the dressing member configured to provide a visual indication of a level of liquid saturation beneath the backing layer.

55. The wound dressing kit of Arrangements 49-54 or any one of the previous arrangements, comprising a viewing window in an opaque backing layer, the viewing window being configured to permit a user to determine a level of saturation within the dressing member.

56. A wound dressing kit for reduced pressure wound therapy, comprising:
   a dressing member having a fluid impermeable backing layer, a transmission layer, and an absorption layer between the transmission layer and the backing layer; and
   a pump assembly positioned within an opening formed in the absorption layer sized and configured such that the pump assembly is positioned in direct contact with the transmission layer.

57. The wound dressing kit of Arrangement 56, wherein the pump has a port that is in direct fluid communication with the transmission layer, such that negative pressure is applied by the pump assembly directly to the transmission layer.

58. The wound dressing kit of any one of Arrangements 56-57, further comprising a liquid barrier or liquid filter in communication with the pump assembly and configured to prevent the passage of liquid into the pump.

59. The wound dressing kit of any one of Arrangements 56-58, wherein the opening does not extend into the transmission layer.

60. The wound dressing kit of any one of Arrangements 56-59, wherein the opening extends through the transmission layer.

61. The wound dressing kit of any one of Arrangements 56-60, further comprising an impermeable film between the absorption layer and the transmission layer, the impermeable film having an opening therein in communication with a port in the pump assembly configured to permit the passage of negative pressure from the pump assembly into the transmission layer.

62. The wound dressing kit of any one of Arrangements 56-61, wherein the pump assembly is configured to transfer liquid from the transmission layer through the pump into the absorption layer.

63. The wound dressing kit of any one of Arrangements 56-62, wherein the pump assembly is covered by the backing layer.

64. The wound dressing kit of Arrangements 63, further comprising a vent hole in the backing layer configured to permit exhaust air from the pump assembly to pass through the backing layer.

65. The wound dressing kit of any one of Arrangements 56-64, wherein the pump assembly comprises a voice coil actuated pump.

66. The wound dressing kit of any one of Arrangements 56-64, comprising a pull tab, button, conductive label, or switch configured to activate the power source.

67. The wound dressing kit of any one of Arrangements 56-66, comprising a pressure indicator supported by the dressing member configured to provide a visual indication of a level of pressure beneath the backing layer.

68. The wound dressing kit of any one of Arrangements 56-67, comprising a saturation indicator or sensor supported by the dressing member configured to provide a visual indication of a level of liquid saturation beneath the backing layer.

69. The wound dressing kit of Arrangement 68, wherein the saturation indicator or sensor is positioned adjacent to the pump assembly.

70. The wound dressing kit of any one of Arrangements 56-69, further comprising a power source configured to provide a source of power to at least the pump assembly.

71. The wound dressing kit of any one of Arrangements 56-70, wherein the backing layer is opaque, and comprising one or more viewing windows in the backing layer configured to permit a user to determine a level of saturation within the dressing member.

72. A method of treating a wound, comprising;
   placing a wound dressing kit of any one of the previous arrangements over a wound;
   applying negative pressure to the wound from the pump assembly.

BRIEF DESCRIPTION OF THE DRAWINGS

Embodiments of the present disclosure will now be described hereinafter, by way of example only, with reference to the accompanying drawings in which:

FIGS. 1A-B illustrate an embodiment of a dressing kit for negative pressure wound therapy.

FIGS. 2A-C illustrate additional embodiments of a dressing kit for negative pressure wound therapy.

FIGS. 3A-C illustrate additional embodiments of a dressing kit for negative pressure wound therapy.

FIGS. 18A-C illustrate additional embodiments of a dressing kit for negative pressure wound therapy.

FIGS. 21A-21C illustrate an additional embodiment of a dressing kit for negative pressure wound therapy.

FIGS. 22A-C illustrate an additional embodiment of a dressing kit for negative pressure wound therapy.

FIGS. 24A-F illustrate an additional embodiment of an activation switch of a dressing kit for negative pressure wound therapy.

FIGS. 27A-D illustrate additional embodiments of a dressing kit for negative pressure wound therapy.

FIGS. 28A-G illustrate additional embodiments of a dressing kit for negative pressure wound therapy.

FIGS. 29A-B illustrate additional embodiments of a dressing kit for negative pressure wound therapy.

FIGS. 35A-B illustrate additional embodiments of a dressing kit for negative pressure wound therapy.

FIGS. 43A-E illustrate additional embodiments of a dressing kit for negative pressure wound therapy.

FIGS. 45A-C illustrate additional embodiments of a dressing kit for negative pressure wound therapy.

FIG. 46 illustrates an additional embodiment of a dressing kit for negative pressure wound therapy.

FIGS. 47A-B illustrate an additional embodiment of a dressing kit for negative pressure wound therapy.

FIGS. 51A-B illustrate an additional embodiment of a dressing kit for negative pressure wound therapy.

FIGS. 54A-C illustrate an additional embodiment of an activation switch of a dressing kit for negative pressure wound therapy.

FIGS. 83A-C illustrate an additional embodiment of a dressing kit for negative pressure wound therapy.

FIGS. 84A-B illustrate an additional embodiment of a portion of a dressing kit supporting or housing the pump assembly.

FIGS. 85A-E illustrate an additional embodiment of a dressing kit for negative pressure wound therapy.

DETAILED DESCRIPTION OF SOME EXEMPLIFYING EMBODIMENTS

Figure 4C:
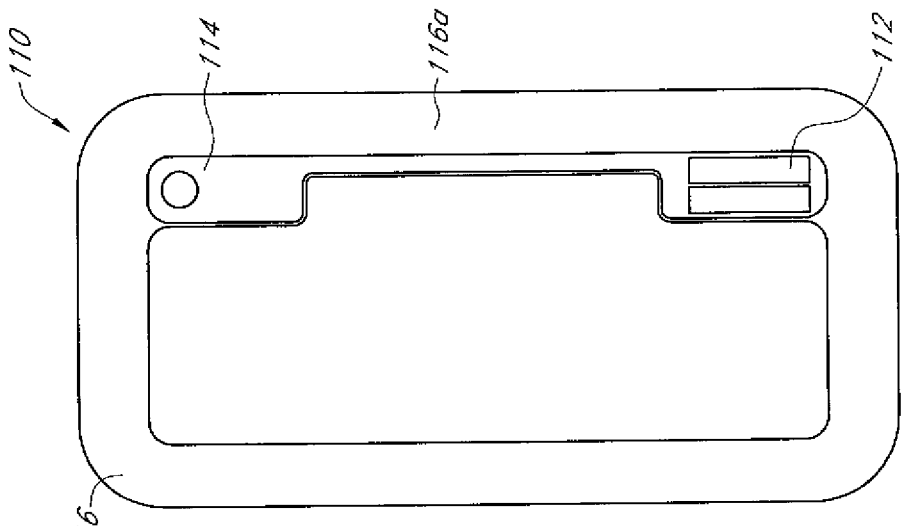
FIGS. 4A-C illustrate additional embodiments of dressing kits for negative pressure wound therapy, showing two different exemplifying sizes of such embodiment.

Embodiments disclosed herein relate to apparatuses and methods of treating a wound with reduced pressure. It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as –X mmHg, represent pressure levels that are below standard atmospheric pressure, which corresponds to 760 mmHg (or t atm, 29.93 inHg, 101.325 kPa, 14.696 psi, etc.). Accordingly, a negative pressure value of –X mmHg reflects absolute pressure that is X mmHg below 760 mmHg or, in other words, an absolute pressure of (760–X) mmHg. In addition, negative pressure that is "less" or "smaller" than X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg).

Any of the wound dressing embodiments disclosed herein can be located over a wound site to be treated. The dressing can form a substantially sealed cavity or enclosure over the wound site. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

In any of the apparatus embodiments disclosed herein, as in the embodiment illustrated in FIG. 1, the pump assembly can be a canisterless pump assembly (meaning that the pump assembly does not have an exudate or liquid collection canister). However, any of the pump embodiments disclosed herein can be configured to include or support a canister. Additionally, in any of the apparatus embodiments disclosed herein, any of the pump assembly embodiments can be mounted to or supported by the dressing, or adjacent to the dressing. Additionally, in any of the apparatus embodiments disclosed herein, the pump assembly can have two or more pumps and one, two, or more power sources. In any of the embodiments disclosed herein, the pump assembly, power source, and or any support member or film supporting or covering the pump assembly or power source can have any of a variety of colors used to match a person's skin including any tone or coloring thereof. Further, in any embodiments disclosed herein, the pump assembly can have any of the components, features, or other details of any of the pump assembly embodiments disclosed in U.S. patent application Ser. No. 13/287,897 (titled "REDUCED PRESSURE THERAPY APPARATUSES AND METHODS OF USING SAME,), filed on Nov. 2, 2011, which disclosure is hereby incorporated by reference as if fully set forth herein.

Any of the wound dressing embodiments disclosed herein can be arranged or configured to operate without the use of an exudate canister. Any dressing embodiments can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. Some embodiments of the pump are designed for an operation period of up to fourteen days, and some for up to twenty days. The pump can be programmed to automatically terminate therapy after a desired number of days, e.g., after seven days, further operation of the pump will not be possible. Some embodiments are designed for longer or repeated usage, and can be configured to support an exudate canister.

In any dressing kit embodiments, including without limitation the illustrated embodiments, the pump assembly can be of a sufficiently small and portable size to be supported on or adjacent to the dressing, or on another location of a user's body or in a user's clothing. For example and without limitation, as will be described in greater detail below, in any of the embodiments disclosed herein, the pump assembly can be attached to a specially formed depression or space on the dressing, can be embedded within, supported on top of or adjacent to one or more absorbent or other dressing layers, or can be otherwise supported by the dressing. Additionally, in any embodiments disclosed or incorporated by reference herein (collectively referred to as "disclosed herein"), the pump assembly can be sized to be attached using adhesive medical tape or otherwise to a person's skin in a comfortable location, adjacent to or on the dressing or otherwise, or can be sized to fit within a person's pants or shirt pocket or tethered to a person's body using a lanyard, pouch, or other suitable device or article.

Any of the dressing kit embodiments disclosed herein can be manufactured in a wide variety of different models or versions, wherein the size of the dressing can be varied to accommodate a wide range of wound sizes. For example, any of the dressing kits can be made having the following sizes of dressings and wound pads or other absorbent elements. In any embodiments disclosed herein, the size of the dressing or the wound pad can be defined by the area of the dressing or the wound pad, wherein the specific length and width (if rectangular) can be varied to accommodate a wider range of wound sizes. For example, the dressings and/or wound pads can be rectangular, circular, ovular, triangular, pentagonal, hexagonal, trapezoidal, or otherwise. The shape and dimensions of the various dressings and wound pads can fall within any of the area ranges listed below, otherwise disclosed in this application, or otherwise. Thus, the dressing dimensions and shapes are not limited to those specified in this disclosure but can be any suitable size and shape.

| Approximate Dressing Size (Dimensions) | Approximate Dressing Size (Area) | Approximate Wound Pad Size (Dimensions) | Approximate Wound Pad Size (Area) |
| --- | --- | --- | --- |
| 10 cm × 30 cm (4 in × 11.75 in) | 300 cm$^2$ (47 in$^2$) | 5 cm × 20 cm (2 in × 8 in) | 100 cm$^2$ (16 in$^2$) |
| 15 cm × 15 cm (6 in × 6 in) | 225 cm$^2$ (36 in$^2$) | 10 cm × 10 cm (4 in × 4 in) | 100 cm$^2$ (16 in$^2$) |
| 15 cm × 20 cm (6 in × 8 in) | 300 cm$^2$ (48 in$^2$) | 10 cm × 15 cm (4 in × 6 in) | 150 cm$^2$ (24 in$^2$) |
| 10 cm × 20 cm (4 in × 8 in) | 200 cm$^2$ (32 in$^2$) | 5 cm × 10 cm (2 in × 4 in) | 50 cm$^2$ (8 in$^2$) |
| 20 cm × 20 cm (8 in × 8 in) | 400 cm$^2$ (64 in$^2$) | 15 cm × 15 cm (6 in × 6 in) | 225 cm$^2$ (36 in$^2$) |

In any embodiments disclosed herein, the dressing can be sized such that the pad or absorptive portion of the dressing is approximately 50×100 mm, 100×150 mm, 100×250 mm, or any size within these ranges. Some embodiments of the dressing can be configured to be universal, so that one dressing size, shape, and configuration can be adhered to the hips, arms, thighs, torso, back, and/or other body parts.

Some embodiments of the overlay or dressing can be substantially impervious to air flow and the flow of bacteria or other contaminants through the overlay layer, while being pervious to vapor transmission.

As described in greater detail in U.S. patent application Ser. No. 13/092,042, which is hereby incorporated by reference in its entirety as if fully set forth herein, in any of the dressing embodiments disclosed herein, a layer of absorbent material can be provided above the transmission layer. The absorbent material which can be a foam or non-woven natural or synthetic material and can optionally include or be super-absorbent material that can form a reservoir for fluid, particularly liquid, removed from the wound site and draws those fluids towards a cover layer. The material of the absorbent layer can prevent liquid collected in the wound dressing from flowing in a sloshing manner. The absorbent layer can also help distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressure, the material of the absorbent layer can be selected to absorb liquid. A number of materials exist that are able to absorb liquid when under negative pressure, for example superabsorber material. For example and without limitation, any embodiments of the absorbent layer can be manufactured using ALLEVYN™ foam, Freudenberg 114-224-4 and/or Chem-Posite™ 11C-450, or any other suitable material. Other materials may be more appropriate for and can be used in and of the dressing embodiments disclosed herein. Suitable superabsorbers can have polyacrylate or carbomethoxycellulose based materials in the form of granules or fibers or combinations thereof.

In any embodiments disclosed herein, the absorbent layer can be a layer of non-woven cellulose fibers having superabsorbent material in the form of dry particles dispersed throughout. In some arrangements, the use of natural and/or synthetic fibres such as cotton, cellulose and viscose fibres can introduce fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action can also assist in bringing liquid into contact with the upper cover layer to aid increase transpiration rates of the dressing. The wicking action can also assist in delivering liquid downward towards the wound bed when exudation slows or halts. This delivery process helps maintain the transmission layer and lower wound bed region in a moist state which helps prevent crusting within the dressing. Crusting could lead to blockage both within the dressing layers or components beneath the cover or backing layer, and also within the port and/or conduit which can inhibit the flow of wound fluids in the dressing and also inhibit a flow of reduced pressure to the wound or portions of the wound. Thus, the delivery process can help maintain an environment optimized for wound healing.

A layer of porous material can be located above the wound contact layer. This porous layer, or transmission layer, allows transmission of fluid including liquid and gas away from a wound site into upper layers of the wound dressing. In particular, the transmission layer can ensure that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalized negative pressure. The layer can be formed of a material having a three dimensional structure. For example, a knitted or woven spacer fabric (for example Baltex 7970 weft knitted polyester) or a non-woven fabric can be used. Other materials can be utilized, and examples of such materials are described in U.S. patent application Ser. No. 13/092,042, which are hereby incorporated by reference and made part of this disclosure.

In any embodiments disclosed herein, the transmission layer can have a 3D polyester spacer fabric layer, such as with any embodiments of the dressing disclosed in U.S. Patent Application Publication No. 2011/0282309 (Ser. No. 13/092,042), (titled WOUND DRESSING AND METHOD OF USE), filed Apr. 21, 2011, which application is hereby incorporated by reference as if fully set forth herein. Some embodiments of the transmission layer can have a top layer (that is to say, a layer distal from the wound-bed in use) which is a 84/144 textured polyester (which can be approximately 24.5%, or from approximately 22% to approximately 27% in terms of material composition), and a bottom layer (i.e., a layer which lies proximate to the wound bed in use) which can be a 100 denier flat polyester (which can be approximately 31.4%, or from approximately 28% to approximately 34% in terms of material composition), and a third layer formed sandwiched between these two layers which is a region defined by a knitted polyester viscose, cellulose or the like monofilament fiber (which can be approximately 44.1%, or from approximately 40% to approximately 48% in terms of material composition). Other suitable materials and other linear mass densities of fiber can be used.

Additionally, any embodiments of the transmission layer can be formed using any of the following needle arrangement parameters.

| Needle Arrangement Dial Set Out | | | | | | | | | | | |
|---|---|---|---|---|---|---|---|---|---|---|---|
| F1 | F2 | F3 | F4 | F5 | F6 | F7 | F8 | F9 | F10 | E11 | F12 |
| TA | AW | KA | WA | AW | TA | | | | | | |
| WB | | TB | TB | | KB | | | | | | |

| Pattern area: 4 wales × 12 courses | | | | |
|---|---|---|---|---|
| F12 | K | K | K | K |
| F11 | W | W | W | W |
| F10 | W | T | W | T |
| F9 | K | K | K | K |
| F8 | W | W | W | W |
| F7 | T | W | K | W |
| F6 | K | K | K | K |
| F5 | W | W | W | W |
| F4 | W | T | W | T |
| F3 | K | K | K | K |
| F2 | W | W | W | W |
| F1 | T | W | T | W |

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Material Layer Composition

Preferably, to improve the liquid flow across the transmission layer (that is to say perpendicular to the channel region formed between the top and bottom spacer layers, the 3D fabric is treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

In some embodiments, the absorbent layer can be an air-laid material. Heat fusible fibers can optionally be used to assist in holding the structure of the pad together. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Optionally, the absorbent layer can include synthetic stable fibers and/or bi-component stable fibers and/or natural stable fibers and/or super-absorbent fibers. Fibers in the absorbent layer can be secured together by latex bonding or thermal bonding or hydrogen bonding or a combination of any bonding technique or other securing mechanism. In any embodiments disclosed herein, the absorbent layer can be formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer can comprise a layer of multiple fibers. Preferably, the fibers are strand-like and made from cellulose, polyester, viscose or the like. Preferably, dry absorbent particles are distributed throughout the absorbent layer ready for use. In any embodiments disclosed herein, the absorbent layer can have a pad of cellulose fibers and a plurality of super absorbent particles. In additional embodiments, the absorbent layer is a non-woven layer of randomly orientated cellulose fibers.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc., or more than 15 times its own weight of 0.9% W/W saline, etc., or, in some embodiments, more than 20 times its own weight of 0.9% W/W saline, etc. Preferably, the material is capable of absorbing more than 30 times its own weight of 0.9% W/W saline, etc. The absorbent layer can have one or more through holes located so as to underlie a suction port. In any embodiments disclosed herein, a hydrophobic filter or other filter or object configured to permit the flow of air or gas through the port or openings in the dressing and prevent the flow of liquid or solids through the port or openings in the dressing can be positioned upstream of the pump to prevent any liquids or solids from entering the pump.

In some embodiments, the wound site can be filled partially or completely with a wound packing material. Deeper wounds can benefit from such packing material. The wound packing material can be used in addition to the wound dressing, or can be integral to the wound dressing. The wound packing material generally can comprise a porous and conformable material, for example foam (including reticulated foams), and gauze. Preferably, the wound packing material is sized or shaped to fit within the wound site so as to fill any empty spaces. The wound dressing can then be placed over the wound site and wound packing material overlying the wound site. When a wound packing material is used, once the wound dressing is sealed over the wound site, TNP is transmitted from a pump through the wound dressing, through the wound packing material, and to the wound site. This negative pressure draws wound exudate and other fluids or secretions away from the wound site.

The dressing of any dressing kit embodiments disclosed herein can have a gas impermeable, but moisture vapor permeable, cover layer extending across the width of the wound dressing. The cover layer, which can for example be a polyurethane film (for example, Elastollan SP9109) or any other suitable material having a pressure sensitive adhesive on one side, is substantially gas impermeable, thereby creating a substantially sealed enclosure over the wound. In this way an effective chamber is made between the cover layer and a wound site where a negative pressure can be established. The cover layer can be sealed to the wound contact layer in a border region around the circumference of the dressing, ensuring that no air is drawn in through the border area, for example via adhesive or welding techniques. The cover layer can protect the wound from external bacterial contamination (bacterial barrier) and allows liquid from wound exudates to be transferred through the layer and evaporated from the film outer surface. The cover layer can have a polyurethane film and an adhesive pattern spread onto the film. The polyurethane film is moisture vapor permeable and can be manufactured from a material that has an increased water transmission rate when wet.

An orifice can be provided in the cover film to allow a negative pressure to be applied to the dressing. As mentioned, in some embodiments, a suction port can be sealed to the top of the cover film over the orifice, which can communicate negative pressure through the orifice, or the pump assembly can be mounted directly over the orifice. The port or pump assembly can be adhered and sealed to the cover film using an adhesive such as an acrylic, cyanoacrylate, epoxy, UV curable or hot melt adhesive. If used, the port can be formed from a soft polymer, for example a polyethylene, a polyvinyl chloride, a silicone or polyurethane having a hardness of 30 to 90 on the Shore A scale.

The dressing can have a filter element that is impermeable to liquids, but permeable to gases. The filter element can act as a liquid barrier, to substantially prevent or inhibit liquids from escaping from the wound dressing, as well as an odor barrier. The filter element can also function as a bacterial barrier. In some embodiments, the pore size of the filter element can be approximately 0.2 µm. Suitable materials for the filter material of the filter element include 0.2 micron Gore™ expanded PTFE from the MMT range, PALL Versapore™ 200R, and Donaldson™ TX6628. The filter element thus enables gas to be exhausted through the orifice. Liquid, particulates and pathogens however are contained in the dressing. Other details regarding the filter are disclosed in U.S. patent application Ser. No. 13/092,042 (2011/0282309) and incorporated by reference herein.

The wound dressing and its methods of manufacture and use as described herein may also incorporate features, configurations and materials described in the following patents and patent applications, each of which is incorporated by reference in their entireties herein as if made part of this disclosure: U.S. Pat. Nos. 7,524,315, 7,708,724, 7,909,805; 7,964,766; 8,062,272; 8,080,702, 8,105,295, 8,282,611, and 8,303,552; U.S. Patent Application Publication Nos. 2009/0254054, 2010/0160880, 2010/0274207, 2011/0009838, 2011/0028918, 2011/0054421, 2011/0054423, and 2011/0118683, as well as U.S. App. Ser. No. 29/389,782, filed Apr. 15, 2011, and Ser. No. 29/389,783, filed Apr. 15, 2011. From these incorporated by reference patents and patent applications, features, configurations, materials and methods of manufacture or use for similar components to those described in the present disclosure can be substituted, added or implemented into embodiments of the present application.

In operation, the wound dressing can be sealed over a wound site forming a wound cavity. The pump assembly can provide a source of a negative pressure to the dressing. Fluid can be drawn toward the orifice through the wound dressing from a wound site below the wound contact layer. The fluid can move towards the orifice through the transmission layer. As the fluid is drawn through the transmission layer, wound exudate can be absorbed into the absorbent layer.

The general shape of the wound dressing can be square, ovular, rectangular, or otherwise. The dressing can have rounded corner regions. It will be appreciated that wound dressings according to other embodiments of the present invention can be shaped differently such as square, circular or elliptical dressings, or the like.

The desired size of the wound dressing can be selected based on the size and type of wound it will be used in. In any embodiments, though not required, the wound dressing can measure between 20 and 40 cm on its long axis, and between 10 to 25 cm on its short axis. For example, dressings can be provided in sizes of approximately 10×20 cm, 10×30 cm, 10×40 cm, 15×20 cm, and 15×30 cm, or any other sizes within these ranges or otherwise.

Whilst some embodiments of the present invention have so far been described in which the transmission layer is formed as a 3D knit layer, e.g., two layers spaced apart by a monofilament layer, it will be appreciated that some embodiments of the present invention are not restricted to the use of such a material. In some embodiments, as an alternative to such a 3D knit material, one or more layers of a wide variety of materials could be utilized. In each case, according to embodiments of the present invention, the openings presented by layers of the transmission layer are wider and wider as one moves away from the side of the dressing which, in use will be located proximate to the wound. In any embodiments disclosed herein, the transmission layer can be provided by multiple layers of open celled foam. Though note required, the foam can be reticulated open cell foam. The foam can be hydrophilic or able to wick aqueous based fluids. The pore size in each layer is selected so that in the foam layer most proximate to the wound side in use the pores have a smallest size. If only one further foam layer is utilized that includes pore sizes which are greater than the pore sizes of the first layer. This helps avoid solid particulate being trapped in the lower layer which thus helps maintain the lower layer in an open configuration in which it is thus able to transmit air throughout the dressing. In any embodiments disclosed herein, two, three, four or more foam layers can be included. The foam layers can be integrally formed, for example, by selecting a foam having a large pore size and then repeatedly dipping this to a lesser and lesser extent into material which will clog the pores or alternatively, the transmission layer formed by the multiple foam layers can be provided by laminating different types of foam in a layered arrangement or by securing such layers of foam in place in a known manner.

Some embodiments of the dressing can be configured to permit the repositionability of the dressing. In any embodiments disclosed herein, the dressing can have a wound contact surface that is covered with an adhesive, such as a silicone based adhesive. As described in U.S. patent application Ser. No. 13/092,042, which disclosure is hereby incorporated by reference as if fully set forth herein, though not required, a lower surface of any of the wound dressing embodiments disclosed herein can have an optional wound contact layer. Any of the dressing embodiments disclosed herein can be made without the wound contact layer. The wound contact layer can be a polyurethane layer or polyethylene layer or other flexible layer which can be made porous or perforated, for example via a hot pin process, laser ablation process, ultrasound process or in some other way or otherwise made permeable to liquid and gas. The perforations can enable fluid and/or gas to flow through the layer. The wound contact layer can help prevent tissue ingrowth into the other material of the wound dressing.

The perforations of the contact layer can be sized small enough to meet this requirement but still allow fluid through. For example, the contact layer can have perforations formed as slits or holes having a size ranging from approximately 0.025 mm to approximately 1.8 mm, or from approximately 1.2 mm to approximately 1.8 mm, which are considered small enough to help prevent tissue ingrowth into the wound dressing while allowing wound exudate to flow into the dressing. In any embodiments, therefore, the perforations can be formed as holes ranging in diameter from approximately 1.2 mm to approximately 2.8 mm, or from approximately 1.2 mm to approximately 1.8 mm. The hole spacing or density in any embodiments can be approximately 8 holes/cm$^2$, or from approximately 6 holes/cm$^2$ to approximately 10 holes/cm$^2$. As used throughout this disclosure, unless otherwise defined, the term approximately can be used to describe a range of +/−10% of the stated value. Additionally, in any embodiments of the contact layer, the holes can be formed at approximately a 3.655 mm triangular pitch. Any of the wound contact layer embodiments disclosed herein can be formed from silicone.

The wound contact layer can help hold the whole wound dressing together and help to create an air tight seal around the absorbent pad in order to maintain negative pressure at the wound. The wound contact layer also acts as a carrier for an optional lower and upper adhesive layer (not shown). For example, a lower pressure sensitive adhesive can be provided on the underside surface of the wound dressing whilst an upper pressure sensitive adhesive layer can be provided on the upper surface of the wound contact layer. The pressure sensitive adhesive, which can be a silicone, hot melt, hydrocolloid or acrylic based adhesive or other such adhesives, can be formed on both sides or optionally on a selected one or none of the sides of the wound contact layer. When a lower pressure sensitive adhesive layer is utilized, this helps adhere the wound dressing to the skin around a wound site.

As mentioned, any dressing embodiments for use in the dressing kits disclosed or incorporated by reference herein can have an adhesive covered bottom (e.g., wound contacting) surface. In any embodiments disclosed herein, as mentioned, the adhesive can be a silicone adhesive including, for example, polysiloxanes or polyorganosiloxanes or other polymeric pressure sensitive silicone adhesives. For example, polydimethylsiloxane or the like can be used. The adhesive formulation can be a mixture of alkyl pendant siloxanes, which can be spread and cast as a two part mix with a catalyst such that a final polymerisation step takes place following casting or spreading. In any embodiments disclosed herein, a dressing layer can have a non-perforated silicone adhesive coating (coat weight 130 gsm nominal) and full spread acrylic adhesive (27 to 37 gsm) coated onto opposite sides of an extruded EU30 polyurethane clear film (27 to 37 gsm). Moisture vapour permeability of such an arrangement can be between approximately 367 gm$^{-2}$/24 hrs to approximately 405 gm$^{-2}$/24 hrs, or a mean moisture vapour permeability of 382 gm$^{-2}$/24 hrs.

Some embodiments or arrangements of a silicone adhesive layer suitable for dressing embodiments disclosed herein can have a moisture vapour transmission rate between approximately 350 gm$^{-2}$/24 hrs and approximately 410 gm$^{-2}$/24 hrs. Aptly, the average moisture vapour permeability of some embodiments or arrangements of a silicone adhesive layer suitable for dressing embodiments disclosed herein can be approximately 380 gm$^{-2}$/24 hrs. Some of the dressing embodiments disclosed herein can have a Wacker silres PSA 45 pressure sensitive adhesive coated thereon.

Additionally, any of the dressing embodiments disclosed herein can have an anti-microbial agent or substance incorporated into the dressing or coated on one or more surfaces of the dressing. For example, without limitation, the dressing can contain anti-microbial e.g. nanocrystalline silver agents on the wound contact layer, or otherwise, and/or silver sulphur diazine in the absorbent layer, or otherwise. These respectively can eliminate micro-organisms in the wound and micro-organisms in the absorption matrix. A wound contact layer of any dressing embodiments disclosed herein can have nanocrystalline silver agents, silver salts, copper salts, or gold salts such as, without limitation, those disclosed in U.S. patent application Ser. No. 11/922,894 (titled ANTIMICROBIAL BIGUANIDE METAL COMPLEXES), filed May 21, 2008, which application is incorporated by reference herein as if made part of this disclosure, PHMB, chlorohexadine, peroxide, hypochloride, or other bleaches therein or thereon.

One or more of such agents can be used separately or together. These can reduce or eliminate micro-organisms in the wound and micro-organisms in the absorption matrix. As a still further option other active components, for example, pain suppressants, such as ibuprofen, can be included. Also agents which enhance cell activity, such as growth factors or that inhibit enzymes, such as matrix metalloproteinase inhibitors, such as tissue inhibitors of metalloproteinase (TIMPS) or zinc chelators could be utilized. As a still further option odor trapping elements such as activated carbon, cyclodextrine, zeolite or the like can be included in the absorbent layer or as a still further layer above the filter layer.

Additionally, adhesive fixation strips can be positioned around the peripheral edges of the any of the dressing embodiments disclosed herein to provide additional support to the dressing. Such fixation strips can be advantageous in some situations so as to provide additional sealing against the skin of the patient surrounding the wound site. For example, the sealing or fixation strips can provide additional sealing for when a patient is more mobile. In some cases, the fixation strips can be used prior to activation of the pump assembly, particularly if the dressing is placed over a difficult to reach or contoured area. In any embodiments disclosed herein, the dressing kit can be provided with up to five sealing strips.

Moreover, some embodiments disclosed herein are directed to systems that include negative pressure therapy apparatuses and dressings, and methods and algorithms for operating such negative pressure therapy apparatuses for use with negative pressure therapy dressings. In some embodiments, a negative pressure therapy apparatus comprises a pump assembly configured to, inter alia, provide negative pressure to a wound. Some embodiments of pump assemblies disclosed herein comprise novel and inventive control logic configured to control the operation of the pump assembly. For example, some embodiments comprise novel and inventive control logic configured to control the operation of a pump assembly in response to monitoring and detecting various operating conditions, such as presence and/or severity of a leak or leaks in the system, rate of flow of fluid (e.g., air, liquid and/or solid exudate, etc.) aspirated from a wound, and the like. In some embodiments, the control logic can be configured to detect a leak or leaks in a system (e.g., leak or leaks in the dressing that is in fluid communication with the pump, leak or leaks in the seal created by the dressing over the wound, etc.) as well as to control the operation of the pump assembly when such leak or leaks are detected. In some embodiments, the pump assembly can be configured to distinguish between at least a normal or low leak (e.g., a leak that has a relatively low flow rate), a high leak (e.g., a leak that has a relatively high flow rate), and a very high leak (e.g., a leak that has a relatively very high flow rate). Some embodiments can further be configured to also distinguish between the aforementioned leaks and an extremely high leak.

The operation of the pump can be controlled by the use of one or more buttons, pull tabs, sliding switches, or other similar features.

In some embodiments, the dressing kit can comprise a source of negative pressure, such as a miniature, disposable pump, powered by a power source. The pump assembly can be configured to provide therapy for a predetermined period of time, such as approximately 1 day, 1 or 2 to 10 days, 1 or 2 to 14 days, etc. In some embodiments, the pump assembly can be required to provide uninterrupted therapy for such period of time. In some embodiments, the pump assembly can be configured to deactivate itself a predetermined period of time (e.g., 7 days) after an initial activation. The algorithms or logic disclosed herein can help the pump assembly operate more efficiently and conserve power, for example but without limitation, battery power.

In any embodiments disclosed herein, the pump, circuit board or other controller, indicator lights, audible or visual alarms, and/or any other electronic components (collectively referred to herein as "pump electronics") of the dressing embodiments disclosed herein can be powered by one or more batteries (for example, two batteries) and can weigh approximately 84 grams, or less than 90 grams, including the weight of the batteries. In some embodiments, the pump assembly can weigh less than 84 grams, including the weight of the batteries, or can weigh from approximately 80 grams to approximately 90 grams, from approximately 75 grams or less to approximately 100 grams, or between any values within the foregoing ranges. The weight and/or size of the pump assembly can be reduced by reducing the battery size and/or weight to, for example, AAA sized batteries, or smaller, or to one or more flat lithium batteries, or by using an array of batteries.

For example, in some embodiments, the pump can be powered by a single 1200 mAh lithium battery. A non-limiting example of a battery that would be suitable is a JAUCH $LiMnO_2$ battery having a nominal voltage of 3.0 volts, a nominal capacity of 1200 mAh, a maximum continuous discharge current of 150 mA, a max pulse discharge current of 300 mA, a length of 40.0 mm, a width of 25.0 mm, a thickness of 5.0 mm, and a weight approximately 9.5 grams or less. The dimensions and/or weight of the battery can be reduced if a smaller capacity, voltage, and/or current is desired. For example, in any of the dressing embodiments disclosed herein, a plurality of lithium batteries can be used, each having a reduced size and weight as compared to the single battery described above. In any embodiments disclosed herein, any number of batteries (including any of the battery types disclosed herein) and/or capacitors can be positioned about the dressing cover layer and/or any of the dressing layers beneath the cover layer, the pump housing, and/or the conduit providing reduced pressure from the pump to the dressing, if such conduit is used. In any dressing embodiments, as described herein, the pump can be positioned directly on the dressing an configured such that no conduit is needed.

Any embodiments of the pump assembly and dressings disclosed herein can have a plurality of small capacitors, flexible batteries, and/or printed batteries supported by the dressing, the pump, and/or the conduit between the pump and the dressing, or otherwise. For example, an array of flat batteries can be distributed across the dressing cover layer, within the dressing layers under the cover layer (including being positioned across a plurality of the dressing layers), and/or across any conduit positioned on the dressing or between the pump and the dressing. Additionally, the weight and/or size of the pump assembly can be reduced by reducing the pump size and/or weight.

The batteries of any of the embodiments disclosed herein can be lithium chloride, lithium ion disulfide, lithium manganese dioxide or any other suitable batteries that are suitable for exposure to ethylene dioxide and/or other sterilization gases. Lithium air or zinc air batteries can also be used with any embodiment disclosed herein. Coin shaped or button shaped batteries of any composition can also be used with any embodiment disclosed herein. The batteries can be supported outside of the pump housing so as to minimize or eliminate the chance of an electrical spark which could cause an explosion in the presence of the sterilization gas or an explosive gas during the sterilization process when supported in the packaging element or elements. Additionally, where there are a plurality of batteries, the batteries can be spaced apart or otherwise separated in the packaging to prevent any power loss or sparking of the batteries during the sterilization process or otherwise before usage.

Additionally, in any embodiments disclosed herein, the power source for the pump can be provided by one or more flexible batteries. For example, one or more flexible printed batteries based on the technology developed by Imprint Energy and/or Solicore. For example, in any embodiments disclosed herein, the power source can comprise one or more lithium polymer batteries manufactured by Solicore, Inc. Solicore Flexion lithium polymer batteries are ultra-thin, flexible, and have a high energy density. For example, in some embodiments, the power source can have a plurality of thin, flexible lithium polymer batteries. In any embodiments disclosed herein, the power source can comprise a plurality of thin, flexible lithium polymer batteries each having a nominal capacity of approximately 10 to approximately 14 mAh or greater, and a voltage of approximately 3.0 V. In some embodiments, the batteries can each have a size of approximately 26 mm by approximately 29 mm, or approximately 49 mm by approximately 23 mm, and a thickness of approximately 0.45 mm.

In any embodiments disclosed herein, the power source can have from approximately 6 to approximately 10 flexible batteries, or from approximately 10 to approximately 50 or more flexible batteries, depending on the spatial area of the battery, having a thickness of approximately 0.5 mm or less. In any embodiments disclosed herein, the power source can have one or more batteries having a thickness of approximately 0.5 mm or less, or approximately 0.45 mm or less, and can be configured to have a total nominal capacity of from approximately 1000 mAh or less to approximately 1200 mAh.

Additionally, in any embodiments disclosed herein, the power can be provided by one or more carbon zinc flexible batteries manufactured by Blue Spark Technologies, built on 1.5V carbon-zinc battery chemistry. Voltages above 1.5V can be provided to the pump embodiments by providing multiple battery cells in series. Providing one or more flexible batteries in parallel can increase the total capacity of the power provided by the plurality of batteries. The Blue Spark Technologies ST series printed batteries can provide peak drain currents of approximately at least 1 mA. Such batteries can have a thickness of less than 500 micron (0.020 in). For example, the Blue Spark Technologies 110-ST1 battery provides 1.5V, has a capacity of 30 mAh, a peak drain current of 1-2 mA, a height of 55 mm (2.17 in), a length of 47 mm (1.87 in), and a thickness of 750 microns (0.029 in). The Blue Spark Technologies 111-ST1 battery provides 1.5V, has a capacity of 54 mAh, a peak drain current of 1-2 mA, a height of 78.7 mm (3.10 in), a length of 47.6 mm (1.87 in), and a thickness of 750 microns (0.029 in). The Blue Spark Technologies 111-ST1 battery provides 1.5V, has a capacity of 37 mAh, a peak drain current of 1-2 mA, a height of 79 mm (3.10 in), a length of 47 mm (1.87 in), and a thickness of 500 microns (0.020 in).

Any of the foregoing printed batteries, or similar printed batteries, can be used to provide a power source to any of the pump electronics of any of the dressing embodiments disclosed herein. Additionally, any of the batteries, including the flexible batteries, disclosed herein can be formed in a flat, planar relaxed shape, curved relaxed shape, or any other desired shape. Though not required, in any embodiments disclosed herein, the power source (including the thin, flexible batteries) can be positioned or distributed over or within the dressing absorption, transmission, and/or backing layers, positioned about the housing for the pump assembly, and/or positioned about the one or more layers comprising the conduit (if any) between the pump assembly and the dressing absorption, transmission, and/or backing layers.

Further, as in any of the dressing kit embodiments disclosed herein, the dressing kits can be configured such that the conductive connections between the power source and the pump assembly can be separated by a pull tab, isolation tab, activation switch, or other isolation mechanism to prevent any power supply from being provided to the pump assembly during sterilization, shipment, or handling prior to initiation of the negative pressure therapy.

In some embodiments, the pump assembly can be configured such that the battery connections or terminals have polarity protection. For example and without limitation, one or more of the battery contacts can be configured to have plastic or other non-conductive protrusions adjacent to the battery terminal contacts to inhibit the contact between the battery contact and the incorrect side of a battery that is inserted into the battery compartment in the incorrect orientation. In some embodiments, the one or more protrusions can be sized and configured to prevent the negative side of a standard cylindrical battery from contacting the battery contact adjacent to the one or more protrusions, while permitting a positive side of such battery to contact the battery contact. Generally, with this configuration, the battery can generally only make contact with the contact if the battery is inserted in the battery compartment in the correct orientation, thereby providing polarity protection to the pump assembly. Alternatively or additionally, a control board of the pump assembly can be configured to have polarity protective features or components. Additionally, a control board of the pump assembly can have one or more fuses to protect against overpower conditions or surge power conditions.

Additionally, any of the dressing embodiments disclosed herein can have one or more photovoltaic cells configured to provide energy to the pump electronics. Though not required, the embodiments having one or more photovoltaic cells can additionally have one or more batteries or capacitors configured to provide energy to the pump electronics. The photovoltaic cells, batteries, capacitors, and/or other suitable power sources of any of the dressing kit embodiments disclosed herein can be positioned about at least one of the dressing cover layer, the pump housing, and the conduit between the pump housing and the dressing cover layer.

In any embodiments disclosed herein, the conduit can have a plurality of articulations in along the length thereof, configured to bias the conduit to a shorter length state. The conduit can be extended if increased length is needed. Additionally, in some embodiments, a connector (or first connector) can be positioned at an end portion of the conduit to connect the conduit to a mating connector (or second connector) on the dressing. In some embodiments, the connector can be configured to activate the pump once the connector is attached to a mating connector fixed to the dressing.

For example and without limitation, in some embodiments, the dressing kit can have a pair of wires or electrical conductors extending from the pump assembly to the first connector. The two conductive wires or electrical conductors can form an open circuit along the length of the conduit. A low voltage can be provided through one of the two conductive wires, sufficient to activate the pump when the two conductive wires are in communication with one another. The two electrical conductors can terminate in a first set of electrical contact points. A second connector supported by the dressing can be configured to engage the first connector and can have a second set of electrical contact points. The second contact points can be electrically connected such that, when the first connector is fully engaged with the second connector supported by the dressing, the first set of contact points will be in contact with the second set of contact points, and close the circuit between the two conductive wires in the conduit to activate the pump.

Some embodiments of the pump assembly can be configured to abate noise and/or vibration of the pump during operation. Noise canceling chips can be used in some embodiments to reduce noise. In some embodiments, the pump output can be configured to ramp in and ramp out or gradually increase and decrease to eliminate sudden changes in the operation of the pump, thereby minimizing or eliminating any sudden transitions. Additionally, in any of the embodiments disclosed herein, the pump assembly or pump motor can be supported within a silicone or foam envelop or layer to attenuate vibration and noise.

Additionally, in any of the embodiments disclosed herein, the pump assembly or dressing member can be configured to support an organic light emitting diode ("OLED") display or other suitable interface display.

Some of the embodiments comprise a pump and/or a pump and dressing kit. Some embodiments are directed to a pump and/or pump and dressing kit that have been sterilized before delivery to the hospital, operating room or theatre, or to the medical practitioner using such devices such that the sterile pump and/or a sterile pump/dressing kit can be applied immediately following the surgical or operating procedures. One advantage of this is that the surgeon can release the patient from the operating room knowing that the reduced pressure pump is operating and that the reduced pressure therapy has been started at the earliest point in time possible. A further advantage of applying the dressing kit immediately following the surgical or other procedure is that doing so can reduce the chance of infection by eliminating a subsequent dressing change that may otherwise be required in the ward. In other words, for those patients where a dressing (but not a pump) is applied in the operating theatre and then a problem is found thereafter, such as a leak or other issue with the dressing, if the dressing is required to be removed to be repositioned, replaced, or otherwise after the patient is released from the operating theater, the patient's wound can be exposed to infection risk when the dressing is repositioned, replaced, or otherwise outside of the operating theater. However, with the embodiments disclosed herein, if the pump is applied and tested while the patient is in the operating theater, any issues with the dressing that may require the dressing to be removed, repositioned, or otherwise, can be handled in the sterile operating room environment, thereby significantly reducing or eliminating the risk of exposure to pathogens, bacteria, or other contaminants. Further, it is generally not possible for a hospital to sterilize a traditional pump once it has been received by the hospital, and therefore the hospital may resort to bagging the pumps in sterile bags but risk compromising the operating room sterile field with this approach, particularly once the device is turned on and pathogens, bacteria, or other contaminants that may be inside the pump are release due to the operation of the pump.

In some embodiments, the pump can be configured to be amenable to gas sterilization, having features, components, and other characteristics that make the pump amenable to full sterilization gas exposure and penetration throughout the components of the pump. For example, without limitation, one or more pump valves have been selected or configured to permit a sufficient flow of sterilization gas therethrough such that the entire fluid pathway within the pump can be exposed to the sterilization gas. As will be explained in greater detail below, in some embodiments, the pump can have other components, such as without limitation, strategically positioned one way flow valves, to complement the other valves within the pump, which can improve the efficiency of the pump by reducing leakage through the flow pathway within the pump assembly.

Additionally, where provided, the sterile pump/dressing kit can also be designed and configured to be amenable to gas sterilization. As described below, the sterile pump/dressing kit can be configured such that all of the components comprising the sterile pump/dressing kit, including the pump assembly, are packaged together in at least a first packaging element before sterilization, permitting all of the components to be sterilized together. Furthermore, as will be described, the components comprising the sterile pump/dressing kit can be arranged in the packaging such that at least some of the components can be removed in a predefined order, making it easier for the surgeon or medical practitioner to assemble and apply the dressing to the patient.

There are a number of benefits to being able to begin treatment of a wound in the operating theater, including without limitation providing a substantially sealed barrier over the wound while the wound is in a sterile condition and environment that will inhibit or prevent bacteria or other contaminants from getting into the wound. Additionally, initiating the reduced pressure treatment at the earliest stage possible is also advantageous to healing of the wound.

The housing of any of the pump assembly embodiments can be configured such that a sterilization gas, such as ethylene dioxide, can penetrate into the housing such that the internal components of the pump assembly are exposed to the sterilization gas during normal sterilization processes. Typically, the pump will be exposed to the sterilization gas in a chamber that has been substantially evacuated of air or any other gas, so that the sterilization gas is drawn into the pump housing and into the other spaces and chambers within the pump assembly. For example, some embodiments of the pump housing can have an unsealed gap surrounding the connector through which the sterilization gas can pass. Also, in some embodiments, the first housing member can be joined to the second housing member without the use of a seal therebetween, and the pump assembly can have one or more valves that permit a sufficient amount of sterilization gas therein to effectively sterilize all of the internal components of the pump.

In some embodiments, the pump assembly can be mounted to any of the dressing embodiments disclosed herein and can have any suitable pump components (including, without limitation, a standard off-the-shelf vacuum pump such as the Koge Electronics KPV8A-3A pump). Some embodiments of the pump can be approximately 37 mm (length)×20 mm (width)×8 mm (depth). In any of the embodiments disclosed herein, one or more of the pumps can be a piezoelectric pump or a diaphragm pump or any other suitable pump. Additionally, in some embodiments, the pump can be a voice coil actuated pump.

The batteries can be lithium or zinc air activatable batteries, though not so required. If the dressing kit is to be sterilized, the batteries can be separated during the sterilization process by positioning a non-conductive barrier between the batteries. Additionally, to accommodate current legislation regarding battery disposal, some embodiments of the pump assembly can be configured such that the batteries are easily removable or separable from the dressing, for example before the dressing is removed from the body, for disposal after the dressing kit and pump assembly have been used.

In some embodiments, the pump can be configured such that the pump needs to be powered on at the start of the treatment cycle. Additionally, the pump can be configured such that the pump needs to be re-started when a leak is detected and dressing has been assessed. Regarding leaks, the pump assembly and dressing kit can be configured such that the device provides the following operation indications, without limitation: communication of device operating correctly; communication of leak being found; communication indicating that the dressing is full; and/or communication of a low or dead battery. The pump can be configured to communicate in multiple different languages. Any embodiments of the pump disclosed herein can be configured to communicate in 19 or more different languages. Any embodiments of the pump disclosed herein can be configured to maintain reduced pressure in the wound site between approximately 60 and approximately 80 mmHg, or between approximately 60 and approximately 130 mmHg.

FIGS. 1-5 illustrate five dressing embodiments, the dressing being configured to support the pump and power source such that the pump and power source is on-board the dressing. In any of the embodiments herein, the power source used to provide power to the pump electronics can have one or more batteries, one or more capacitors, one or more photovoltaic cells, one or more fuel cells, or any combination of the foregoing. Such power sources are collectively referred to herein as "power source."

Any of the embodiments illustrated in FIGS. 1-5 or elsewhere in this disclosure can comprise any feature, component, material, and/or details of any or all of the other embodiments described herein. FIGS. 1A-B illustrate one embodiment of a dressing kit 50 having a pump assembly 52 supported by the dressing 54 at a corner 54a of a dressing 54. The power source 52 of this embodiment or any dressing kit embodiment disclosed herein can have any of the types of batteries disclosed herein or otherwise, including printed and/or flexible batteries, lithium batteries, and/or air activatable batteries 56, or can have one or more capacitors, photovoltaic cells, fuel cells, or otherwise. Having the pump assembly 52 on the corner 54a of the dressing 54 can improve the handleability of the dressing 50.

In some embodiments, the power source 52 can be positioned along the short edge of the dressing 54 and the pump assembly 52 can be positioned along the long edge of the dressing 54, or vice versa. In any of the dressing embodiments disclosed herein, a control board and/or user interface, which can include operation buttons, visual displays, alarms, indicator lights, or otherwise, can be positioned in any desired position on the dressing, including above or below the backing layer (the backing layer being the outermost dressing layer), integrated within the dressing layers positioned beneath the backing layer, or otherwise.

As further illustrated by FIG. 1A, some embodiments of the invention can include a removable label 58. The removable label 58 can be made of an airtight polymer material or any other suitable material. The removable label can be removably fixed to the batteries 56 via an adhesive or any other suitable mechanism. Removing the label 58 can expose the batteries 56 to air, thereby activating the batteries 56.

FIG. 1B illustrates the dressing 50 with the label 58 removed. When the dressing 50 is applied to a wound, the corner placement of the pump assembly 52 and batteries 56 can frame the wound. For example, the pump assembly 52 and the batteries 56 can lay outside the periphery of the wound and attach to healthy skin. Further, the pump assembly 52 and batteries 56 can be raised from the surface of the skin, such that if the patient bumps into an object, the raised surface prevents damage to the wound.

Though not required, in some embodiments, the pump assembly can be positioned on one end of the dressing and the batteries or other power source can be positioned on another side or end of the dressing, such as the opposite side. This arrangement can result in a more balanced dressing in terms of weight, rigidity, and/or size.

In some embodiments, as with the dressing kit 70 embodiment illustrated in FIG. 2B, the pump 72 and power source 76 can be positioned at opposite ends of the dressing 74. With reference to FIG. 2, the pump assembly 72, printed circuit board (PCB) or other pump controller, and battery assembly 76 can be positioned in recesses or openings formed in the dressing material or foam 78, or can be embedded within the foam or dressing material 78. The foam or dressing material 78, with the pump 72 and/or power source therein, can be flexible and conformable to curved or contoured body surfaces. An elastomeric carriage 84 can line the dressing material or foam 78 close to the pump 72, PCB, and battery 76. The elastomeric carriage 84 can provide flexibility to the dressing 70. The pump assembly 72, PCB, and battery assembly 76 can be configured such that the components are flexible to permit the wound dressing 70 to bend about the body or flex with the movement of the body. For example, a hinge can be provided between the pump assembly 72, PCB, and/or the battery 76 to permit flexibility. Additionally, the portion of the dressing 74 supporting the pump 72 and/or battery 76 can be configured to provide a handle, to improve the handleability of the dressing during placement of the dressing on the body. Separating the battery 76 on the dressing 70 also has the benefit of permitting the battery or batteries 76 to be easily removed after use for separate disposal.

In any of the dressing kit embodiments disclosed herein (which includes the pump embodiments supported remote to the dressing, such as adjacent to the dressing), the PCB or pump controller can be a flexible circuit board and/or can have one or more flexible components. A flexible circuit board is generally a patterned arrangement of printed circuitry and components that utilizes flexible based material with or without flexible overlay. These flexible electronic assemblies can be fabricated using the same components used for rigid printed circuit boards, but allowing the board to conform to a desired shape (flex) during its application. In their simplest form, flexible circuits are PCBs made of materials that allow for a non-planar positioning within the end product. Typical materials a polyimide-based, and can go under trade names such as Kapton (DuPont). Additionally, any of the control boards or controllers disclosed herein can have a combination of flexible and rigid substrates laminated into a single package.

Additionally, in any embodiments, the circuit boards can be printed on any desired substrate, including printing the circuits on one or more surfaces of the pump housing, on one or more dressing layers or surfaces, on one or more conduit and/or port layers or surfaces, or any combination of the foregoing.

In any of the dressing embodiments disclosed herein, with reference to FIG. 2A, malleable metal or other materials (such as metal wires or strips) 84 can be added to the dressing 70 to maintain the shape of the dressing 70 after it has been molded to the body surface. The malleable material 84 can be under, within, or above the gauze. Additionally, the malleable material 84 can be positioned under, within, or above the cover layer. The malleable material 84 can be positioned in a parallel arrangement, as illustrated by FIG. 2, or in any other suitable arrangement.

Additionally, in any embodiments disclosed herein, a hinge (such as a living hinge) can be positioned between the various components comprising the pump assembly, such as between a control board and the pump motor 72, or between an power source 76 and the pump 72, to improve the flexibility of the pump assembly and/or dressing kit. Printed connectors could be used to provide electrical connections between the PCB and the pump motor 72 and/or between the batteries 76 and the PCB or pump motor 72. Additionally, in any embodiments disclosed herein, if both the pump assembly 72 and the batteries 80 are positioned at one end of the dressing 70, a foam handle could be positioned at the other end to improve the handleability of the dressing 70.

As illustrated in FIG. 3, the dressing kit 90 can be configured such that both the pump assembly 92 and the power source 94 can be positioned on one end 96a of the dressing 96. As shown in FIG. 3B, a cover 98 can be positioned over the pump 92 and power source 94 to contain those components. The cover 98 can be supported by the dressing 92 with a living hinge 100 or by any other suitable mechanism. The dressing contact layer 102, the packing layer 104, and the cover 106 can have rounded corners. The dressing can come in a variety of lengths and sizes, as illustrated by FIG. 3C. Additionally, a pull tab, as further described herein, can be used for activation and deactivation of the pump. Additionally, in this and any other dressing embodiments disclosed herein, the border around the dressing can be baggy or have additional slack or material therein to for increased user movement.

Figure 4B:
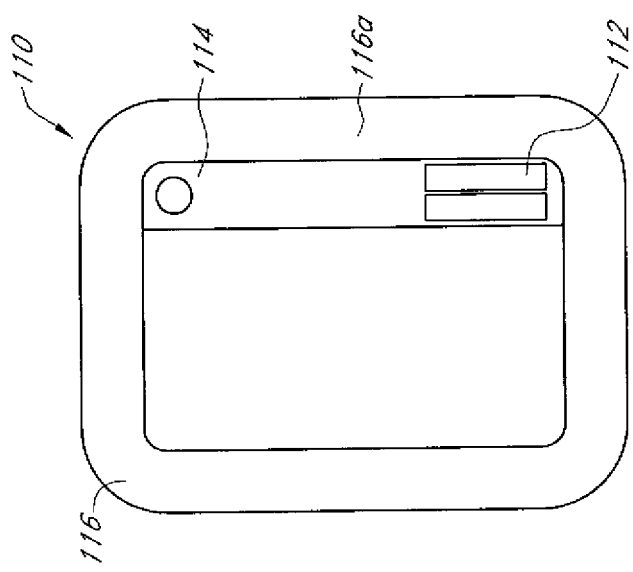
Figure 4A:
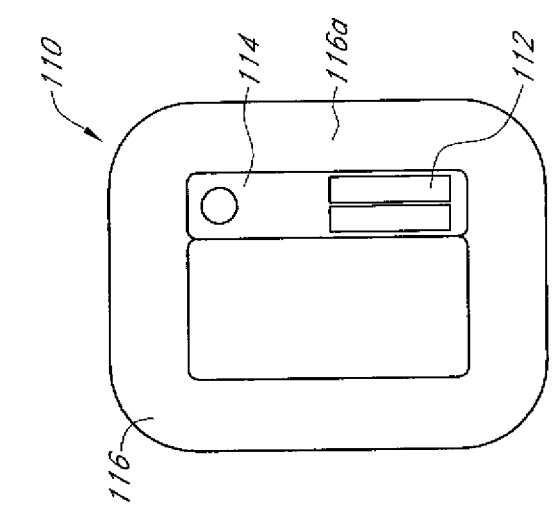

With reference to FIG. 4, in some embodiments of the dressing 110, the power source 112 (which can comprise one or more batteries) and pump assembly 114 can be positioned along the lengthwise side 116a of the dressing 116. Referring to FIGS. 4A-C, the dimensions of the dressing 110 according to some embodiments of the invention can be approximately 50 mm×100 mm, 100 mm×150 mm, or 100 mm×250 mm, respectively. In these embodiments, the power source 112 and pump assembly 114 can be placed along the side of the dressing measuring 100 mm, 150 mm, and 250 mm, respectively. Although FIG. 4A illustrates various dimensions of the dressing 116, it will be appreciated that the dimensions can be of any suitable length and width.

The power source 112 (which can have one or more batteries) and pump assembly 114 can be separated, as shown in FIG. 4C, or can be positioned adjacent to one another, as illustrated in FIGS. 4A and 4B. This arrangement can result in the pump assembly 114 being more flush to the user's body, to prevent or reduce the risk of dislodgement and discomfort. Additionally, positioning the pump 114 at one end and the batteries 112 at the other end can result in greater conformability of the dressing kit 110 to the body, and increased comfort and performance of the dressing kit 110. Referring to FIG. 4C, separating the power source 112 and the pump assembly 114 can increase the flexibility of the dressing 110. Both enhance flexibility and enhanced conformability can improve the dressing's seal to the body, to reduce leakage pathways to the space between the dressing and the wound.

Figure 5B:
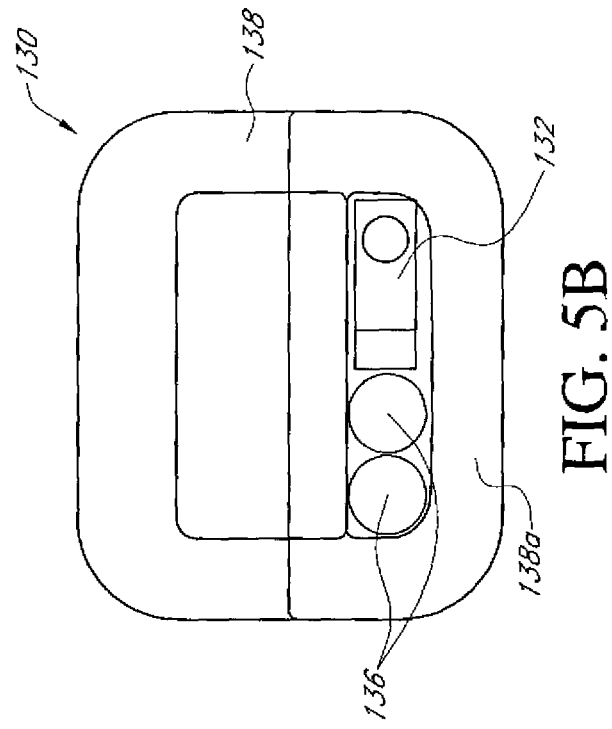
FIGS. 5A-B illustrate additional embodiments of a dressing kit for negative pressure wound therapy, showing two different exemplifying sizes of such embodiment.
Figure 5A:
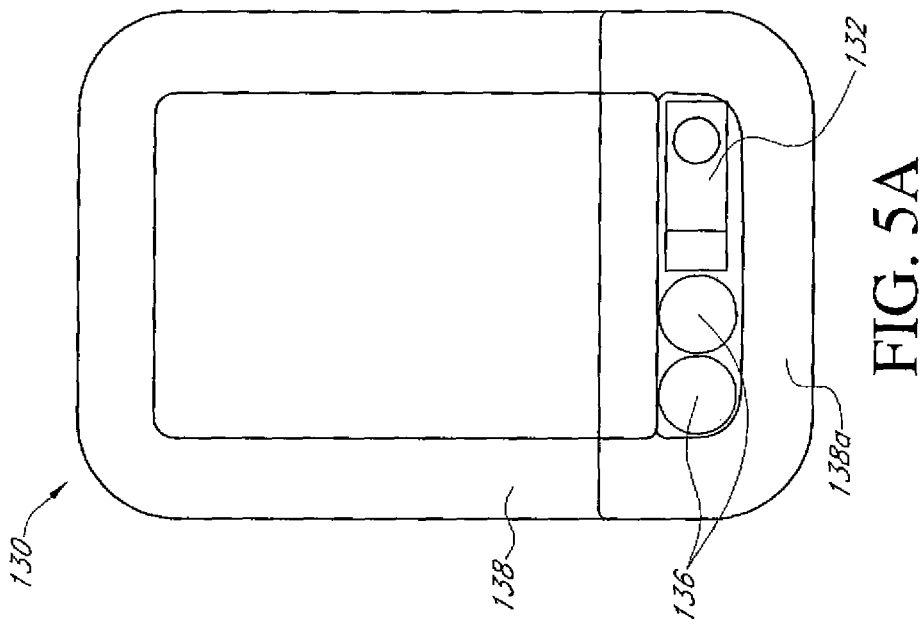

With reference to FIGS. 5A-B, any embodiments disclosed herein of the dressing kit 130 can have one or more zinc air activated batteries 136 that can activate the pump 132 with air that is introduced to the batteries 136. The batteries 136 and pump assembly 132 can be positioned along an end portion 138a of the dressing 138. The batteries 136 can be low profile to reduce the profile of the dressing 130. As illustrated by FIGS. 5A-B, the batteries 136 and pump assembly 132 can be placed on an end portion 138 of the dressing 130 according to some embodiments of the invention. The batteries 136 and pump assembly 132 can be placed along the shorter side (as illustrated in FIG. 5A) or the longer side (as illustrated in FIG. 5B) of the dressing 138. Therefore, in any embodiments disclosed herein, the pump and power source can be positioned adjacent to one or more packing layers of the dressing, and can be positioned adjacent to an edge of a cover layer to reduce the likelihood that the power source and/or pump will be positioned over the wound.

Figure 6B:
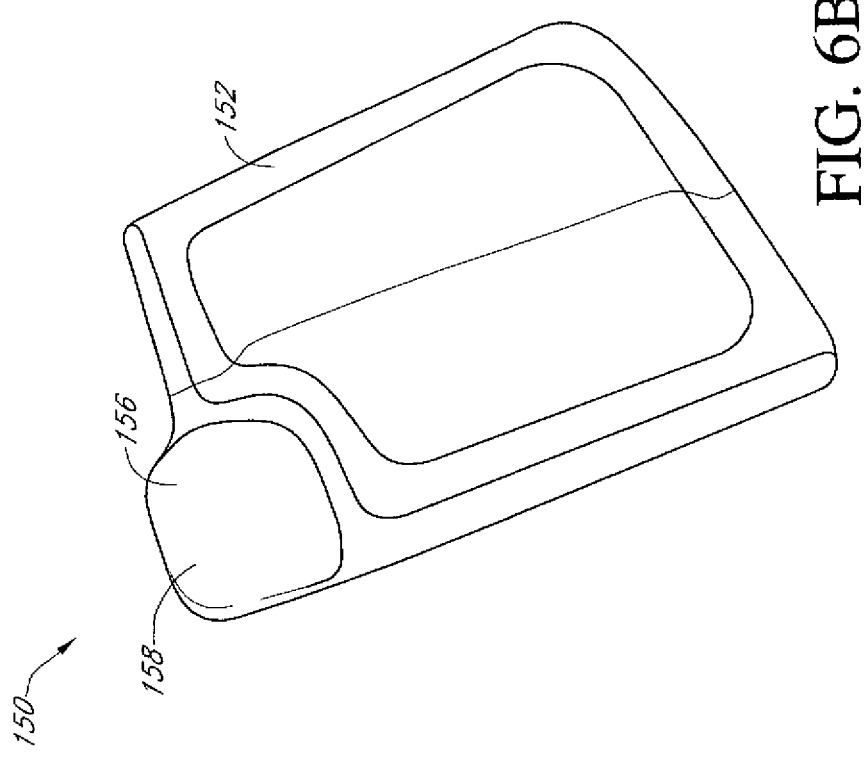
FIGS. 6A-B illustrate additional embodiments of a dressing kit for negative pressure wound therapy.
Figure 6A:
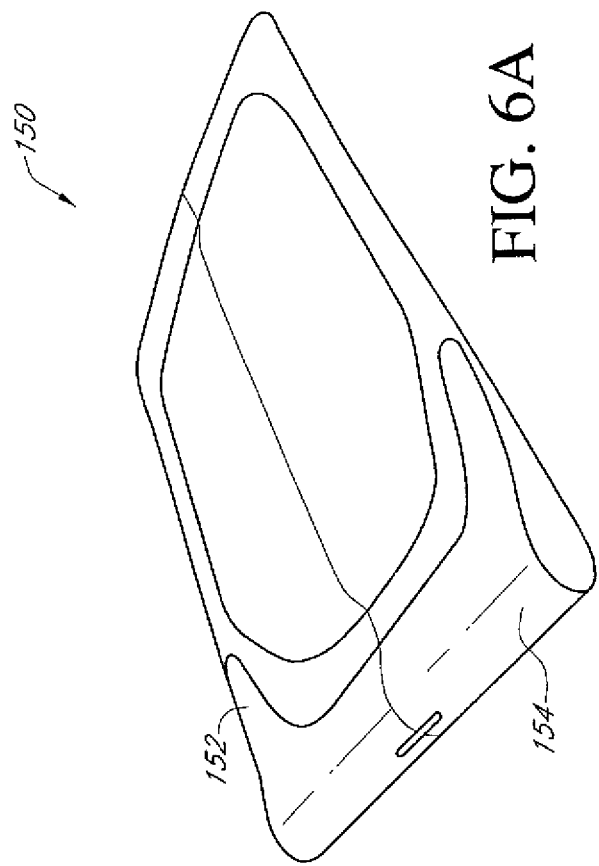

As shown in FIG. 6A, in any embodiments disclosed herein, the dressing film or cover layer 152 can extend beyond the dressing borders and form a loop 154 at one end to improve the handleability of the dressing 150 and prevent the dressing from flopping around or becoming limp and unhandleable during application of the dressing to the body. The looped over support layer could be removable, to permit the support layer to be removed after positioning the dressing on the body. Additionally, in some embodiments, the pump 156 and/or battery source 158 can be positioned in a corner of the dressing 152 or in any other suitable location. In this or any other embodiment disclosed herein, the dressing 152 and/or pump assembly 156 can have one or more press studs to provide mechanical attachment between the dressing and the pump assembly, and/or to loop and removably hold the dressing layer in the desired looped configuration.

Figure 7B:
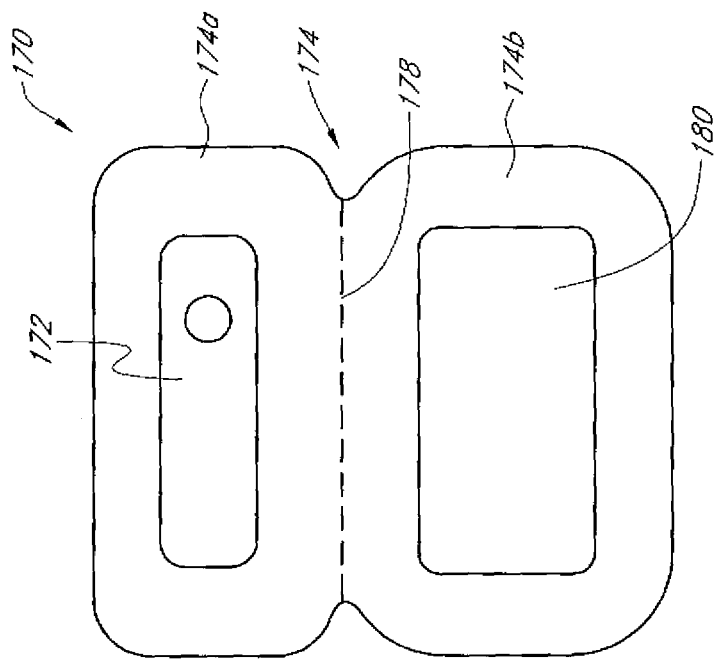
FIGS. 7A-B illustrate additional embodiments of a dressing kit for negative pressure wound therapy, showing two different exemplifying sizes of such embodiment.
Figure 7A:
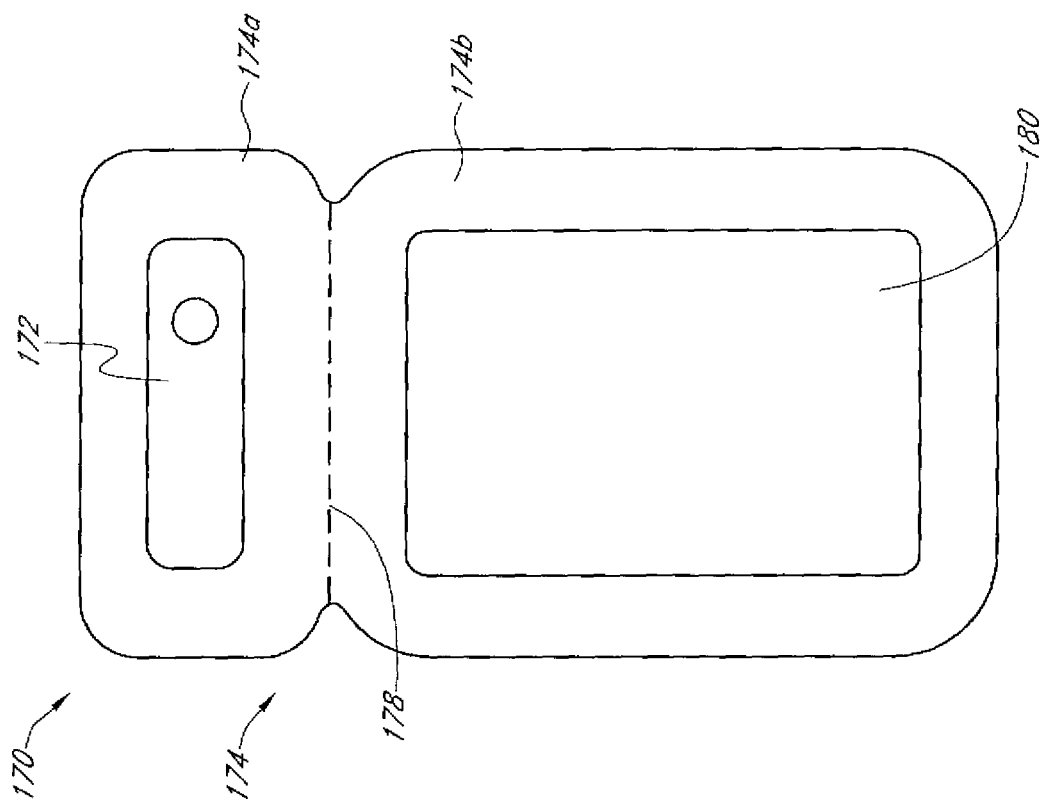

With reference to FIG. 7, the dressing kit 170 can be arranged such that the pump assembly 172 can be supported by the dressing 174 in an offset position so that the pump assembly 172 is not positioned over any portion of the dressing 174. A conduit can be used to communicate the reduced pressure produced by the pump assembly 172 to the dressing 174 and wound. The dressing kit 170 can be configured such that the pump portion 172 can be easily removed for disposal of the pump assembly separate from the dressing. In any embodiments disclosed herein, the dressing can have a one or more cuts, channels, scores, reduced thickness portions, partial thickness cuts, or perforations 178 between a first portion 174a of the dressing 174 supporting the pump assembly and a second portion 174b of the dressing 174 having one or more absorbing layers 180 to be positioned over the wound.

As such, any dressing member disclosed herein can be configured to have at least a first portion and a second portion configured to be separable from the first portion by hand and without the use of tools. The dressing member can be configured to be torn by hand to separate the first portion from the second portion. Additionally, positioning the pump 172 and power source (e.g., batteries) adjacent to the wound site instead of over the wound site can improve the comfort to the user by preventing the pump assembly and/or power source from contacting the sensitive wound bed. The dressing 174 can have at least one continuous layer that covers the entire dressing 174. The dressing member 174 can be approximately air-tight adjacent to the perforations or boundary between the first and second portions so that, upon separation of the second portion from the first portion of the dressing, no air leaks result.

Figure 8B:
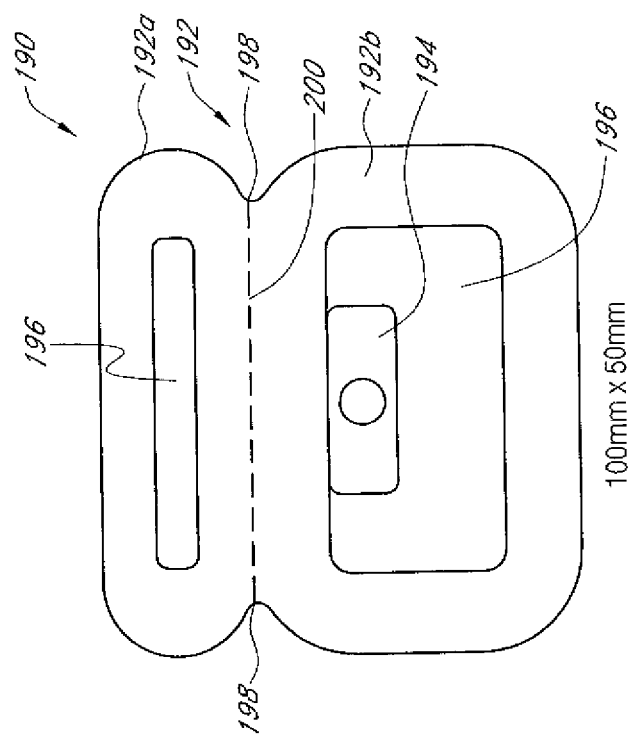
FIGS. 8A-B illustrate additional embodiments of a dressing kit for negative pressure wound therapy, showing two different exemplifying sizes of such embodiment.
Figure 8A:
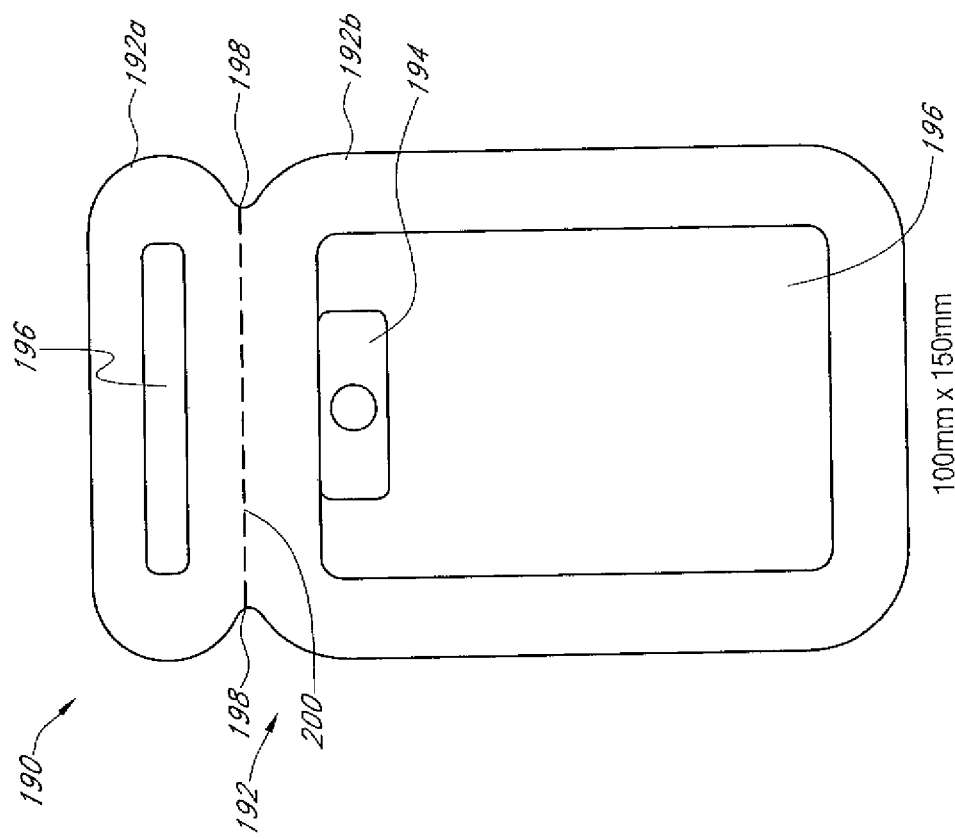

FIG. 8 is an illustration of another embodiment of a dressing kit 190 having a dressing 192, a pump 194, and an power source 196. As illustrated in FIG. 8, the pump assembly 194 can be positioned over or within the wound packing material 196 over the wound, while the power source 196, which can have one or more batteries, can be positioned in an offset position on the dressing. For example, in some embodiments, the power source 196 can be positioned on a first portion 192a of the dressing 192, which the pump assembly 194 can be positioned on a second portion 192b of the dressing 192. The absorbing or packing layers 196 can be positioned on the second portion 192b of the dressing 192.

In some embodiments, one or more cutouts 198 can be formed in the dressing between the first portion 192a and the second portion 192b to improve the flexibility of the dressing and to permit better articulation of the dressing. In this configuration, the dressing can have a narrowed or necked portion between the first and second portions. In some embodiments, a perforation 200 can be formed in the dressing 192 to permit separation of the first portion from the second portion of the dressing 192. This can facilitate the separation of the power source 196 from the rest of the dressing upon termination of the treatment for disposal of the two portions.

Figure 9B:
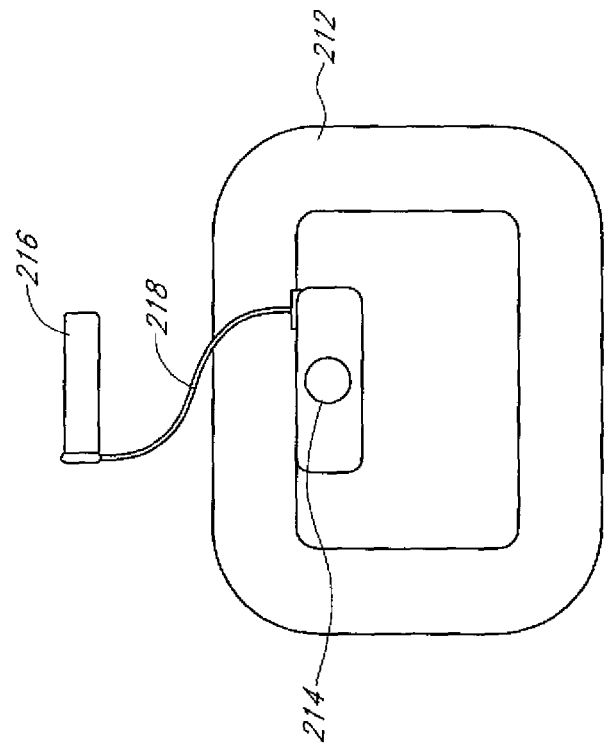
FIGS. 9A-B illustrate additional embodiments of a dressing kit for negative pressure wound therapy, showing two different exemplifying sizes of such embodiment.
Figure 9A:
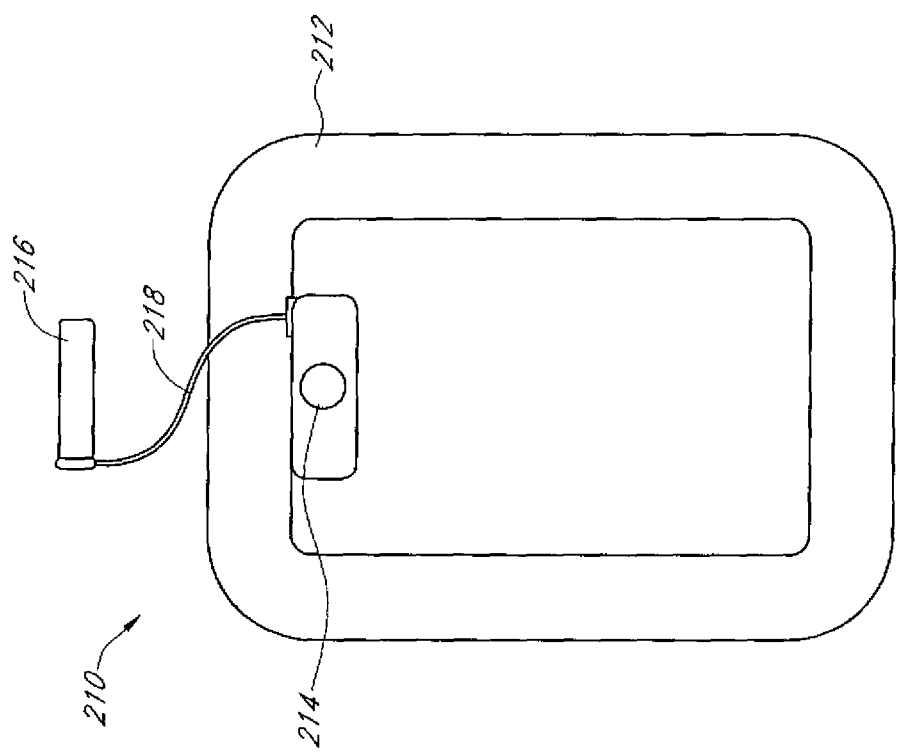

FIG. 9 illustrates an additional embodiment of a dressing kit 210, having a dressing 212, a pump assembly 214, and an power source 216. As with any of the embodiments disclosed herein, the power source 216 can have one or more flexible or rigid batteries of any of the configurations disclosed herein. In any embodiments disclosed herein, as illustrated in FIG. 9, the power source 216 can be freely positionable relative to the dressing 212, either on or adjacent to the dressing 212. A printed ribbon or wiring 218 can provide an electrical connection between the power source 216 and the pump assembly 214. This arrangement can improve the ability of the user or medical practitioner to change the batteries during operation of the dressing kit, can improve the flexibility of the dressing 212, and can move heavy and/or semi-rigid objects away from the wound surface. Additionally, detaching and reattaching the batteries can be used for deactivating and activating the pump.

Figure 10A:
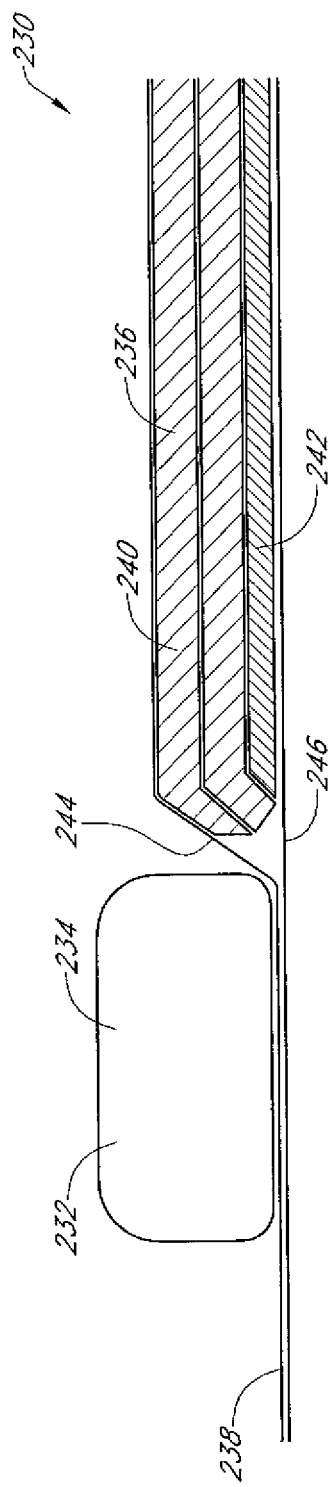
FIGS. 10A-C illustrate additional embodiments of a dressing kit for negative pressure wound therapy, showing such dressing kit schematically in section, isometrically, and in a top view, respectively.
Figure 10B:
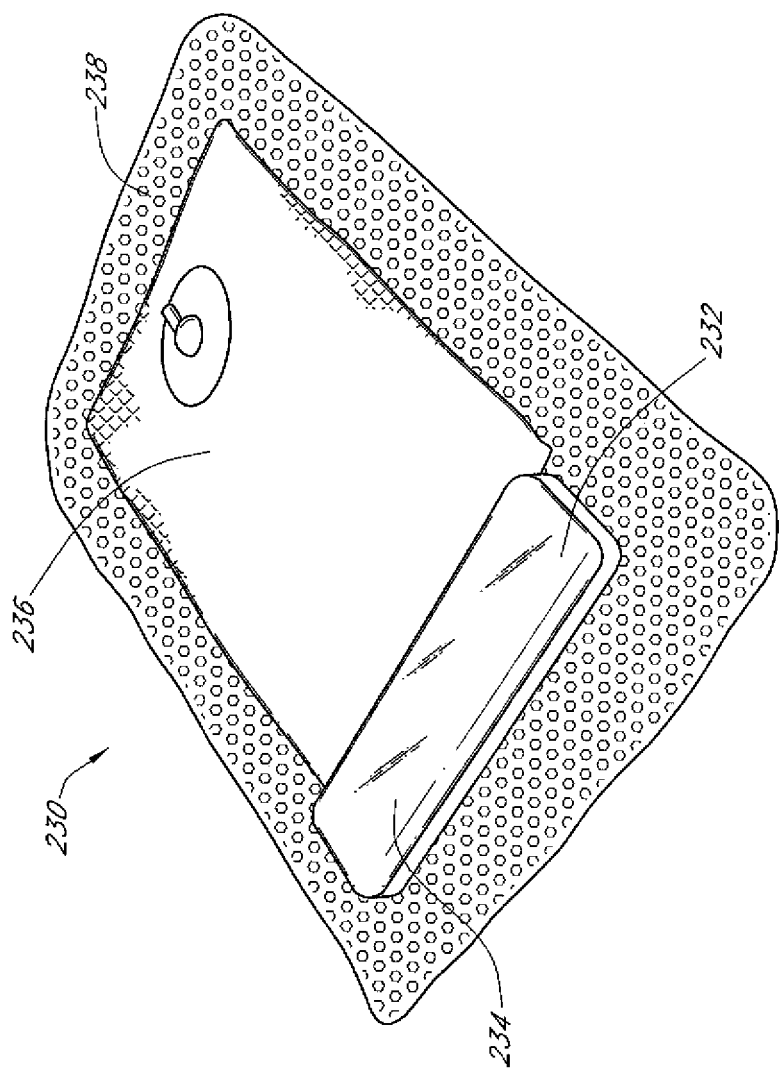
Figure 10C:
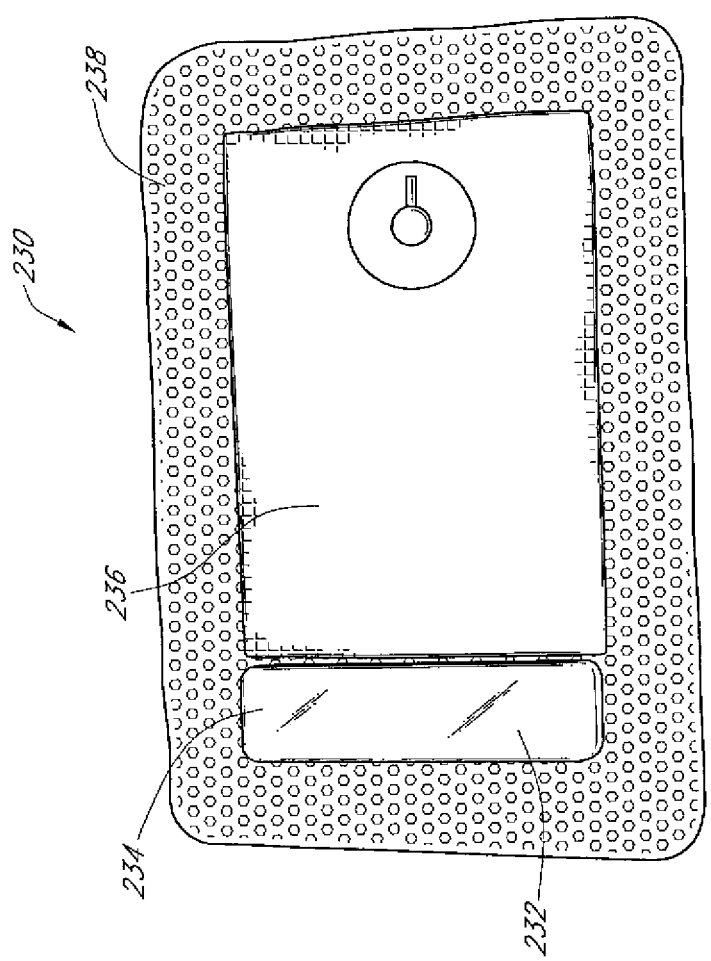

FIG. 10 illustrates an embodiment of a dressing kit 230 wherein the pump assembly 232 and batteries 234 are positioned adjacent to the dressing packing or absorption layers 236 of the dressing 238. In some embodiments, the dressing member 240 and the transmission layer 242 can terminate adjacent to the pump assembly 232 and the batteries 234 such that the pump 232 and batteries 234 can be positioned on an outside surface of the backing layer 240, with no dressing absorbing layers 240 or transmission layer 242 beneath the pump 232. Only the backing layer 244 and the wound contact layer 246 are positioned under the pump assembly 232 and batteries 234.

Figure 11A:
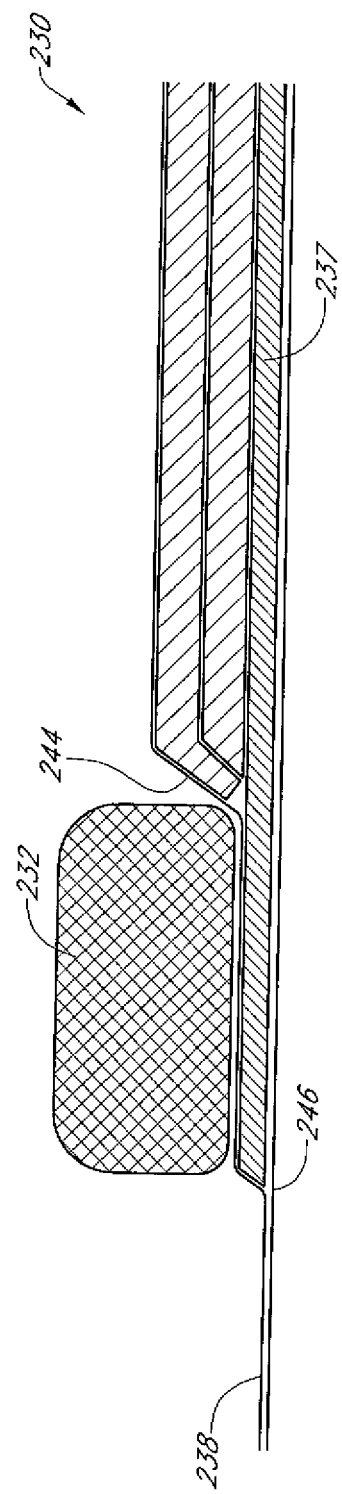
FIGS. 11A-C illustrate additional embodiments of a dressing kit for negative pressure wound therapy, showing such dressing kit schematically in section, isometrically, and in a top view, respectively.
Figure 11B:
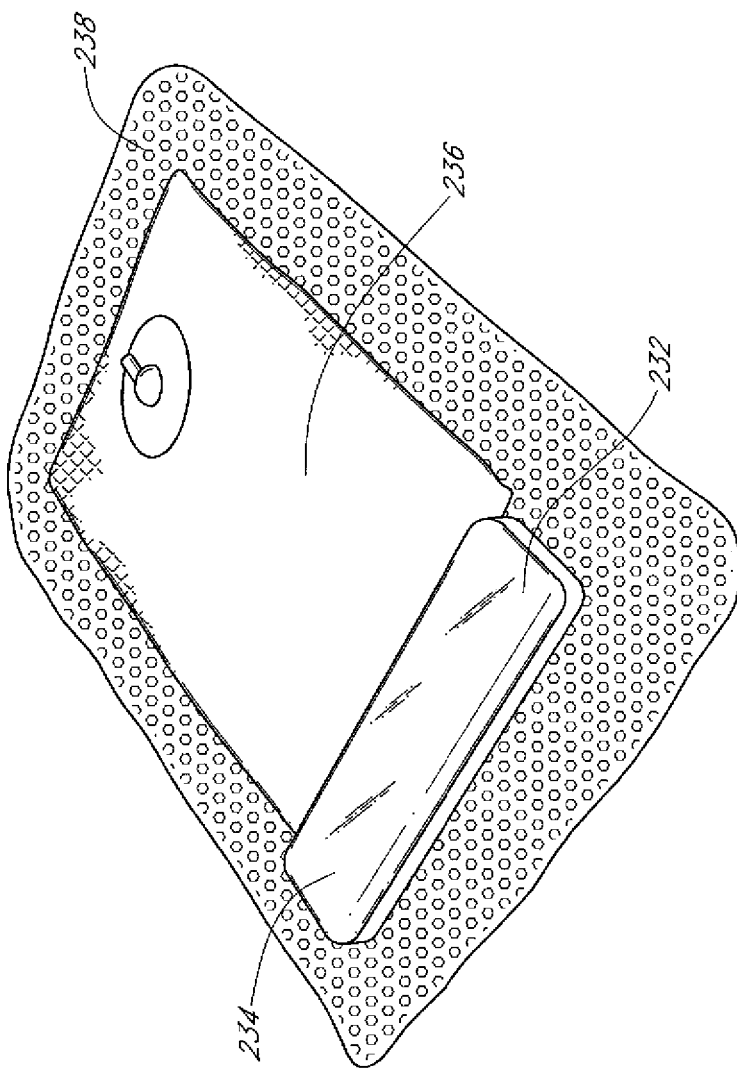
Figure 11C:
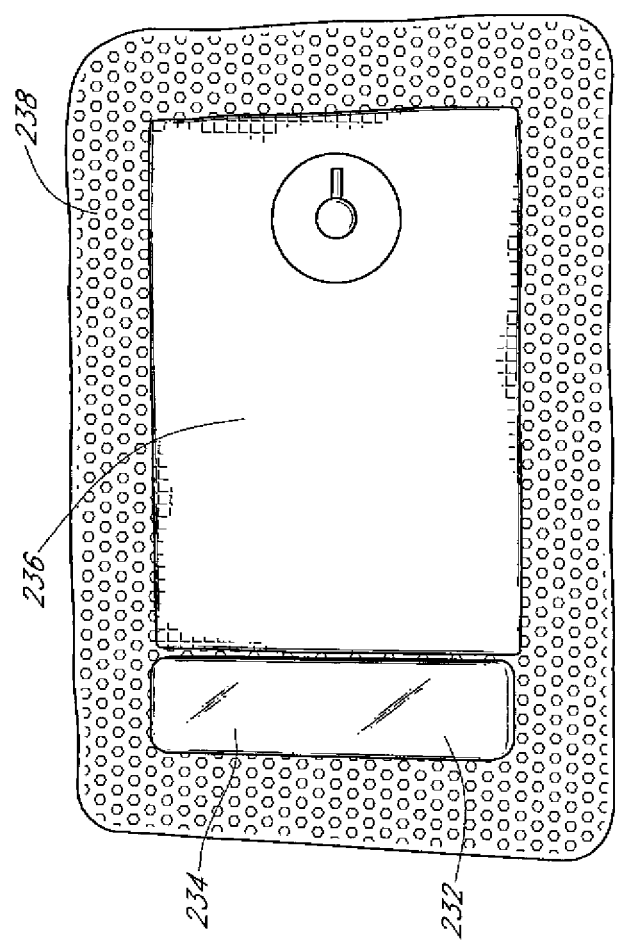

Alternatively, with reference to FIG. 11, in some embodiments, an additional layer (which can be a transmission layer, spacer layer, absorption layer, and/or a 3D knitted or 3D fabric layer) can be positioned under the pump 232, between the backing layer and the wound contact layer 246. For example, in any embodiments, the pump can be positioned over a 3D knitted and/or fabric layer (such as the 3D knitted and/or fabric layer 237 shown in FIG. 11) of any of the compositions disclosed herein, either with or without a liquid filter being positioned between the pump and the 3D knitted and/or fabric layer. A port in the pump 232 can be in fluid communication with the 3D knitted and/or fabric layer. In any embodiments, the backing layer 244 can be positioned over the pump 232, with an exhaust valve and/or filter to prevent pathogens, bacteria, odors, or other contaminants from leaving the pump. Positioning the pump over the transmission of 3D knitted and/or fabric layer layer can reduce the risk of maceration of the skin beneath the pump assembly and batteries that can result from the buildup of moisture against the skin, and can improve the comfort of the dressing by providing additional cushion between the pump assembly 232 and/or batteries 234 and the skin. This arrangement can also reduce the profile height of the dressing kit.

In the embodiment illustrated in FIG. 11, or in any other embodiments disclosed herein, the dressing kit 230 can have one or more filters or valves upstream of the pump assembly 232 configured to prevent liquids and solids from entering the pump 232, but permitting the flow of air or gas through the filter or valve. In the case of a filter, the filter can be a hydrophobic filter, a hydrophilic filter, an occlusive filter, for example a membrane having a hydrogel and/or superabsorber material, or any other suitable type of filter or valve configured to prevent the passage of liquids or solids therethrough. In some embodiments, the filter or valve can be positioned adjacent to a port member, beneath the pump assembly, or otherwise positioned upstream of the pump assembly. For example, for the embodiment illustrated in FIG. 11, the filter can be positioned between the pump assembly 232 and the backing layer 244, between the backing layer 244 and the wound packing layer 246 beneath or adjacent to the pump assembly 232, or in any other suitable location. In the embodiment illustrated in FIG. 11, the backing layer 244 can have a puncture, opening, or other port feature adjacent to the filter to provide the passage of air through the backing layer 244 to the pump assembly 232.

Additionally, in some embodiments, the pump can be directly positioned on top of the wound contact layer, but have a port in communication with the 3D knitted and/or fabric layer so as to provide a source of negative pressure directly to the 3D knitted and/or fabric layer. As mentioned above, a liquid filter or liquid barrier can be positioned between the pump 232 and the 3D knitted and/or fabric layer to prevent liquid from entering the pump. In any of these embodiments, an absorption layer (which can be a superabsorbing layer) can be positioned above the 3D knitted and/or fabric layer or other transmission layer and can be configured to wick fluid out of the 3D knitted and/or fabric layer or other transmission layer.

Figure 12A:
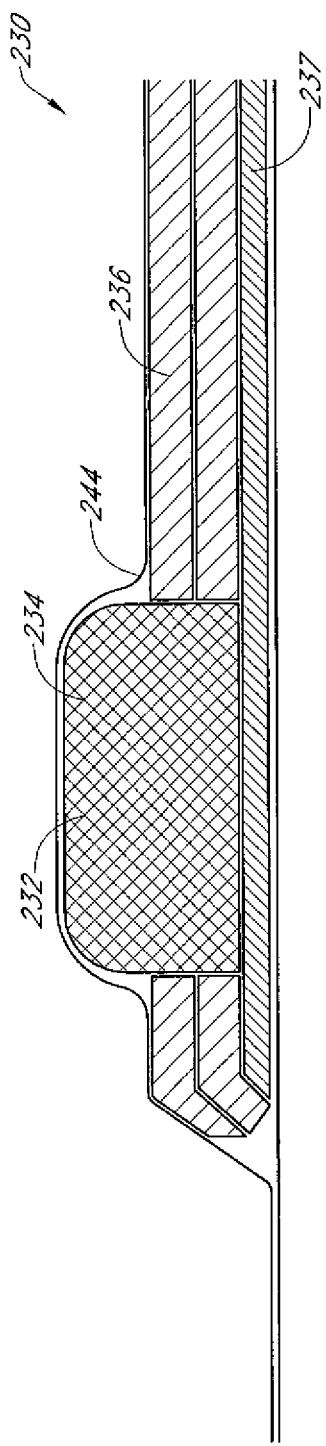
FIGS. 12A-B illustrate additional embodiments of a dressing kit for negative pressure wound therapy, showing such dressing kit schematically in section and isometrically.
Figure 12B:
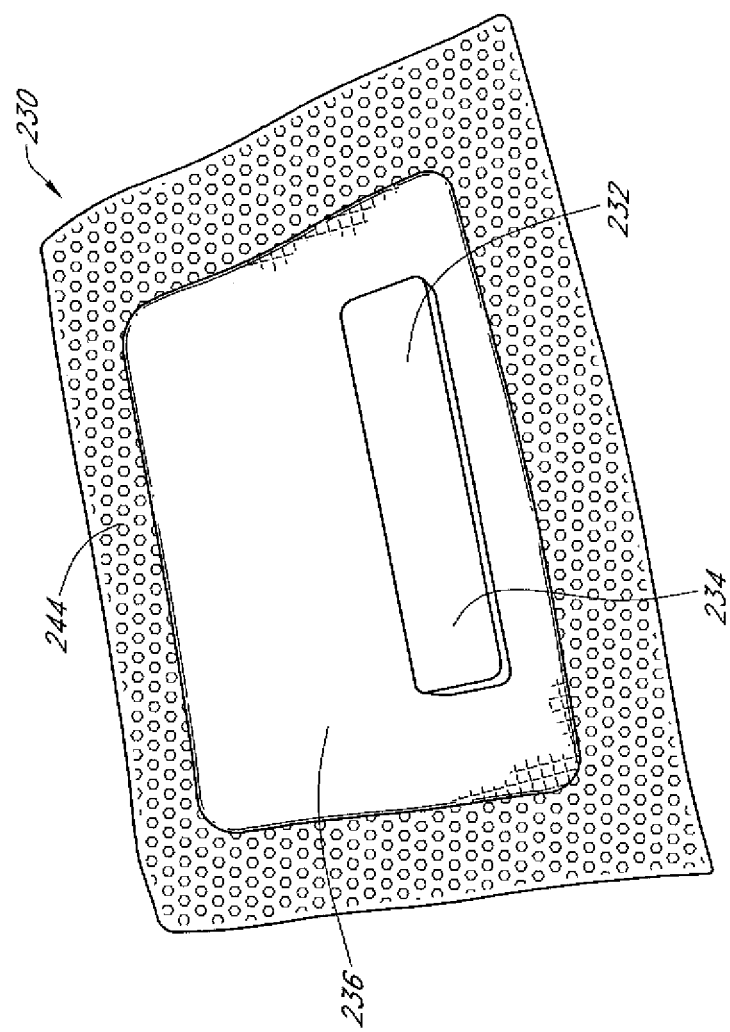

The pump assembly 232 and/or batteries 234 can be positioned at an edge portion of the dressing 238, as illustrated in FIG. 11, or can be positioned inside of an edge portion of the dressing, as illustrated in FIG. 12. A double layer of absorptive material 238 can surround the pump assembly 232. Some embodiments only have a single layer of absorptive material 238. Additionally, with reference to FIG. 13, in any dressing kit embodiment disclosed herein, the pump assembly 232 and/or batteries 234 can be positioned inside an edge portion of the dressing 238 and beneath the backing layer of the dressing in a depression or cutout that passes through the entire thickness of the absorptive layers so as to be positioned on top of the transmission layer 237. A port from the pump can be in communication with the transmission layer 237 so as to provide negative pressure to the transmission layer 237. A liquid filter to prevent liquid from passing through the pump can be positioned between the pump and the 3D knitted and/or fabric layer or other transmission layer, such as the 3D knitted and/or fabric layer 237 shown in FIG. 12.

Additionally, in any embodiments, the pump can be positioned in a depression formed in the absorption layer so as to be positioned directly on top of the transmission layer. A port in the pump can be positioned so as to be in communication with the absorption layer so that negative pressure is applied directly to the absorption layer. Some embodiments can have a perforated or permeable polymeric film between the absorption layer and the transmission layer, such as a polyurethane or polyethylene layer.

Further, in any embodiments disclosed herein, the pump can be positioned directly over the transmission layer (which can be a 3D knitted and/or fabric layer, or any other suitable transmissive material), either embedded within one or more absorption layers or positioned adjacent to one or more absorption layers. In such arrangements, an impermeable film can be positioned between the transmission layer and the absorption layer, surrounding the pump. The pump can be configured to apply negative pressure directly to the transmission layer and to draw liquid from the transmission layer through the pump and exhaust such liquid into the absorption layer. An impermeable backing layer can be, but is not required to be, positioned over the pump assembly. In any arrangements wherein the pump is located under the backing layer, a filtered or unfiltered exhaust port can be formed in the backing layer to ensure that gas can be exhausted from the dressing. In some embodiments, a bacteria, pathogen, or other contaminant filter can be positioned within the pump assembly.

In any dressing kit embodiments disclosed herein, the 3D knitted and/or fabric layer can have any of the properties of any of the dressing layers disclosed in U.S. Patent Application Publication No. 2011/0282309 (Ser. No. 13/092,042), (titled WOUND DRESSING AND METHOD OF USE), filed Apr. 21, 2011, and/or PCT Patent Application Publication No. WO 2011/087871 (International Patent Application No. PCT/US2010/061938), (titled APPARATUS AND METHODS FOR NEGATIVE PRESSURE WOUND THERAPY), filed internationally on Dec. 22, 2010, which applications are hereby incorporated by reference as if fully set forth herein.

Figure 13A:
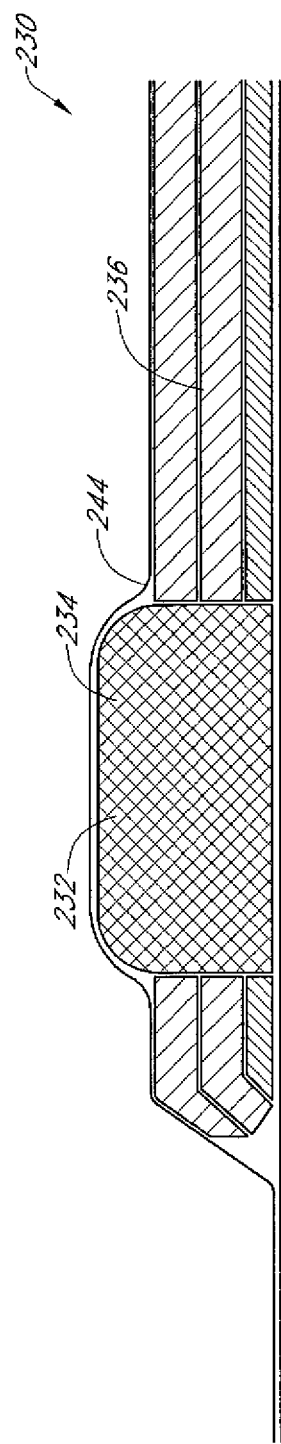
FIGS. 13A-B illustrate additional embodiments of a dressing kit for negative pressure wound therapy, showing such dressing kit schematically in section and isometrically.
Figure 13B:
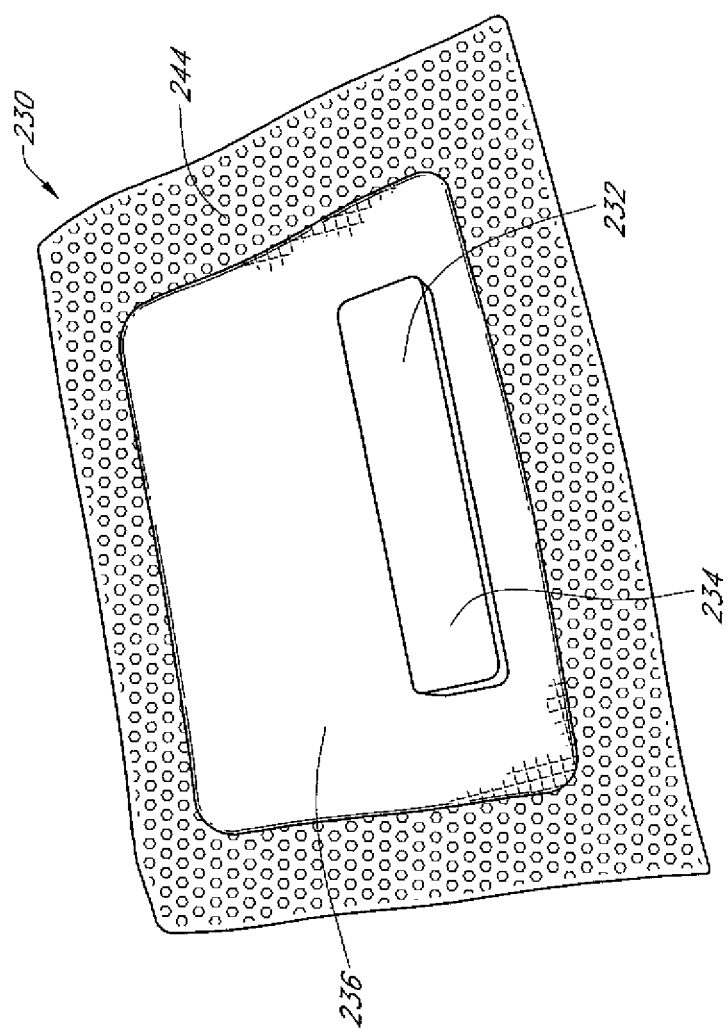

The power source for any of these embodiments can be positioned within the pump assembly housing, can be positioned adjacent to the pump assembly housing and supported by the dressing, either within or above the absorptive layers adjacent to or apart from the absorptive layers, can be positioned on top of the absorptive layers, or can be positioned in a remote position apart from the pump assembly. With reference to FIG. 13, in any embodiments, the pump assembly 232 and/or batteries 234 can be positioned inside an edge portion of the dressing 238 and beneath the backing layer of the dressing in a depression or cutout that passes through the entire thickness of the absorptive or transmission layers so as to be positioned on top of the wound contact layer 246.

Further, any of the dressing kit embodiments disclosed herein can have an exhaust filter downstream of the pump assembly. The exhaust filter can be configured to prevent the spread of any bacteria, pathogens, or other harmful constituents from leaving the dressing through the exhaust port in the dressing kit. The exhaust filter can be supported by the pump assembly, or supported by any other layer or component of the dressing kit. For example, with reference to the embodiment illustrated in FIG. 12 or in any other embodiment wherein the pump assembly is positioned beneath the backing layer, the exhaust filter can be supported by the backing layer or within or adjacent to an opening or port in or on the backing layer.

In any of the embodiments disclosed herein, including without limitation the embodiments illustrated in FIGS. 12 and 13, the pump assembly 232 and/or batteries 234 can be positioned under the backing layer 244. Additionally, in some embodiments, the pump assembly 232 and/or batteries 234 can be embedded within one or more of the absorption layers 236 of the dressing 238. This configuration can reduce the profile of the dressing kit 230, improve the ability of the pump assembly and/or batteries to withstand impact, and provide a more aesthetic design. In some embodiments, the backing layer 244 can be perforated or gas permeable to permit gas exhausted by the pump assembly to pass through the backing layer 244. Additionally, in any of the embodiments disclosed herein, the backing layer 244 can be water vapor permeable to permit vapor from the liquid within the dressing to pass through the cover layer 244.

Figure 14A:
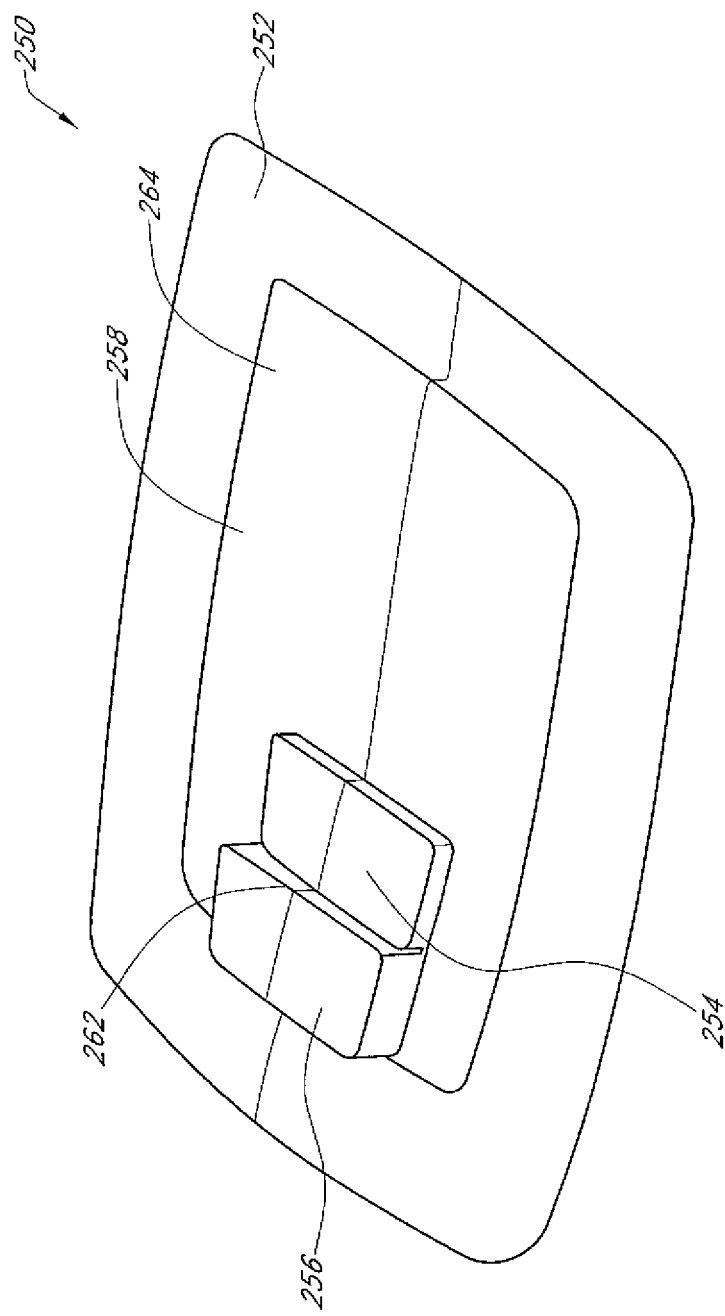
FIGS. 14A-14D illustrate additional embodiments of a dressing kit for negative pressure wound therapy.

FIG. 14A illustrates another embodiment of a dressing kit 250 having a dressing 252, a pump 254, and a power source 256. In some embodiments, as with any of the embodiments of the dressing kits disclosed herein, the pump 254 and or power source 256 can be positioned above, within, partially within, adjacent, or remote to the absorptive and transmission layers 258 of the dressing 252. Additionally, in any of the embodiments disclosed herein, as illustrated in FIG. 14A, a hinge 262 such as a living hinge can be positioned between the pump assembly 254 and the power source 256, which can have one or more batteries. The hinge 262 can improve the flexibility and conformability of the dressing 250 between the pump assembly 254 and the power source 256. In any embodiments disclosed herein, the pump assembly 254 and/or the power source 256 can be configured to be positioned in a casing that does not have a bottom surface, such that the batteries and/or pump assembly are more compact. For example, the pump assembly 254 and/or the power source 256 can be positioned above one or more of the transmission and/or absorptive layers 258 of the dressing 252 or a backing layer 264 of the dressing 252 without having any additional layers or materials beneath the pump assembly 254 and/or the power source 256.

Figure 15:
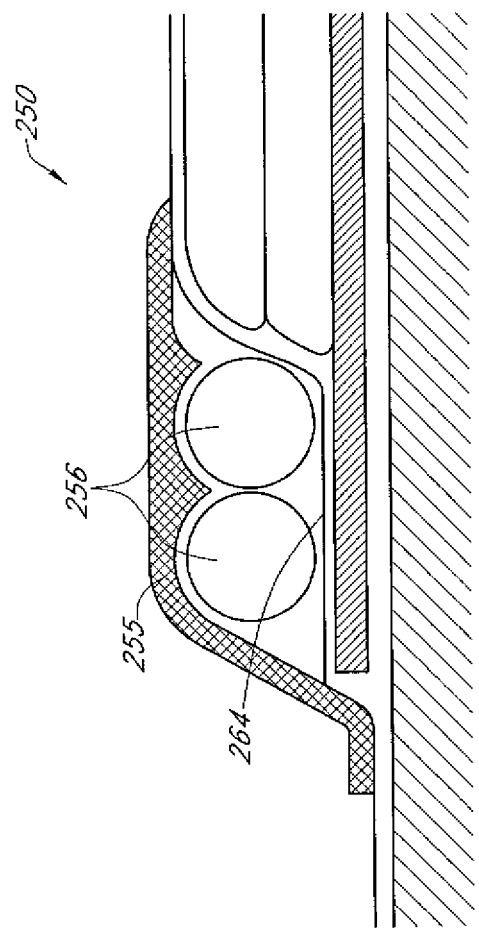
FIG. 15 illustrates an additional embodiment of a dressing kit for negative pressure wound therapy.

For example, with reference to FIG. 15, the power source 256 (which, in this illustration, consists of two batteries) is positioned directly on top of the backing layer 264 so as to minimize the profile of the dressing kit 250 in the region of the power source 256. Additionally, as illustrated, any embodiments disclosed herein can have a molding 255 configured to cover and support the power source 256 and/or the pump assembly 254.

This arrangement can reduce the profile of the pump assembly and/or the one or more batteries and improve the flexibility of the pump assembly and the one or more batteries. This can be produced in a single molding with internal components held captive between the one or more dressing layers and the upper casing of the pump assembly and/or the one or more batteries or between very thin layers within the pump assembly and the one or more batteries. The dressing kit illustrated in FIG. 14 can have any suitable pump type, including without limitation a diaphragm pump, a voice coil pump, a crank pump, or any other suitable pump.

Figure 16:
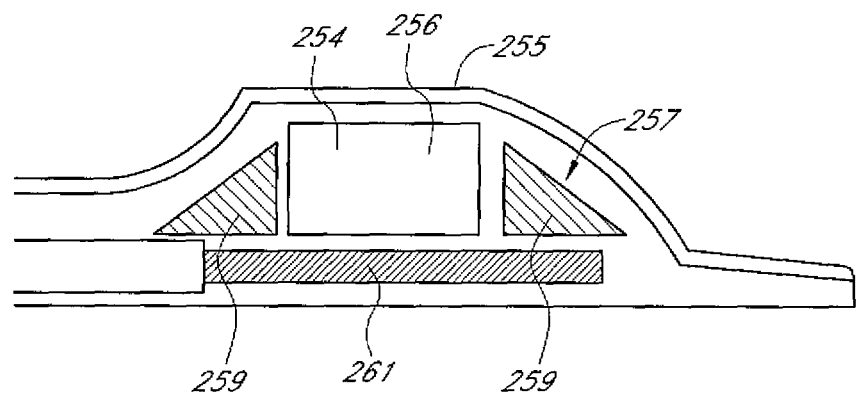
FIG. 16 illustrates an additional embodiment of a dressing kit for negative pressure wound therapy.

Additionally, in some embodiments, as illustrated in FIG. 16, one or more transitional members 257 can be positioned adjacent to the pump assembly 254 and/or the power source 256 to provide a smooth transition to the height or profile of the pump assembly 254 and/or the power source 256, underneath the component cover 255. The transitional members 257 can be formed from foam, silicone or other rubber, or other soft or malleable materials to provide flexibility and comfort to the dressing and the user. Additionally, though not required, a thin spacer 261 can be positioned beneath the pump assembly 254 and/or the power source 256.

Figure 14B:
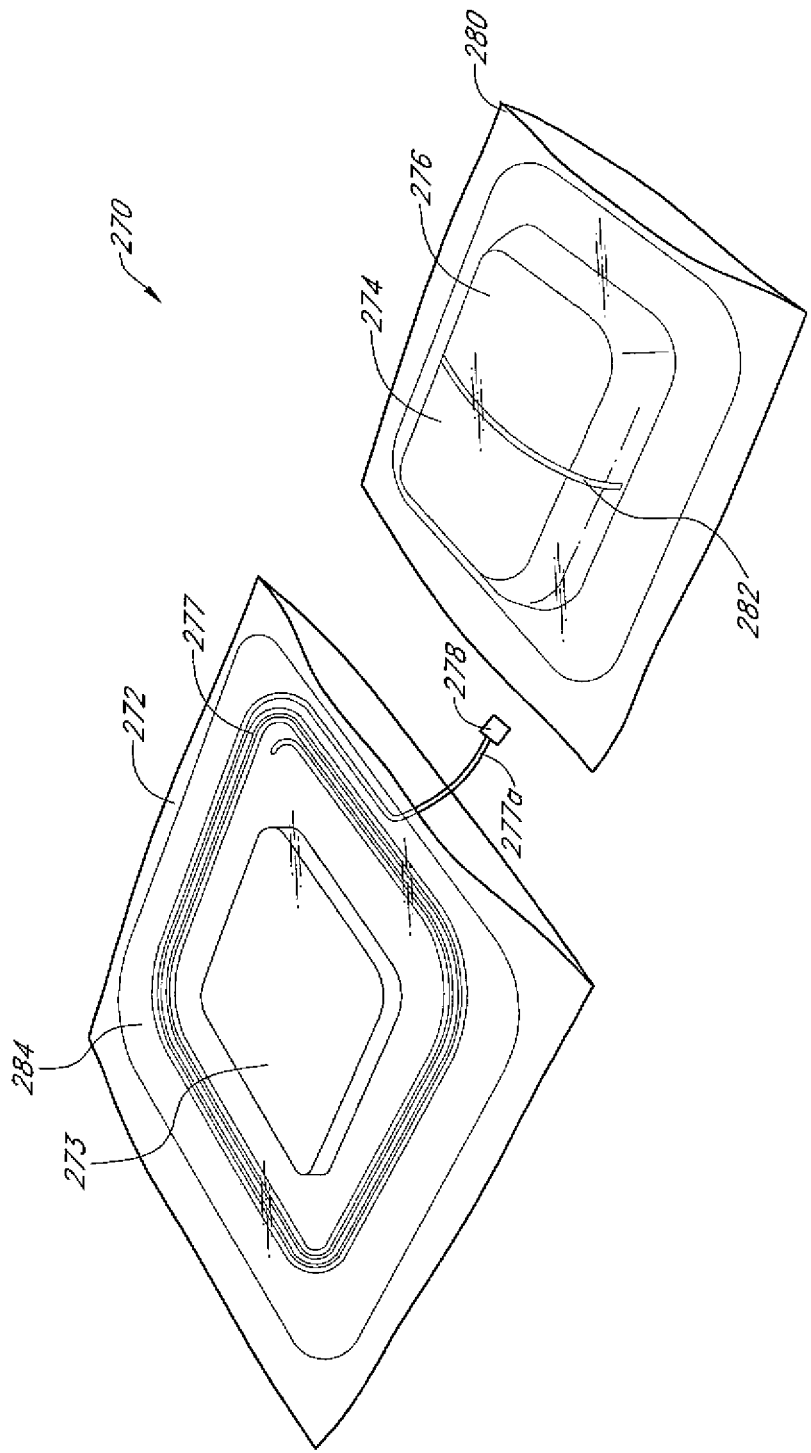
Figure 14C:
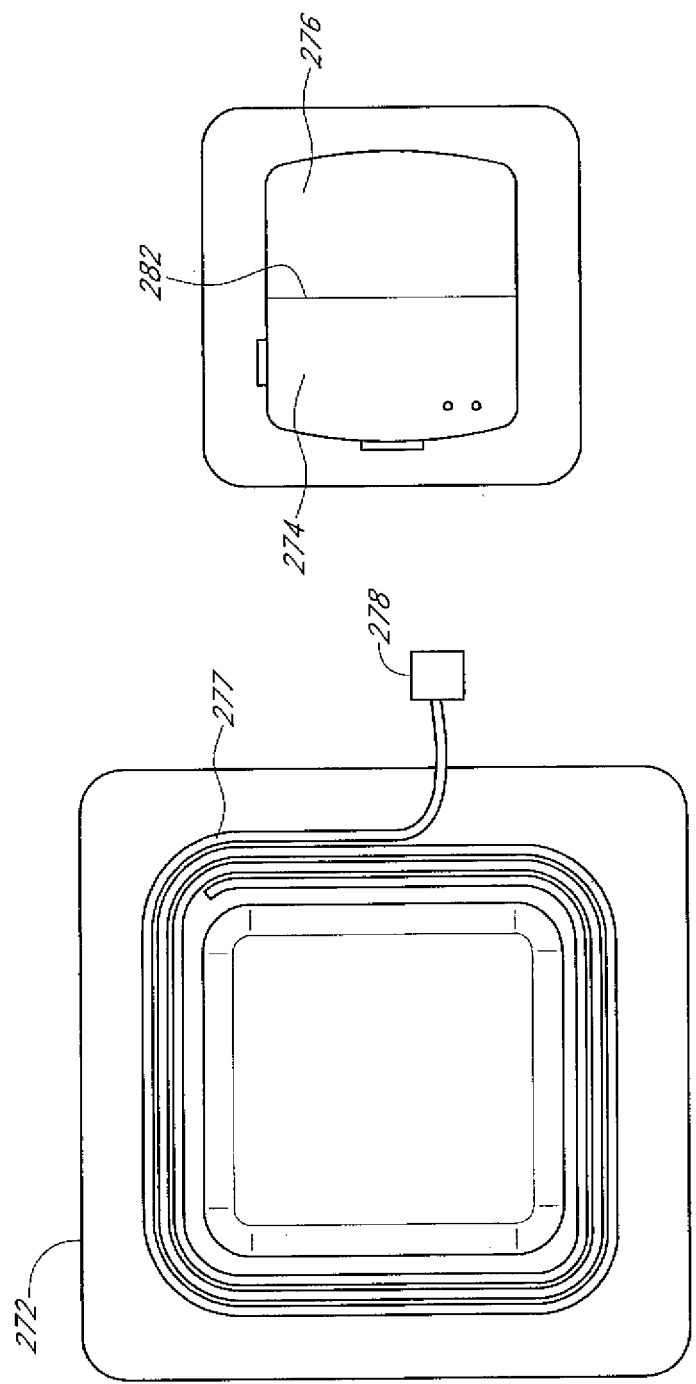
Figure 14D:
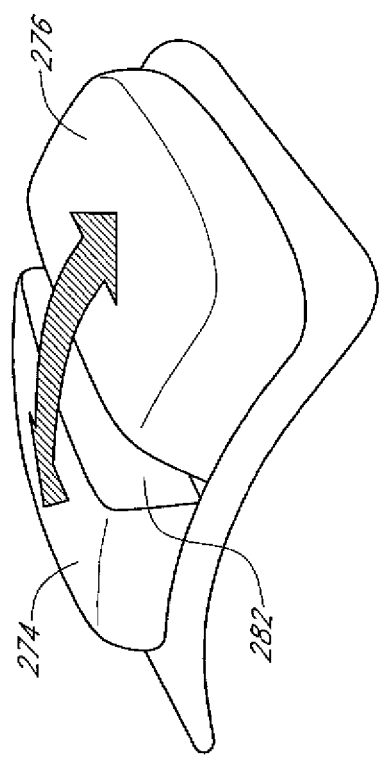

FIGS. 14B-14D illustrates another embodiment of a dressing kit 270 having a wound dressing 272, a pump assembly 274, a power source 276, and a conduit 277 configured to communicate the negative pressure produced by the pump assembly 274 to the space between the dressing 272 in the wound. In some embodiments, the conduit 277 can have a connector 278 fixed to a distal end 277a of the conduit 277 configured to connect with the pump assembly 274. A complementary coupling or mating feature can be supported by the pump assembly 274 to receive the connector 278 and provide a substantially sealed connection therewith. In some arrangements, the conduit 277 can be supported on the dressing 272 in a helical or winding arrangement around the absorptive layers 273 of the dressing 272. Additionally, the conduit 277 can be held in place with a supplemental backing layer 284 configured to adhere to the top of the conduit 277 and the dressing 272 and to hold the conduit 277 in the desired position. The supplemental backing layer 284 can be configured to permit a medical practitioner or user to remove a desired length of conduit 277 from the coil conduit so as to position the pump assembly 274 at any desired position either on the dressing 272 or remote to the dressing 272. Additionally, in some embodiments, the supplemental backing layer 284 can have a cut out or opening in the middle thereof over the portion that covers the dressing and/or absorptive layers 273 so as to not inhibit vapor transmission from within the dressing. Additionally or alternatively, the supplemental backing layer 284 can have a plurality of perforations therein configured to permit vapor transmission through the dressing layers.

Alternatively, the conduit 277 can be adhered to the top of the dressing 272 around a perimeter of the dressing and/or transmission layers 273 using adhesive or any other suitable mechanism that will removably secure the conduit 277 in the desired location, but permit a medical practitioner or user to remove a desired length of conduit 277 from the coil so as to position the pump assembly 274 at any desired position either on the dressing 272 or remote to the dressing 272. In any embodiments disclosed herein, the pump assembly 274 and power source 276 can be supported on a separate support member 280 so that the pump assembly 274 and the power source 276 can be positioned at any desired location either remotely relative to the dressing 272, adjacent to the dressing 272, or even on board the dressing 272. The support member 280 can have adhesive on a bottom surface thereof for each into any desired surface, or any other desired fastening mechanism such as book and loop connectors, snaps, wires, or otherwise. Additionally, as described above, a flexible hinge 282 can be positioned between the pump assembly 274 and the power source 276 to increase the flexibility and conformability of the support member 280. Any of the dressing kit embodiments disclosed herein can have a similar arrangement of conduit as disclosed for the dressing kit 270, or any of the other features, details, or configurations disclosed were shown for dressing kit embodiment 270.

Figure 17:
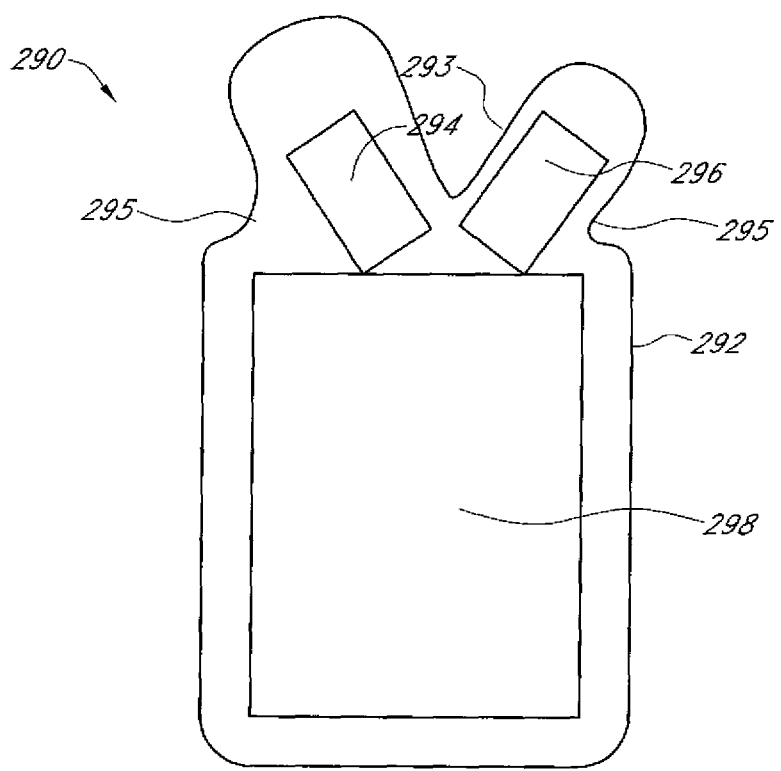
FIG. 17 illustrates an additional embodiment of a dressing kit for negative pressure wound therapy.

FIG. 17 illustrates another embodiment of a dressing kit 290 having a dressing 292, a pump assembly 294, and a power source 296 supported by the dressing 292 in some embodiments, the pump assembly 294 and the power source 296 can be positioned adjacent to the one or more absorptive and/or transmission layers 298 of the dressing kit 290. As illustrated therein, the pump assembly 294 and the power source 296 can be supported on portions of the dressing 292 extending in a V-shaped pattern away from the dressing pad 298. In other words, a cut out 293 can be formed in the dressing 292 to permit greater flexibility and conformability of the dressing in the region of the pump assembly 294 and the power source 296. In some embodiments, the cut out can have a V-shape. In some embodiments, the cut out 293 can have a U-shaped, or a smooth cutout shape.

Additionally or alternatively, any of the embodiments disclosed herein of the dressing 292 can also have additional cutouts 295 formed in the dressing 292 to the outside of the pump assembly 294 and/or the power source 296 to also increase the flexibility and conformability of the dressing. As mentioned, this arrangement can improve the conformability and flexibility of the dressing and enable the pump assembly 294 and/or the power source 296 to better mold around a curved body surface. Additionally, in some embodiments, this arrangement can have a pinpoint hinge rather than a lengthwise hinge to permit the components to better mold over curved or complex surface contours. Any of the dressing kit embodiments disclosed herein can have the pump assembly and the power source arranged on the dressing in this configuration, and can have a dressing of this shape.

FIG. 18 illustrates another embodiment of a dressing kit 310 wherein the pump assembly 314 and the power source 316 are supported by the dressing 312 and can have a hinge 322 therebetween. In some embodiments, the hinge 322 can be a living hinge. The hinge 322 can improve the flexibility of the dressing and the components supported thereby. Additionally, in some embodiments, the edges of the pump assembly 312 and/or the power source can be tapered and can be flexible.

Figure 19B:
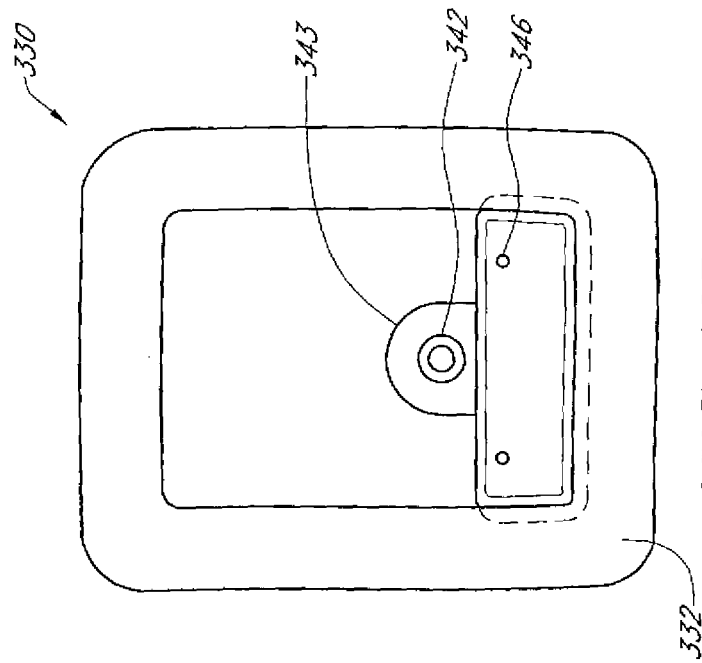
FIGS. 19A-C illustrate additional embodiments of a dressing kit for negative pressure wound therapy.
Figure 19C:
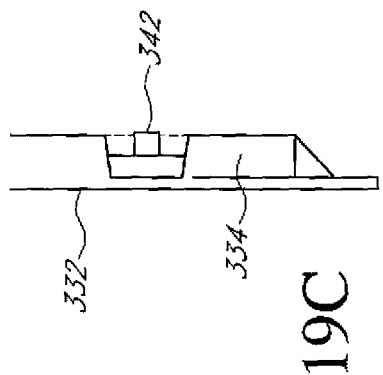
Figure 19A:
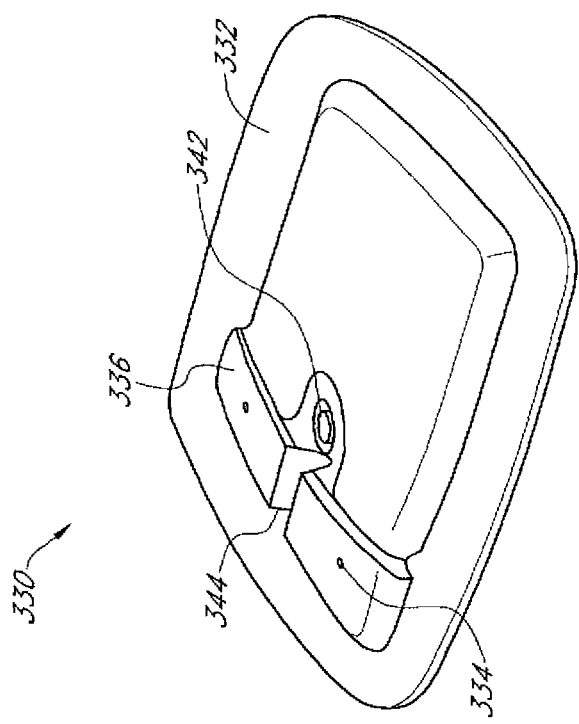

Additionally, in any embodiments disclosed herein, for example, FIG. 19 illustrates an embodiment of the dressing kit 330 that can have a dressing member 332, a pump assembly 334, a power source 336, and a pressure indicator 342 supported by the dressing 332. Additionally, in some embodiments, a flexible hinge 344 can be molded into, formed on, or positioned on the support layer or support material used to house or support the pump assembly 334 and the power source 336, the hinge 344 being positioned between the pump assembly 334 and the power source 336. The pressure bubble or pressure indicator can be positioned 342 were supported by the dressing 332 in any desired location on the dressing 332.

Additionally, as with any other embodiments disclosed herein, one or more press studs 346 can be supported on an outside surface of the cover layer of the dressing 332, the press studs being configured to receive complementary fastening features on the power source 346 and/or the pump assembly 334. In some embodiments, as is illustrated in FIG. 19, a filter layer can be positioned beneath the pressure indicator 342.

Figure 20:
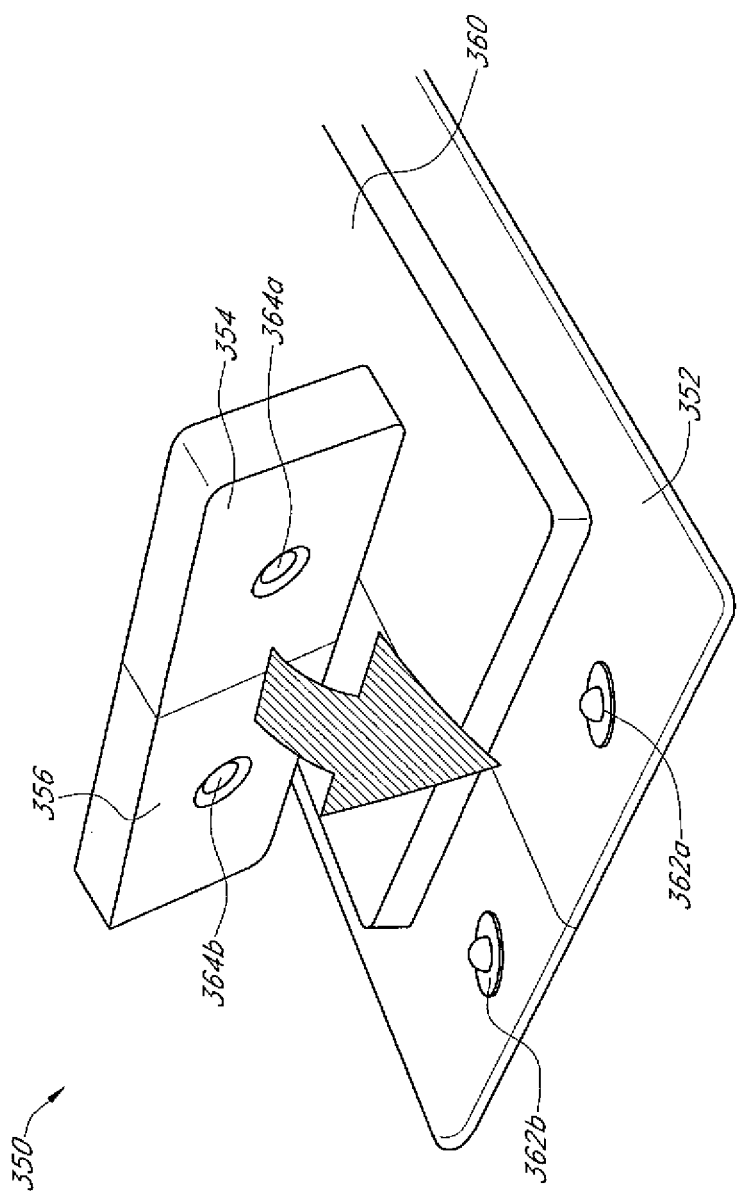
FIG. 20 illustrates an additional embodiment of a dressing kit for negative pressure wound therapy.

FIG. 20 illustrates another embodiment of a dressing kit having a dressing 352, a pump assembly 354, and a power source 356. In some embodiments, the pump assembly 354 and/or the power source 356 can be removably attached to the dressing member 352 using one or more stud connectors 362 fixed to the dressing member 352. The use of stud connectors 362 (also referred to herein as metal connectors or snap connectors) to support the battery and/or pump assembly on the dressing can enable the removability of the pump and/or power source from the dressing for replacement or for disposal. Additionally, the snap connectors can be used to not only removably support the battery and/or pump assembly on the dressing, but also to provide an electrical connection between the one or more batteries and the pump assembly.

In some embodiments, a first snap connector 362a can engage a first female receiver 364a positioned on a housing for the pump assembly 354. Similarly, a second snap connector 362a can engage a second female receiver 364a positioned on housing for the power source 356. The first snap connector 362a can be electrically connected or in communication with the second snap connector 362b so that a current supplied from the power source connected to the second snap connector 362b can be communicated to the pump assembly through such electrical connection or wiring between the two snap connectors. Additionally, in any embodiments disclosed herein, the pump and battery module could have a hinge therebetween for added conformability and flexibility. A hinge could also be used to connect the pump and battery module to the dressing kit. Further, in any embodiments disclosed herein, the battery and the pump assembly can be separate modules that can be independently removed and/or replaced.

In any of the embodiments disclosed herein, the batteries can be positioned and supported apart from the dressing. The batteries can be secured to the body or to the dressing using tape, a local pad, snaps, a clip supported by the dressing, Velcro, and/or any other desired fastening member. The batteries can be inserted and removed to facilitate activation and deactivation of the pump, and to permit replacement and/or disposal of the batteries.

Additionally, in any embodiments disclosed herein, one or more press studs can be supported by the dressing. The one or more press studs can be configured to engage complementary connectors supported by the pump assembly and/or the one or more batteries to permit the pump assembly and/or the one or more batteries to be removably snap supported by the dressing. The stud connectors can also be used to create an electrical connection between one or more batteries and the pump assembly and, accordingly, can be used to activate the pump.

The press studs or snap connectors can allow the one or more batteries to be electrically disconnected from the pump assembly until one or both of the components is snapped into the snap connectors. Additionally, if there are two or more batteries, such batteries can also have stud type electrically conductive connectors that permit the batteries to be separately supportable by the dressing so that the power circuit can be completed by snapping each of the one or more batteries into the dressing. In this configuration, the batteries and/or pump assembly can be snapped into position following sterilization of the dressing kit. Such assembly can also serve to activate the pump.

Additionally, any of the dressing embodiments disclosed herein can be configured to support one or more power source modules or pump assemblies on or adjacent to the dressing. For example, having a multiple number of power sources (e.g., a plurality of batteries, or any combination of batteries, fuel cells, capacitors, and photovoltaic cells) can improve the flexibly and conformability of the dressing and can reduce the profile of the dressing. The dressing can be configured such that the batteries are replaceable or interchangeable with similar or different batteries, selectable depending on the duration of time the dressing is to be on the patient. In configurations wherein the power source is preferably removable, the power source can be snapped into the dock or otherwise removably attachable and detachable from the dressing and configured to be lifted out of the dock or otherwise removed from the dressing when it is time to either disposed of or replace the batteries or power source.

The batteries can be positioned within or supported by the docks prior to positioning the dressing on the patient's body. In embodiments using conductive connectors fixed to the dressing and or the pump assembly, starting or restarting the pump can be achieved by inserting or re-inserting the one or more batteries in the docks, so as to permit a user to control an operation of the pump by inserting or re-inserting the batteries.

FIG. 21A-21C illustrates another dressing kit embodiment 370 having a pump assembly 374 and a power source 376 supported on either of a dressing member 372 or a separate support member. In some embodiments, the dressing member 372 can have a depression 373 therein configured to receive the pump assembly 374 and/or power source 376. With reference to FIG. 21A-21C, in any embodiments disclosed herein, one or more batteries can be supported in a removable cartridge configured to be removably engageable with a housing 377 surrounding at least a portion of the power source 376. In some embodiments, the housing 377 can also support or surround the pump assembly 374. With reference to FIG. 21B, in some embodiments, the housing 377 used to support the power source 376 can have a lid, cover, or hatch 379 that can be opened to access the power source 376, which can be batteries.

In some embodiments, the hatch 379 can have one or more battery terminals or electrical connections thereon configured such that, during sterilization or before the pump is to be activated, the battery terminals are out of contact with the power source 376. After sterilization or before therapy is to be initiated, the hatch can be closed to create an electrical connection between the power source 376 and the pump assembly 374, thereby initiating the negative pressure wound therapy.

FIG. 22 illustrates another dressing kit embodiment 390 having a pump assembly 394 and a power source 396 supported on either of a dressing member 392 or a separate support member. With reference to FIG. 22, similar to the dressing kit embodiment 370, in any embodiments disclosed herein, one or more batteries can be supported in a removable cartridge configured to be removably engageable with a housing 397 supported by the dressing member 392. In some embodiments, the housing 397 can also support or surround the pump assembly 394 if desired. However, in some embodiments, as in the illustrated embodiment, the pump assembly 394 can be separately supported by the dressing member 392. The dressing kit 390 can be configured such that the power source can be removable and disposed of and/or replaceable with a replacement power source when desired. For example, any of the dressing kits disclosed herein can come with a first power source and a second power source that can be used sequentially.

Figure 23A:
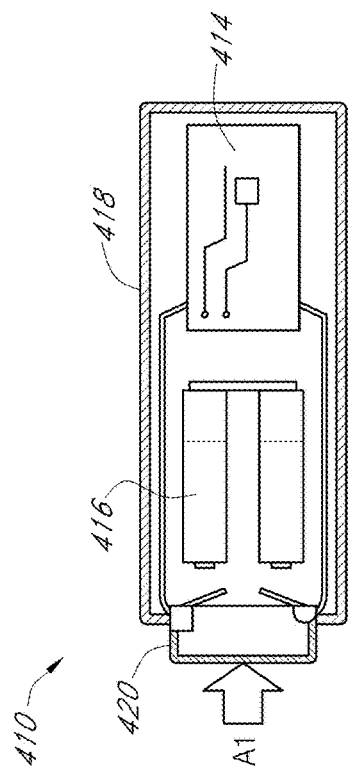
FIGS. 23A-C illustrate an additional embodiment of a dressing kit for negative pressure wound therapy.
Figure 23B:
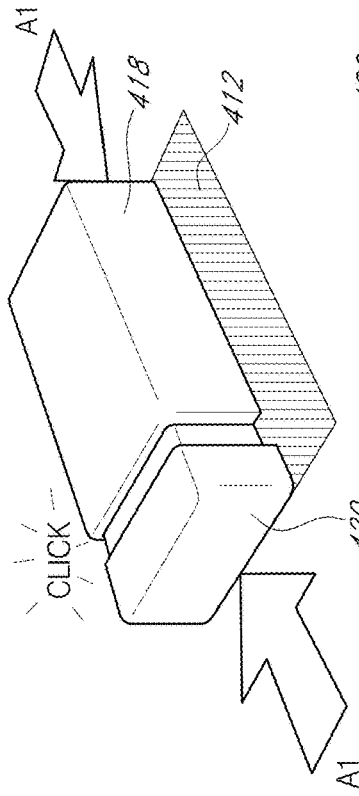

FIG. 23 illustrates an embodiment of a dressing kit 410 having a support layer 412, a pump assembly 414, a power source 416, and a housing or support member 418 configured to support the power source 416 and/or a pump assembly 414. In some embodiments, the power source 416 can be removably attachable to or engageable with the support member 418. The support member 418 can be configured to have conductive terminals such that, when the power source 416 is engaged therewith, power is automatically provided to the pump assembly 414 to either provide the power to the pump assembly 414 (but requiring a switch or button to activate the pump assembly) or to power and activate the pump assembly 414 to initiate negative pressure. Additionally, in some embodiments, multiple batteries or sources of power can be provided with the dressing kit 410. For example, a first battery pack 416 and a second battery pack 416 can be provided with the dressing kit 410 to provide interchangeable power sources. In some embodiments, the support member 418 can be attached directly to a dressing backing layer, or can be attached to a separate support layer, such as support layer 412, to enable the pump assembly and the power source to be attached adjacent to the wound and the dressing member positioned over the wound.

As an example, as illustrated in FIG. 23, one or more batteries can be supported in a removable cartridge or carrier 420 configured to be removably engageable with a housing 418 supported by the support layer 412. In some embodiments, the housing 418 can also support or surround the pump assembly 414 if desired. However, in some embodiments, as in the illustrated embodiment, the pump assembly 414 can be separately supported by the support layer 412. The dressing kit 410 can be configured such that the power source can be removable and disposed of and/or replaceable with a replacement power source when desired. Any of the dressing kits disclosed herein can come with a first power source and a second power source that can be used sequentially.

Figure 23C:
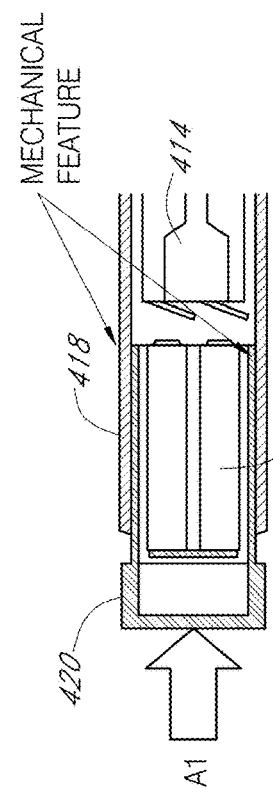

With reference to FIG. 23C, the dressing can be configured such that sliding the batteries into engagement with the battery terminals (in the direction indicated by arrow A1 in the figures) will result in an audible click, to alert a user regarding the position of the components of the battery enclosure that the battery circuit is closed. Any of the dressing kit embodiments disclosed herein can be supported in packaging configured such that, while the dressing kit is supported in the packaging, the components of the battery pack or pump assembly are held in a first or non-operational position and prevented from moving to a second operational position. In this configuration, when the components are in the first position, the pump is non-operational due to the fact that the battery terminals are not in contact with the one or more batteries. For example, the packaging supporting the dressing kit can prevent a lid of the battery housing from moving to the second position by holding the housing lid or cap in the first position. The packaging can have protrusions that are positioned between the housing lid or cap and the body of the battery housing that separate the battery housing lid from the body of the battery housing. Once the dressing kit is removed from the packaging, the battery housing lid or cartridge can be slid inward, permitting the terminals to contact the batteries so that the pump can be activated. In this configuration, the battery housing can serve as an activation button. Sliding the lid out of contact from the batteries can stop the operation of the pump.

Figure 24D:
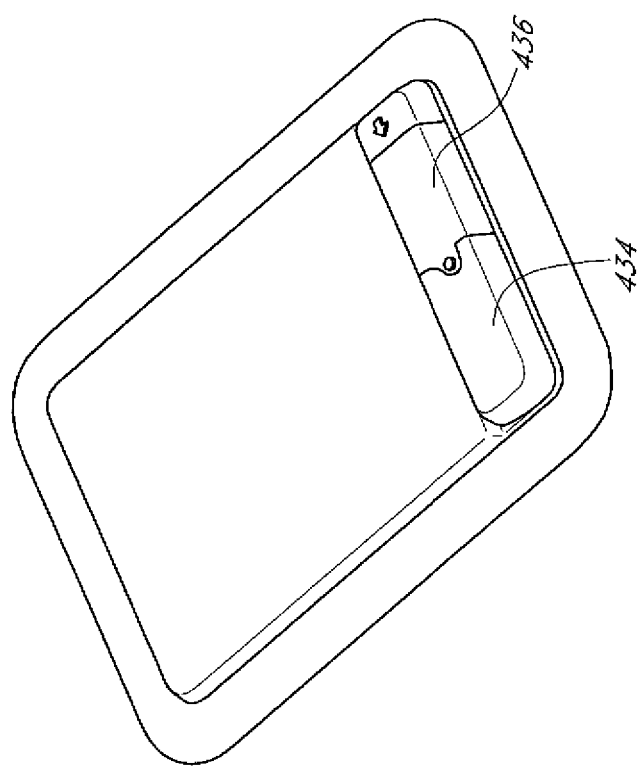
Figure 24E:
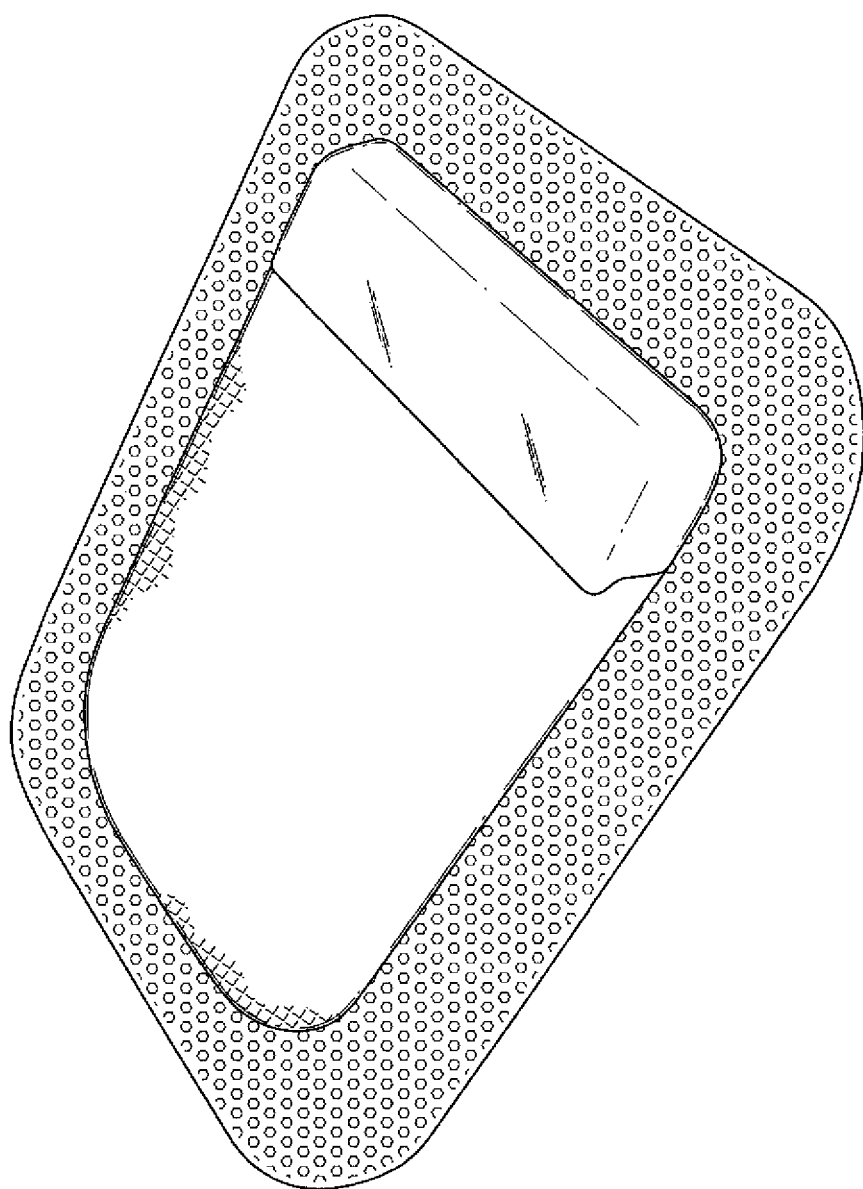
Figure 24F:
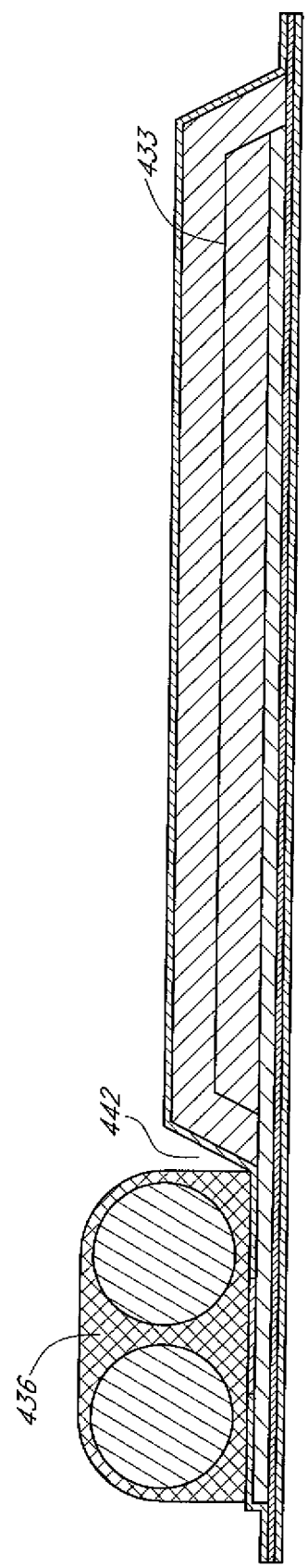

The dressing kit 430 embodiment of FIG. 24 is similar to the dressing kit 410 embodiment of FIG. 23, having a slideable carriage 420 configured to move the power source 436 in contact with the pump assembly 434. Additionally, the dressing kit 430 can have a flexible hinge 442 positioned between the housing used to support the power source and pump assembly, and the absorption and/or transmission layers 433 of the dressing 432 to permit greater flexibility and conformability of the dressing 432.

Figure 25A:
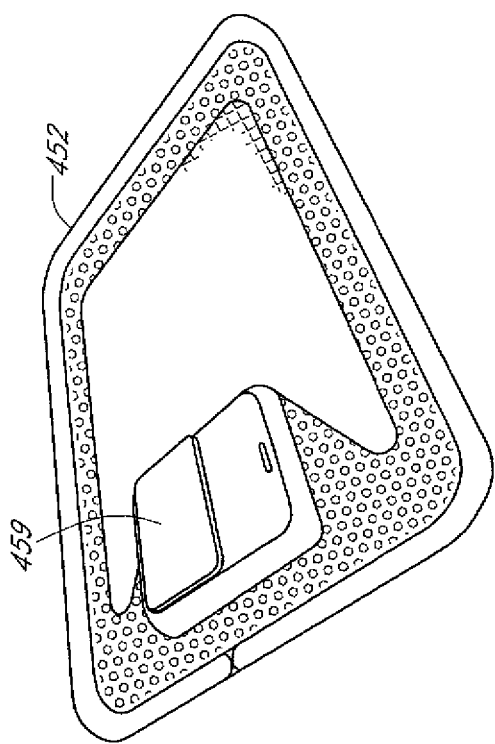
FIGS. 25A-B illustrate an additional embodiment of a dressing kit for negative pressure wound therapy.
Figure 25B:
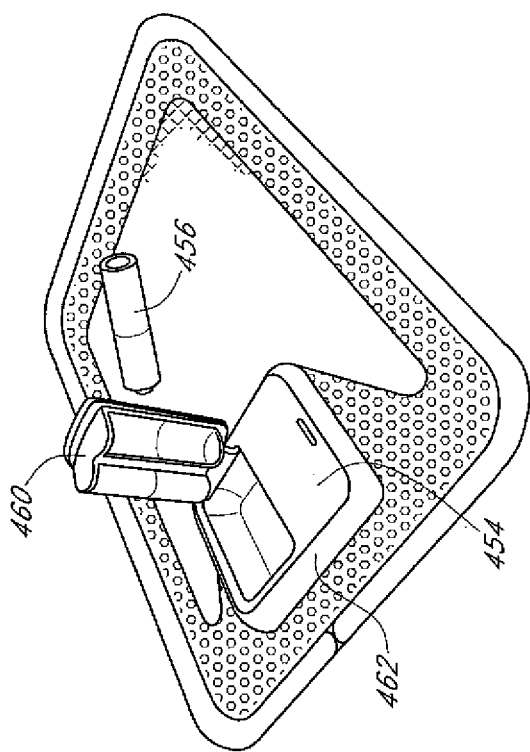
Figure 26A:
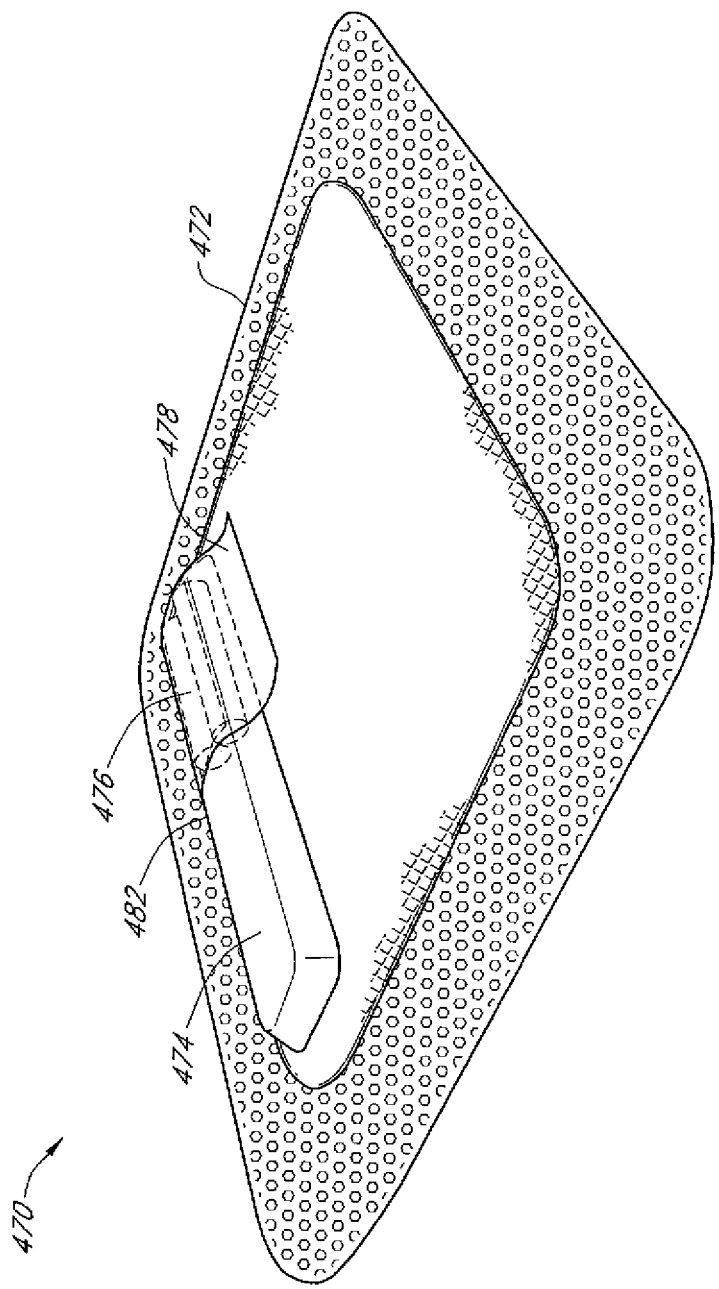
FIGS. 26A-G illustrate additional embodiments of a dressing kit for negative pressure wound therapy.
Figure 26B:
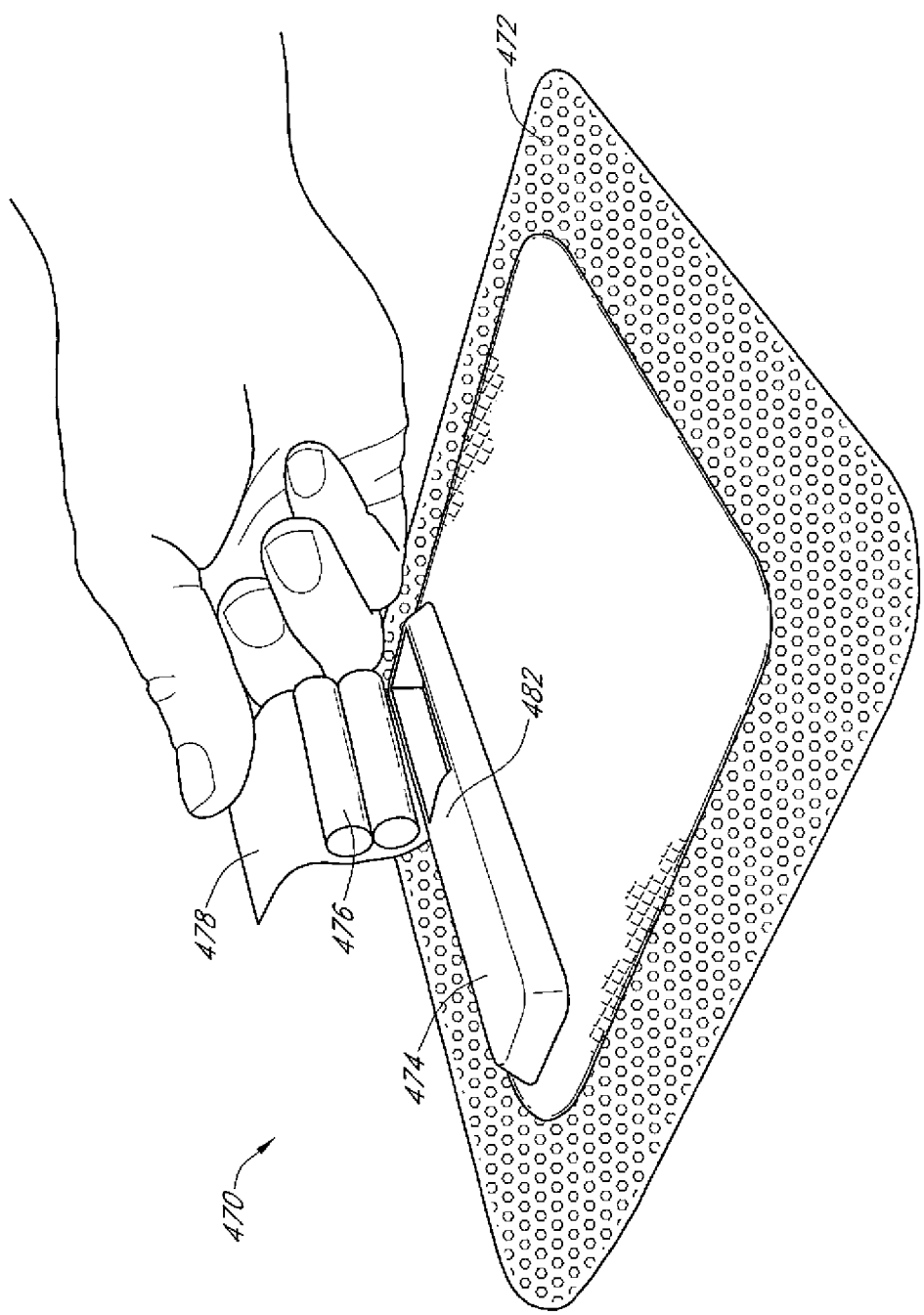
Figure 26C:
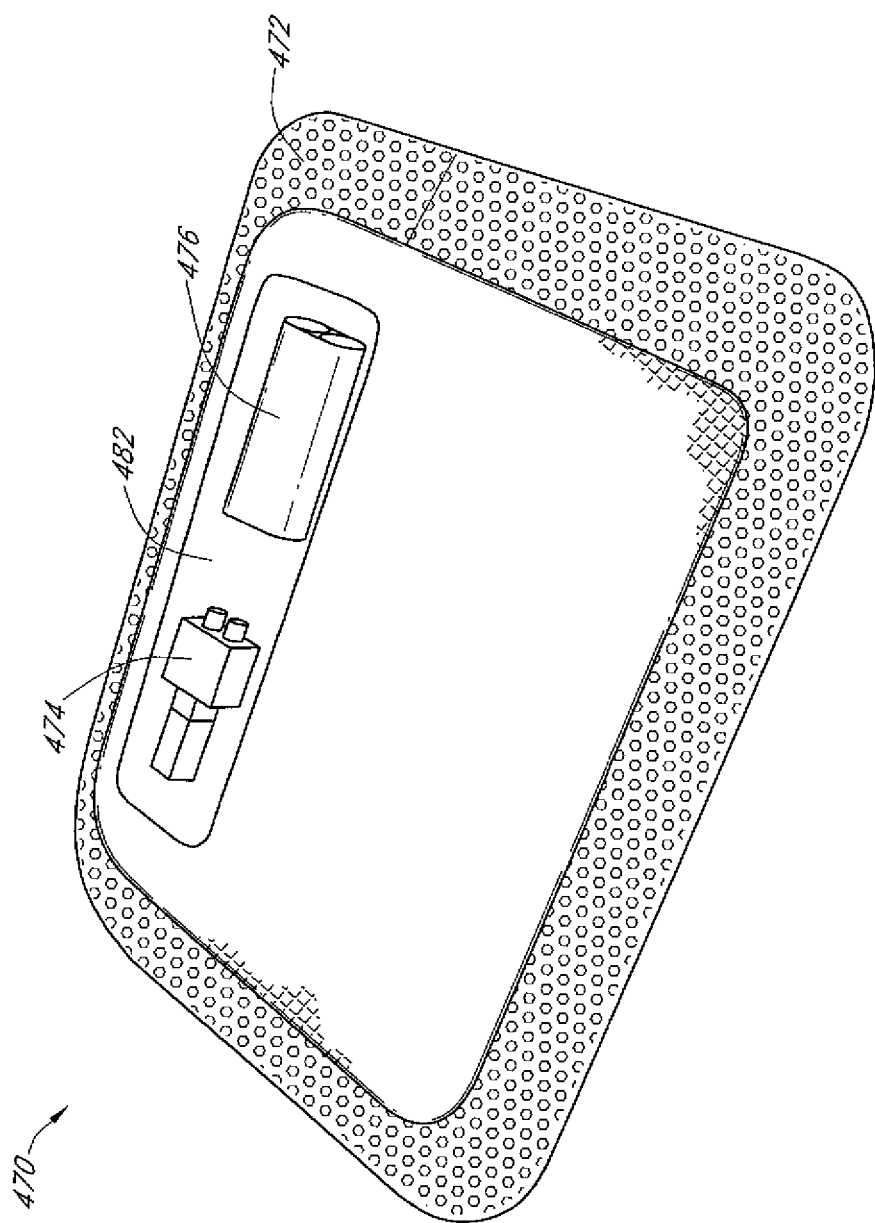
Figure 26D:
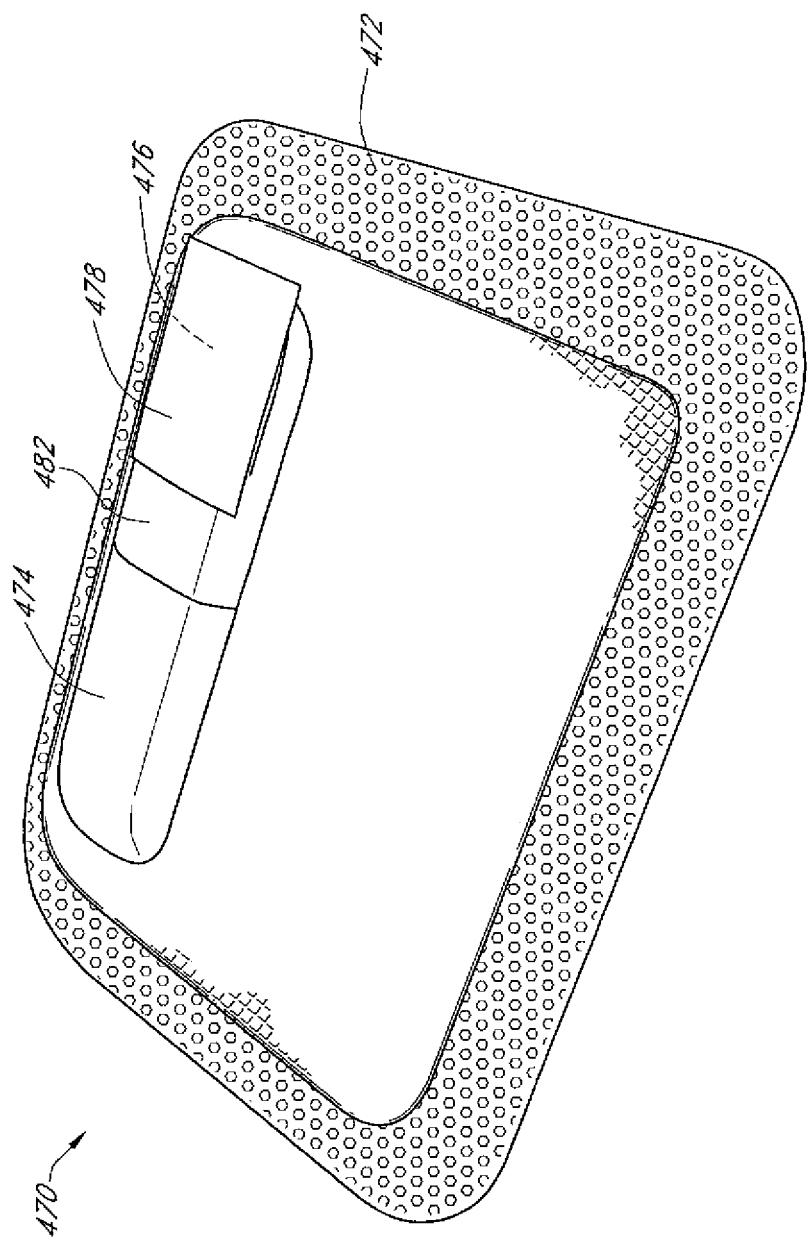
Figure 26E:
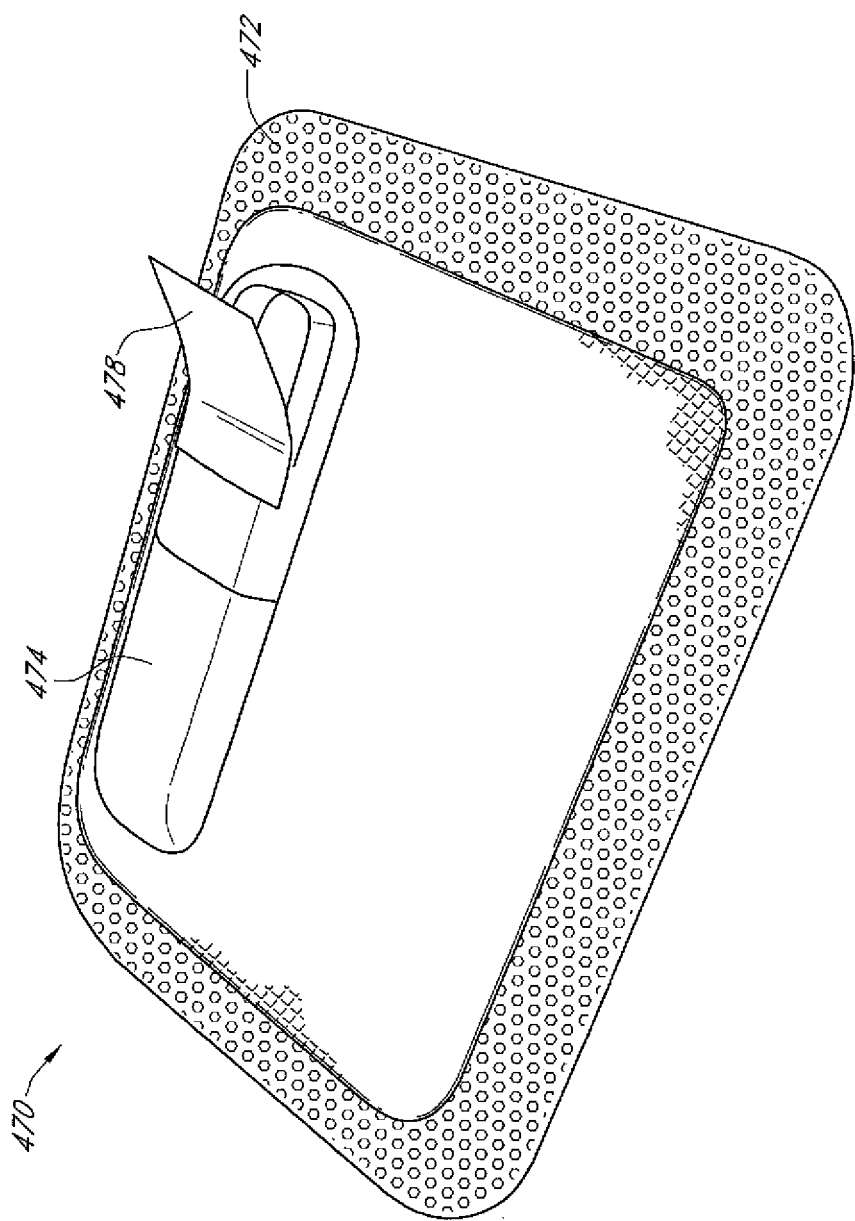
Figure 26F:
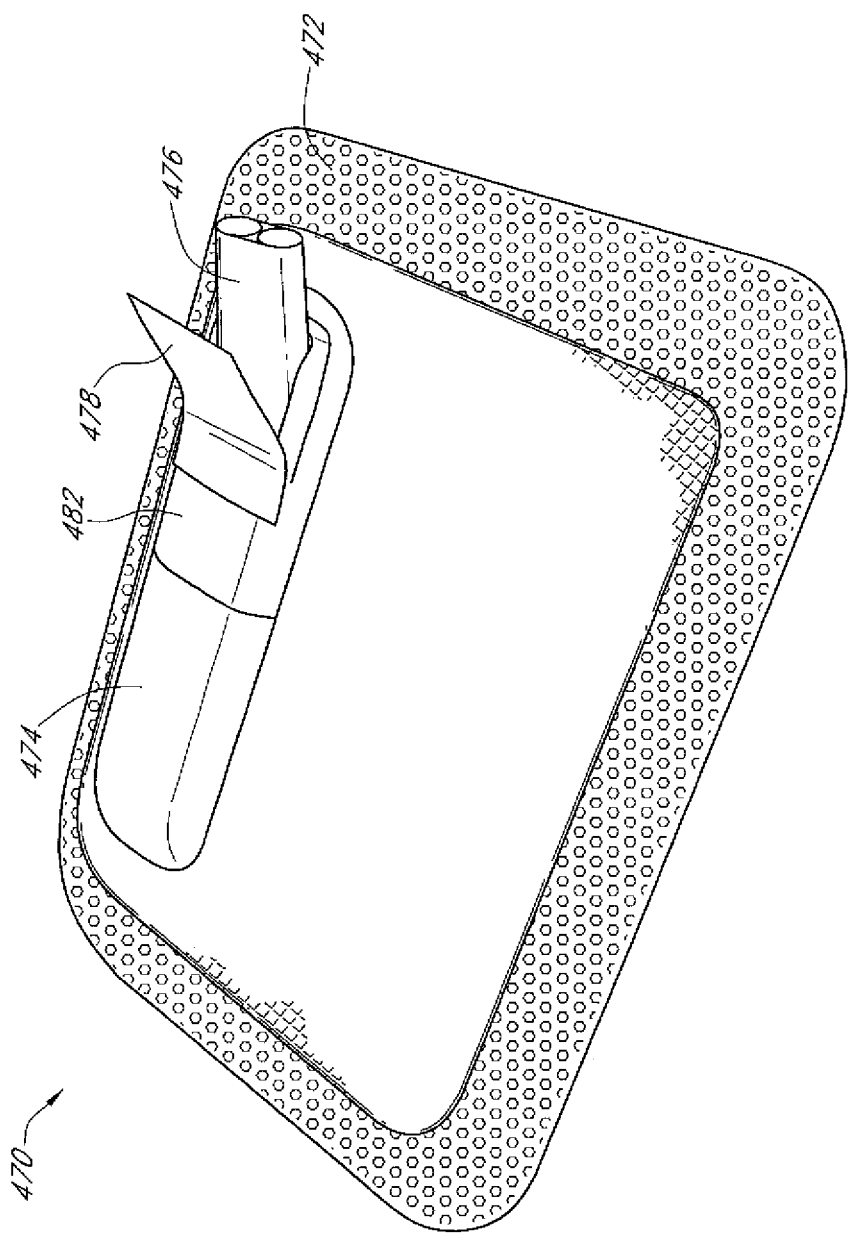
Figure 26G:
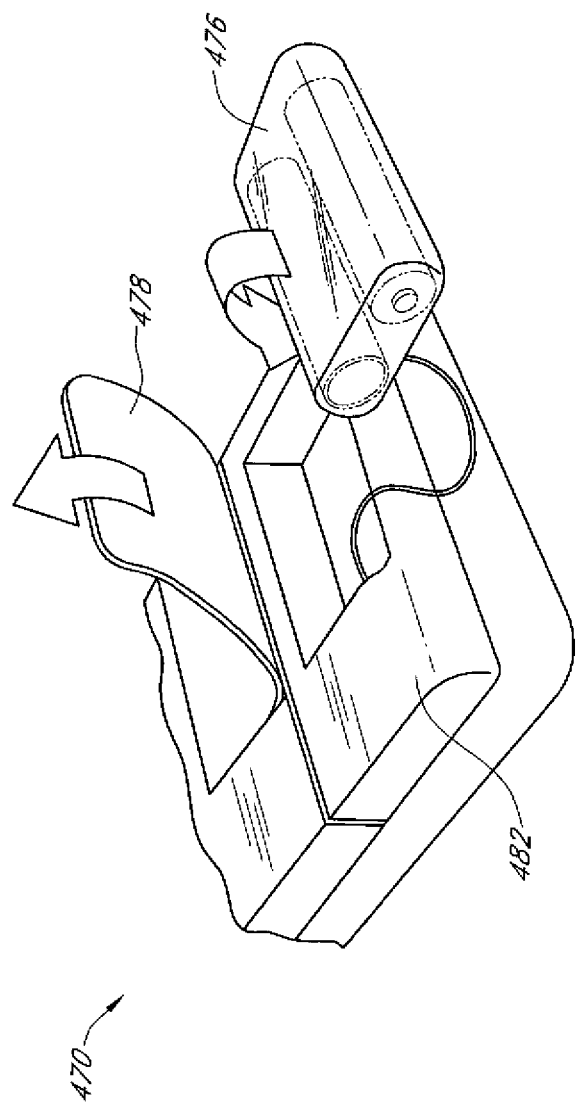

Additionally, with reference to FIG. 25, in some embodiments, the dressing kit 450 can have a dressing 452, a pump assembly 454, a power supply 456, and a support member 462 configured to support the pump assembly 454 and the power supply 456. The support member 462 can be supported by the dressing member 452 and can enable the power supply 456 to be removably supported by the dressing member 452. In some embodiments, the power supply 456 can be supported in a carriage 460 hingeably supported by the support member 462 or having an adhesive cover that can hold the power supply in the desired position within the support member 462.

FIG. 26 illustrates another embodiment of a dressing kit 470 having a dressing 472, a pump assembly 474, a power supply 476, and a support member 482 configured to support the pump assembly 474 and/or the power supply 476. The support member 482 can be supported by the dressing member 472 and can enable the power supply 476 to be removably supported by the dressing member 472. In some embodiments, the power supply 476 can be supported by an adhesive strap 476 having one end thereof fastened or secured to the support member 482. The adhesive strap 476 can be sealingly closed over the support member 482 to provide a mechanism for holding the power source 476 in the support member 482. The strap can have a tabbed portion for grasping, and can be flexible enough to deflect away from the dressing when the user wishes to withdraw the battery. The adhesive strap can be colored and/or labeled to alert a user that the batter should be removed before the medical device is incinerated or otherwise disposed of. In some embodiments, as illustrated in FIG. 26C, the power source can be positionable in a compartment in the support member 482 and not attached to the strap 476.

Figure 27C:
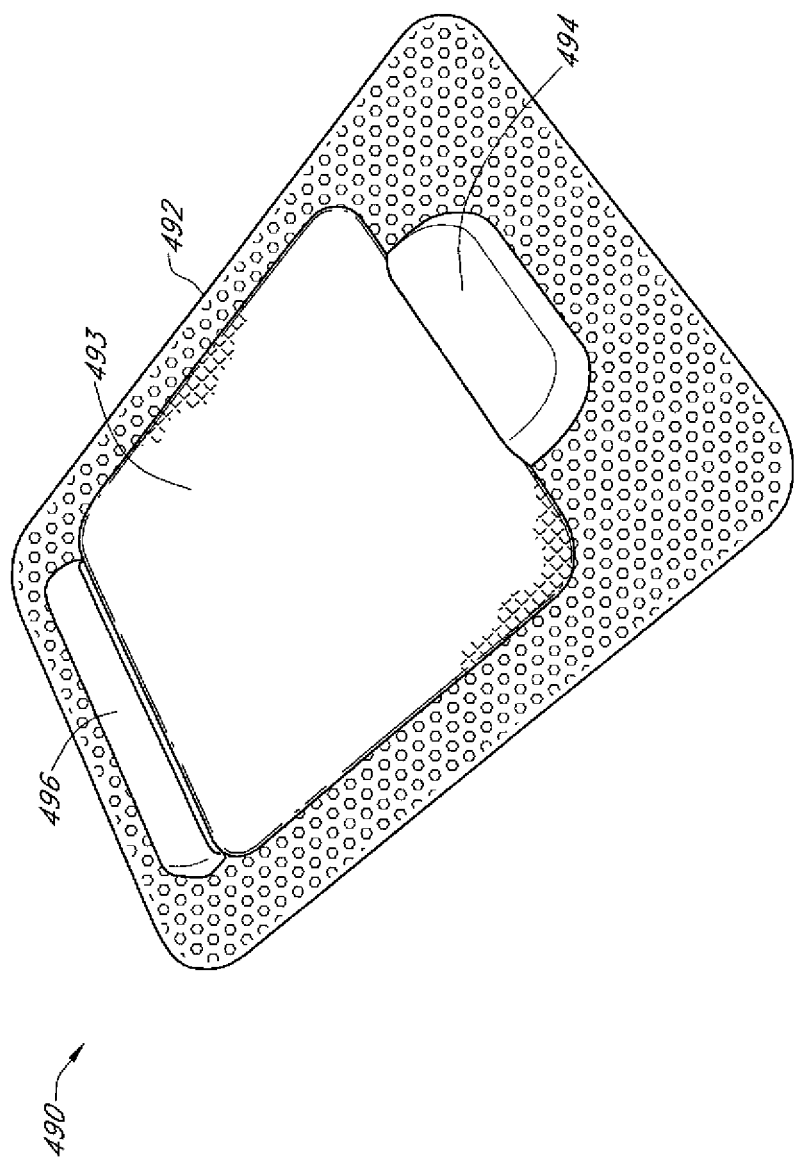
Figure 27D:
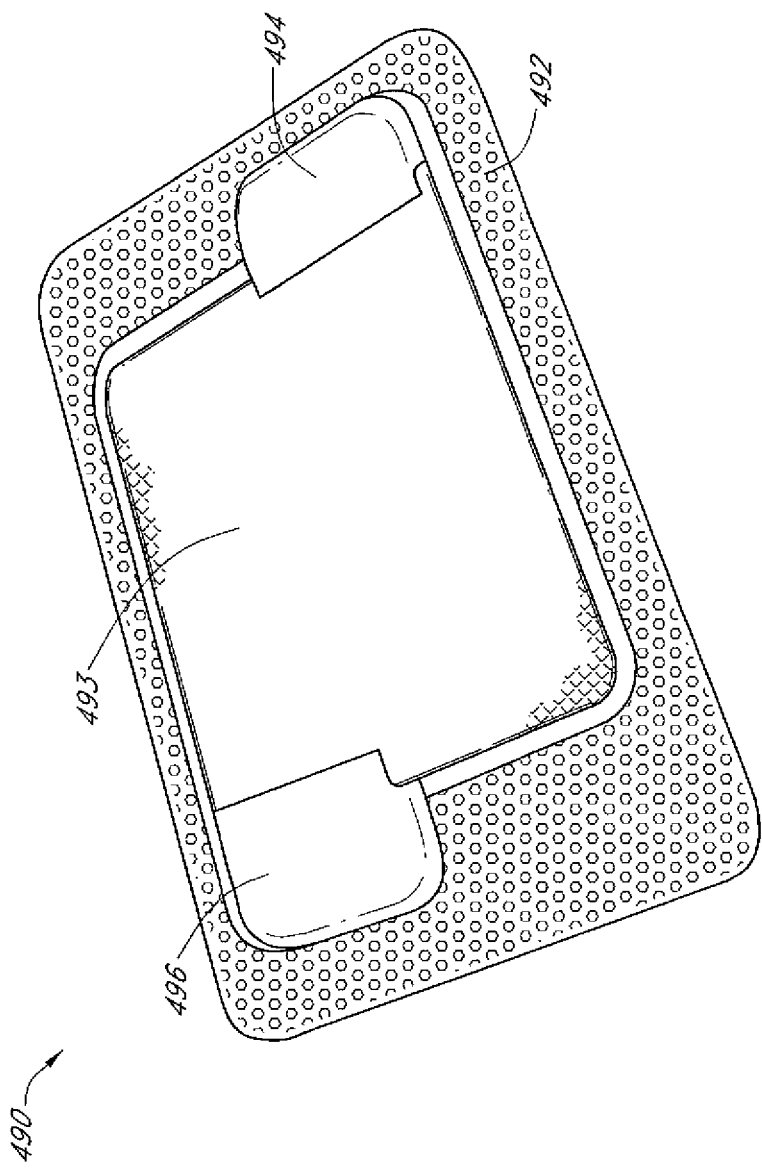
Figure 28A:
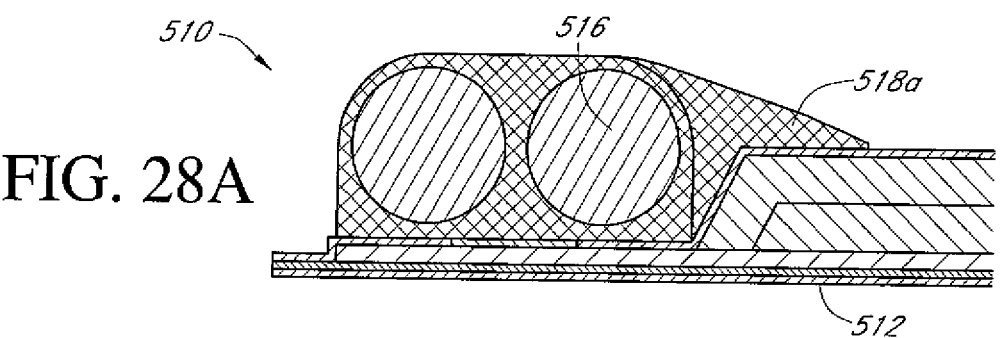
Figure 28B:
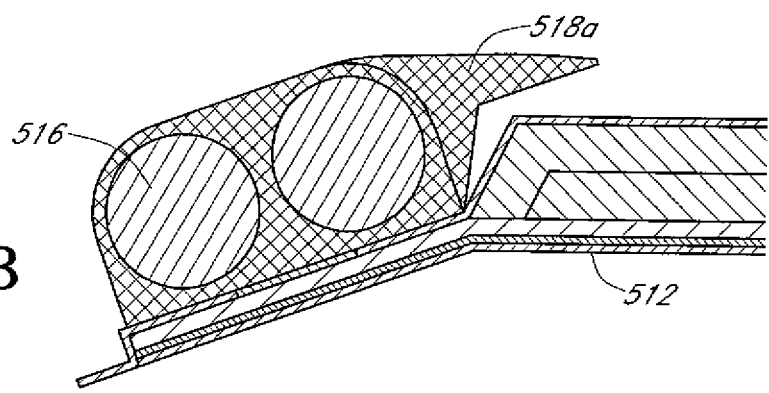
Figure 28C:
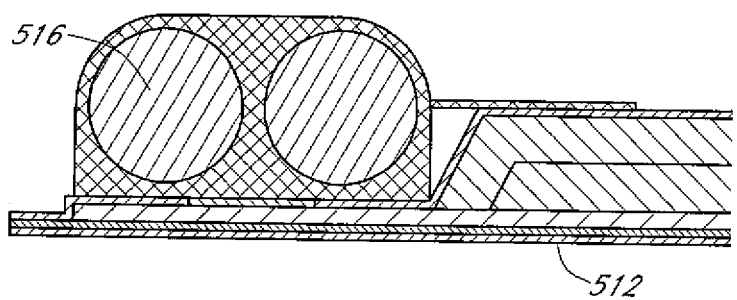
Figure 28D:
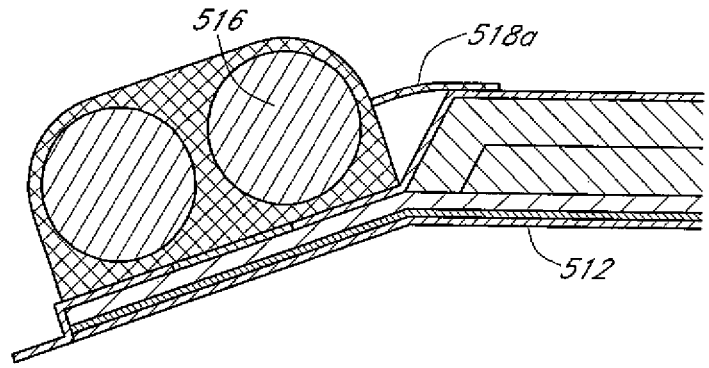
Figure 28E:
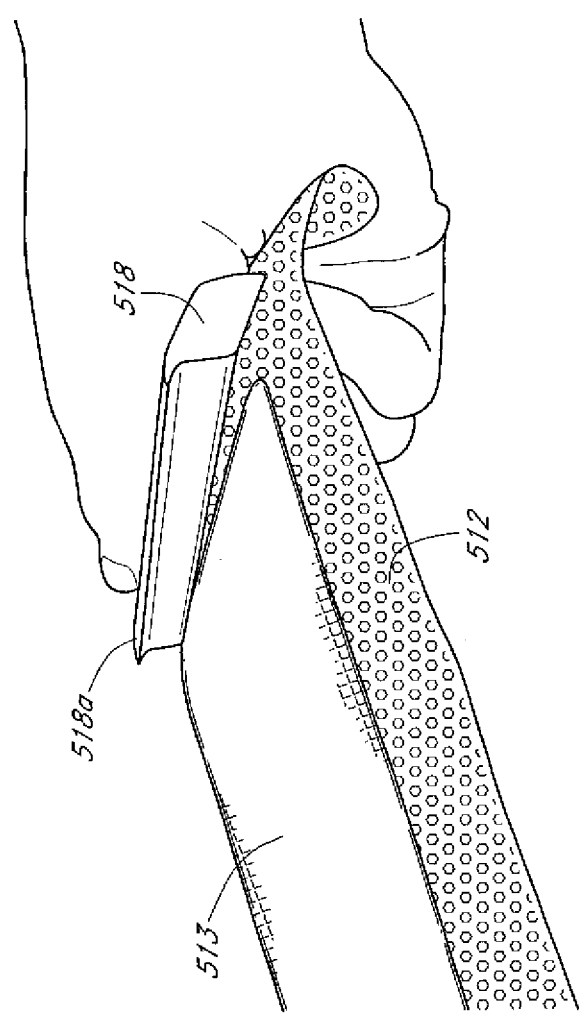

In the embodiment of the dressing 490 illustrated in FIG. 27, the pump assembly 494 and the power source 496 can be positioned at opposite ends or on different portions of the dressing 492. For example, the pump assembly 494 and the power source 496 can be adjacent to opposite edges of the absorption and/or transmission layers 493. As shown in FIG. 27A, the pump 494 and power source 496 modules can be positioned at opposite corners of the dressing 492. The circuitry used for this arrangement or any other dressing kit embodiments disclosed herein can be flexible so that the dressing 492 is conformable and flexible to the user.

With reference to the dressing kit 510 embodiment illustrated in FIG. 28, the pump assembly 514 can be supported on an edge portion of the dressing 512. A support member 518 can be used to support either or both of the pump assembly 514 and the power source 516. An overhang or extended portion 518a can extend over or overlap an adjacent portion of the dressing 512 having the absorptive and or transmission layers 513. In some embodiments, as in FIG. 28A, the overhang 518a can have a curved and smooth profile. In some embodiments, as in FIG. 28C, the overhang 518b can have a straight and flexible profile. The overhang or extended portion 518a can extend over the adjacent edge portion of the dressing to provide a more integrated look and feel With reference to the dressing kit 530 embodiment illustrated in FIG. 29, the pump assembly 534 can be supported on an edge portion of the dressing 532. A support member 540 can be used to support either or both of the pump assembly 534 and the power source 536. An overhang or extended portion 540a can extend over or overlap an adjacent portion of the dressing 532 having the absorptive and or transmission layers 533. In some embodiments, as in FIG. 28A, the overhang 538a can have a curved and smooth profile. Additionally, in some embodiments, a joint or flexible hinge 538 can be positioned between the pump assembly 534 and the power source 536. The overhang or extended portion 540a can extend over the adjacent edge portion of the dressing to provide a more integrated look and feel.

Figure 30:
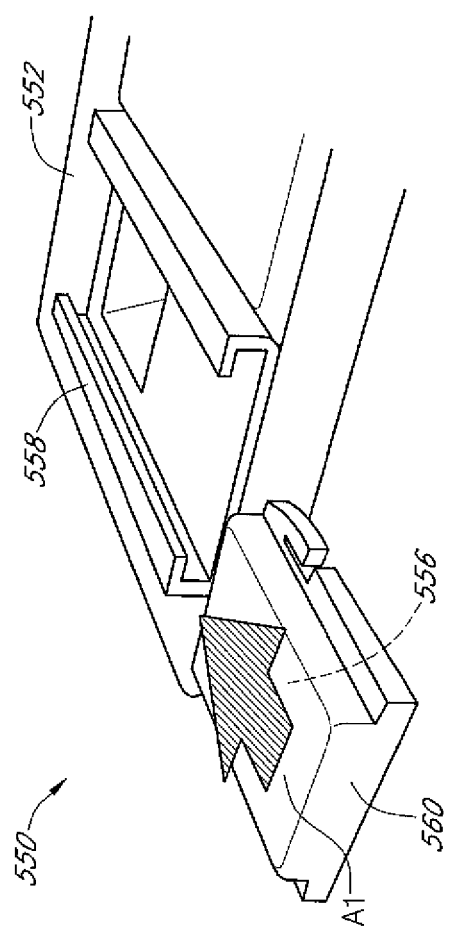
FIG. 30 illustrates an additional embodiment of a dressing kit for negative pressure wound therapy.

FIG. 30 illustrates an embodiment of a dressing kit 550 having a support layer 552, a pump assembly (not illustrated), a power source 556, and a housing or support member 558 configured to support the power source 556 and/or a pump assembly 554. In some embodiments, the power source 556 can be removably attachable to or engageable with the support member 558. The support member 558 can be configured to have conductive terminals such that, when the power source 556 is engaged therewith, power is automatically provided to the pump assembly 554 to either provide the power to the pump assembly 554 (but requiring a switch or button to activate the pump assembly) or to power and activate the pump assembly 554 to initiate negative pressure. Additionally, in some embodiments, multiple batteries or sources of power can be provided with the dressing kit 550. For example, a first battery pack 556 and a second battery pack 556 can be provided with the dressing kit 550 to provide interchangeable power sources. In some embodiments, the support member 558 can be attached directly to a dressing backing layer, or can be attached to a separate support layer, such as support layer 552, to enable the pump assembly and the power source to be attached adjacent to the wound and the dressing member positioned over the wound.

Further, one or more batteries 556 can be supported in a removable cartridge or carrier 560 configured to be removably engageable with a housing 558 supported by the support layer 552. In some embodiments, the housing 558 can also support or surround the pump assembly 554 if desired. However, the pump assembly 554 can be separately supported by the support layer 552. The dressing kit 550 can be configured such that the power source can be removable and disposed of and/or replaceable with a replacement power source when desired. Any of the dressing kits disclosed herein can come with a first power source and a second power source that can be used sequentially.

With reference to FIG. 30, the dressing can be configured such that sliding the batteries into engagement with the battery terminals (in the direction indicated by arrow A1 in the figures) will result in an audible click, to alert a user regarding the position of the components of the battery enclosure that the battery circuit is closed. Any of the dressing kit embodiments disclosed herein can be supported in packaging configured such that, while the dressing kit is supported in the packaging, the components of the battery pack or pump assembly are held in a first or non-operational position and prevented from moving to a second operational position. Ptional position and prevented from moving to a second operational position. In this configuration, when the components are in the first position, the pump is non-operational due to the fact that the battery terminals are not in contact with the one or more batteries. For example, the packaging supporting the dressing kit can prevent a lid of the battery housing from moving to the second position by holding the housing lid or cap in the first position. The packaging can have protrusions that are positioned between the housing lid or cap and the body of the battery housing that separate the battery housing lid from the body of the battery housing. Once the dressing kit is removed from the packaging, the battery housing lid or cartridge can be slid inward, permitting the terminals to contact the batteries so that the pump can be activated. In this configuration, the battery housing can serve as an activation button. Sliding the lid out of contact from the batteries can stop the operation of the pump.

Figure 31:
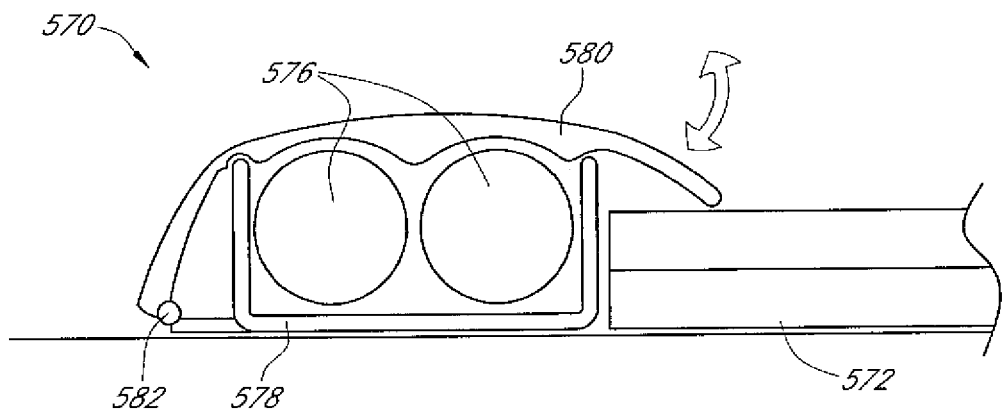
FIG. 31 illustrates additional embodiments of a dressing kit for negative pressure wound therapy.

FIG. 31 illustrates a dressing kit 570 having a dressing member 572, a power source 576 positioned within a support member 578, and a hinged lid 580 hingably positioned over an opening in the support member 578. The lid 580 can rotate about an axis or joint 582. In some embodiments, the hinge can be configured such that, when the hinge is moved to a closed position, the power source 576 will be secured within the support member 578 and an electrical connection will be created between the power source 576 and a pump assembly (not illustrated) so that the pump can be changed to an operational state. The hinged door can have a living hinge, soft pivot, an axle, or other suitable mechanism.

Figure 32A:
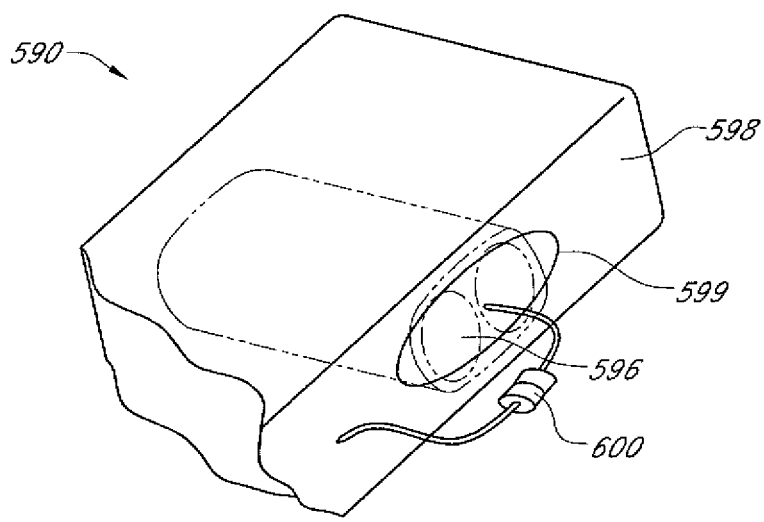
FIGS. 32A-B illustrate an additional embodiment of a dressing kit for negative pressure wound therapy.
Figure 32B:
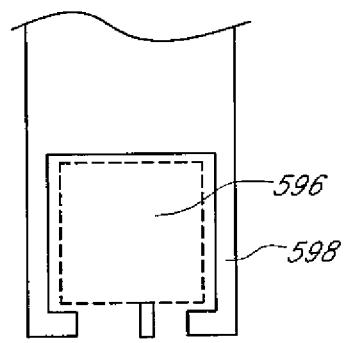
Figure 33A:
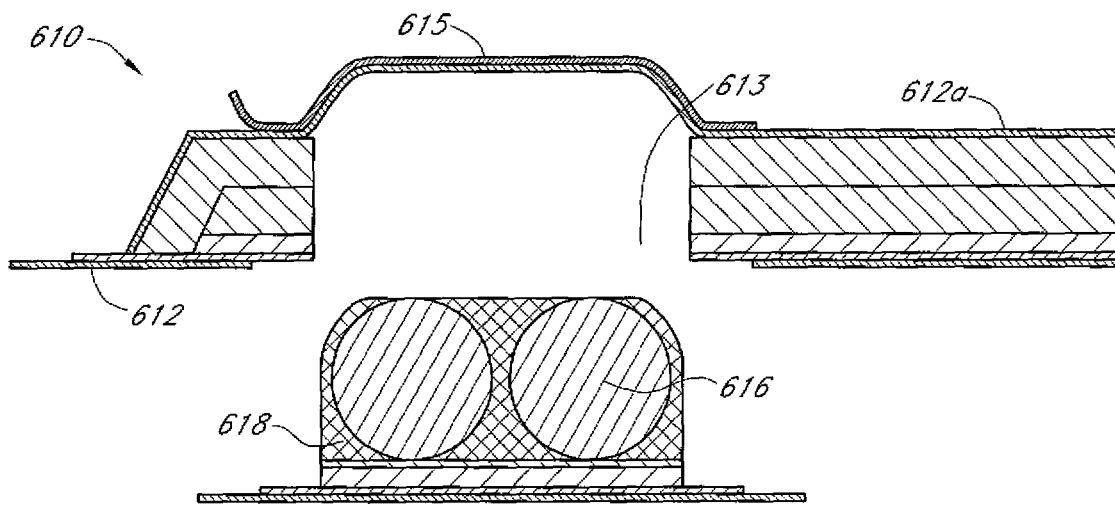
FIGS. 33A-E illustrate additional embodiments of a dressing kit for negative pressure wound therapy.
Figure 33B:
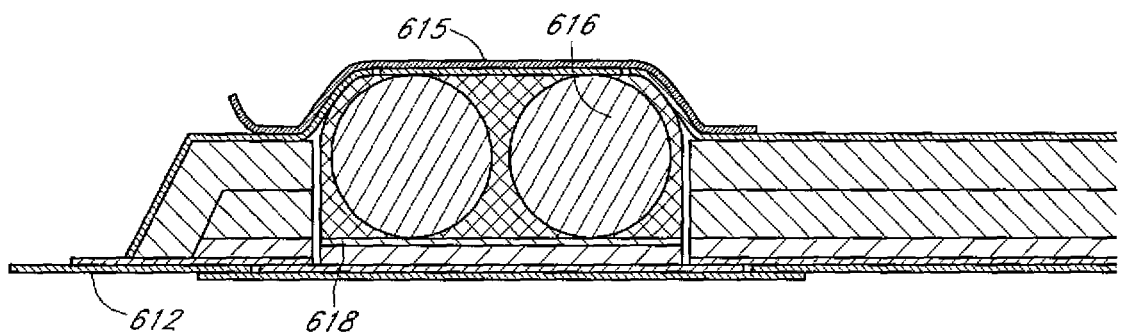
Figure 33C:
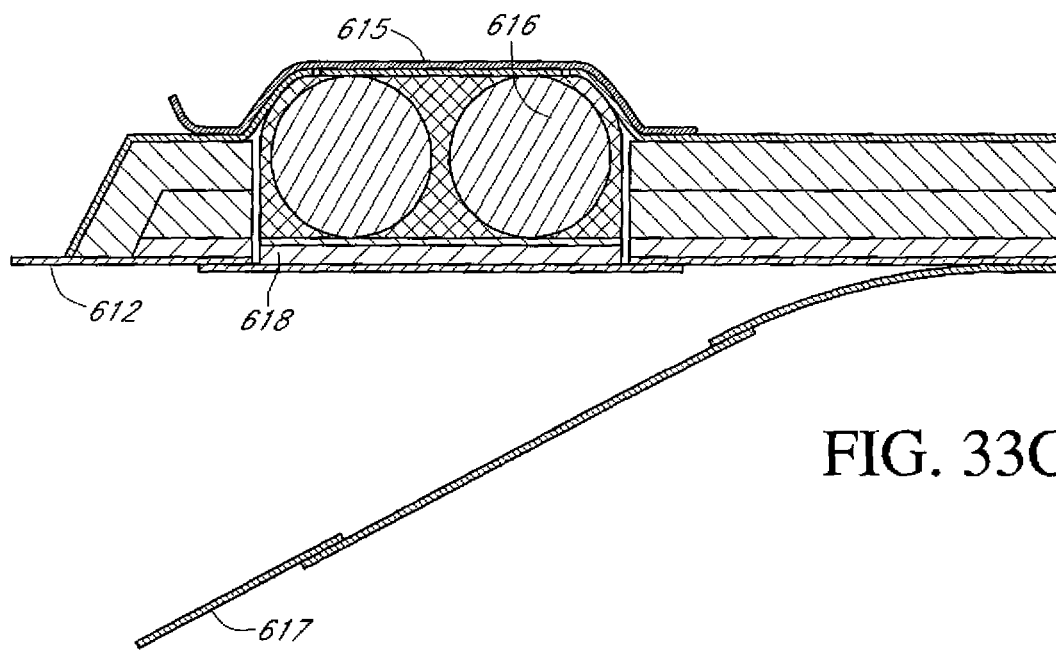
Figure 33D:
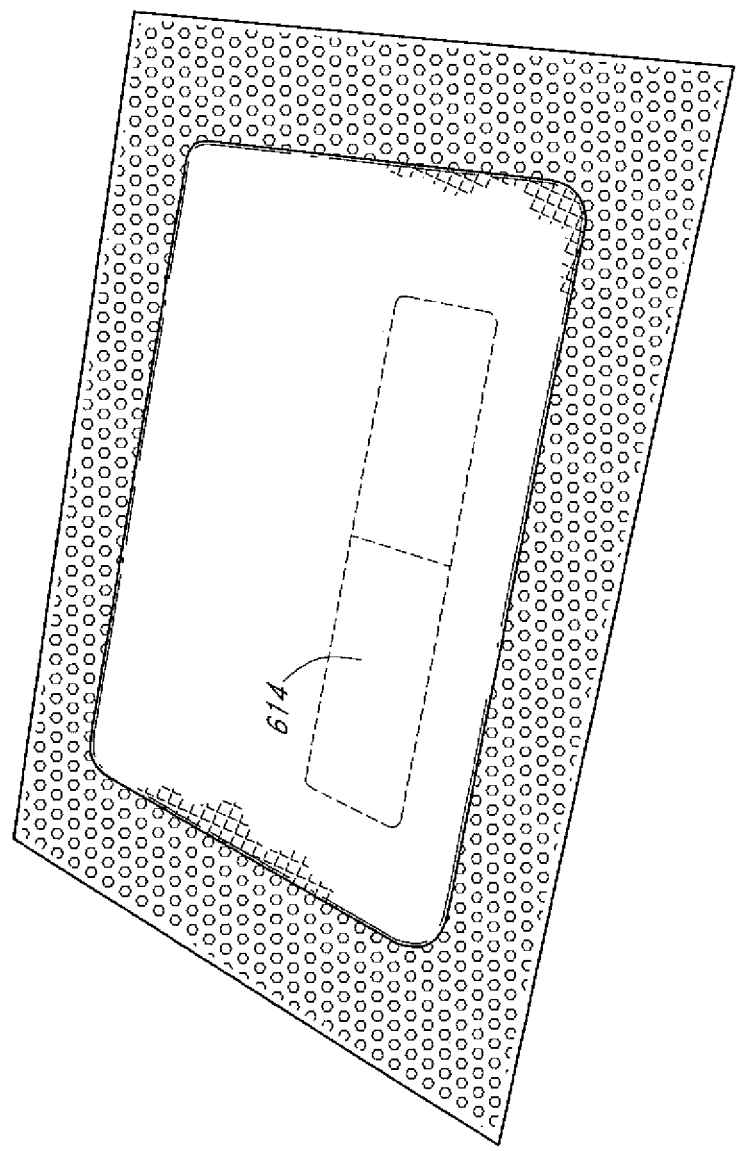
Figure 33E:
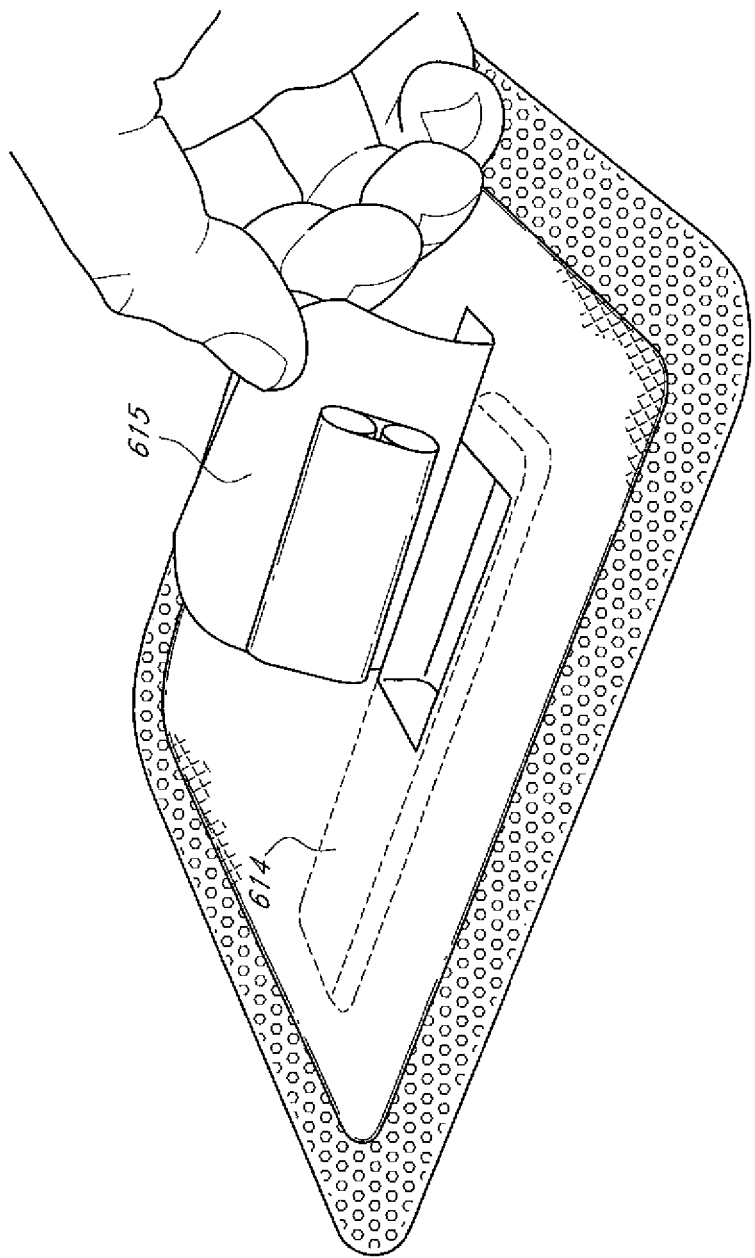

In some embodiments, as illustrated in FIG. 32, the dressing kit 590 can have a housing 598 made from a resilient, thin-walled material having an opening 599 therein can be used to hold the power source 596 within the housing 598. The power source 596 can be squeezed through the opening 599 with sufficient force to cause the opening 599 to widen sufficiently to permit the passage of the power source therethrough. Thereafter, being formed of a resilient material, the opening in the housing can reduce in size, thereby securely holding the power source 596 within the housing 598. A plug connection 600 can be used to electrically connect the power source to the pump assembly.

FIG. 33 illustrates an embodiment of a dressing kit 610 having a dressing member 612, a pump assembly 614, a power source 616, and a housing or support member 618 configured to support the power source 616 and/or a pump assembly 614. In some embodiments, the support member 618 can be configured to pass through an opening 613 in a bottom or base portion of the dressing member 612 so that the power source 616 and/or the pump assembly 614 are positioned within the opening 613. A cover layer 615, which can be removable or hingably attached to the dressing member 612, can be positioned over a top surface of the power supply 616, pump assembly 614, and/or the support member 618. In some embodiments, the power source 616 and the pump assembly 614 can be positioned within the dressing member 612 so as to be flush or beneath a top surface 612a of the dressing member 612.

The battery and/or pump module can be loaded from the bottom to give the dressing a more integrated look and feel. Further, the device could be positioned beneath the backing layer (i.e., outermost layer away from the wound).

In some embodiments, the dressing kit 610 can be configured to have conductive terminals such that, when the power source 616 is engaged therewith or positioned within the opening 613, power is automatically provided to the pump assembly 614 from the power source 616 to either provide the power to the pump assembly 614 (but requiring a switch or button to activate the pump assembly) or to power and activate the pump assembly 614 to initiate negative pressure. A bottom layer 617 can be used to secure the housing and/or power source in the opening 613 on a bottom or base surface of the dressing member 612.

Multiple batteries or sources of power can be provided with the dressing kit 610. For example, a first battery pack 616 and a second battery pack 616 can be provided with the dressing kit 610 to provide interchangeable power sources. In some embodiments, the support member 618 can be attached directly to a dressing backing layer, or can be attached to a separate support layer, such as support layer 612, to enable the pump assembly and the power source to be attached adjacent to the wound and the dressing member positioned over the wound.

In some embodiments, the housing 618 can also support or surround the pump assembly 614 if desired. However, the pump assembly 614 can be separately supported by the support layer 612. The dressing kit 610 can be configured such that the power source can be removable and disposed of and/or replaceable with a replacement power source when desired. Any of the dressing kits disclosed herein can come with a first power source and a second power source that can be used sequentially. In some embodiments, the cover layer over the top of the dressing member 612 can form a continuous layer over the opening 613 such that a separate cover tab or layer 615 is not required. The cover layer over the top of the opening can be perforated or porous to permit air exhausted from the pump to exit the dressing.

Figure 34A:
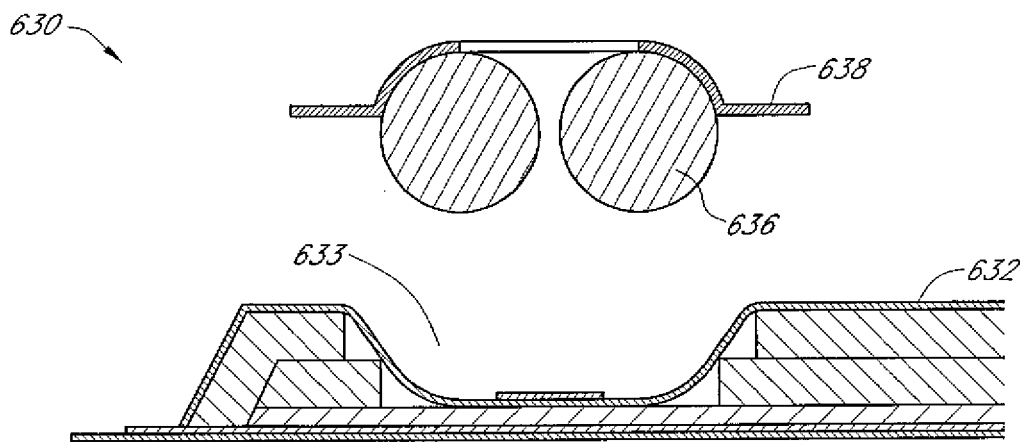
FIGS. 34A-C illustrate additional embodiments of a dressing kit for negative pressure wound therapy.
Figure 34B:
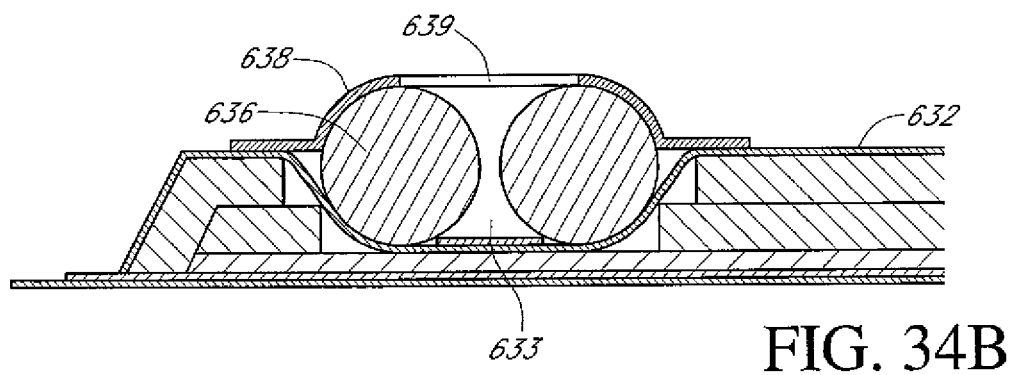

FIG. 34 illustrates an embodiment of a dressing kit 630 having a dressing member 632, a pump assembly (not illustrated), a power source 636, and a support layer 638 configured to support the power source 636 and/or a pump assembly 634. In some embodiments, the support layer 638 can be configured to cover an opening 633 in the dressing member 632 so that the power source 636 and/or the pump assembly 634 are positioned within the opening 633. In some embodiments, the power source 636 and the pump assembly 634 can be positioned within the dressing member 632 so as to be flush or beneath a top surface 632a of the dressing member 632.

In some embodiments, the dressing kit 630 can be configured to have conductive terminals such that, when the power source 636 is engaged therewith or positioned within the opening 633, power is automatically provided to the pump assembly 634 from the power source 636 to either provide the power to the pump assembly 634 (but requiring a switch or button to activate the pump assembly) or to power and activate the pump assembly 634 to initiate negative pressure.

Figure 34C:
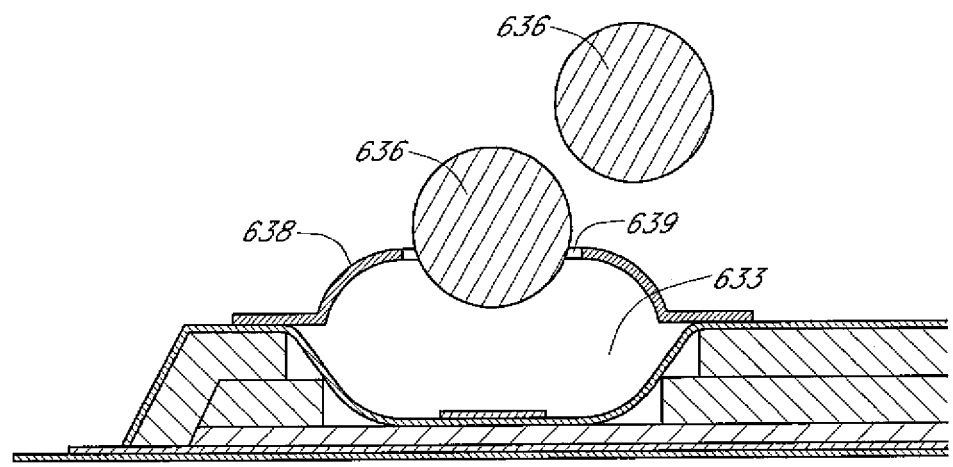

Additionally, in some embodiments, multiple batteries or sources of power can be provided with the dressing kit 630. For example, a first battery pack 636 and a second battery pack 636 can be provided with the dressing kit 630 to provide interchangeable power sources. In some embodiments, as shown in FIG. 34C, the cover layer 638 can have an opening 639 therein, the opening being configured to permit the removal of the power supply 636 from the opening or compartment 633 when disposal or replacement of the power supply is desired.

The pump assembly can also be supported within the opening 633 and can be covered by the cover layer 638. The cover layer 638 can be perforated to permit exhaust gas to exit the opening or compartment 633. In some embodiments, the cover layer over the top of the dressing member 632 can form a continuous layer over the opening 633 such that a separate cover tab or layer 638 is not required. The cover layer over the top of the opening can be perforated or porous to permit air exhausted from the pump to exit the dressing.

FIG. 35 illustrates another embodiment of a dressing kit 650 having a dressing member 652, a pump assembly (not illustrated), a power source 656, and a support layer 658 configured to support the power source 656 and/or a pump assembly 654 over the cover layer 653 of the dressing. In some embodiments, the support layer 658 can be configured to cover the power source 656 and/or the pump assembly 654. The support layer 658 can have a tabbed portion 658a configured to permit a user to grasp the support layer 658 for removal thereof. The support layer 658 can be fastened to the top layer 653 of the dressing member 652 using adhesive 659. When the power source 656 is desired to be removed for replacement or disposal, a user can grasp the support layer 658 by the tabbed portion 658a and lift the support layer 658 off of the power source 656. In some embodiments, where a pump assembly 654 can be supported under the support layer 658, an opening 660 formed in the upper layer 653 of the dressing member 652 can permit the passage of gas from within the dressing member or between the dressing member and the wound to pass through the pump assembly 654 and out of the dressing kit 650.

In some embodiments, the dressing kit 650 can be configured to have conductive terminals such that, when the support layer 658 is closed against the upper layer 653 of the dressing 652 on both sides of the power source 656, power is then provided to the pump assembly 654 from the power source 656 to either provide the power to the pump assembly 654 (but requiring a switch or button to activate the pump assembly) or to power and activate the pump assembly 654 to initiate negative pressure.

Additionally, in some embodiments, multiple batteries or sources of power can be provided with the dressing kit 650. For example, a first battery pack 656 and a second battery pack 656 can be provided with the dressing kit 650 to provide interchangeable power sources. The cover layer 658 can be perforated to permit exhaust gas to exit through the cover layer 658. In some embodiments, the cover layer over the top of the dressing member 652 can form a continuous layer over the opening 653 such that a separate cover tab or layer 658 is not required.

Figure 36B:
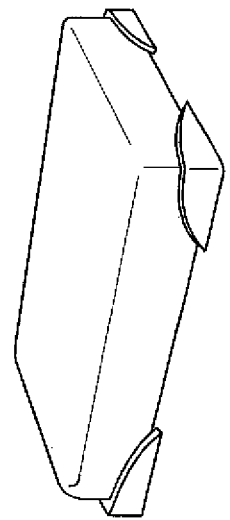
FIGS. 36A-B illustrate an additional embodiment of a dressing kit for negative pressure wound therapy.
Figure 36A:
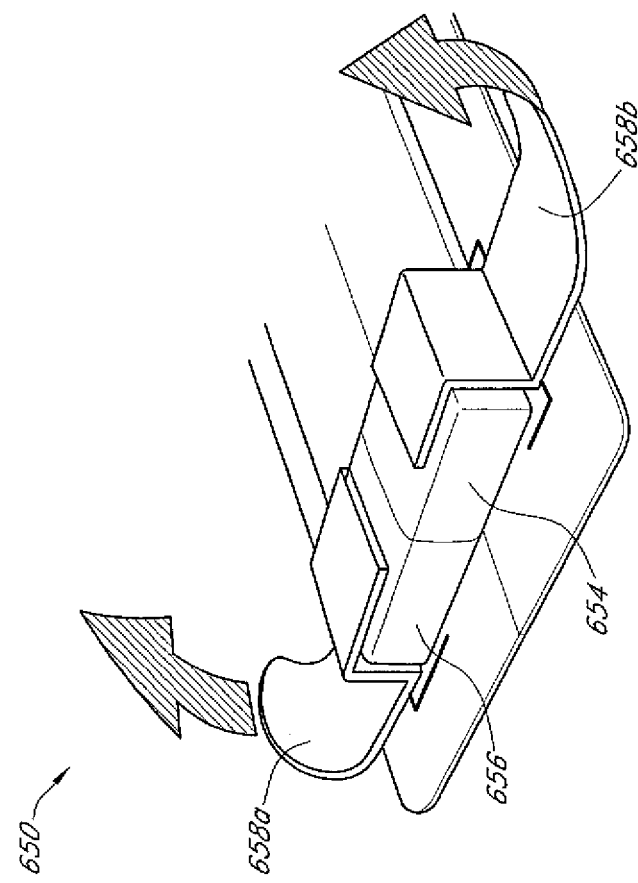

As illustrated in FIG. 36, some embodiments of the dressing kit 650 can have multiple support layers were release tabs 658 used to releasably fasten the pump assembly 654 and/or the power source 656 to the dressing. For example, as illustrated in FIG. 36, a first tab 658a and the second tab 658b can be positioned on mutually opposing ends of a housing used to support the pump assembly 654 and the power supply 656.

Figure 37A:
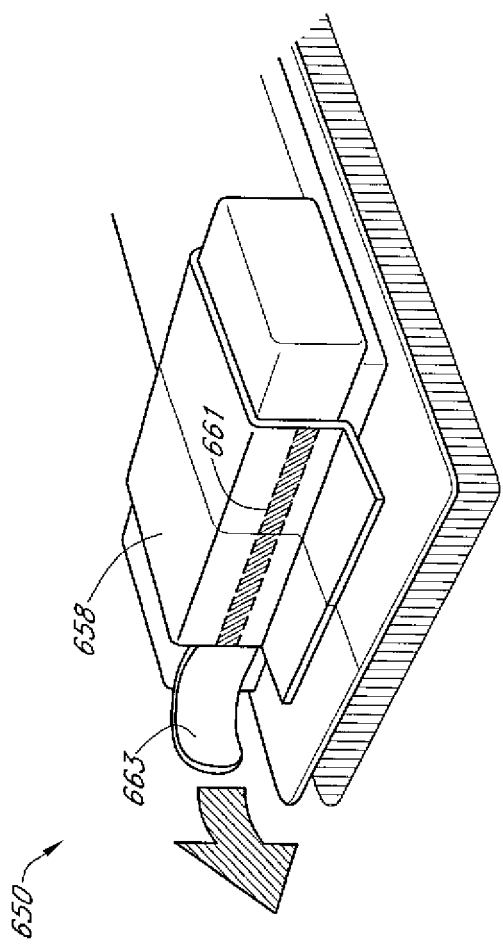
FIGS. 37A-B illustrate an additional embodiment of a dressing kit for negative pressure wound therapy.
Figure 37B:
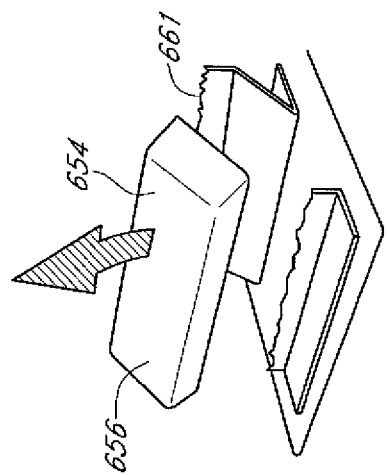

Furthermore, in some embodiments, the dressing kit can have a tearable strap covering at least one of a pump assembly and a power source that can be perforated or slit to facilitate the tearing of the strap. Additionally, the strap could be non-tearable but could be adhered to the supporting surface using Velcro or other similar adhesive materials. With some embodiments of the pull-tab arrangement, the batteries can be removed by pulling on a label or pull tab. This can be achieved with either side or end ejection. As illustrated in FIG. 37, the cover layer 658 of some embodiments of the dressing kit 650 or any other dressing kit disclosed herein can have one or more perforated or tearable portions 661 configured to tear open to permit the removal of the pump assembly 654 and/or the power source 656. A tab 663 can be grasped to initiate the tear.

Figure 38:
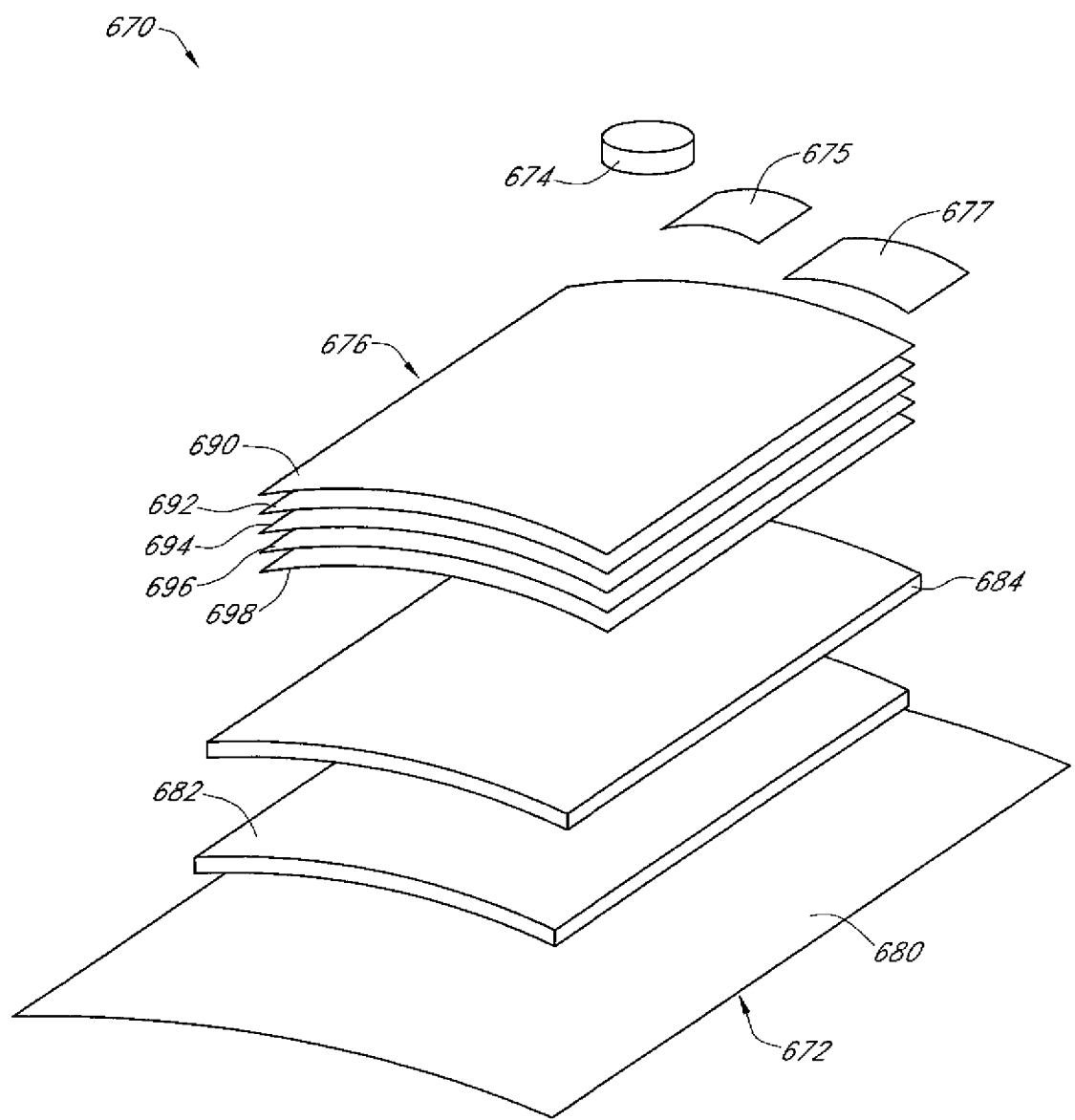
FIG. 38 illustrates an additional embodiment of a dressing kit for negative pressure wound therapy.

FIG. 38 illustrates another embodiment of a dressing kit 670 having a dressing member 672, a pump assembly 674, and a power source 676. In any of the dressing kit embodiments disclosed herein, the dressing member 672 can but is not required to have a wound contact layer 680, one or more layers of spacer material 682 (also referred to herein as a transmission layer or layers), one or more layers of absorbent material 684, and a cover layer (not illustrated) configured to cover at least the layer of spacer material 682 and the layer of absorbent material 682. Additionally, in any of the embodiments disclosed herein, the power source can have a flexible battery 676 configured to cover a portion of the absorption and transmission layers.

In some embodiments, the flexible battery 676 can have a plurality of different material layers coupled with one another. For example, in some embodiments, the flexible battery 676 can have a current collector layer 690, above an anode layer 692, followed by a separator layer 694, the cathode layer 696, and finally a current collector layer 698 on the bottom thereof. Additionally, any embodiments of the dressing kit disclosed herein can be powered by one or more flexible printed batteries based on the technology developed by Imprint Energy, or by one or more carbon zinc flexible batteries manufactured by Blue Spark Technologies, built, such as any of those described above. The size of the flexible battery 676 can depend on the power requirements of the pump assembly and duration desired for the negative pressure wound therapy. In some embodiments, however, the flexible battery 676 can be approximately the same size as the absorption layers in the dressing and can be configured to cover the absorption layers in the dressing.

Further, in any of the dressing kit embodiments disclosed herein, such as dressing kit 670, the pump assembly 674 can be controlled by a flexible control board. Further, any dressing kit embodiments disclosed herein can further have an organic light emitting diode ("OLED") display or other suitable interface display.

Figure 39:
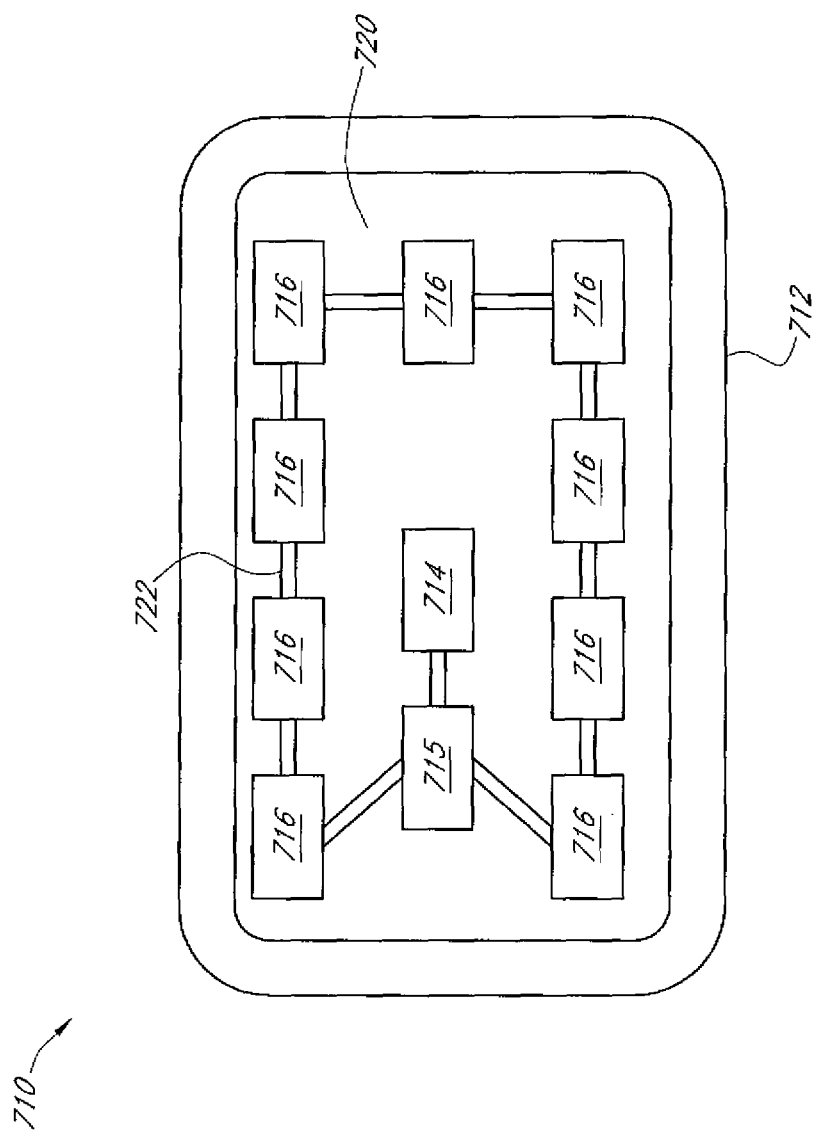
FIG. 39 illustrates an additional embodiment of a dressing kit for negative pressure wound therapy.

FIG. 39 is an illustration of another embodiment of a dressing kit 710 configured to be positioned over a wound. The dressing kit 710 can have any of the features of any other dressing kits disclosed herein. In some embodiments, the dressing kit 710 can have a dressing member 712 a pump assembly 714 powered by a flexible PCB 715, and plurality of power sources 716 position about the dressing member 712. For example, in some embodiments, each of the power sources 716 can be a flexible battery such as a flexible printed battery, a thin lithium battery, a photovoltaic cell, and/or any other suitable power source. The plurality of power sources 716 can be interconnected by electrical wiring 722 in any suitable configuration or arrangement to permit the optimal level of current flow and voltage to the pump assembly. The electrical wiring 722 can be connected to the control board 715 configured to control an operation of the pump assembly 714.

Figure 40:
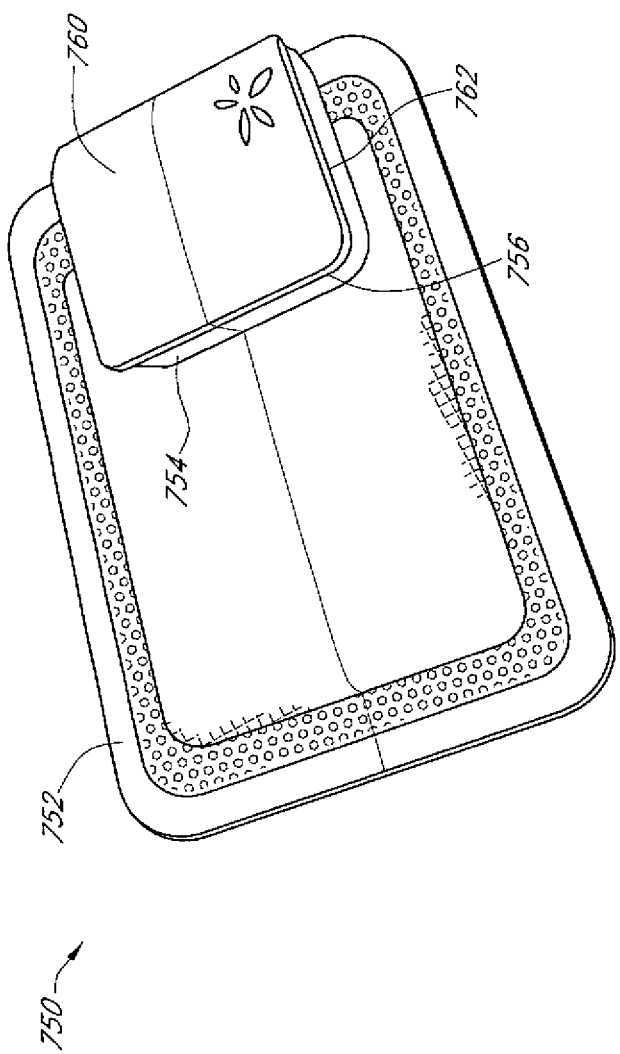
FIG. 40 illustrates an additional embodiment of a dressing kit for negative pressure wound therapy.

FIG. 40 illustrates another embodiment of a dressing kit 750 having a dressing member 752, a pump assembly 754, and a power source 756. The dressing kit can be packaged with the pump assembly 754 and the power source 756 positioned on top of the dressing member 752. The dressing kit 750 is configured such that the pump assembly 754 and the power source 756 can remain positioned above the dressing member during treatment. Or, alternatively and at the user's preference, releasable backing layer 760 can be removed from the pump assembly 754 and the power source 756 so that the pump assembly 754 and the power source 756 can be flipped or folded out and adhere to the skin adjacent to the wound dressing member 752. A conduit can communicate the negative pressure generated by the pump assembly 754 to the dressing member 772 and/or to the space between the dressing member 772 and the wound.

Figure 41A:
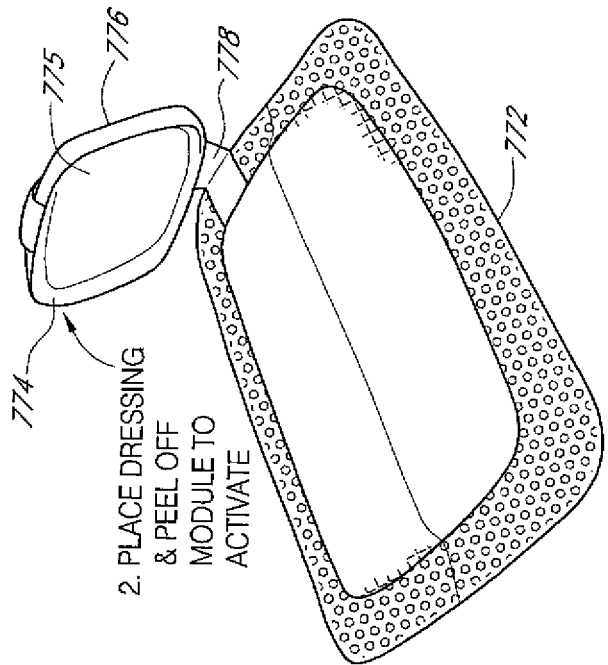
FIGS. 41A-C illustrate an additional embodiment of a dressing kit for negative pressure wound therapy.
Figure 41B:
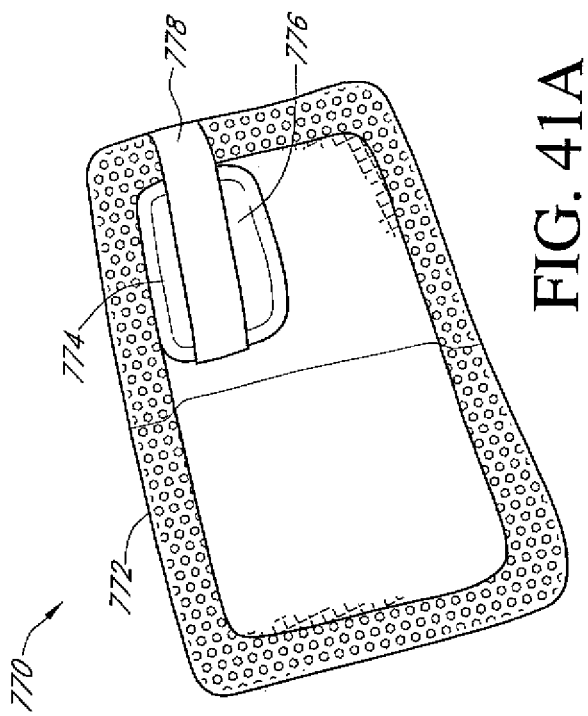
Figure 41C:
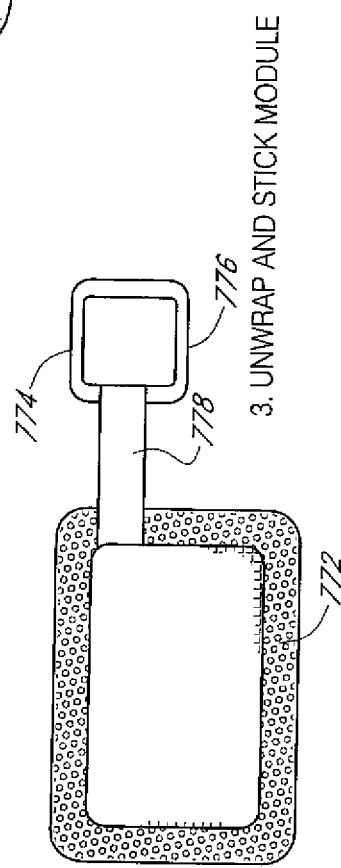

FIG. 41 illustrates another embodiment of a dressing kit 770 having a dressing member 772, a pump assembly 774, and a power source 776. The dressing kit can be packaged with the pump assembly 774 and the power source 776 positioned on top of the dressing member 772. The dressing kit 770 is configured such that the pump assembly 774 and the power source 776 can remain positioned above the dressing member during treatment. Or, alternatively and at the user's preference, releasable backing layer 780 can be removed from the pump assembly 774 and the power source 776 so that the pump assembly 774 and the power source 776 can be flipped or folded out and adhere to the skin adjacent to the wound dressing member 772. A flexible conduit 778 can communicate the negative pressure generated by the pump assembly 774 to the dressing member 772 and/or to the space between the dressing member 772 and the wound. A film layer 775 adhered to a surface of the power source or the pump assembly, or a non-conductive material separating electrical connections between the power source and the pump assembly can be removed to activate the pump assembly.

In any embodiments disclosed herein, including the embodiment illustrated in FIG. 41, the conduit 778 can have a foam, a transmission layer or 3d knit fabric, and/or other porous material therein to prevent or significantly prevent the collapse of the conduit during operation from kinking, crushing, etc., while permitting the passage of fluids therethrough. For example and without limitation, in any embodiments disclosed herein, the conduit can have a top and a bottom layer constructed from a liquid impermeable material, a 3D knitted or 3D fabric material located between the top and bottom layers, an opening in fluid communication with the 3D knitted or 3D fabric material, and an elongate channel extending between the top and bottom layers containing the 3D knitted or 3D fabric material. The opening can be in fluid communication with any of the transmission and/or absorption layers within the dressing member. In any embodiments disclosed herein, the conduit can be integrally formed with the remainder of the dressing member. Additionally, in any embodiments disclosed herein, the conduit can have a width from approximately 0.5 inches or less to approximately 0.75 inches or more, from approximately 0.75 inch to approximately 1.5 inches or more, having a low profile height of from approximately 0.1 or less to approximately 0.25 or more inches.

Figure 42:
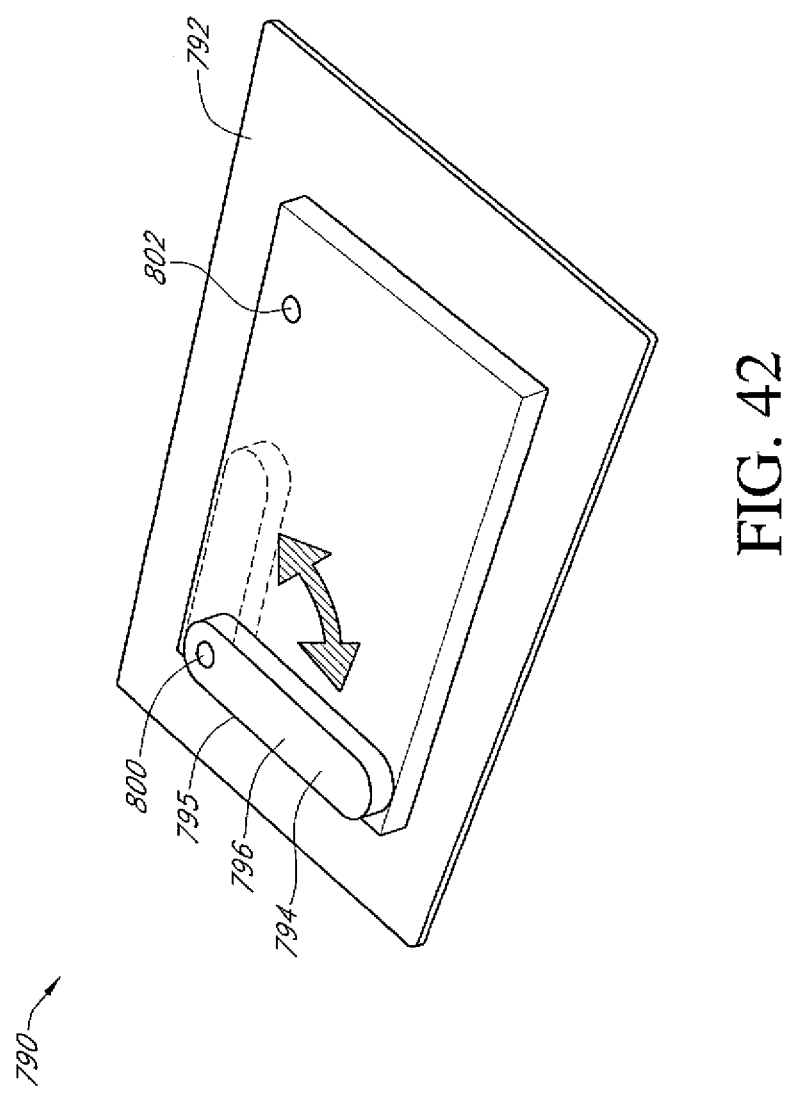
FIG. 42 illustrates an additional embodiment of a dressing kit for negative pressure wound therapy.

FIG. 42 illustrates another embodiment of a dressing kit 790 having a dressing member 792, a pump assembly 794, and a power source 796. The dressing kit can be configured such that the pump assembly 794 and the power source 796 are supported within a module 795 that is rotatable an axis. In some embodiments, the axis of rotation can be coincident with a port member 800 configured to communicate the negative pressure generated by the pump assembly to the dressing. Thus, in some embodiments, the dressing kit 790 can be configured such that the battery 796 and/or pump assembly 794 are pivotably positionable on the dressing so that the position and/or orientation of the battery module and/or pump assembly can be adjusted or adjustable depending on the contour of the body. Additionally, a second sealable port 802 can be formed in the top layer of the dressing member 792 to permit the user to select which port to use for the pump assembly 794. An angular orientation of the module 795 can be adjusted in position from a first orientation to a second orientation. In the first orientation, the module 795 can be positioned along a lengthwise edge or a first edge of the dressing member 792. In a second orientation, the module 795 can be positioned along a short edge or a second edge of the dressing member 792. Additionally, the module 795 can be positioned at any desired orientation between the first and second positions or orientations.

Figure 43C:
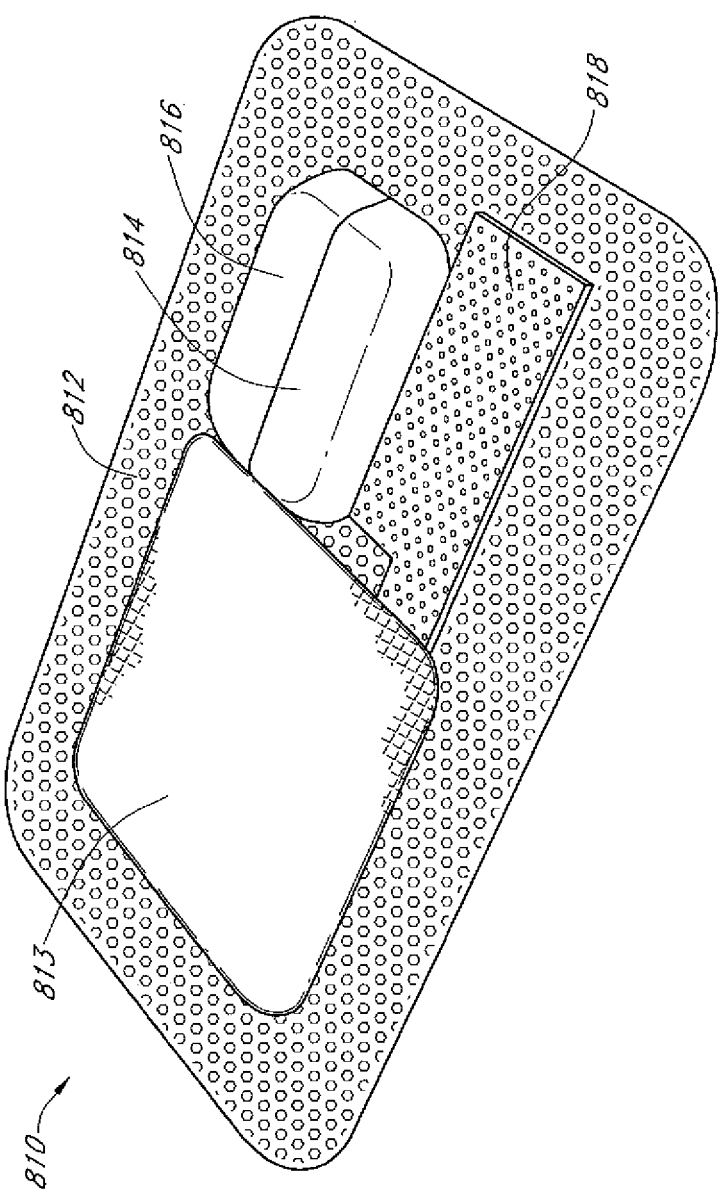
Figure 43D:
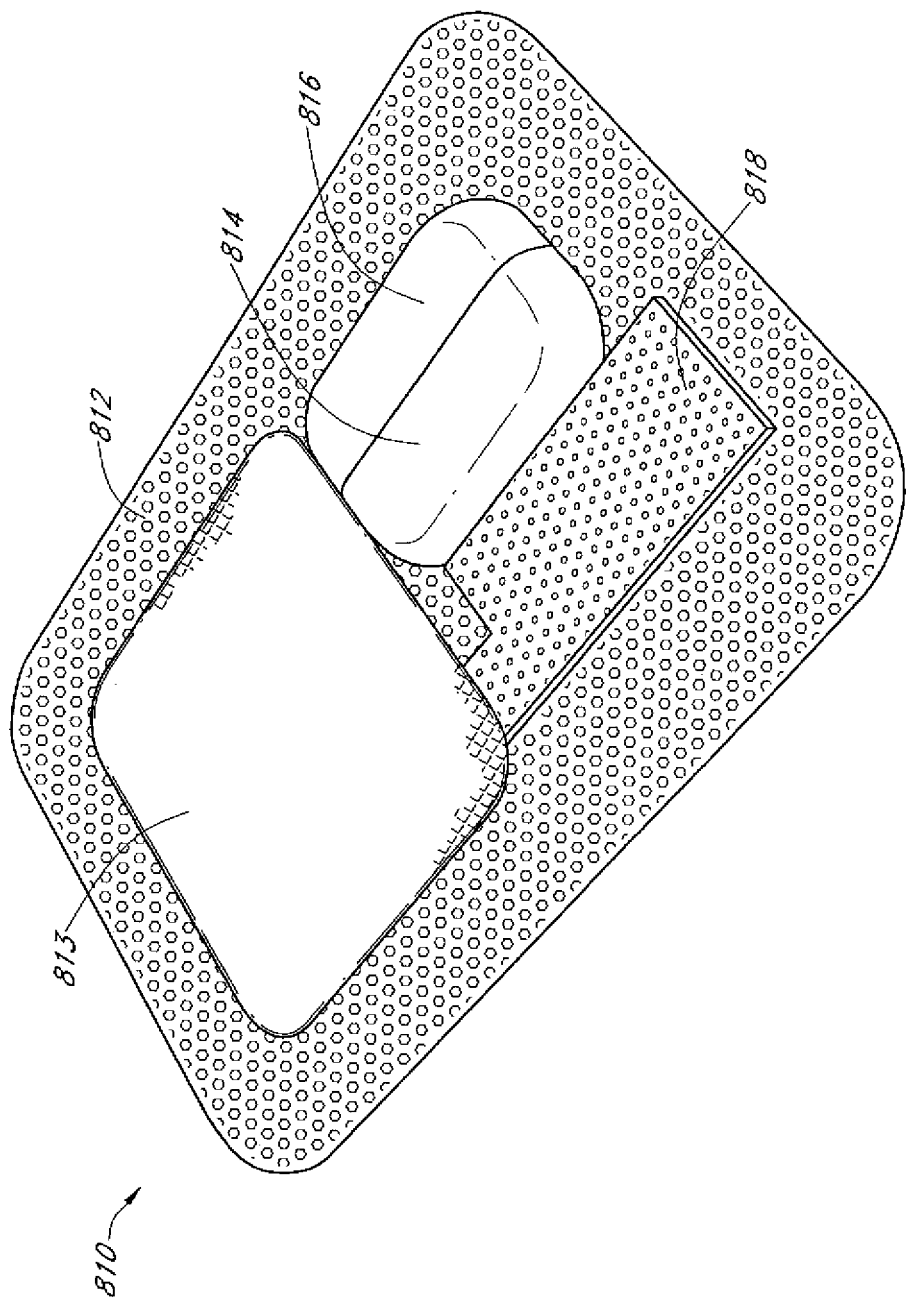
Figure 43E:
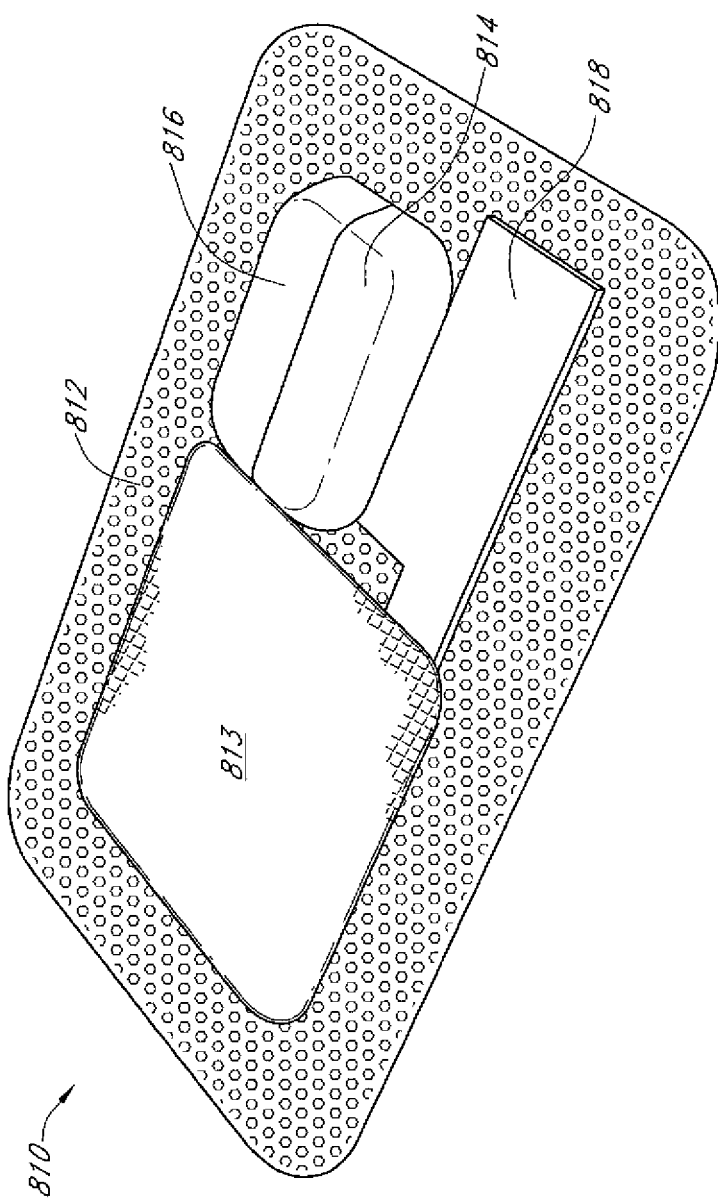

FIG. 43 illustrates another embodiment of a dressing kit 810 having a dressing member 812 having one or more absorption and/or transmission layers 813, a pump assembly 814, and a power source 816. The embodiment illustrated in FIG. 43 can have a length of conduit 818 between the pump and the dressing that permits the dressing to be mounted adjacent to or on top of the dressing. The dressing kit can be packaged with the pump assembly 814 and the power source 816 positioned on top of the dressing member 812 or adjacent to the dressing member. The dressing kit 810 is configured such that the pump assembly 814 and the power source 816 can remain positioned above the dressing member during treatment, being adhered or removably fastened to the top of the dressing using a Velcro, adhesive, one or more clips, a pouch, or otherwise. Or, alternatively and at the user's preference, the pump assembly 814 and/or the power source 816 can be moved away from the wound so that the pump assembly 814 and the power source 816 can be positioned remote to the dressing 812. For example, the pump assembly 814 and/or the power source 816 can be adhered to the skin adjacent to the wound dressing member 812.

A flexible conduit 818 can communicate the negative pressure generated by the pump assembly 814 to the dressing member 812 and/or to the space between the dressing member 812 and the wound. In any embodiments disclosed herein, including the embodiment illustrated in FIG. 43, the conduit 818 can have a foam, a transmission layer or 3d knit fabric, and/or other porous material therein to prevent or significantly prevent the collapse of the conduit during operation from kinking, crushing, etc., while permitting the passage of fluids therethrough. In some embodiments, with reference to FIGS 43C-43E, the conduit 818 can comprise a small sheet of a transmission material forming a conduit between the pump assembly 814 and the absorption material 812. In this arrangement, the transmission material can have a foam, a transmission layer or 3d knit fabric, and/or other porous material therein to prevent or significantly prevent the collapse of the conduit during operation from kinking, crushing, etc., and can have a cross-sectional area transverse to the flow direction that is approximately one-third the width of the absorption and/or transmission layers 813, or from approximately one-quarter to approximate one-half the width of the absorption and/or transmission layers 812. This extra width of the conduit 818 can help prevent blockage of the conduit that may affect the transmission of reduced pressure to the dressing layers 813.

In any embodiments, the dressing layers 813, pump assembly 814, the power source 816, and the conduit 818 can be supported by the dressing member 812. Additionally, the conduit 818 can have any of the materials, features, or other details of any of the other conduit arrangements disclosed herein.

Figure 44B:
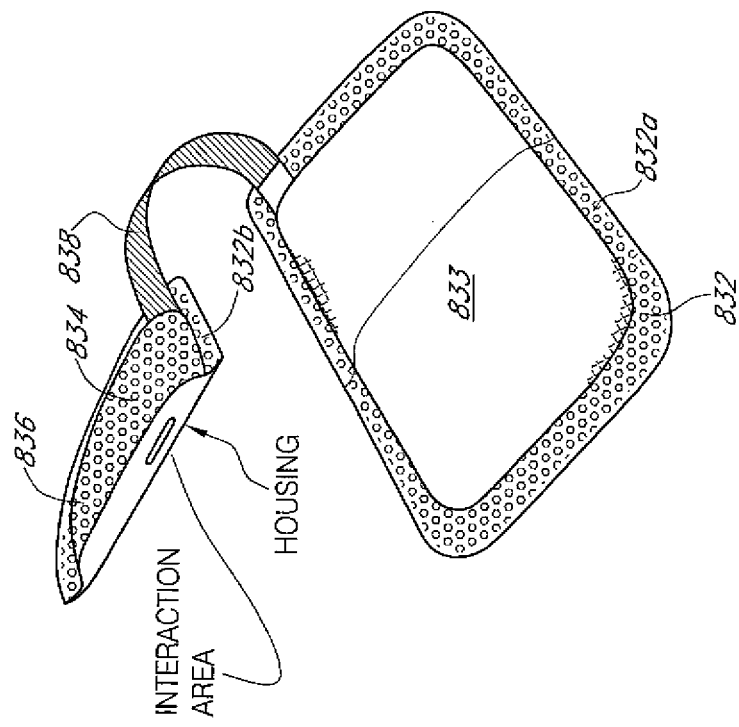
FIGS. 44A-B illustrate additional embodiments of a dressing kit for negative pressure wound therapy.
Figure 44A:
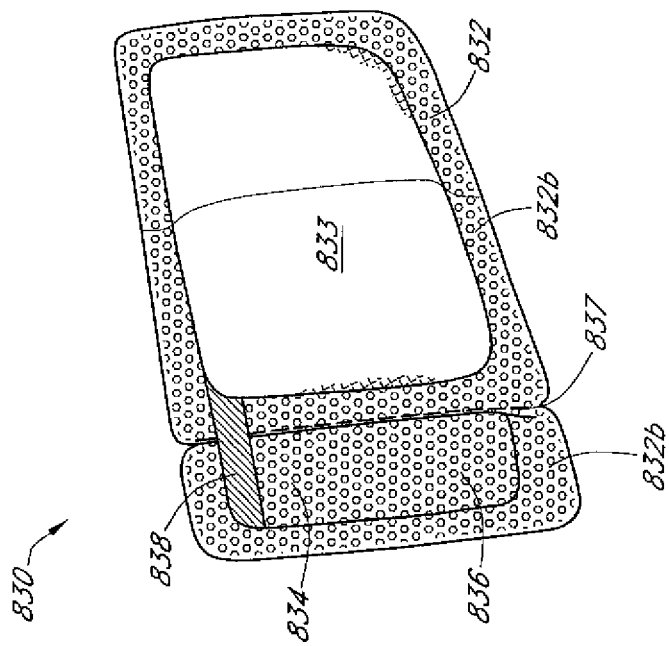

FIG. 44 illustrates another embodiment of a dressing kit 830 having a dressing member 832 having one or more absorption and/or transmission layers 833, a pump assembly 834, and a power source 836. The dressing kit can be packaged with the pump assembly 834 and the power source 836 positioned adjacent to one or more absorption and/or transmission layers 833 but being removably attached to the dressing member 832 supporting the one or more absorption and/or transmission layers 833.

The dressing kit 830 can be configured such that the pump assembly 834 and the power source 836 can remain positioned adjacent to the dressing member 832 during treatment. Or, alternatively and at the user's preference, the pump assembly 834 and the power source 836 can be positioned on a portion of the dressing member 832 that can be detached from the portion of the dressing member 832 supporting the one or more absorption and/or transmission layers 833. For example, in some embodiments, the one or more absorption and/or transmission layers 833 can be positioned on a first portion 832a of the dressing member 812, and the pump assembly 834 and the power source 836 can be positioned on a second portion 832b of the dressing member 832 that can be detached from the first portion 832a of the dressing member 832. In some embodiments, the dressing member 832 can have a perforation, indentations, reduced thickness, or one or more cutouts between the first portion 832a and the second portion 832b of the dressing member 832 to facilitate the detachability of the first portion 832a from the second portion 832b of the dressing. This can facilitate the detachment of the second portion 832b of the dressing 832 from the first portion 832a of the dressing for placement of the second portion 832b of the dressing 832 in a desired location spaced apart from the first portion 832a of the dressing, and hence, spaced apart from the wound. The second portion 832b of the dressing member 832 can have a different adhesive thereon as compared to the adhesive on the first portion 832a of the dressing member 832 for adhesion to the skin or otherwise.

A flexible conduit 838 can communicate the negative pressure generated by the pump assembly 834 to the dressing member 832 and/or to the space between the dressing member 832 and the wound. A film layer adhered to a surface of the power source or the pump assembly, or a non-conductive material separating electrical connections between the power source and the pump assembly can be removed to activate the pump assembly.

In any embodiments disclosed herein, including the embodiment illustrated in FIG. 44, the conduit 838 can have a foam, a transmission layer or 3d knit fabric, and/or other porous material therein to prevent or significantly prevent the collapse of the conduit during operation from kinking, crushing, etc., while permitting the passage of fluids therethrough, and can have a width from approximately 0.5 inches or less to approximately 0.75 inches or more, from approximately 0.75 inch to approximately 1.5 inches or more, having a low profile height of from approximately 0.1 or less to approximately 0.25 or more inches.

FIG. 45 illustrates another embodiment of a dressing kit 850 having a dressing member 852, a pump assembly 854, and a power source 856. In some embodiments, the dressing kit 850 can have any of the features, details, or components of any of the other dressing kit embodiments disclosed herein. In any dressing kit or pump assembly embodiments herein, including the embodiment of the dressing kit 850 shown in FIG. 45, the pump assembly can have one or more indicator lights (such as LED indicator lights), and one or more control buttons or switches. The dressing kit can be packaged with the pump assembly 854 and the power source 856 positioned adjacent to the dressing layers 853. The dressing kit 850 can be configured such that the pump assembly 854 and the power source 856 can remain positioned adjacent to the absorption and/or transmission layers 853 (collectively referred to as the dressing layers) during treatment. Or, alternatively and at the user's preference, the pump assembly 854 and the power source 856 can be positioned on a portion of the dressing member 852 that can be detached from the portion of the dressing member 852 supporting the one or more absorption and/or transmission layers 853.

For example, in any dressing kit embodiments disclosed herein, the one or more absorption and/or transmission layers 853 can be positioned on a first portion 852a of the dressing member 812, and the pump assembly 854 and the power source 856 can be positioned on a second portion 852b of the dressing member 852 that can be detached from the first portion 852a of the dressing member 852. Additionally, in any embodiments disclosed herein, the conduit 858 can be positioned on a third portion 852c of the dressing member 852 that can be detached from the first portion 852a of the dressing member 852 and/or the second portion 852b of the dressing member 852.

In any embodiments, the dressing member 852 can have one or more intermittent or continuous scores, perforation, indentations, notches, cuts, cutouts, partial thickness cuts, or reduced thickness 855 between the first portion 852a and the second portion 852b of the dressing member 852, between the second portion 852b and the third portion 852c of the dressing member 852, and/or between the first portion 852a and the third portion 852c of the dressing member 852 to facilitate the detachability of the first portion 852a from the second portion 852b of the dressing member 852. This can facilitate the detachment of the second portion 852b of the dressing member 852 from the first portion 852a of the dressing member for placement of the second portion 852b of the dressing 852 in a desired location spaced apart from the first portion 852a of the dressing, and hence, spaced apart from the wound. The second portion 852b of the dressing member 852 can have a different adhesive thereon as compared to the adhesive on the first portion 852a of the dressing member 852 for adhesion to the skin or otherwise. Further, as with any embodiments disclosed herein, the pump assembly 854 can have pull tabs or strips configured to activate the pump or permit the conduction of current from the power source to the pump assembly.

Additionally, as illustrated in FIG. 45, a conduit 858 can communicate the negative pressure produced by the pump assembly 858 to the dressing layers 853. The conduit can be attached to or formed as part of the dressing cover layer used to cover the dressing layers 813. In some embodiments, at least one of an outer or top layer used to form the conduit in any embodiments disclosed herein can be vapor permeable. In this configuration, the conduit 858 can be sealed along a length thereof and can have perforations along the length thereof so that any desired length of conduit 858 can be detached from the dressing member 852, with the remaining portion of the conduit 858 remaining attached to the dressing member 852, as illustrated in FIG. 45B.

For example, in some embodiments, as illustrated in FIG. 45A, the dressing member 852 have a plurality of perforations, including without limitation first perforation 855a, second perforation 855b, third perforation 855c, and so on. A user can tear and detach the conduit 858 along any desired number of the perforations to permit any desired length of conduit 858, while the remaining portion of the conduit remains removably attached to the dressing member 852. In any embodiments, the perforations 855 can be arranged in a parallel orientation, as illustrated in FIGS. 45A and 45B. Alternatively or additionally, one or more perforations 855 can be arranged about a perimeter of the dressing member 852, which can surround the dressing layers 853, as illustrated in FIG. 45C.

Additionally, with reference to FIG. 45C, the dressing member 852 can support a plurality of power sources (which can be any of the flexible battery or any other power source embodiments disclosed herein) 856 distributed about a first portion 852a of the dressing member 852, either under, within or on top of any of the layers, materials, or members comprising the dressing layers 853 or dressing member 852. The power sources 856 can be interconnected in any desired fashion using one or more electrical connectors or wires 857. In some embodiments, the wire connectors 857 can extend along or within the conduit 858 to provide power to the pump assembly 854 located on the second portion 852b of the dressing member 852. The pump assembly 854 in any embodiments disclosed herein, including dressing kit embodiment 850, can be a miniature pump have a voice coil, a diaphragm, or otherwise.

In any embodiments disclosed herein, including the embodiment illustrated in FIG. 45, the conduit 858 can have a foam, a transmission layer or 3d knit fabric, and/or other porous material therein to prevent or significantly prevent the collapse of the conduit during operation from kinking, crushing, etc., while permitting the passage of fluids therethrough, and can have a width from approximately 0.5 inches or less to approximately 0.75 inches or more, from approximately 0.75 inch to approximately 1.5 inches or more, having a low profile height of from approximately 0.1 or less to approximately 0.25 or more inches.

In any embodiments disclosed herein, the conduit can be formed of two layers of liquid and air impervious material (such as a thin polymer film) and have one or more layers of foam or other porous material to prevent the conduit from collapsing, formed in a circular, square, or other shaped length of material having foam or other porous material therein. As such, the dressing can be configured such that a user can adjust the length of the conduit by the amount of the conduit removed from the dressing.

Additionally, with reference to the dressing kit embodiment 870 illustrated in FIG. 46, in any of the embodiments disclosed herein, the dressing kit can have a conduit 878 that is arranged in a spiral or helical arrangement adjacent to the one of more dressing layers 873 of the dressing member 872. The conduit can be spirally wound about the pump assembly and/or power source. In some embodiments, the dressing kit 870 can have any of the features, details, or components of any of the other dressing kit embodiments disclosed herein, including without limitation those of dressing kit 850, including without limitation any of the details regarding the power source, pump assembly, dressing member, or conduit described with respect to any of the other embodiments, such as for dressing kit 850. For example, in some embodiments, the conduit can be perforated along a length thereof for selective detachment from the dressing member 872.

In any of these arrangements, the conduit 878 can be unwound or extended to permit the user to select the appropriate length of the conduit 878. The dressing can be used in the completely wound up arrangement illustrated in FIG. 45, or can be partially unwound and used with the conduit partially wound up around the pump assembly 878, or the conduit 878 can be fully extended such that the pump assembly is positioned apart from the dressing. A bottom surface of the pump assembly can be coated with an acrylic or other suitable adhesive or fastener (such as any of the other fasteners disclosed herein) for attaching the pump and/or conduit to the body or even to the dressing member 872, as desired.

FIG. 47 illustrates another embodiment of a dressing kit 890 having a dressing member 892, a pump assembly 894, and a power source 896. In some embodiments, the dressing kit 890 can have any of the features, details, or components of any of the other dressing kit embodiments disclosed herein. The dressing kit can be packaged with the pump assembly 894 and/or the power source 896 positioned adjacent to the dressing layers 893. In some embodiments, the power source can be separable from the dressing member 892 and positionable in any desired position on the dressing member 892 and/or on the body adjacent to the dressing member or wound or otherwise. The power source 896 can be connected to the pump assembly 894 using a wired connection 897 that can have a connector for easy removal of the power source 896 for disposal or replacement.

Additionally, the dressing can be configured such that a perforated or weakened band of material is routed around the portion of the dressing that supports the battery. This can form a detachable portion of the dressing that supports the battery. Such configurations can facilitate battery removal, replacement, and/or proper disposal. Additionally, the battery module can be supported on a removable or separate portion of the dressing that tape or otherwise adhered to the main portion of the dressing and is easily removed therefrom for easy disposal of the battery module. The portion of the dressing that can support the battery module can be connected to the remaining portion of the dressing by tape, a local pad, or otherwise. The pump can be supported by the main dressing area. This could have a benefit for sterilization or sterilization of particular parts of the dressing, and could permit frequent (e.g., daily) battery changes. Additionally, in some embodiments, the batteries can be supported in a battery tray that can be easily supported by the dressing. The battery tray can be configured to be snapped into and out of the receiving portion of the dressing or pump assembly. This can reduce the wall thickness of the battery module and battery compartment.

Figure 48B:
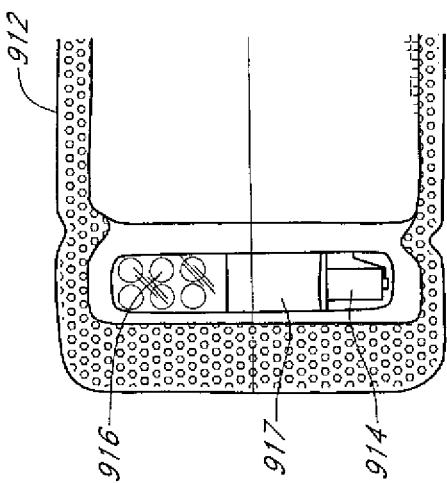
FIGS. 48A-B illustrate an additional embodiment of a dressing kit for negative pressure wound therapy.
Figure 48A:
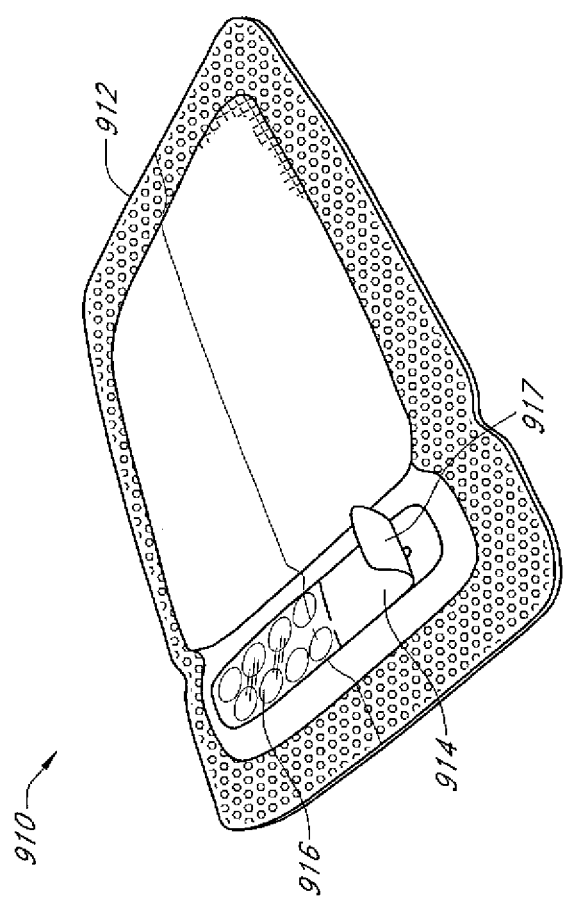

In the embodiment of the dressing kit 910 illustrated in FIG. 48, the battery module can have one or more zinc air activated batteries 916 as the power source for the pump assembly 914. In this arrangement, removing a pull-tab 917 so as to expose the batteries 916 to air will activate the batteries 916 and start the operation of the pump 914. The pull-tab or label 917 can cover the openings or air passageways in communication with the batteries 916 and can be peeled back or removed to activate or re-activate the batteries 916. The pull-tab 917 can be configured to cover only a portion of the dressing member 912 or the battery module 916, or can be integral to larger dressing support for added stiffness during application of the dressing to the body. Any of the dressing kit embodiments disclosed herein can use any of the features, details, or components of the dressing kit 910 therein, including without limitation the air activated batteries.

Figure 49:
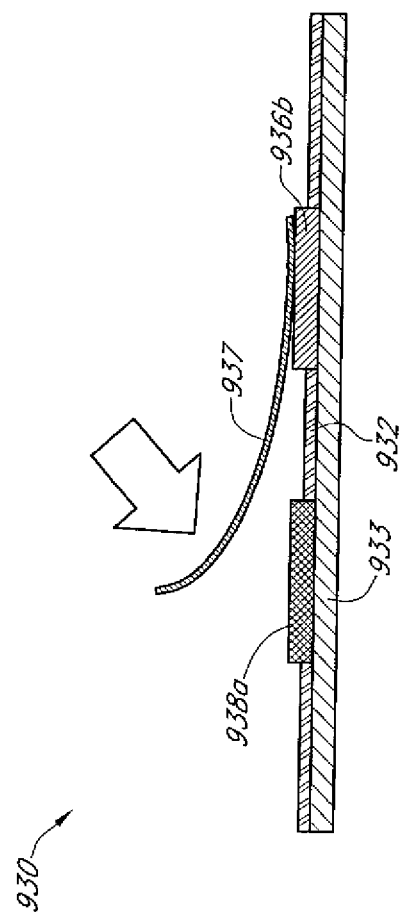
FIG. 49 illustrates an embodiment of a switch or activation mechanism.

With reference to FIG. 49, which illustrates a dressing kit 930 having a dressing member 932, and a pump assembly having a PCB 933, the power source or pump assembly can have one or more conductive labels 937 that, when in a first position, do not provide an electrical connection between a first terminal 938a and a second terminal 938b supported by the dressing member 932 or the PCB 933. When the conductive label or tab 937 is moved to a second position, the conductive tab 937 can provide an electrical connection between the first terminal 938a and the second terminal 938b, so as to activate the pump assembly. The packaging supporting the dressing can be configured such that such conductive label is held fixed in the first position to ensure that the batteries are not electrically connected to the pump assembly or other components during sterilization or prior to application to a patient or user. The conductive label 937 could be used as a pause button, or to terminate the operation of the pump.

In any dressing kit embodiments disclosed herein, the dressing kit can have one or more pull tabs (such as pull tabs 957 illustrated in FIGS. 50A-D) configured to activate and deactivate the pump assembly. In this arrangement, each pull tab 957 can be configured to be positioned, or have a portion thereof that is positioned, between a first terminal 958a and a second terminal 958b to selectively control an activation of the pump assembly 954. When the pull tab 957 is positioned between the first terminal 958a and the second terminal 958b, thereby separating the first and second terminals 958a, 958b, no power will be provided to the pump assembly 954. By retracting the pull tab 957, the first and second terminals 958a, 958b can be placed in contact with one another such that power can be provided to the pump assembly.

Figure 50B:
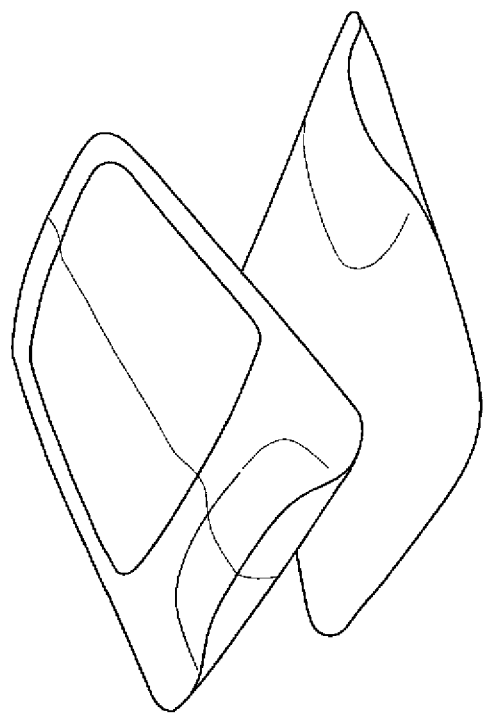
FIGS. 50A-D illustrate an embodiment of a switch or activation mechanism.
Figure 50A:
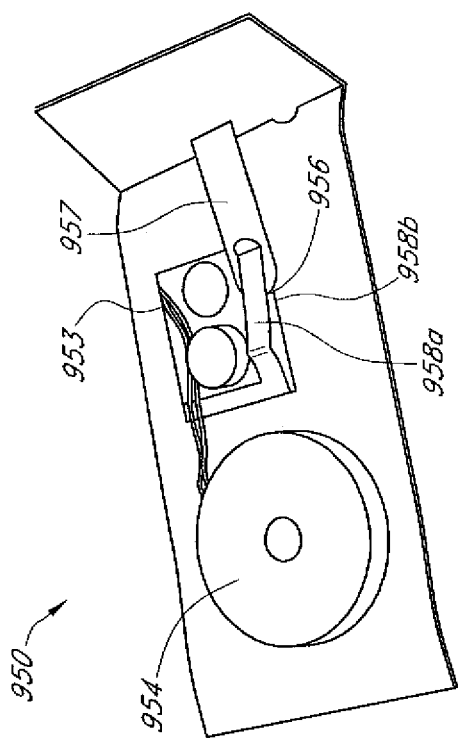
Figure 50C:
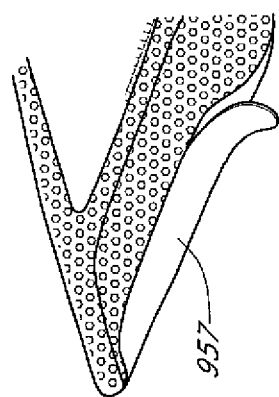
Figure 50D:
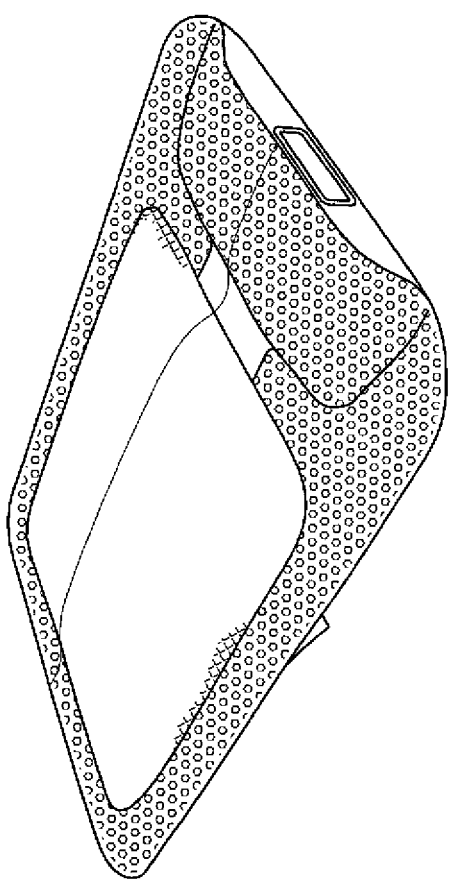

Additionally, in any embodiments, the packaging supporting the dressing kit can be configured such that such tab or isolator is fixedly positioned between the components in the electrical circuit to ensure that the batteries are not electrically connected to the pump assembly or other components during sterilization (if used) or prior to activation. For example, as illustrated in FIGS. 50B-50D, a pull tab can be positioned over any desired surface of the dressing, power supply, or pump assembly, of any of the dressing or pump assembly embodiments disclosed herein. As is disclosed in other embodiments, the label or tab can be conductive such that the first and second terminals are in communication with one another when the label is connected to both terminals.

As shown in FIG. 51, in any embodiments disclosed herein, the dressing kit (such as dressing kit 970 disclosed in FIG. 51) can have one or more buttons 979 supported by the dressing member 972. The buttons 979 can be fixed to the backing layer 975 of the dressing member 972 and can be positioned near an edge portion of the dressing (such as outside of the perimeter of the dressing layers 973) where operation of the buttons will not irritate or cause discomfort or damage to the wound. The controls can comprise one or more keypad buttons that can be positioned anywhere on the wound. The dressing can have one or more printed cables 981 to provide electrical connections between the batteries, activation buttons, LED or other lights 986 for indicating a condition under the dressing or with regard to the pump assembly 974, and/or power source 976.

Figure 52C:
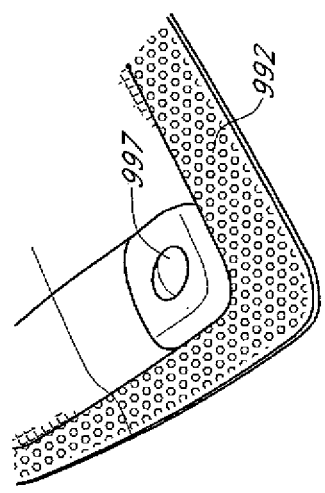
FIGS. 52A-C illustrate an additional embodiment of a dressing kit for negative pressure wound therapy.
Figure 52B:
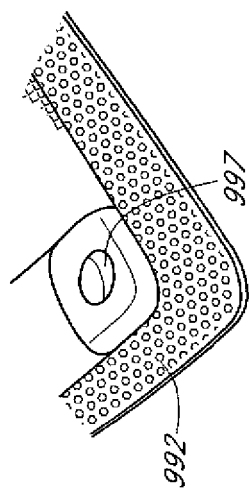
Figure 52A:
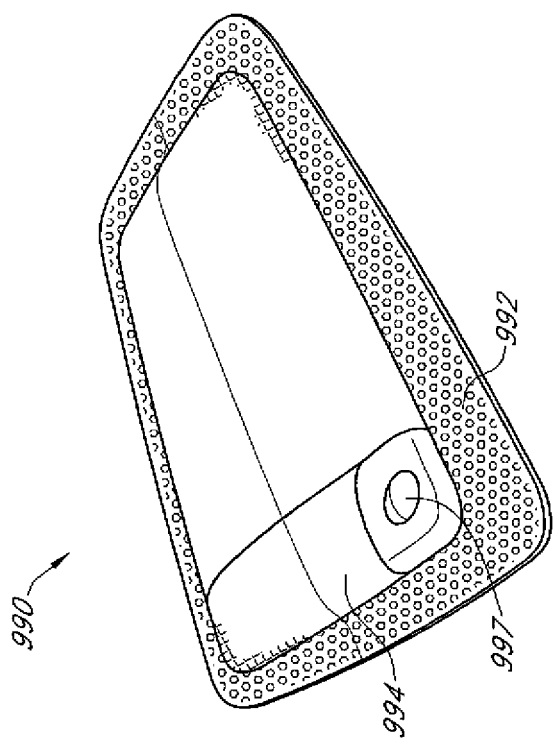

With reference to the dressing kit 990 shown in FIG. 52, in any embodiments disclosed herein, the pump assembly 994 can be activated using one or more pop buttons 997. Each pop button 997 can be configured such that, when the pump is activated and the conditions under the overlay are within threshold parameters, the pop button will remain depressed and the pump will continue to operate. The circuitry of the pump assembly 994 can be configured to maintain the button 997 in the depressed position during optimal or threshold conditions, for example when a sufficient vacuum has been achieved. The button can be configured to pop up when a sufficient vacuum has not been achieved, or when other operating conditions under the overly are not within the threshold parameters. As such, the button can be used to provide a visual indication of the operating conditions of the dressing. The button can be depressed to initially activate operation of the pump.

Figure 53A:
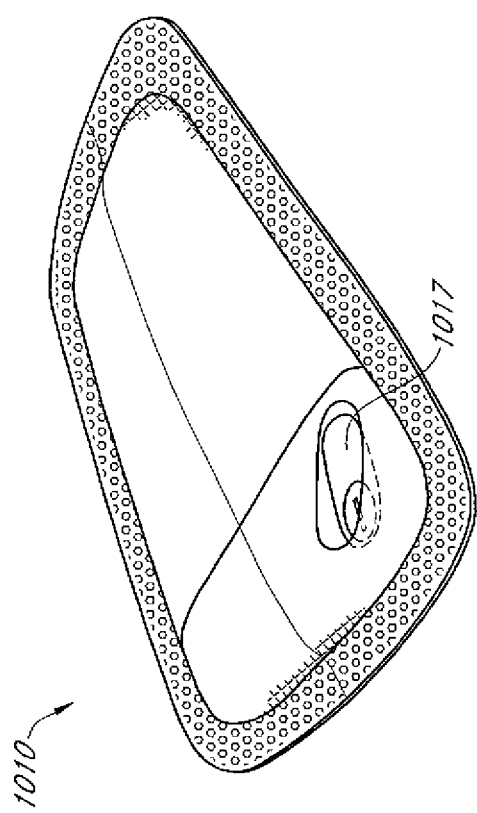
FIGS. 53A-B illustrate an additional embodiment of an activation switch of a dressing kit for negative pressure wound therapy.
Figure 53B:
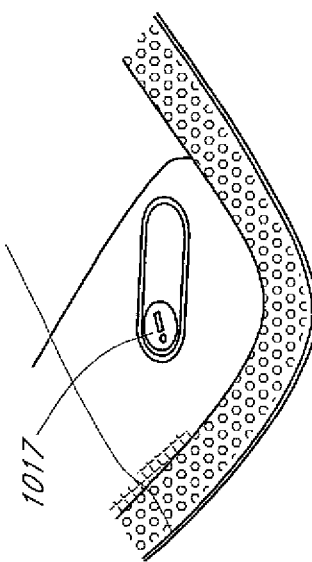

The switch 1017 (which can be a trip switch) illustrated in FIG. 53 can also be used to activate or control any of the pump assembly or dressing kit embodiments disclosed herein, and can also provide a visual indication of the operating conditions of the dressing. Depressing the switch 1017 can activate a pump. The switch 1017 can move between a first, relaxed position to a second, depressed position.

In some embodiments, the circuitry of the pump can be used to maintain the switch in the depressed state when the operating conditions under the backing layer are within threshold parameters. In some embodiments, the switch 1017 can have one or more components made from a shape memory material, or have a memory bistable dome or diaphragm therein that can hold the switch 1017 in a depressed position for a predetermined period of time during initial pump down until the level of reduced pressure under the overlay is sufficient to maintain the switch in the depressed (or second) position. In some embodiments, a pressure sensor within the dressing or pump assembly can be configured to provide a current of electricity to a shape memory, piezoelectric material sufficient to hold the switch in the depressed or second position.

The switch can be configured to pop up if there is a leak in the dressing (detected based flow rate through the pump or on duty cycle feedback or other parameters), or if one or more other parameters or conditions are not met, such as but not limited to insufficient battery power or insufficient negative pressure within the dressing after a predetermined period of time. For example, the switch of this or any other embodiment disclosed herein can be configured to move between a first on position and a second off position, and to remain in the first position when a threshold level of negative pressure is maintained beneath the backing layer. The switch of this or any other embodiment disclosed herein can be configured to move to the second position when the level of negative pressure under the backing layer is less than a threshold level of negative pressure and the pump assembly exceeds a threshold flow rate for a threshold period of time, which can be caused by the presence of a leak in the system. For example, any of the embodiments disclosed herein can be configured to trigger an alarm or change the switch or button from a first operational position to a second non-operational position when the pressure beneath the dressing is less than 60 mmHg (i.e., less meaning 59 mmHg or lower) and the pump assembly has been operating for a threshold period of time, such as for approximately 5 minutes, from approximately 5 minutes to approximately 8 minutes, or from approximately 2 minutes to approximately 5 minutes, or any values within any of the foregoing ranges. Additionally, depressing the switch can produce an audible click to alert the user that the switch has been activated.

The embodiment of the dressing kit 1030 illustrated in FIG. 54 can have a pump assembly 1034 supported on the dressing member 1032. The pump assembly 1034 can have a flexible activation switch 1037 that can activate or control any of the pump assembly or dressing kit embodiments disclosed herein. The activation switch can be configured to be a flexible tab 1041 having one or more buttons 1039 supported there. The flexible tab 1041 can be rotated upward away from the pump assembly to a first position to permit a user to grasp and activate the button or buttons 1039. In any embodiments disclosed herein, the button 1039 can be activated by squeezing the button 1039, so that no force or very little force is imparted on the wound dressing or wound bed. When in the stowed or second position, the activation switch or tab 1037 can have a low profile and lie substantially flat against the pump assembly.

Alternatively, in any embodiments, the activation switch can be a slide activation switch (such as slide activation switch 1057 illustrated in FIG. 55 or slide activation switch 1077 illustrated in FIG. 56) or a squeeze activation button or switch (such as switch 1097 illustrated in FIG. 57) to reduce the forces imparted on the wound. Though not required, the slide switches of the embodiments shown in FIGS. 55 and 56 can be a reed switch with a sliding magnet. The slide switches can be configured to provide an illustration or indication of the position of the switch, for example, to alert a user that the switch is in a particular position, such as in the on or active position. The switch mechanism can be used for battery isolation prior to operation of the pump or during sterilization, if sterilization is used. The switches in any of these embodiments can move the batteries into and out of contact with the pump assembly such that, prior to operation, the battery can be out of contact with the battery terminals or other electrical connections between the batteries and the pump assembly.

Figure 55:
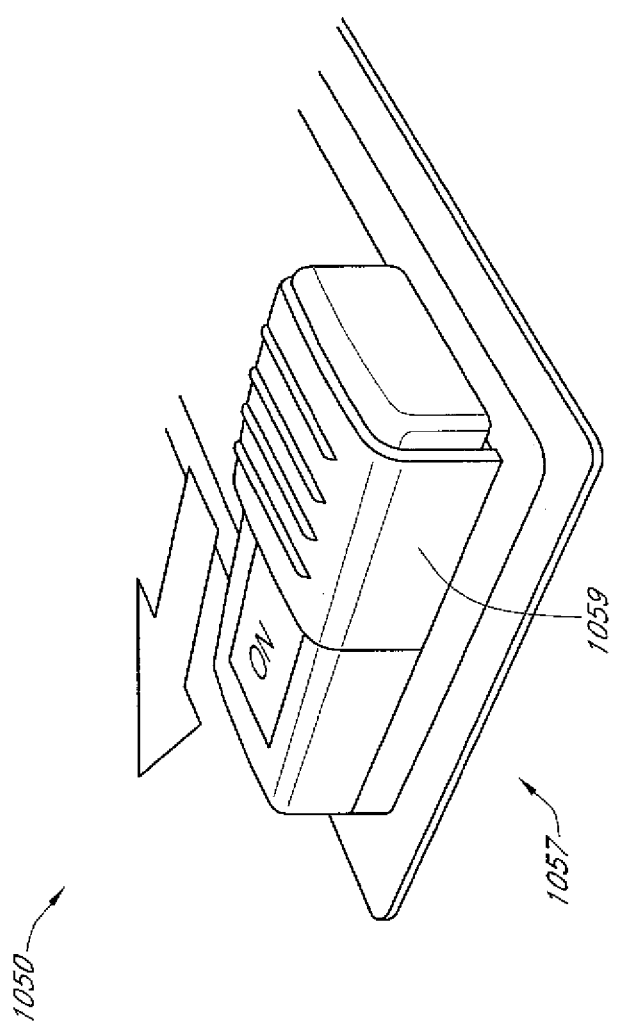
FIG. 55 illustrates an additional embodiment of an activation switch of a dressing kit for negative pressure wound therapy.
Figures 56A, 56B:
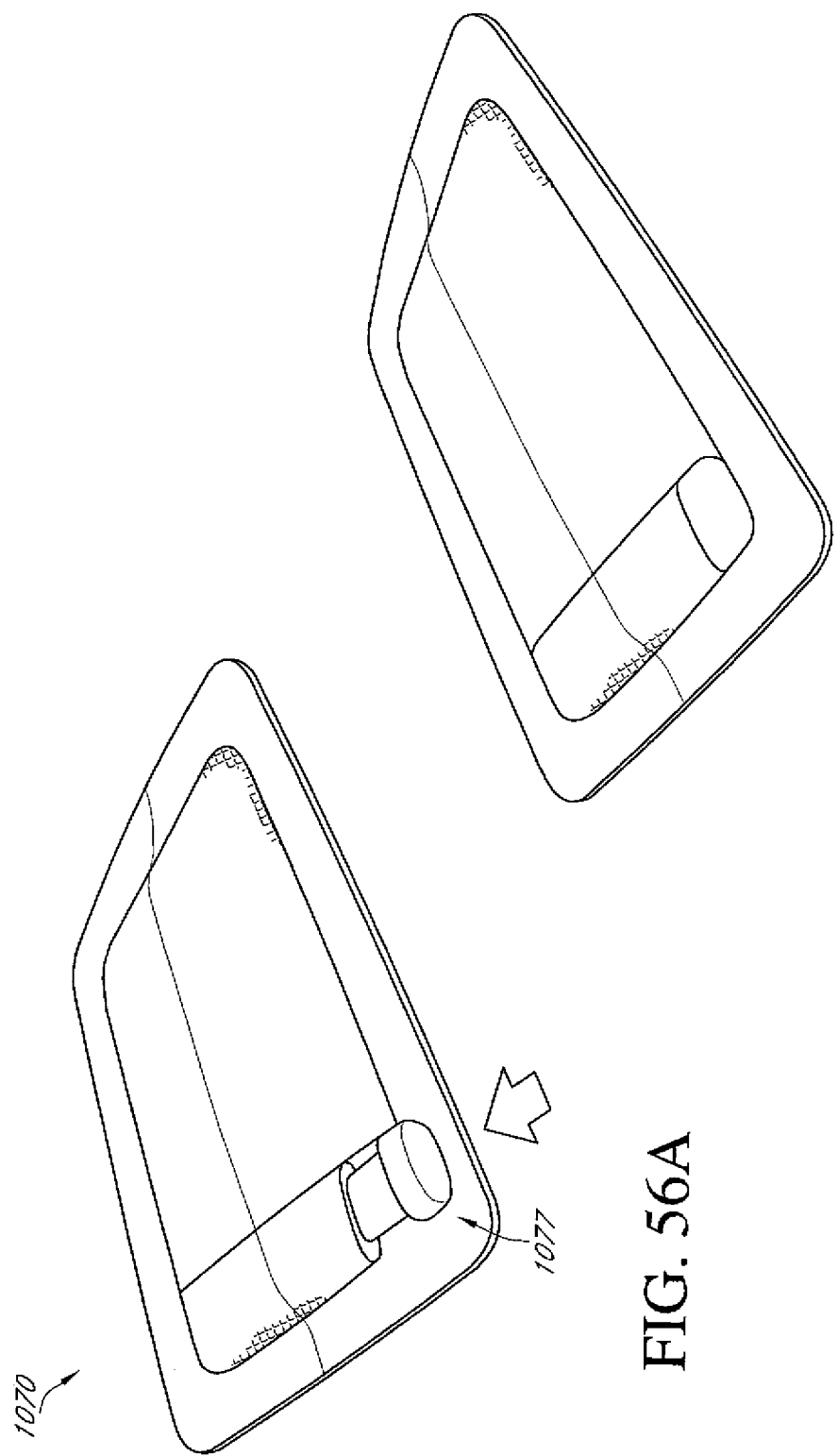
FIGS. 56A-B illustrate an additional embodiment of an indicator light of a dressing kit for negative pressure wound therapy.
Figure 57:
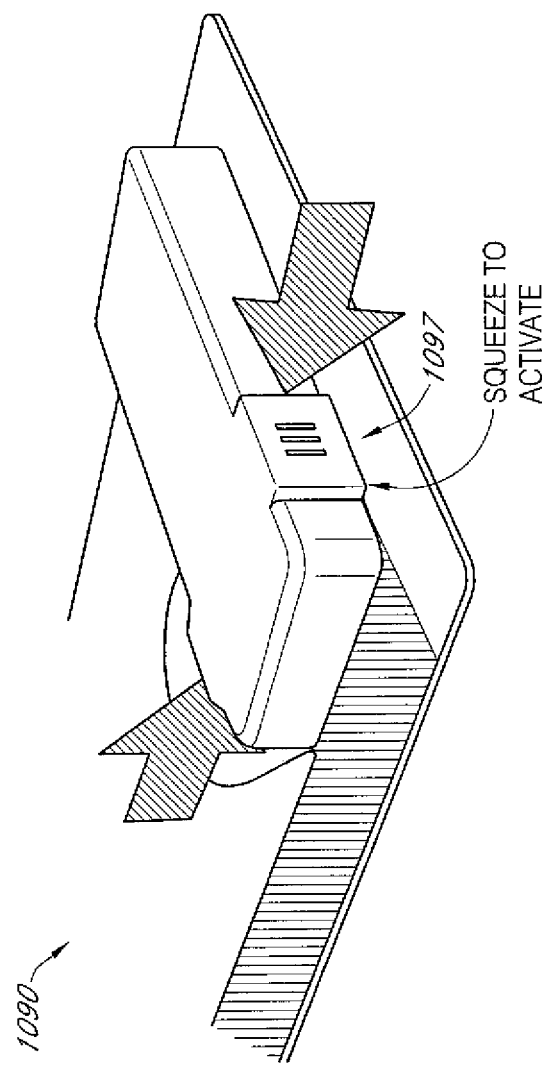
FIG. 57 illustrates an additional embodiment of an activation switch of a dressing kit for negative pressure wound therapy.

Any of the embodiments disclosed herein wherein the activation mechanism has a sliding mechanism, a sliding switch, or other moving activation mechanism, including without limitation the embodiments illustrated in FIGS. 55-57, can have any of the features configured to prevent the premature activation of the pump in the packaging supporting the dressing kit and pump assembly or otherwise. Additionally, any such embodiments can be configured such that the packaging can be configured to securely hold the pump assembly and/or battery module in a disconnected state.

For example, the dressing kit embodiments can be supported in the packaging such that, while the dressing kit is supported in the packaging, the components of the battery pack or pump assembly are held in a first or non-operational position and prevented from moving to a second operational position. In this configuration, when the components are in the first position, the pump is non-operational due to the fact that the battery terminals are not in contact with the one or more batteries. For example, the packaging supporting the dressing kit can prevent a lid of the battery housing from moving to the second position by holding the housing lid or cap in the first position. The packaging can have protrusions that are positioned between the housing lid or cap and the body of the battery housing that separate the battery housing lid from the body of the battery housing. Once the dressing kit is removed from the packaging, the battery housing lid or cartridge can be slid inward, permitting the terminals to contact the batteries so that the pump can be activated. In this configuration, the battery housing can serve as an activation button. Sliding the lid out of contact from the batteries can stop the operation of the pump. Further, the dressing kit can be configured such that sliding the batteries into engagement with the battery terminals will result in an audible click, to alert a user regarding the position of the components of the battery enclosure or regarding whether the battery circuit is open or closed.

Figure 58C:
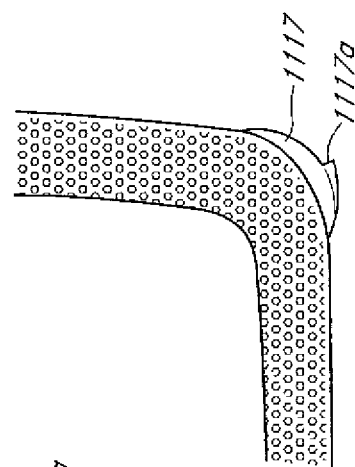
FIGS. 58A-C illustrate an additional embodiment of an activation switch of a dressing kit for negative pressure wound therapy.
Figure 58B:
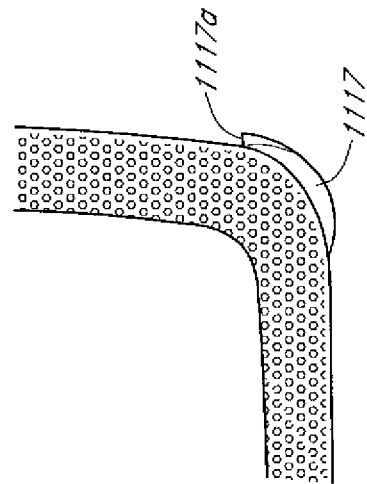
Figure 58A:
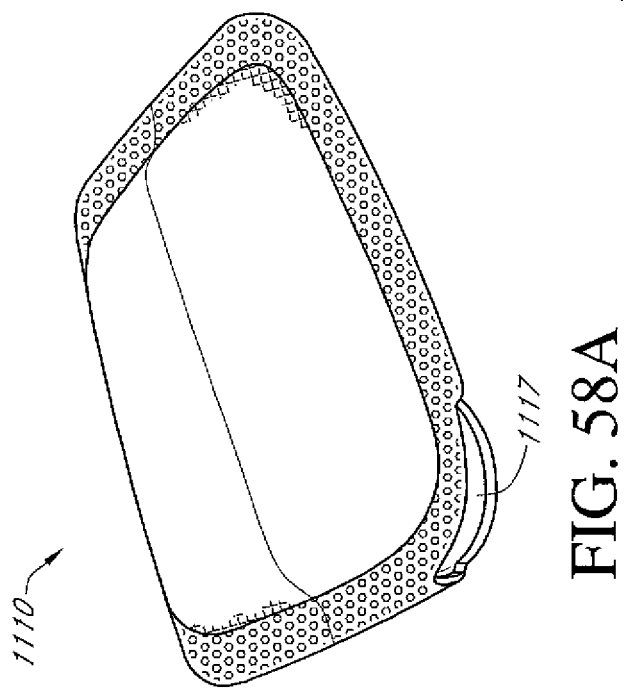
Figure 59:
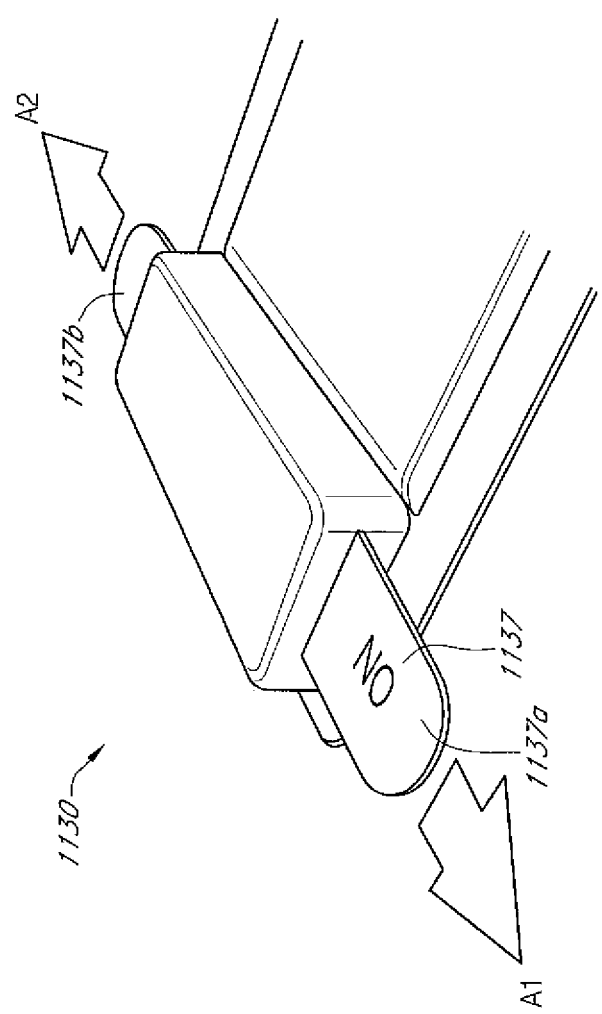
FIG. 59 illustrates an additional embodiment of an activation switch of a dressing kit for negative pressure wound therapy.

Any of the dressing kit embodiments disclosed herein can have a rotating or wheel activation switch (such as the rotating switch 1117 illustrated in FIG. 58) or an axial sliding tab or reed (such as the sliding tab switch 1137 illustrated as shown in FIG. 59) having two or more positions corresponding to two or more pump operation positions. For example, the wheel switch 1117 can define an off position, as shown in FIG. 58B and an on position shown in FIG. 58C. A protrusion or bump 1117a on the wheel 1117 can be used to limit the rotational range of the switch 1117, and one or more detents can be used to give tactile feedback regarding the switch position and/or bias the switch to remain in the positions associated with the detents.

Similarly, the pull tab 1137 in FIG. 59 can trigger an operational state if moved to a first position (such as by pulling the tab in the direction indicated by arrow A1) and a non-operational state if moved to an opposite, second position (such as by pushing or pulling the tab in the direction indicated by arrow A2). In some embodiments, though not required, the pull tab 1137 can have two end portions that can be grasped, such as first end portion 1137a and second end portion 1137b. Though not required, any of the switches or buttons of any of the dressing kit embodiments disclosed herein can have one or more intermediary positions corresponding to different operation states, such as different operational programs or otherwise. Detents or tabs on any of the switches can be used to define the two or more operational states or positions.

Additionally, as mentioned, for any of the switches or buttons of any of the dressing kits disclosed herein, the pump assemblies and/or battery modules can be configured such that the position of the switch or button dictates the position of the batteries relative to the battery terminals or other electrical connections with the pump assembly. Further, as with any other embodiment disclosed herein, the packaging surrounding the dressing kit having the pull tab arrangement illustrated in FIG. 59 can be configured such that the dressing kit with the pull tab fits in the packing only when the pull tab is in the non-operational position.

Figure 60:
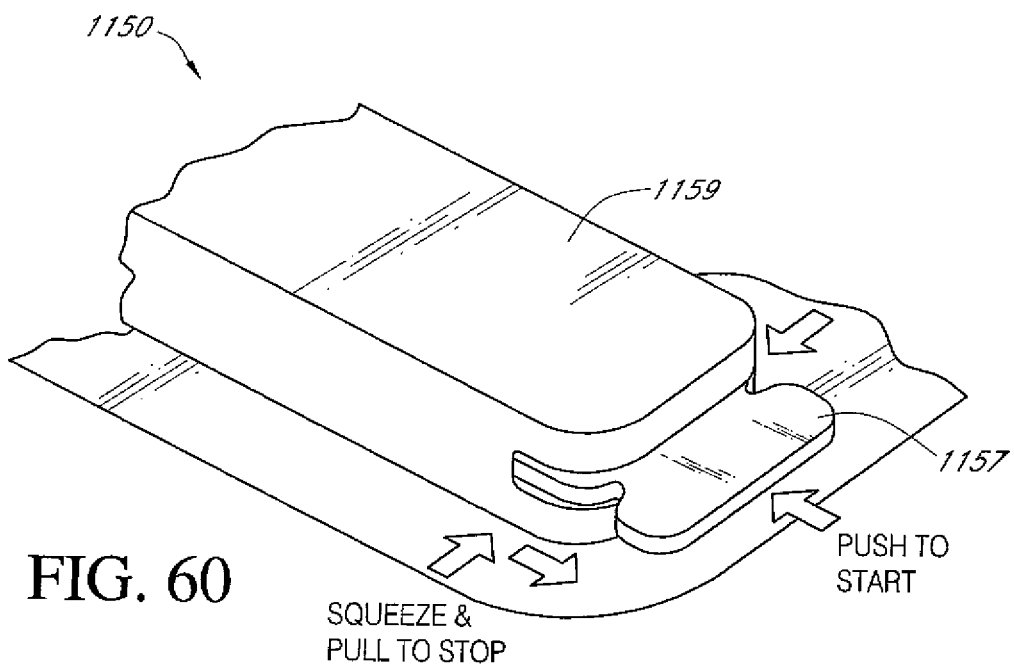
FIG. 60 illustrates an additional embodiment of an activation switch of a dressing kit for negative pressure wound therapy.

In any of the pull tab arrangements disclosed herein, with reference to FIG. 60, the receiver or support 1159 for the pull tab 1157 can be configured such that the receiver or support 1159 must be squeezed inwardly to permit the pull tab 1157 to be slideable relative to the receiver or support 1159. This can prevent or reduce the likelihood that the pull tab 1157 will be inadvertently moved to a different position. In use, a user can squeeze the receiver or support 1159 while simultaneously moving the switch 1157 to the desired position.

Figures 61A, 61B:
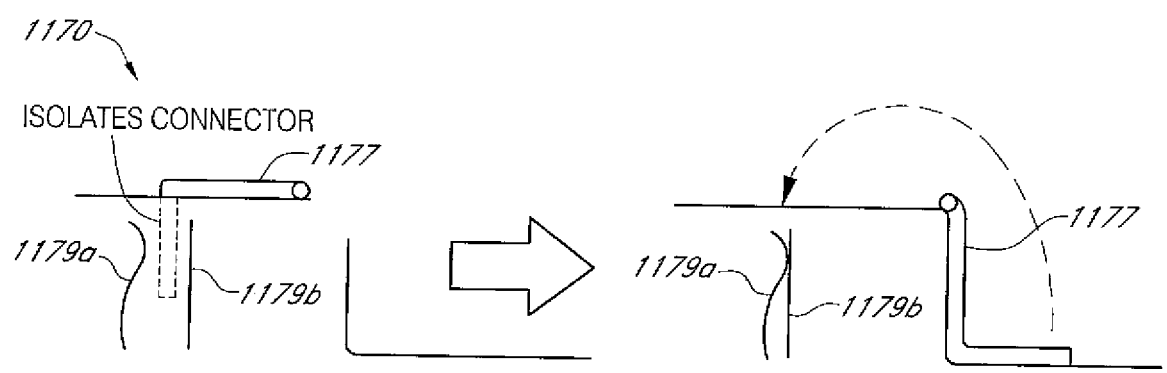
FIGS. 61A-B illustrate an additional embodiment of an activation switch of a dressing kit for negative pressure wound therapy.

FIG. 61 illustrates an embodiment of a dressing kit 1170 having an arrangement of an isolator switch 1177 that can be used with any of the dressing kit embodiments disclosed herein, including the sliding switch embodiments. For example, the rotating or sliding switch 1177 can be formed from a non-conductive material and can be configured to open a switch or spread a pair of contact terminals, such as first contact terminal 1179a and 1179b apart to prevent the flow of electricity between the two terminals 1179a, 1179b, when the switch 1177 is in a first position (as illustrated in FIG. 61A). In some embodiments, the isolator can be a plastic tab or switch that rotates about a living hinge. When moved to a second position (as illustrated in FIG. 61B), the contact terminals 1179a, 1179b can in contact such that the electrical connection can be closed and permit a flow of electricity through the electrical connection. The batteries can be electrically isolated from each other and/or from the rest of the circuitry in this arrangement.

Figure 62:
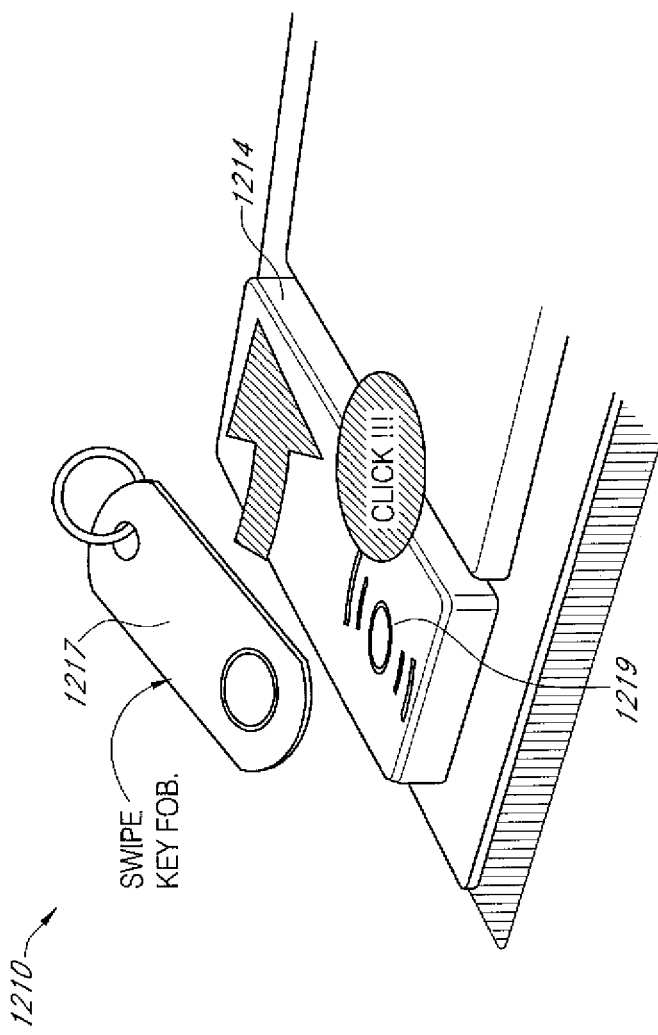
FIG. 62 illustrates an additional embodiment of an activation switch of a dressing kit for negative pressure wound therapy.
Figure 63:
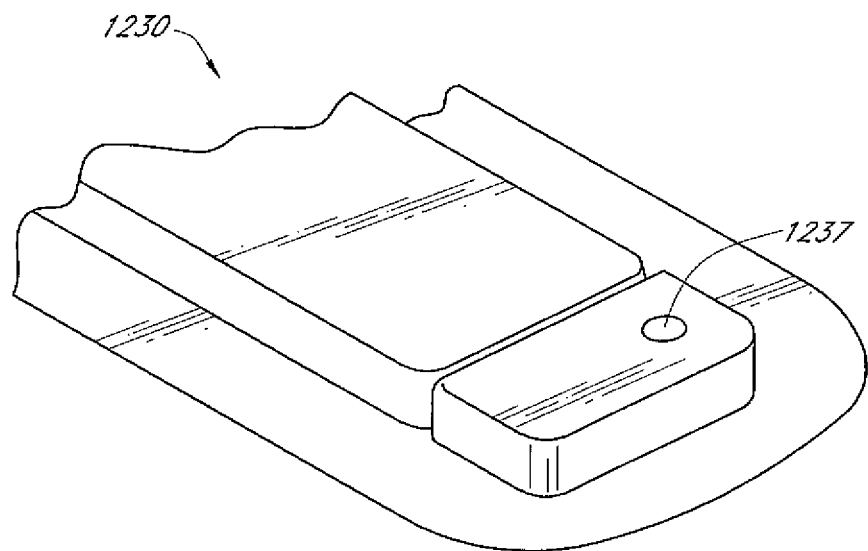
FIG. 63 illustrates an additional embodiment of a dressing kit for negative pressure wound therapy.

In any embodiments disclosed herein, as illustrated in FIG. 62, the pump can be activated by passing a key fob or activator 1217 over an RF ID receiver 1219 positioned on the pump assembly 1214. This can eliminate the force that would otherwise be imparted on the wound dressing during activation of the wound dressing. In some arrangements, as illustrated in FIG. 63, the activation button 1237 can be activated by infrared radiation, light, or by touch. This can reduce or eliminate the pressure exerted on the wound when switching the pump assembly between an on and an off state.

Figure 64A:
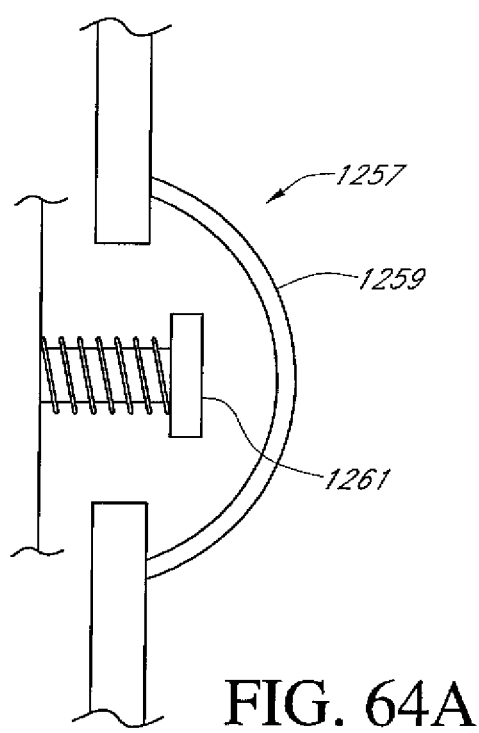
FIGS. 64A-B illustrate an additional embodiment of a dressing kit for negative pressure wound therapy.
Figure 64B:
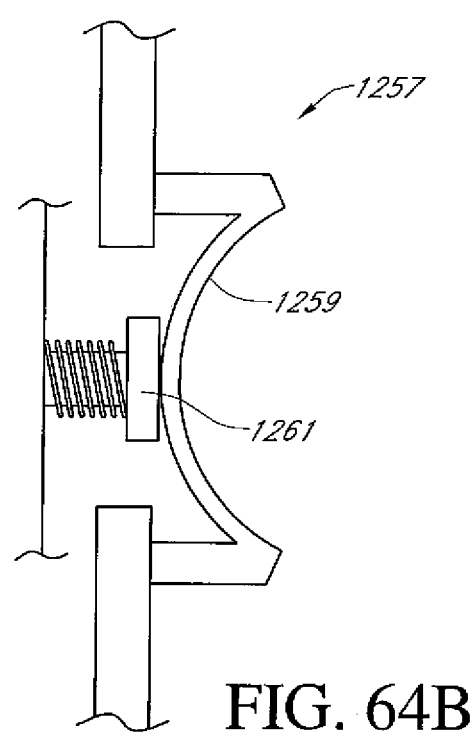

FIG. 64 illustrates a push button arrangement 1257 that can be used to activate any of the pump assemblies disclosed herein. The push button can have a flexible dome switch 1259 over a surface mount tact switch 1261. A threshold level of reduced pressure can hold the flexible dome 1259 in place as visual indicator that a sufficient level of reduced pressure is being exerted on the wound bed. In this arrangement, the button can serve as an activation switch and a tactile or visual indicator. The indicator can be used to alert the user to any or any combination of the following conditions: user device is operating correctly; leak detected; battery dead; and/or dressing saturated or full.

As mentioned, any of the dressing kit embodiments disclosed herein can have a visual pressure indicator configured to provide a visual indication of the pressure beneath the backing layer. The visual pressure indicator can be configured to change position in response to a differential in pressure between the space beneath the backing layer and atmospheric pressure. In some embodiments, the pressure indicator or bubble can be configured to retract or collapse toward the wound surface in response to increasing levels of reduced pressure beneath the backing layer.

In some embodiments, the pressure indicator can have a different color as compared to the remainder of the dressing, or can be configured to change color in response to threshold pressure differentials between the space beneath the backing layer and atmospheric pressure. The pressure indicator can be positioned in an opening or depression formed in the dressing to shield the pressure indicator from impact and to protect the pressure indicator. For example, as described above, the dressing kit 330 of FIG. 19 can have one or more pressure indicators thereon.

Figure 65A:
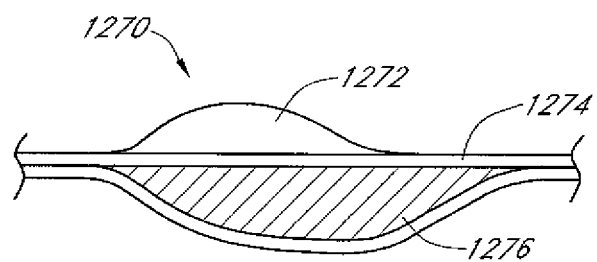
FIGS. 65A-B illustrate several embodiments of a pressure indicator of a dressing kit for negative pressure wound therapy.
Figure 65B:
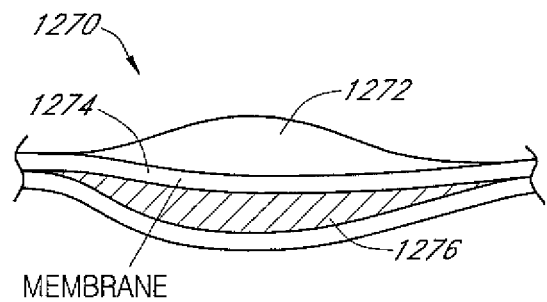

The one or more pressure indicators can be supported in any desired location on the dressing. With reference to FIG. 65, the pressure indicator 1270 can have a pressure bubble 1272 configured to be in an expanded position (as shown in FIG. 65A) when the dressing is in a first, low or no reduced pressure state and in a collapsed position (as shown in FIG. 65B) when the dressing is in a second, increased reduced pressure state. In any embodiments disclosed herein, the dressing can have a pressure bubble (such as pressure bubble 1272) positioned over a membrane (such as membrane 1274), which can be stretchable or substantially stretchable. The membrane 1274 can be formed from a material that is gas permeable, but liquid impermeable in some embodiments. The membrane 1274 can be configured to be substantially or completely opaque in a first, relaxed state and less opaque (i.e., more translucent) in a second, more depressed state. Alternatively, the membrane material can be somewhat translucent in the first, unstretched state and more translucent in a second, stretched state. Reduced pressure imparted on the dressing can cause the membrane to depress or move from the first toward the second state.

In some embodiments, the membrane can be substantially opaque except when in contact with the colored material or liquid 1276 beneath the membrane 1274. When the membrane 1274 contacts the liquid or solid material 1276 beneath the membrane 1274, the color of such liquid or solid material 1276 can become more visible such that the color becomes apparent when a threshold level of reduced pressure is exerted on the membrane 1274, causing it to more toward the colored material.

As mentioned, a colored material such as ink or other material can be positioned under the membrane. The dressing can be configured such that the membrane layer between the pressure bubble and the colored material is substantially more visible in the second state than in the first state, permitting the user to visually inspect the level of reduced pressure in the overlay by visually monitoring the color under the pressure bubble. In some arrangements, the pressure bubble can be visually observed after depressing the button.

Figure 66A:
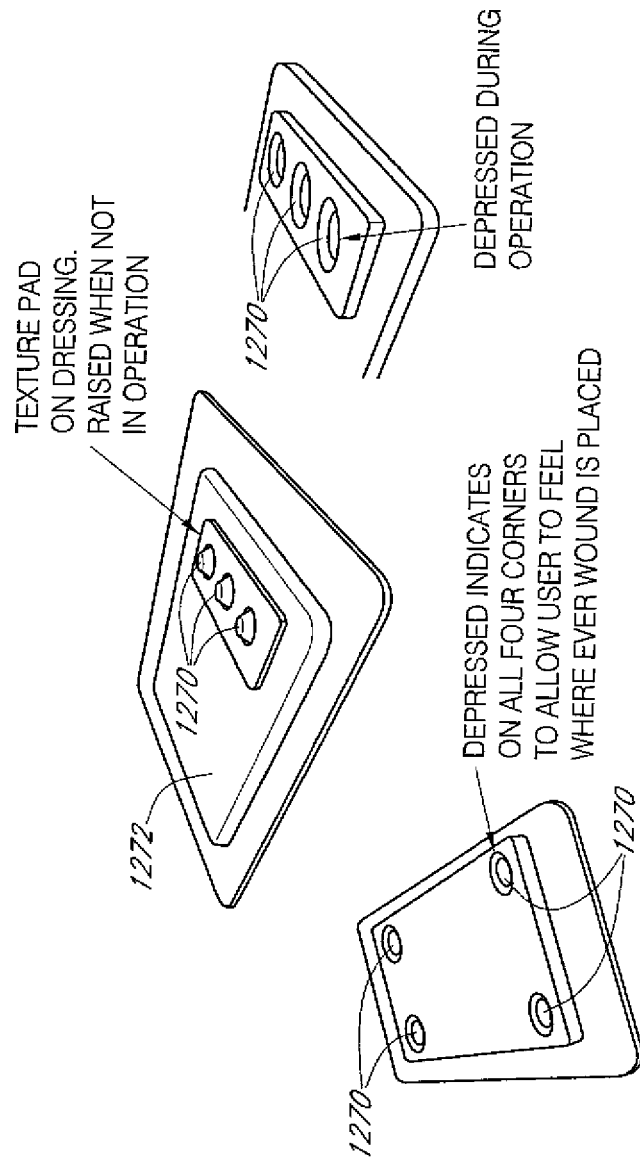
FIGS. 66A-C illustrate additional embodiments of a dressing kit for negative pressure wound therapy.
Figure 66B:
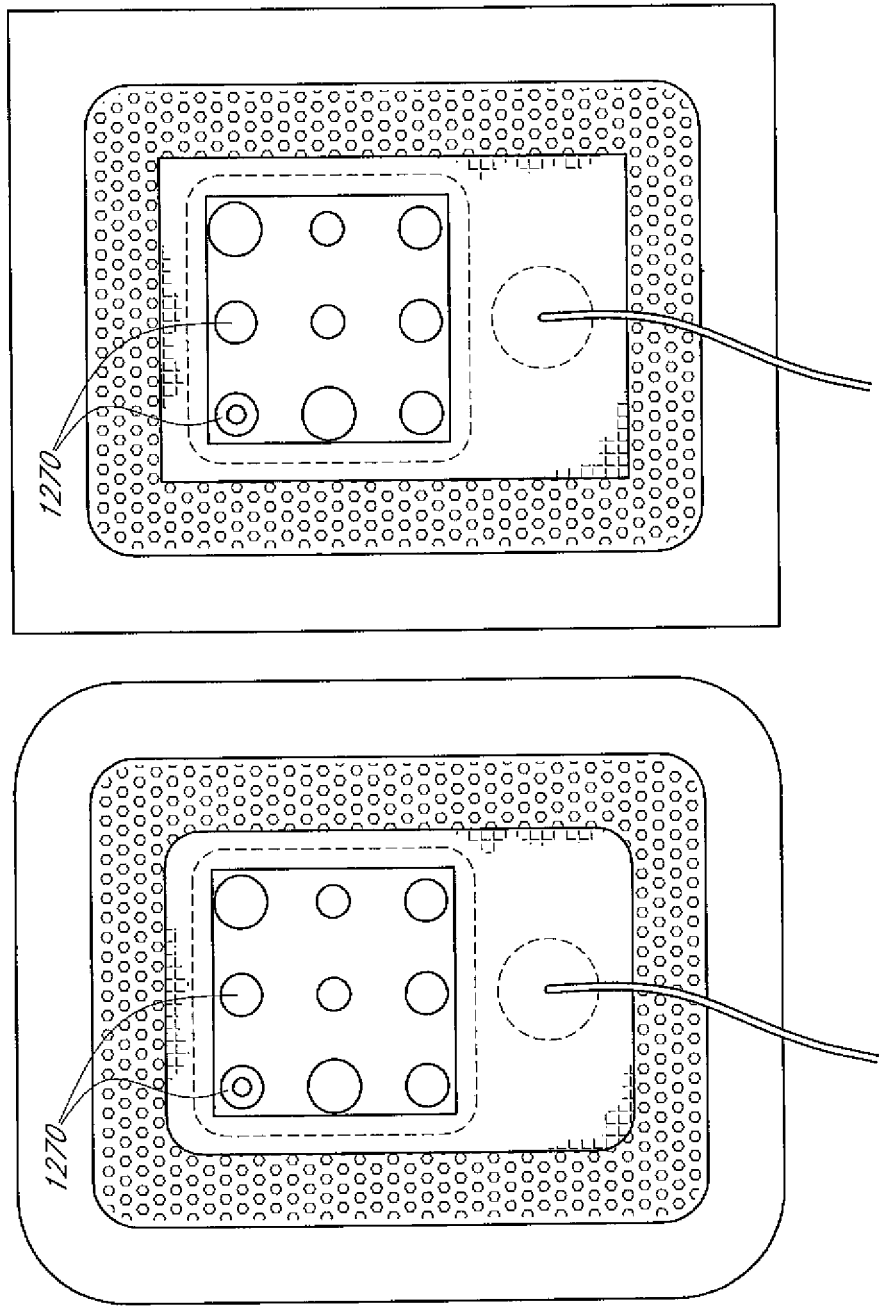
Figure 66C:
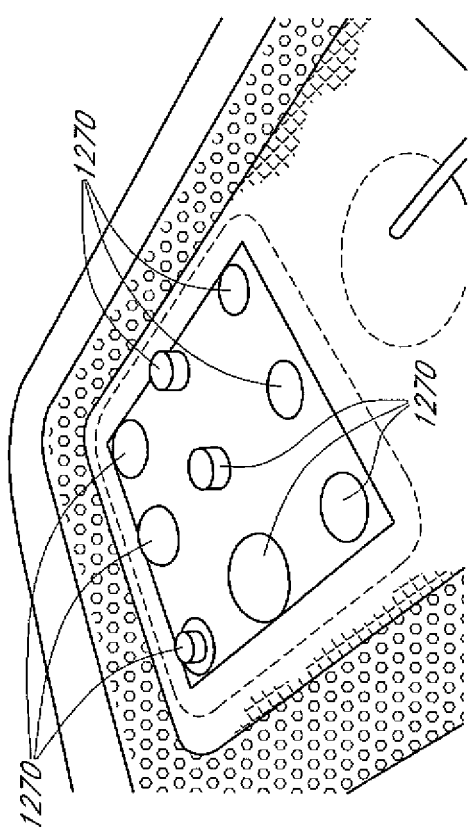
Figure 67:
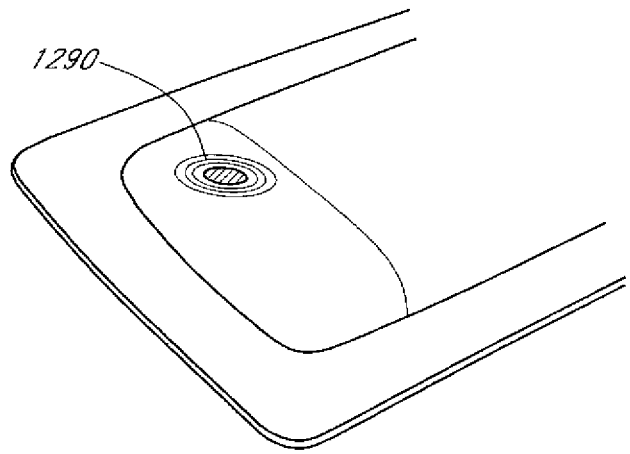
FIGS. 67-70 illustrate additional embodiments of dressing kits for negative pressure wound therapy having one or more indicator lights thereon.

Other pressure indicators can be supported by the wound dressing. For example, as illustrated in FIG. 66, a wound dressing can have a plurality of pressure indicators 1270 (of any suitable configuration or configuration disclosed with respect to any embodiments disclosed herein) positioned about a top surface of the dressing to provide a visual and/or a tactile indication of a level of negative pressure beneath the dressing overlay 1272. The plurality of indicators 1270 can have a plurality of pressure bubbles activated by reduced pressure. In some embodiments, the pressure bubbles or indicators can have a colored substance or material beneath the dome of the indicator, or a light beneath the indicator to enhance the visual appearance of the indicator. In some embodiments, the pressure indicators 1270 can be configured to define two states or positions—a depressed or collapsed position when a threshold level of reduced pressure is present under the overlay and an extended or inflated position when no pressure or less than the threshold pressure is present under the overlay. In some embodiments, the pressure indicators 1270 can also define intermediate positions.

The pressure indicators or bubbles can be mounted on a panel or formed in a panel arrangement and can have any suitable shape or size. The pressure indicators can be integrally formed with the overlay material, or can be integrally formed in a panel arrangement that can be attached to or mounted on the overlay. Additionally, the pressure indicators can be individually formed. In any embodiments disclosed herein, a pressure indicator can be positioned in each of four corners on the overlay.

With reference to FIGS. 67-70, any dressing kit embodiments disclosed herein can have an indicator light 1290 supported by or embedded within the dressing to provide a visual indication of one or more of the operating parameters of the dressing, pump assembly, or battery modules. In some embodiments, the light 1290 can be positioned such that it is visible from two or more planes or directions. Additionally, the light can be supported on a protrusion projecting from an outside surface of the dressing so that the light 1290 is more visible from a greater number of angles. The light 1290 can be an incandescent light, and LED light, or any other suitable light and can be constant or pulsating, or programmable. Additionally, the light 1290 can be configured to change intensity of the light output and can be programmed to gradually increase and decrease the light output.

Figure 68:
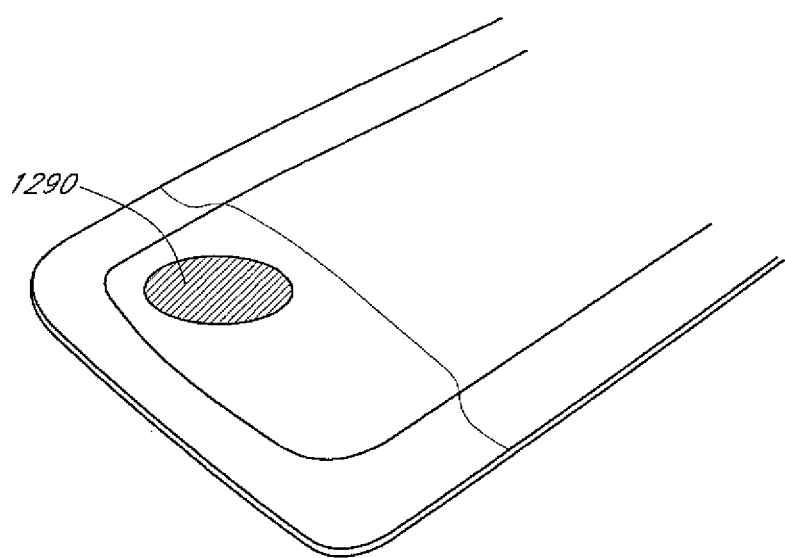
Figure 69:
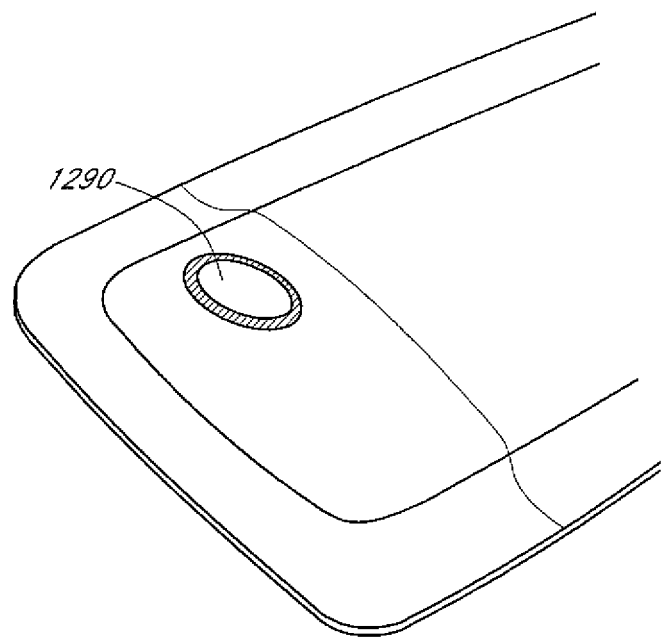
Figure 70:
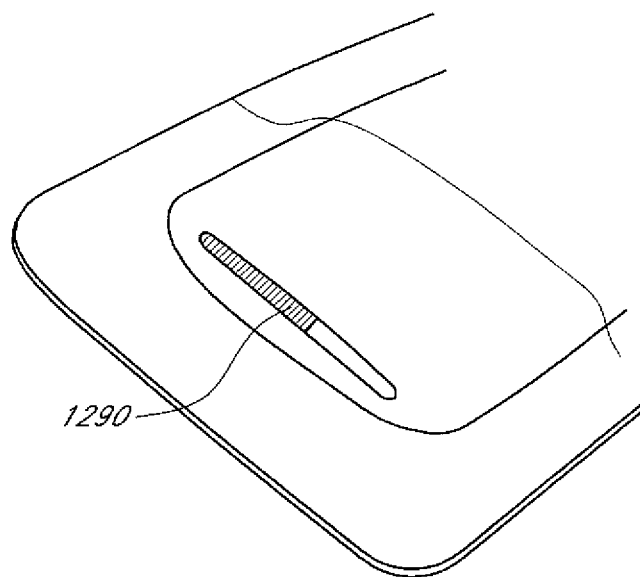

With reference to FIGS. 68, 69, and 70, in some embodiments, the dressing can have a soft or diffused light (as in FIG. 68), a light ring (as in FIG. 69), or an array of lights (as in FIG. 70). As shown in FIG. 68, the dressing can have a discrete diffused light area. The light area can be a continuously lit area, providing reassurance that the dressing and pump assembly is operating correctly.

As shown in FIG. 70, the dressing can support a panel of lights 1290 that is configured to provide an indication of a magnitude of a reading or level within the overlay, or a level of power in the power source. For example, in any embodiments disclosed herein, for light based pressure sensors, temperature sensors, or saturation sensors or indicators, the number of lights illuminated in an array of lights can increase as a level of reduced pressure, level of temperature, or saturation level under the overlay increases. The lights can also be used to indicate a duration of therapy, or a remaining duration of therapy. Multiple light arrays can be used to indicate multiple indications. Additionally, any of the lights disclosed herein can be configured to pulse or flash to provide a variety of signals regarding a variety of conditions to a user. Any of the lights disclosed herein can be LED lights.

Further, as shown in FIG. 69, any of the user buttons on the dressing can have lights integrated into the button design. In any embodiments disclosed herein, the light can surround the button so that a user can easily locate the button.

Figure 71A:
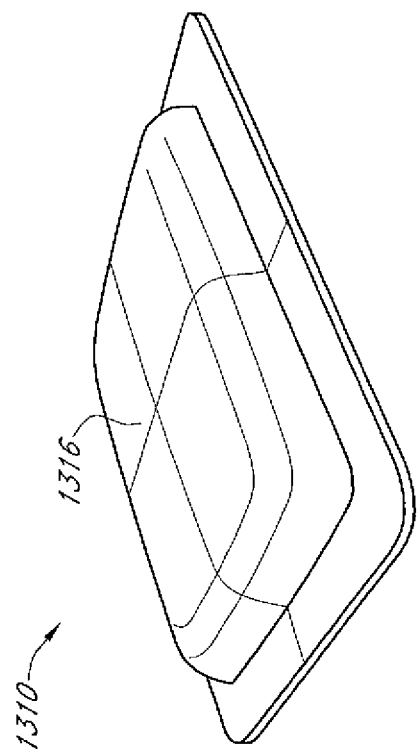
FIGS. 71A-72D illustrate additional embodiments of a dressing kit for negative pressure wound therapy having one or more pressure indicators thereon.
Figure 71B:
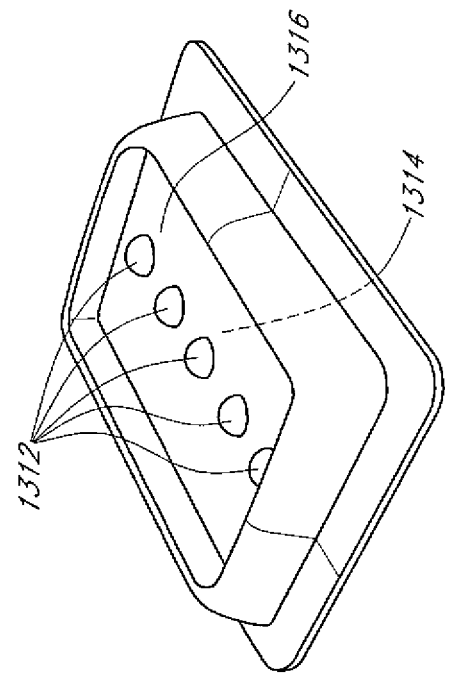
Figure 72B:
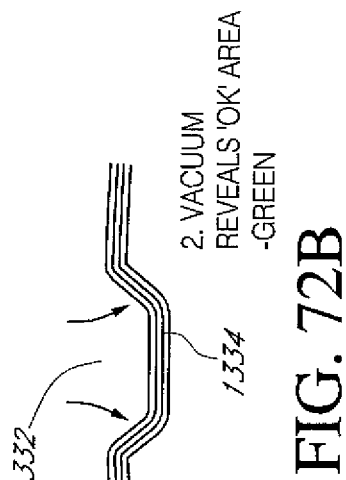
Figure 72C:
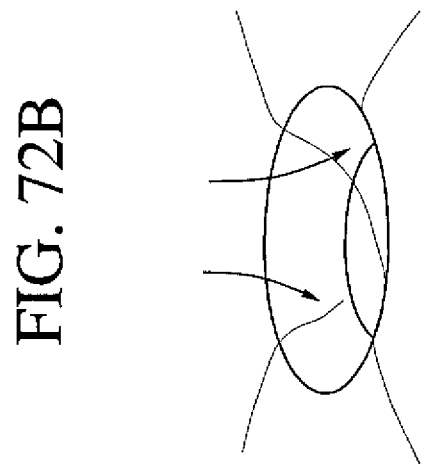
Figure 72D:
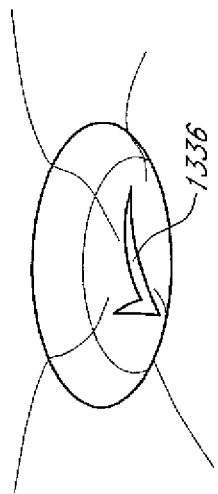
Figure 72A:
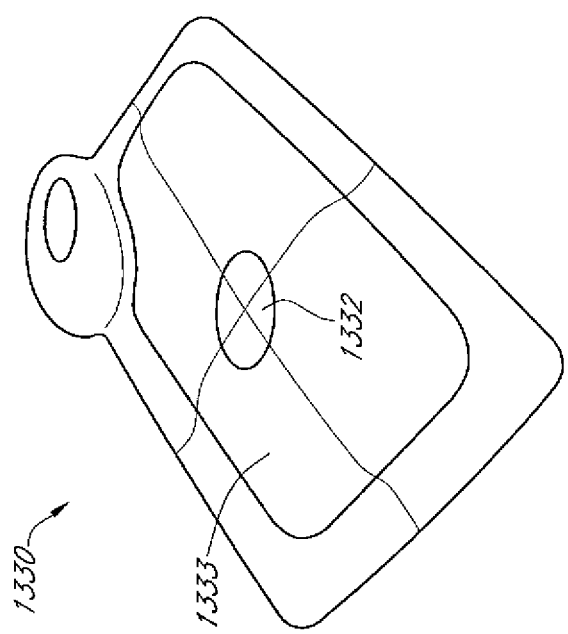

In any embodiments disclosed herein, as is shown for the embodiment of the dressing kit 1310 shown in FIG. 71, the dressing can have shaped features 1312 positioned on a surface of the dressing 1314 that are fully revealed and identifiable by touch only when a threshold level of reduced pressure is achieved in the dressing. FIG. 71A shows the dressing 1310 in first state, where less than a threshold level of reduced pressure exists under the overlay 1316. The dressing can be in a first state when the pump is not operational or when less than the optimal level of reduced pressure is present under the overlay 1316. Dressing components or the strength of the overlay layer 1316 can hold the overlay layer 1316 in a raised position so that the overlay layer 1316 (i.e., the outermost layer) does not collapse under gravity against the foam or other materials below the overlay layer 1316. The dressing 1310 can be configured such that, when a sufficient or threshold level of reduced pressure exists under the overlay 1316, the overlay layer 1316 collapses against a top surface or a top layer 1314 of the packing material or materials, as shown in FIG. 71B. When this occurs, in some embodiments, a color of the packing material layer 1314 can be revealed through the overlay 1316.

Additionally, with reference to FIG. 72, in any embodiments disclosed herein, the dressing can have a one or more discrete openings or depressions 1332 for detecting a level or a threshold level of reduced pressure under the hacking layer 1333. In any embodiments disclosed herein, the top surface or top layer 1334 of the packing material can define one or more raised, depressed, and/or colored features 1336 that have a shape that departs from the surface of the packing material. For example, though not required, the packing material 1334 can have one or more protrusions or tactile bubbles 1336 projecting away from the surface of the packing material 1334. Further, in some embodiments, the features can be depressions or even holes or openings formed through or into the top surface 1334 of the packing material. The features can be sized, positioned, and configured such that a user can see and/or feel the features more when the dressing backing layer is in the second state than in the first state.

In any embodiments disclosed herein, at least the top layer or top surface of the packing material can be a different color than the other materials comprising the dressing. The dressing can be configured such that the color of the packing material is substantially only visible, or is visibly darker or different, when the dressing is in the second reduced pressure state than when it is in the first state.

With reference to FIG. 72, the dressing 1333 can be configured such that the deflecting membrane 1332 changes color in the presence of moisture and/or pressure. In some embodiments, the dressing can be configured such that the dressing reveals a different color substrate under the backing layer 1333 when the backing layer 1333 is collapsed against the packing material. Any of the dressing kit or dressing embodiments disclosed herein can have any or any combination of the features disclosed in the embodiment of the dressing illustrated in FIG. 71 or 72, or otherwise.

Figure 73:
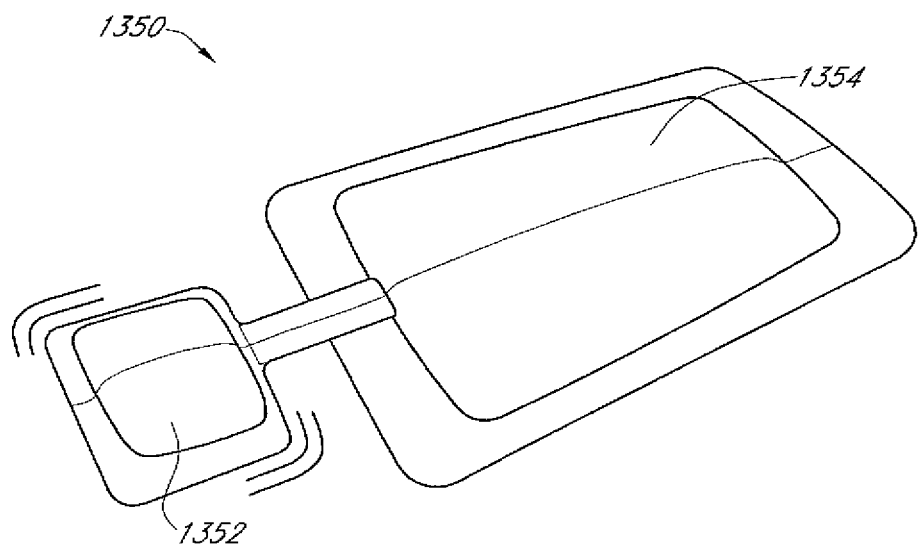
FIGS. 73-74 illustrate additional embodiments of a dressing kit for negative pressure wound therapy.
Figure 74:
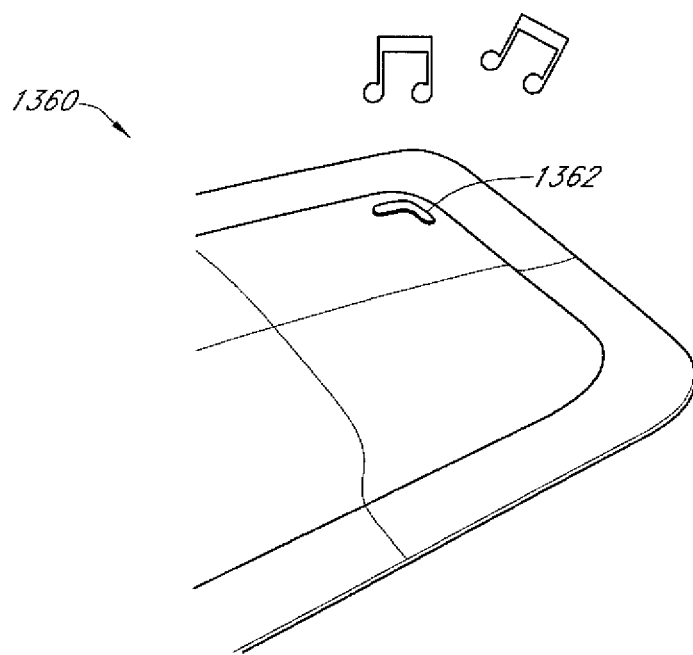

Any of the dressing kit embodiments disclosed herein can have a vibration buzzer 1352 that can be tethered to the dressing 1354 (as shown in FIG. 73), or can have an audible alarm or alert function 1362 (as shown in FIG. 74). The vibration alarm or buzzer 1352 or audible alarm or buzzer 1362 can be configured to alarm or alert a user to a particular condition regarding the wound dressing, pump, batteries, or any other component of the dressing kit. This can provide the user with feedback regarding the performance of the pump without requiring the user to see the pump, which can be particularly beneficial when the pump is worn under clothing or in any other fashion or manner that conceals the dressing or pump. The vibration buzzer can be mounted directly to a patient's skin, to the dressing, or otherwise. The vibration buzzer can have combination of any of the other features disclosed herein. In some embodiments, the vibration buzzer use the pump assembly to provide the vibration. On/off patterns of the pump can be used to provide the desired vibration or alert. Additionally, the audible alarm or buzzer can be positioned or supported apart from the dressing.

In any embodiments disclosed herein, the dressing can have one or more sensors therein that can trigger an alarm when a threshold level or when one or more predetermined levels of saturation within the dressing has been reached. For example, the dressing can be configured to trigger a first alarm when a first level of saturation has been reached, to trigger a second alarm when a second level of saturation has been reached, to trigger a third alarm when a third level of saturation has been reached, and so on, wherein the level of saturation is the level of fullness of the dressing. In some embodiments, the sensors can be positioned within the absorption layers of the dressing and can be configured to generate a signal based on exposure to liquid within the dressing. For example, one or more hygroscopic sensors could be positioned under the backing layer of the overlay. The sensors can be positioned within the dressing layers, and discrete locations about the dressing layers to monitor the amount of liquid throughout the dressing layers. For example, in any embodiments disclosed herein, between 2 and 4 sensors can be positioned symmetrically about the dressing layers, or between 4 and 6 sensors can be positioned symmetrically about the dressing layers. Some embodiments of the dressing kit can have one sensor positioned under the backing layer. In any embodiments disclosed herein, one or more sensors can be positioned adjacent to the port to the pump assembly. Without limitation, the first level can be at approximately 60% saturation, the second level can be at approximately 75% saturation, and the third level can be at approximately 90% saturation. In some embodiments, the first level can be from approximately 60% saturation to approximately 70% saturation, the second level can be from approximately 70% saturation to approximately 80% saturation, and the third level can be from approximately 80% saturation to approximately 90% saturation. In some embodiments, the saturation level can be detected using one or more resistance or capacitance sensors (such as a humidity or moisture sensor based on resistivity or capacitance) positioned within the dressing. In any embodiments disclosed herein, the moisture sensor can be positioned close to or adjacent the wound facing side of the filter or otherwise adjacent to the pump assembly or port to indicate the dressing is saturated or the fluid level is close to the level that will result in blockage to the filter, which could inhibit further negative pressure transmission from the pump assembly.

Figure 75:
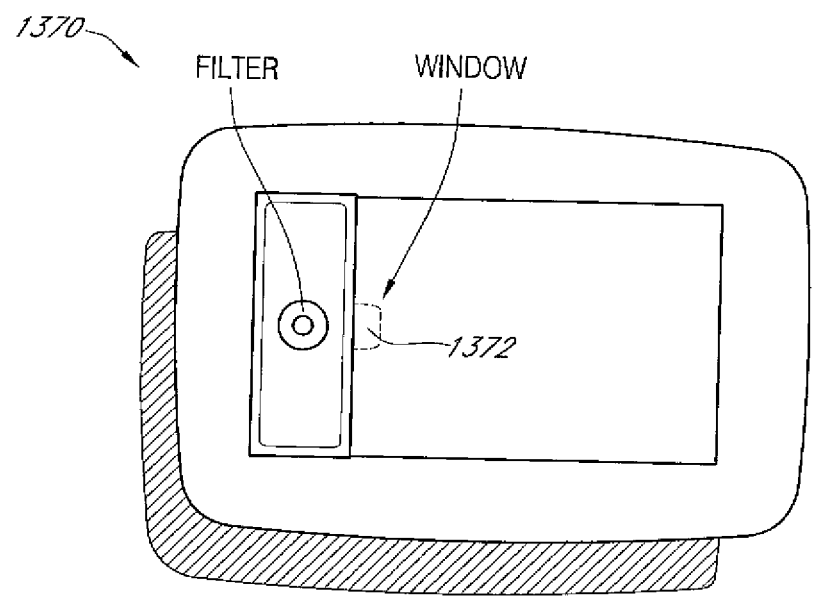
FIGS. 75-77 illustrate additional embodiments of a dressing kit for negative pressure wound therapy having one or more fill indicators thereon.

In any of the embodiments disclosed herein, with reference to FIG. 75, the dressing 1370 can have one or more saturation indicators 1372. For example, without limitation, any of the dressings can have one or more markings or indicators 1372 on the backing layer to indicate or reveal a level of exudate in the dressing when the exudate reaches a threshold level. The indicator can be a clear or transparent window in an otherwise opaque dressing. The dressing can have instructional text around or adjacent to the window to provide a user with instructions regarding how to use the saturation indicator. Additionally, such saturation indicators could be positioned at a variety of different locations on the dressing. Any of the dressing embodiments disclosed herein can have this feature.

Figure 76:
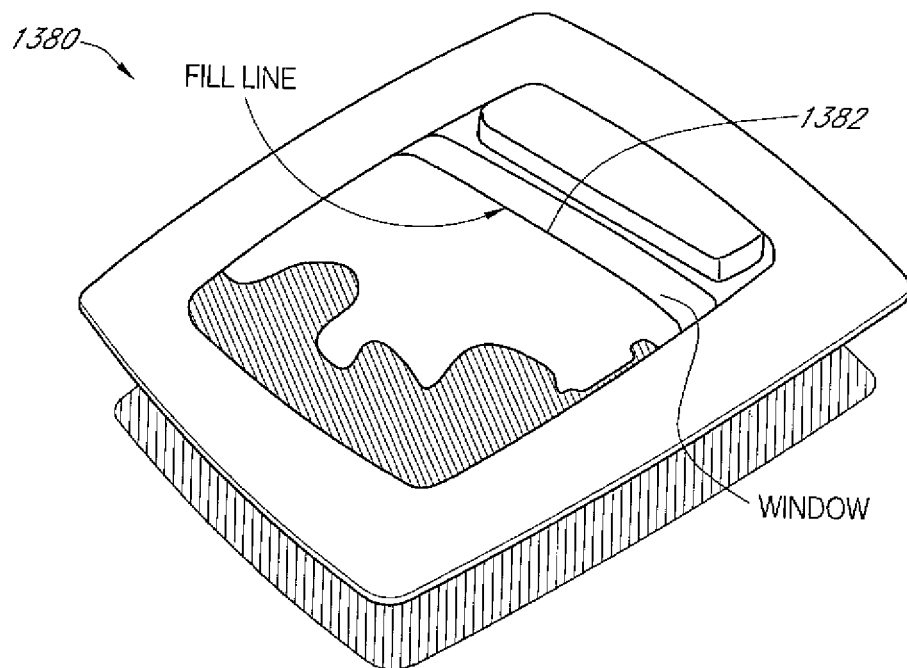
Figure 77:
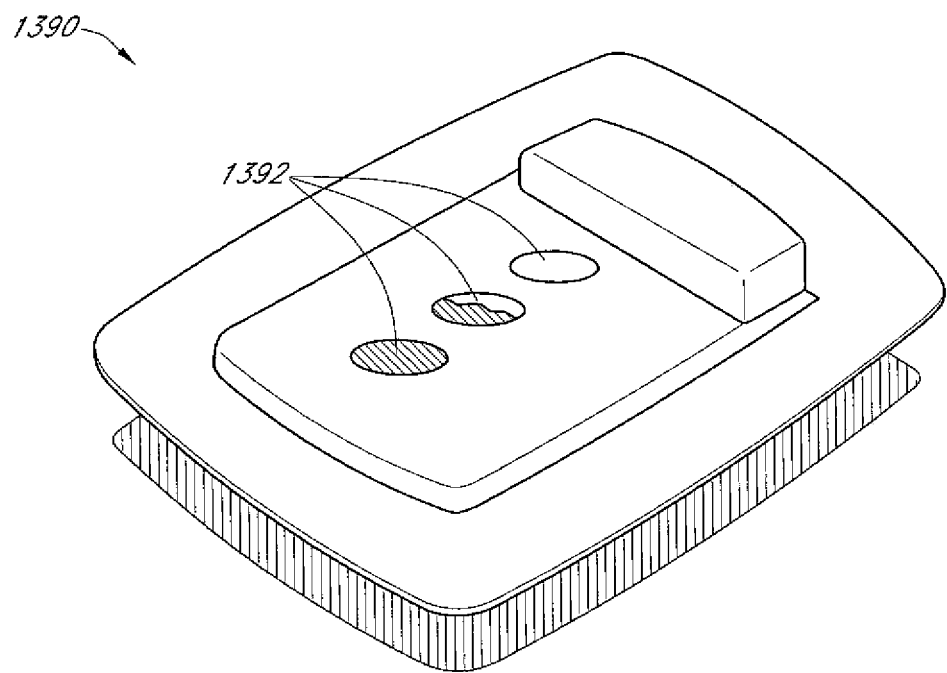

Similarly, with reference to FIG. 76, any dressing embodiments disclosed herein can have one or more fill line indicators 1382 to help a user or medical practitioner assess a level of exudate within a dressing. The fill line indicators 1382 could be lines of substantially transparent appearance across a surface of the dressing, or could be printed lines or markings on the overlay. The fill line indicator can be used to assess when a dressing is ready for changing. With reference to FIG. 77, any embodiments disclosed herein can have a plurality of viewing windows 1392 supported by the backing layer or can have one or more openings or depressions formed in the packing material to permit a user to detect a level of exudate or saturation of the dressing.

Figure 78:
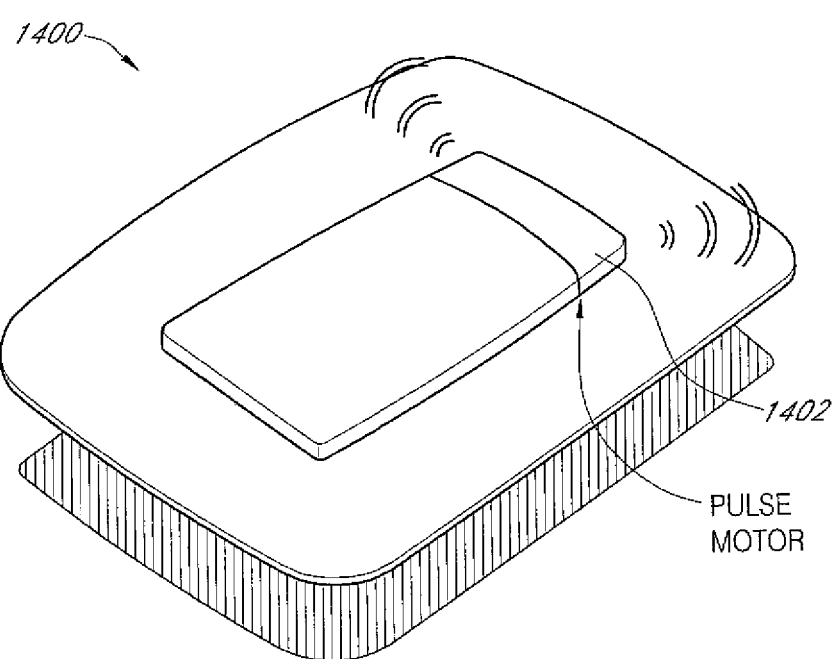
FIG. 78 illustrates an additional embodiment of a dressing kit for negative pressure wound therapy.

As illustrated in FIG. 78, any dressing kit embodiments disclosed herein can be configured to produce a motor pulse or sound to indicate in a controlled manner that the device is working correctly. For example, the dressing kit 1400 can have a pump motor 1402 that can be configured to produce a sound and/or vibration that repeats at regular intervals or following regular patterns.

Figure 79A:
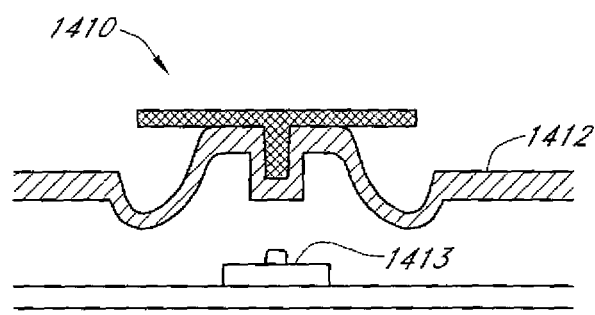
FIGS. 79A-B illustrate an additional embodiment of an activation switch and/or pressure indicator for a dressing kit for negative pressure wound therapy.
Figure 79B:
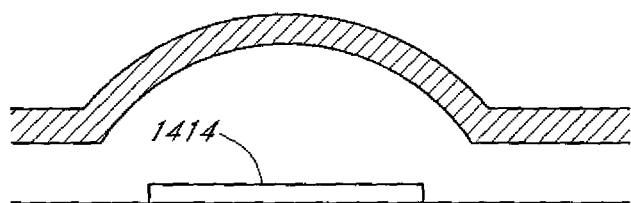

With reference to FIG. 79A, any embodiments disclosed herein can be configured to have a bubble indicator 1410 that serves as a pressure indicator, but which also activates the device, similar to one or more of the other embodiments described above. The bubble indicator will be in communication with the space between the cover layer 1412 and the wound, and can be configured to depress a switch 1413 when depressed. This establishes a clear communication between a working device and the interaction to restart it. As with other embodiments disclosed herein, with a color change material positioned under the bubble, as shown in FIG. 79B, the collapse of the pressure bubble under reduced pressure can reveal a colored bottom to the indicator 1412.

Figure 80A:
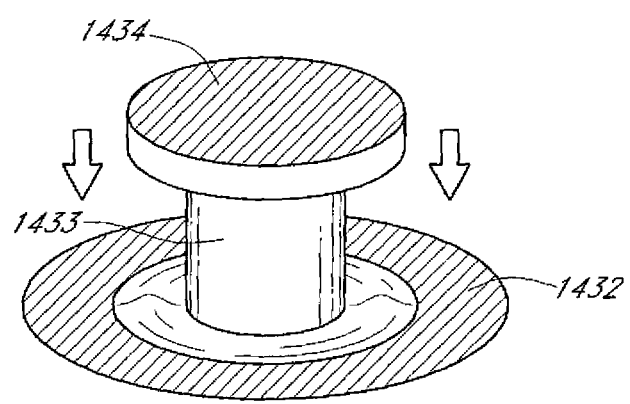
FIGS. 80A-B illustrate an additional embodiment of a pressure indicator for a dressing kit for negative pressure wound therapy.
Figure 80B:
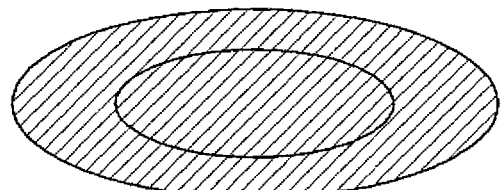

With reference to FIG. 80, any of the pressure indicators disclosed herein can have two or more different colors to help a user better visualize the position of the indicator and, hence, the condition under the overlay. For example, a first colored ring 1432 could be positioned around the protrusion 1433, and the protrusion 1433 can have a similarly colored top surface such that, when the protrusion is collapsed, the color of the top 1434 of the protrusion 1433 matches the color surrounding the protrusion so that it is clear that the protrusion is collapsed. When less than a sufficient amount of reduced pressure is exerted on the overlay such that the protrusion 1433 extends away from the cover of the overlay, a different colored portion of the protrusion can contrast with the color surrounding the overlay to provide a clear indication to a user that the protrusion 1433 is extended and that a less than optimal amount of reduced pressure is present under the overlay. In some embodiments, the color separation or differentiation on the protrusion or indicator can add an extra visual indication that the device requires re-activation. A red side wall can indicate that the device has lost the vacuum or that less than the threshold vacuum level is present.

Figure 81A:
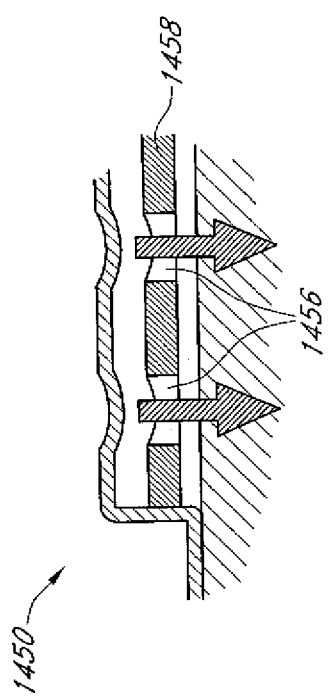
FIGS. 81A-B illustrate an additional embodiment of a dressing kit for negative pressure wound therapy having one or more pressure indicators thereon.
Figure 81B:
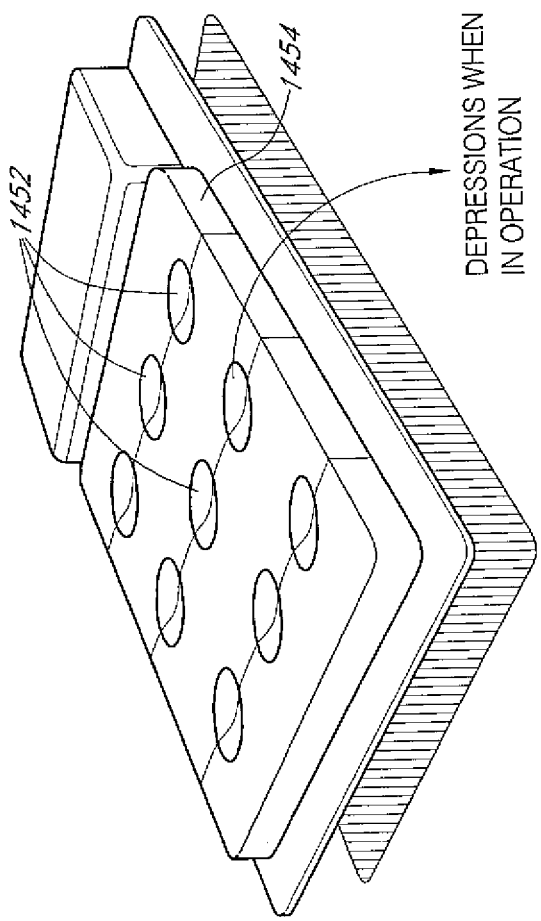

With reference to the embodiment depicted in FIG. 81, any of the dressing kit embodiments disclosed herein can have a plurality of discrete depressions, openings, or other features 1452 formed in a top surface of the packing layers 1454 that can be used to provide a visual and/or tactile indication of the level of reduced pressure beneath a backing layer. In some embodiments, openings 1456 can pass through to a lower layer 1458 of the dressing 1450. In this configuration, when the dressing 1450 is in an operational state, the backing layer to be drawn into or toward the depressions, but relaxed when the dressing is not in an operational state.

Figure 82B:
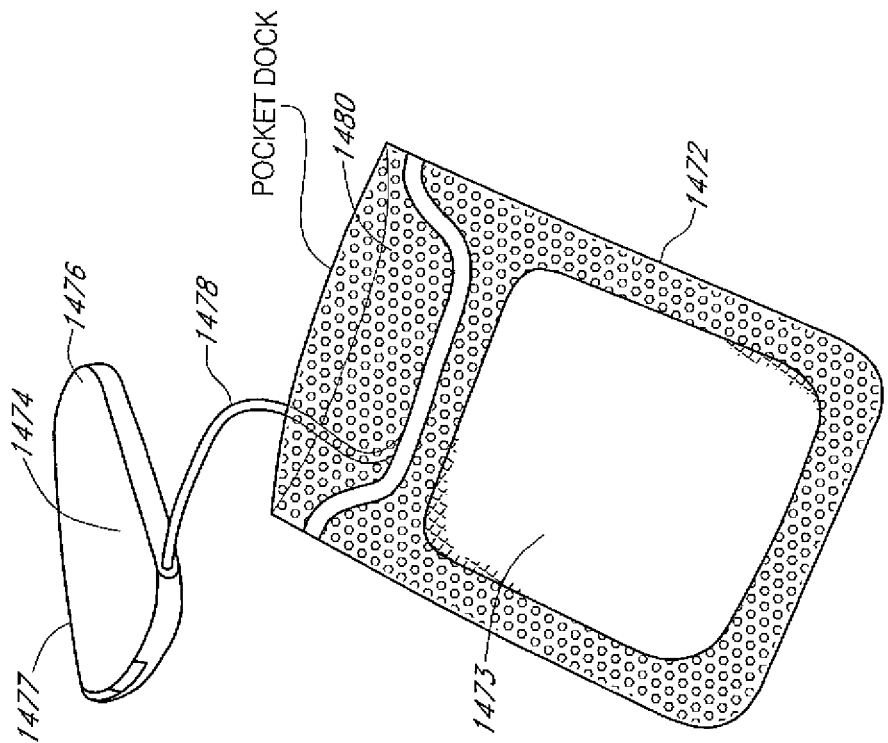
FIGS. 82A-B illustrate an additional embodiment of a dressing kit for negative pressure wound therapy.
Figure 82A:
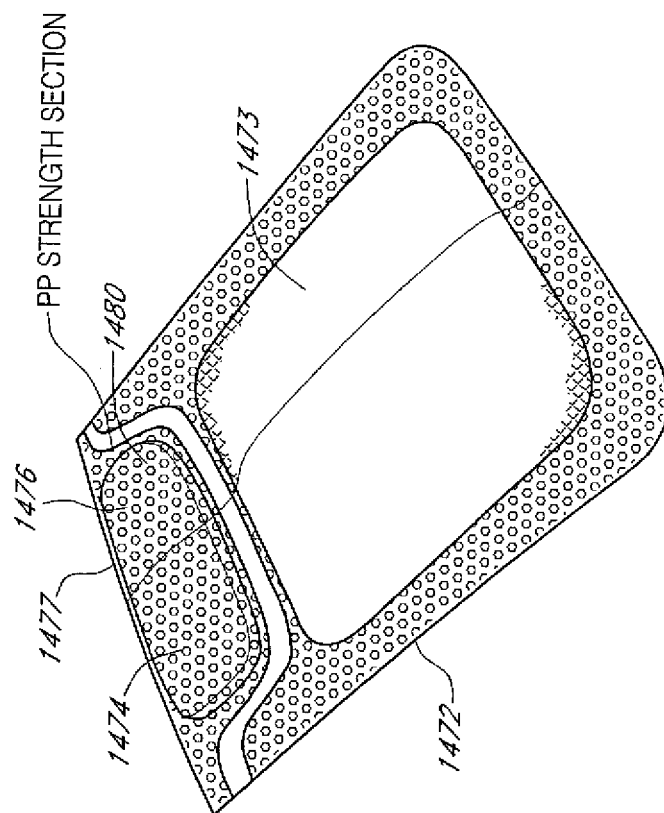
Figure 85E:
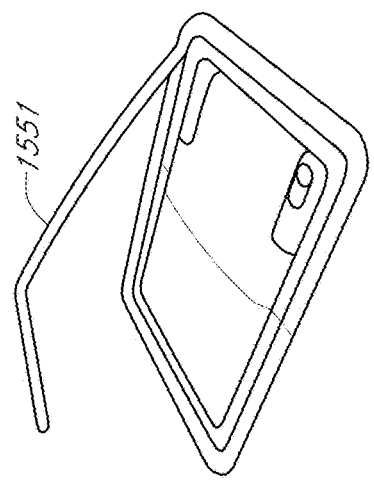
Figure 85D:
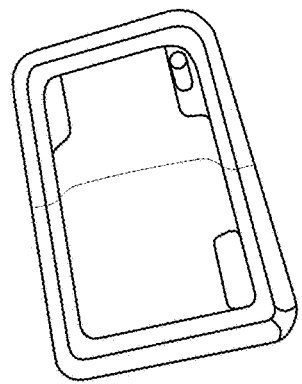
Figure 85C:
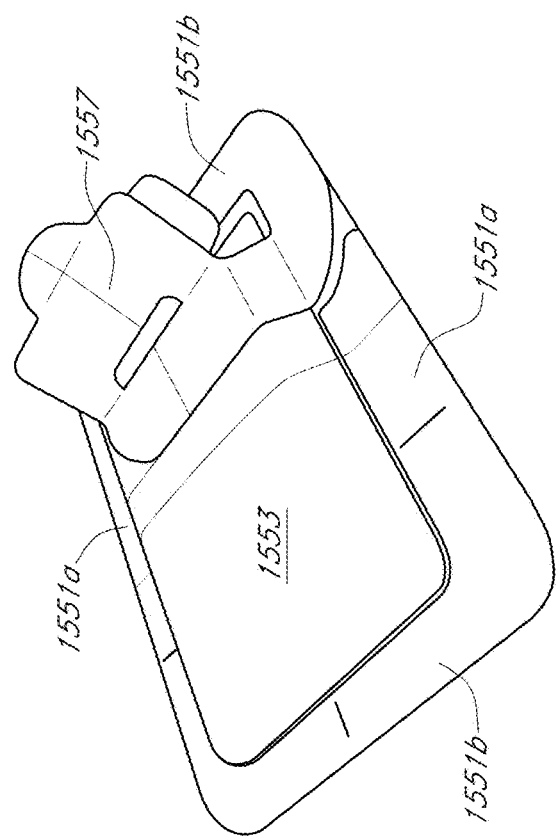

FIG. 82 illustrates another embodiment of a dressing kit 1470 having a dressing member 1472, a pump assembly 1474, and a power source 1476 (which can be housed within a housing 1477 that also houses the pump assembly, or can be distributed across the dressing member 1472, or otherwise). A conduit 1478 can be used to transfer the negative pressure from within the pump assembly 1474 to the dressing member 1472. The dressing member 1472 can have a pocket member 1480 positioned adjacent to the dressing layers 1473 or positioned above the dressing layers 1473 and can be used to removably support the housing 1477 for the pump assembly 1474 and/or the power source 1476. With reference to FIG. 82B, the housing 1477 can be removed from the pocket member 1480 for servicing, battery replacement, or to position the housing 1477 in a different location apart from the dressing for comfort, etc.

FIG. 83 illustrates a carrier 1490 for a pump assembly 1494 that can be used with any of the pump assemblies or dressing kits disclosed herein. The carrier 1490 can be worn on a person's belt or otherwise clipped onto a person's clothing.

In some embodiments, such as the embodiment of the noise attenuating system 1510 illustrated in FIGS. 84A-B, a special pouch or overmold 1512 can be formed to surround any of the pump assemblies disclosed herein. The overmold 1512 can be formed from silicone, rubber, foam, and/or any other material available configured to attenuate the noise and/or vibration of the pump assembly. Additionally, a special pouch or overmold 1514 can be formed to surround any of the pump motor embodiments disclosed herein. The overmold 1514 can be formed from silicone, rubber, foam, and/or any other material available configured to attenuate the noise and/or vibration of the pump motor. In some embodiments, an overmold 1516 for a pump motor can have a slot 1518 therein along a length of the wall portion of the overmold 1516. In one embodiment, the noise attenuating system comprises foam and a silicone boot. In another embodiment, it comprises silicone overmolding on motor and pump.

With reference to FIGS. 85A-E, any of the dressing kit embodiments disclosed herein can have one or more support handle member 1551 removably positioned around a periphery of the dressing 1552 to provide support to the dressing 1552 during application of the dressing 1552 to the body. The support handle member 1551 can increase the stiffness and, hence, reduce the floppiness, of the dressing 1552 to facilitate handleability of the dressing 1552. Providing the additional support on the dressing can be very important to the application of the dressing 1552 to the body, in light of the weight of the pump assembly and batteries on the dressing 1552. The support can be formed from paper, and plastic film, or any other suitable material. Additionally, instructions or other information can be printed on the support material.

In some embodiments, the support handle member 1551 can have a first lengthwise portion 1551a and a second lengthwise portion 1551a positioned between the dressing layers 1553 and an outer perimeter 1552a of the dressing member 1552. In some embodiments, the first and second lengthwise portions 1551a can be interconnected. Additionally, the support handle member 1551 can have a first end portion 1551b and a second end portion 1551b positioned between the dressing layers 1553 and an outer perimeter 1552a of the dressing member 1552. In some embodiments, the first and second end portions 1551b can be interconnected. Additionally, in some embodiments, the support handle member 1551 can have a housing or third portion 1557 configured to cover an end portion of the dressing member 1552. For example, one or more buttons, switches, a pump assembly, a power source, and/or other features can be protectably supported under the third portion 1557 of the support handle member 1551. The support handle member 1551 can be configured to activate the pump upon removal. In some embodiments, the support handle member can be continuous such that each portion is interconnected.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Accordingly, the scope of the present disclosure is intended to be defined only by reference to the appended claims. The accompanying claims and their equivalents are intended to cover such forms or modifications as would fall within the scope and spirit of the protection. Furthermore, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

Further embodiments of this patent application include the embodiments described in U.S. patent application Ser. No. 13/092,042, filed on Apr. 21, 2011. These embodiments are described further below, with reference to the figures from this application that are incorporated by reference herein.

FIG. 3 of U.S. patent application Ser. No. 13/092,042 shows a plan view of a wound dressing including baffle elements that reduce the rate at which wound exudate moves towards the orifice according to one embodiment of the invention. The wound dressing illustrated in FIG. 3 of U.S. patent application Ser. No. 13/092,042 is similar to that shown in FIGS. 1 and 2 of U.S. patent application Ser. No. 13/092,042, but includes a number of baffle elements 310 disposed across the central raised region 201. The baffle elements 310 form barriers in the central region of the dressing, which arrest the movement of wound exudate towards the orifice.

Embodiments of baffle elements that may be used in the wound dressing described herein are preferably at least partly flexible, so as to permit the wound dressing to flex and conform with the skin of the patient surrounding the wound site. When so present in the wound dressing, the baffle elements are preferably constructed so as to at least partially prevent liquid from flowing directly to the wound dressing port or orifice and its associated filter, if so provided. The baffle elements thus increase the distance that liquids may require to reach the port, which may help in absorbing these fluids into the absorbent or superabsorbent material of the wound dressing.

According to some embodiments of the invention, the baffle element may comprise a sealing region in which the absorbent layer 110 and transmission layer 105 are absent and cover layer 140 is sealed to the wound contact layer 101. Thus, the baffle element presents a barrier to the motion of the wound exudate, which must therefore follow a path that avoids the baffle element. Thus the time taken for the wound exudate to reach the orifice is increased.

In some embodiments, the baffle elements may be an insert of a substantially non-porous material, for example a closed-cell polyethylene foam, placed inside the dressing. In some cases, it may be preferable to place such an inserted baffle element in a sealing region where one or more of the absorbent layer 110 and/or transmission layer 105 are absent. A sealant, for example a viscous curing sealant such as a silicone sealant, could be placed or injected as a thin strip so as to form a baffle element that is substantially liquid impermeable. Such a baffle element could be placed or injected into a region of the transmission layer 105 and/or absorbent layer 110, or also a sealing region where the absorbent layer 110 and/or transmission layer 105 are absent.

FIG. 6 of U.S. patent application Ser. No. 13/092,042 illustrates a wound dressing including a baffle element according to a further embodiment of the invention. A single baffle element 610 provides a cup shaped barrier between the bulk of the absorbent layer 110 and the orifice 145. Thus wound exudate that is initially drawn from the wound site within the region defined by the baffle element 610, must follow a path around the outside of the cup shaped barrier to reach the orifice 145. As will be recognized, the baffle element 610 reduces the effect of gravity on reducing the time taken for the wound exudate to move to the orifice 145, as for most orientations of the wound dressing at least a part of the path taken by the wound exudate will be against the force of gravity.

The embodiments of FIGS. 3 and 6 of U.S. patent application Ser. No. 13/092,042 have been described with respect to a wound dressing having a structure as shown in FIG. 1 of U.S. patent application Ser. No. 13/092,042. However, it will be understood that the baffle elements could equally be applied to a wound dressing in which the transmission layer 105 was absent.

FIG. 4 of U.S. patent application Ser. No. 13/092,042 shows a plan view of a wound dressing including the at least one element according to one embodiment of the invention in which a number of baffle elements 410 are provided that extend across the width of the central region 201 of the wound dressing, with further baffle elements 412 formed in a semi-circular path around the orifice 145.

FIG. 5 of U.S. patent application Ser. No. 13/092,042 illustrates the configuration of baffle elements 410 according to some embodiments of the invention. The baffle element comprises a channel of absorbent material 510 underlying the transmission layer 105. A channel in the absorbent layer 110 is located over the baffle element 410 so that the transmission layer is in contact with the cover layer 140 in the region of the baffle element 410. Thus, wound exudate that is moving along a lower surface of the transmission layer 105, and has therefore not been drawn into absorbent layer 110, will come into contact with and be absorbed by the channel of absorbent material 510.

Alternatively, or additionally, baffle elements may comprise one or more channels provided in the surface of the transmission layer 105 underlying and abutting the absorbent layer 110. In use, when negative pressure is applied to the wound dressing, the absorbent layer 110 will be drawn into the channel. The channel in the transmission layer may have a depth substantially equal to the depth of the transmission layer, or may have a depth less than the depth of the transmission layer. The dimensions of the channel may be chosen to ensure that the channel is filled by the absorbent layer 110 when negative pressure is applied to the wound dressing. According to some embodiments, the channel in the transmission layer comprises a channel of absorbent material in the transmission layer 105.

The baffle elements may be formed into a range of shapes and patterns, for example FIGS. 14A to 14L of U.S. patent application Ser. No. 13/092,042 illustrate wound dressings having a number of different exemplifying configurations of baffle elements. FIG. 14A of U.S. patent application Ser. No. 13/092,042 illustrates a linear baffle element in a vertical configuration aligned in the direction of the port or orifice. FIG. 14B of U.S. patent application Ser. No. 13/092,042 illustrates an X-shaped baffle element. FIGS. 14C-E of U.S. patent application Ser. No. 13/092,042 illustrate embodiments of wound dressings with multiple baffle elements, aligned in a generally diagonal, horizontal, or vertical manner.

FIG. 14F of U.S. patent application Ser. No. 13/092,042 illustrates baffle elements arranged in a six-armed starburst configuration, with a center portion left open. FIG. 14G of U.S. patent application Ser. No. 13/092,042 illustrates a W-shaped baffle element on the wound dressing in a position distal to the port or orifice. In FIG. 14H of U.S. patent application Ser. No. 13/092,042, an 3-by-3 array of X-shaped baffle elements is provided on the wound dressing, although it will be understood that more or less X-shaped baffle elements may be used. FIG. 14I of U.S. patent application Ser. No. 13/092,042 shows an embodiment with a plurality of rectangular baffle elements, and wherein one or more baffle elements are located underneath the port in the wound dressing. FIGS. 14J-K of U.S. patent application Ser. No. 13/092,042 illustrate wound dressing embodiments with longer diagonal and horizontal baffle elements. In FIG. 14L of U.S. patent application Ser. No. 13/092,042, rectangular baffle elements are present on this embodiment of a wound dressing, wherein the baffle elements are of different sizes.

What is claimed is:

1. A negative pressure wound therapy device comprising:
    a wound dressing including a backing layer having an opening and adapted for close contact with an outer periphery of a wound site; and
    a pump unit including a housing and a pump,
    wherein the housing includes
        a joint portion joined to the wound dressing, and
        an inlet communicating with the pump,
    wherein the housing is adapted for communicating with a closed space formed by the backing layer and the wound site via the opening of the backing layer and the inlet of the housing,
    wherein the negative pressure wound therapy device further includes an absorbing member adapted for being disposed in the closed space to absorb a liquid, and an exudate passage preventing member with the absorbing member interposed between the exudate passage preventing member and the opening, and
    wherein the absorbing member is configured to absorb and store exudate from the wound site.

2. The negative pressure wound therapy device according to claim 1,
    wherein the housing includes a pressure sensor configured to detect a pressure value, and
    wherein the pump unit includes:
    a battery supplying a power to the pump,
    a controller controlling a driving of the pump, and
    a second housing storing the battery and electrically connected to the housing through a wire.

3. The negative pressure wound therapy device according to claim 2, wherein the pump includes a valve.

4. The negative pressure wound therapy device according to claim 3, wherein the pump is driven by a piezoelectric element.

5. The negative pressure wound therapy device according to claim 2, wherein the pump is driven by a piezoelectric element.

6. The negative pressure wound therapy device according to claim 1, wherein the pump is driven by a piezoelectric element.

7. The negative pressure wound therapy device according to claim 1, wherein the housing is adapted for directly communicating with a closed space formed by the backing layer and the wound site via the opening of the backing layer and the inlet of the housing.

8. The negative pressure wound therapy device according to claim 1, further comprising flow openings configured to allow exudate to flow from the wound site to the absorbing member.

9. The negative pressure wound therapy device according to claim 8, wherein the flow openings are provided around the exudate passage preventing member.

10. The negative pressure wound therapy device according to claim 1, further comprising a filter, wherein the absorbing member is interposed between the filter and the exudate passage preventing member.

11. The negative pressure wound therapy device according to claim 1, wherein the exudate passage preventing member is at a position opposed to the opening.

\* \* \* \* \*